US012371668B2

(12) United States Patent
Radisic et al.

(10) Patent No.: US 12,371,668 B2
(45) Date of Patent: Jul. 29, 2025

(54) METHODS FOR TISSUE GENERATION

(71) Applicant: Milica Radisic, Toronto (CA)

(72) Inventors: Milica Radisic, Toronto (CA); Yimu Zhao, Mississauga (CA); Peter Backx, Toronto (CA); Naimeh Rafatian, Toronto (CA)

(73) Assignee: Milica Radisic, Toronto (CA)

( * ) Notice: Subject to any disclaimer, the term of this patent is extended or adjusted under 35 U.S.C. 154(b) by 1111 days.

(21) Appl. No.: 17/286,865

(22) PCT Filed: Nov. 27, 2019

(86) PCT No.: PCT/US2019/063637
§ 371 (c)(1),
(2) Date: Apr. 20, 2021

(87) PCT Pub. No.: WO2020/113025
PCT Pub. Date: Jun. 4, 2020

(65) Prior Publication Data
US 2021/0380950 A1      Dec. 9, 2021

Related U.S. Application Data

(60) Provisional application No. 62/772,515, filed on Nov. 28, 2018.

(51) Int. Cl.
| C12N 5/071 | (2010.01) |
| C12N 5/077 | (2010.01) |
| C12N 13/00 | (2006.01) |
| G01N 33/50 | (2006.01) |

(52) U.S. Cl.
CPC .......... *C12N 5/0697* (2013.01); *C12N 5/0656* (2013.01); *C12N 5/0657* (2013.01); *C12N 13/00* (2013.01); *G01N 33/5061* (2013.01); *G01N 33/5088* (2013.01); *C12N 2502/1323* (2013.01); *C12N 2502/1329* (2013.01); *C12N 2513/00* (2013.01); *C12N 2533/54* (2013.01); *C12N 2533/56* (2013.01)

(58) Field of Classification Search
CPC .. C12N 5/0697; C12N 5/0656; C12N 5/0657; C12N 13/00; C12N 2502/1323; C12N 2502/1329; C12N 2513/00; C12N 2533/54; C12N 2533/56; C12N 2502/1388; C12N 2506/02; C12N 2506/45; C12N 2529/00; C12N 2531/00; G01N 33/5061; G01N 33/5088; G01N 33/5082
See application file for complete search history.

(56) References Cited

U.S. PATENT DOCUMENTS

2012/0027807 A1\*  2/2012  Chien ...................... A61P 9/00
                                                               435/325
2016/0282338 A1    9/2016  Miklas et al.

FOREIGN PATENT DOCUMENTS

WO    WO-2017156762 A1 \*  9/2017 ........... C12N 5/0031

OTHER PUBLICATIONS

Sidorov, V. Y., et al., "I-Wire Heart-on-a-Chip I: Three-dimensional cardiac tissue constructs for physiology and pharmacology," Acta Biomater 48: 68-78. doi: 10.1016/j.actbio.2016.11.009. Epub Nov. 4, 2016. (Year: 2016).\*
Hernandez, D., et al., "Electrical Stimulation Promotes Cardiac Differentiation of Human Induced Pluripotent Stem Cells," Stem Cells Int. 2016: 1718041. doi: 10.1155/2016/1718041. Epub Dec. 14, 2015. (Year: 2015).\*
Piccini, I., et al., "Human pluripotent stem cell-derived cardiomyocytes: Genome-wide expression profiling of long-term in vitro maturation in comparison to human heart tissue," Genom Data 4:69-72. doi: 10.1016/j.gdata.2015.03.008. (Year: 2015).\*
Lev, M., and Lerner, R., "The theory of Kent: a histologic study of the normal atrioventricular communications of the human heart," Circulation 12(2): 176-184. (Year: 1955).\*
Ott, H., et al., "Perfusion-decellularized matrix: using nature's platform to engineer a bioartificial heart," Nat Med 14(2): 213-221. doi: 10.1038/nm1684. (Year: 2008).\*
Lemme, M., et al., "Atrial-like Engineered Heart Tissue: An In Vitro Model of the Human Atrium," Stem Cell Reports 11(6): 1378-1390. doi: 10.1016/j.stemcr.2018.10.008. Epub Nov. 8, 2018. (Year: 2018).\*
Tan, C. M. J., and Lewandowski, A. J., "The Transitional Heart: From Early Embryonic and Fetal Development to Neonatal Life," Fetal Diagn Ther 47:373-386. DOI: 10.1159/000501906 (Year: 2019).\*
Gabriel, G. C., et al., "Establishment of Cardiac Laterality," Adv Exp Med Biol 2024:1441: 167-183. doi: 10.1007/978-3-031-44087-8_9. (Year: 2024).\*
Boudou, Thomas, et al., "A Microfabricated Platform to Measure and Manipulate the Mechanics of Engineered Cardiac Microtissues", Tissue Engineering: Part A, vol. 18, Nos. 9 and 10, 2012, Dec. 29, 2011, pp. 910-919.
De Boer, Bouke A., et al., "Growth of the developing mouse heart: An interactive qualitative and quantitative 3D atlas", www.elsevier.com/locate/developmentalbiology, May 14, 2012, pp. 203-213.
Doppler, Stefanie A., et al., "Cardiac fibroblasts: more than mechanical support", http://dx.doi.org/10.21037/jtd.2017.03.122, Mar. 4, 2017, pp. S36-S51.
Lemme, Marta, et al., "Atrial-like Engineered Heart Tissue: An In Vitro Model of the Human Atrium", Stem Cell Reports, vol. 11, Dec. 11, 2018, pp. 1378-1390.
Ronaldson-Bouchard, Kacey, et al., "Advanced maturation of human cardiac tissue grown from pluripotent stem cells", www.nature.com/nature, Apr. 2018, pp. 1-30.

(Continued)

*Primary Examiner* — Tracy Vivlemore
*Assistant Examiner* — Eric J Rogers
(74) *Attorney, Agent, or Firm* — Smart & Biggar LP

(57) ABSTRACT

The present disclosure provides ex vivo chamber-specific cardiac tissues, methods for generating the cardiac tissues in a bioreactor, and methods of using the cardiac tissues. Examples of cardiac tissues that can be generated include, but are not limited to, atrial tissues, ventricular tissues, and composite tissues having an atrial tissue connected to a ventricular tissue.

14 Claims, 80 Drawing Sheets

(56) References Cited

OTHER PUBLICATIONS

Sidorov, Veniamin Y., et al., "I-Wire Heart-on-a-Chip I: Three-dimensional cardiac tissue constructs for physiology and pharmacology", Acta Biomater, Jan. 15, 2017, pp. 1-22.

Sun, Xuetao, et al., "Biowire platform for maturation of human pluripotent stem cell-derived cardiomyocytes", http://dx.doi.org/10.1016/j.ymeth.2015.11.005, Nov. 4, 2015, pp. 21-26.

Thavandiran, Nimalan, et al., "Design and formulation of functional pluripotent stem cell-derived cardiac microtissues", www.pnas.org/cgi/doi/10.1073/pnas/1311120110, Nov. 18, 2013, pp. 1-10.

Zhao, Yimu, et al., "A platform for generation of chamber specific cardiac tissues and disease monitoring", Cell. 2019, Feb. 7, 2019, 176(4): 913-927.e18.doi: 10.1016/j.cell.2018.11.042., pp. 1-34.

Xhao, Yimu, et al., "Engineering microenvironment for human cardiac tissue assembly in heart-on-a-chip platform", Matrix Biol., Oct. 11, 2020, pp. 1-24.

\* cited by examiner

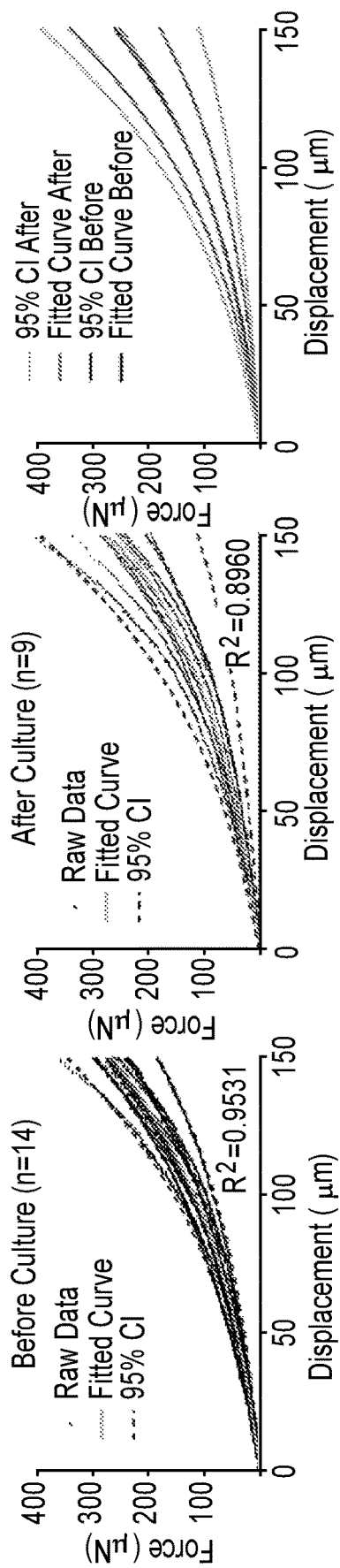
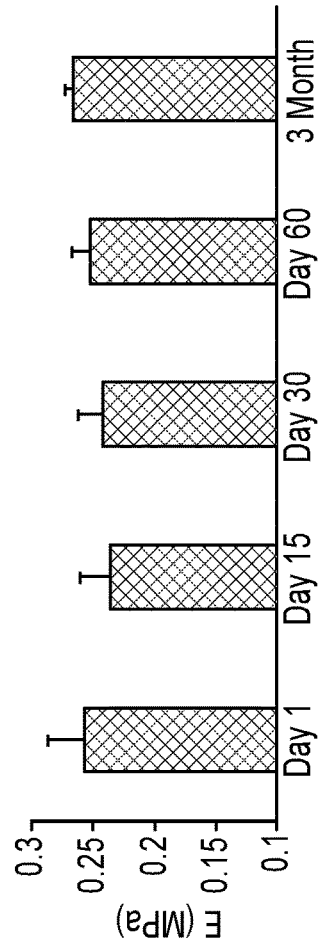
FIG. 2C
FIG. 2D

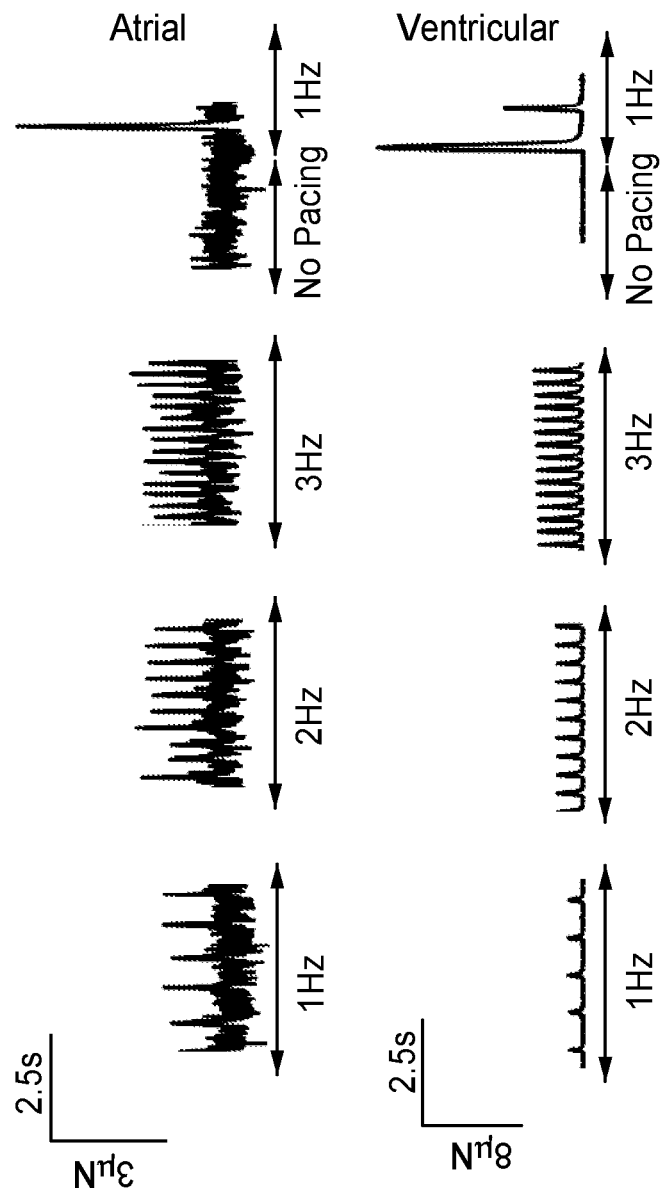
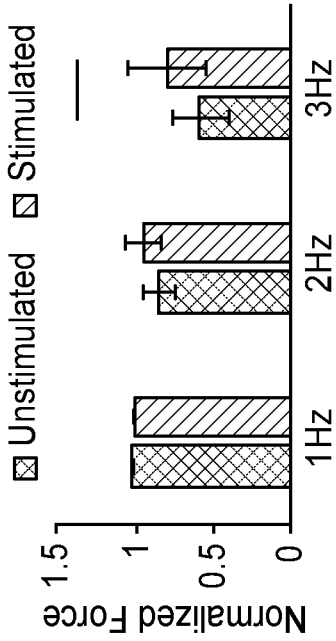
FIG. 4A
FIG. 4B

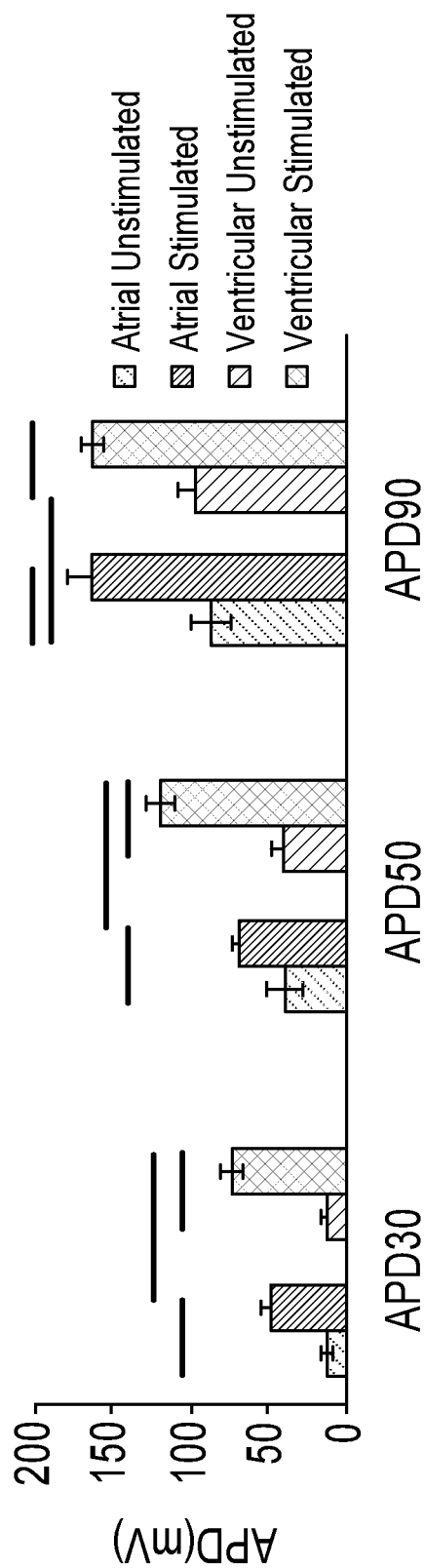
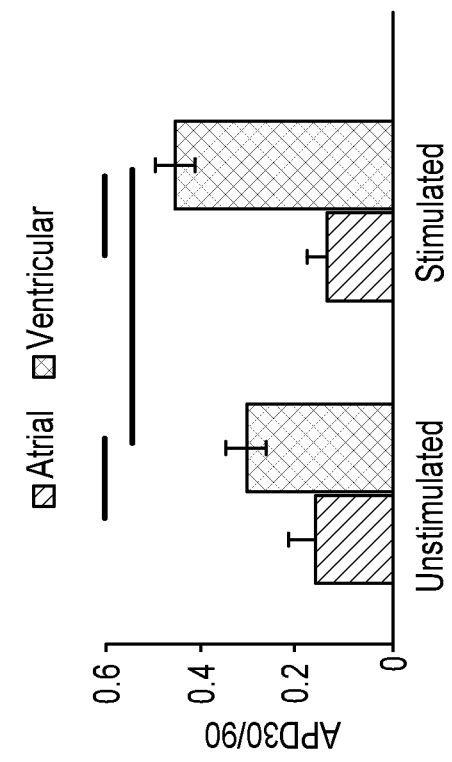
FIG. 4L
FIG. 4M

| Publication ID | Gender | Age | lvmht27 | EF |
|---|---|---|---|---|
| Non-Affected A | Female | 37 | 34.8 | 66 |
| Non-Affected B | Female | 37 | 24.9 | 60 |
| Non-Affected C | Female | 60 | 48.3 | 71 |
| AffectedD | Female | 42 | 97.7 | 59 |
| AffectedE | Female | 43 | 61.4 | 61 |
| AffectedF | Male | 40 | 78.4 | 56 |

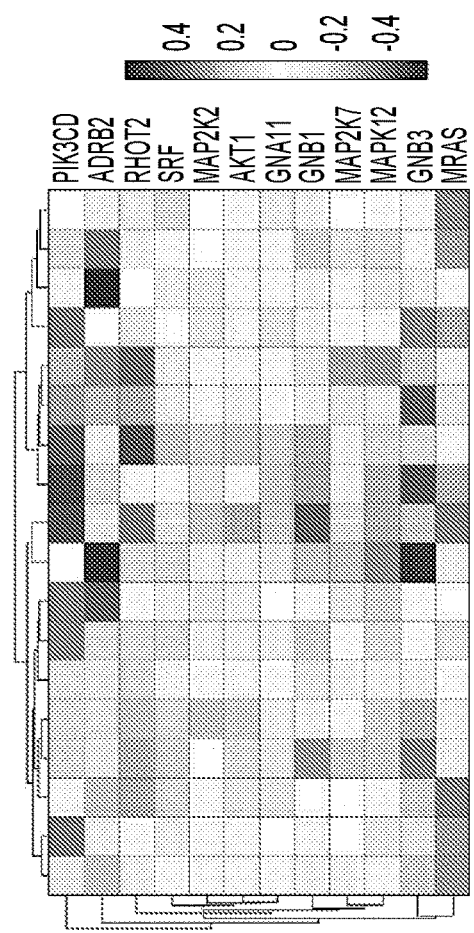
FIG. 6E
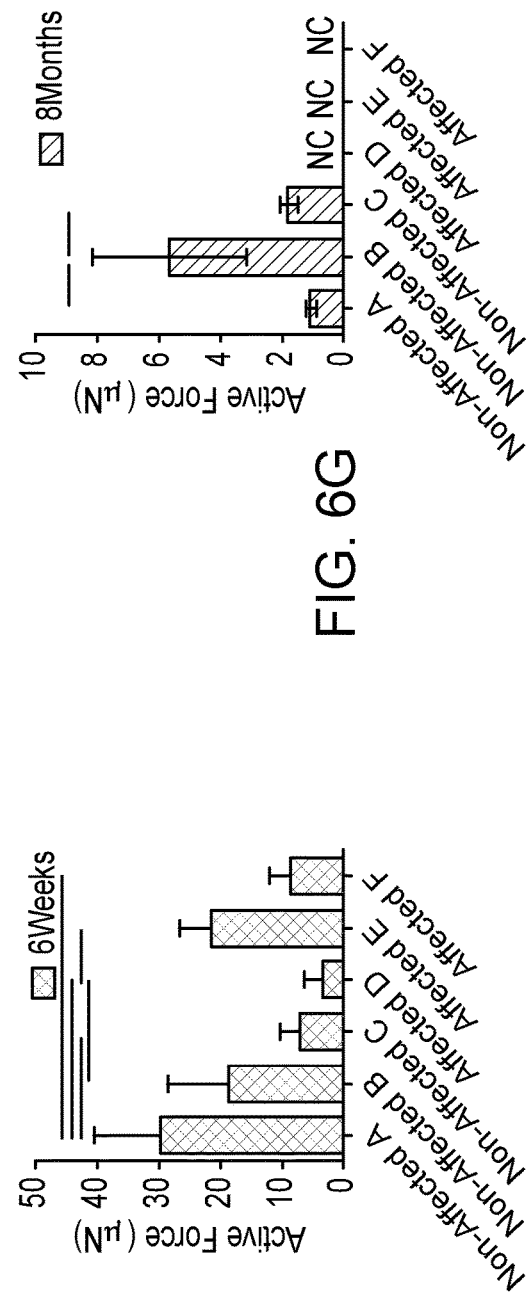
FIG. 6F
FIG. 6G

|  | Atrial | Mid Region | Ventricular | P (a vs v) | P (a vs m) | P (v vs m) |
|---|---|---|---|---|---|---|
| Amplitude (dF/Fo) | 0.040±0.015 | 0.044±0.023 | 0.080±0.032 | 0.062 | 0.958 | 0.100 |
| Time to Peak (s) | 0.051±0.006 | 0.051±0.013 | 0.049±0.012 | 0.964 | 1 | 0.972 |
| Rising Slope (dF/Fo/s) | 0.832±0.401 | 0.909±0.449 | 1.69±0.481 | 0.025* | 0.959 | 0.042* |
| Time from Peak (s) | 0.290±0.038 | 0.297±0.045 | 0.290±0.051 | 1 | 0.970 | 0.966 |
| Tau decay (s) | 0.157±0.045 | 0.183±0.060 | 0.127±0.044 | 0.616 | 0.705 | 0.222 |
FIG. 7E
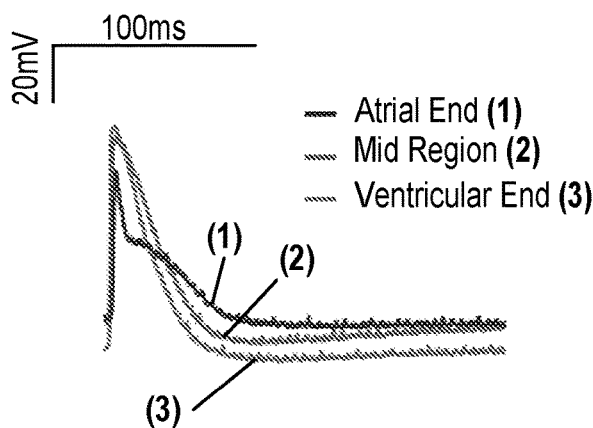
FIG. 7F
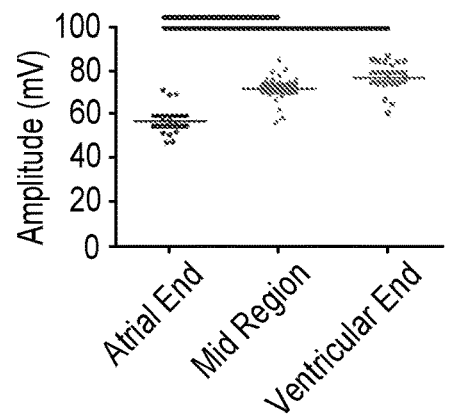
FIG. 7G

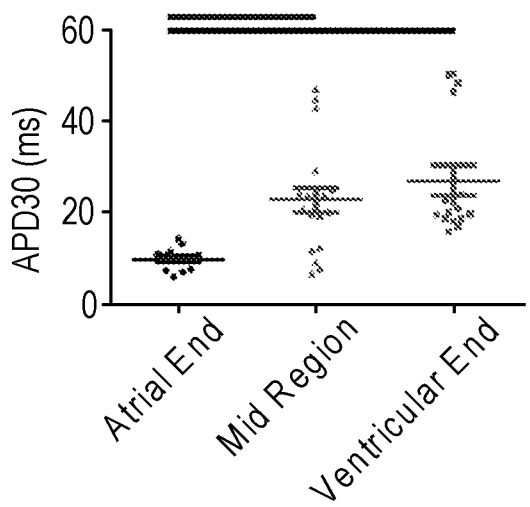 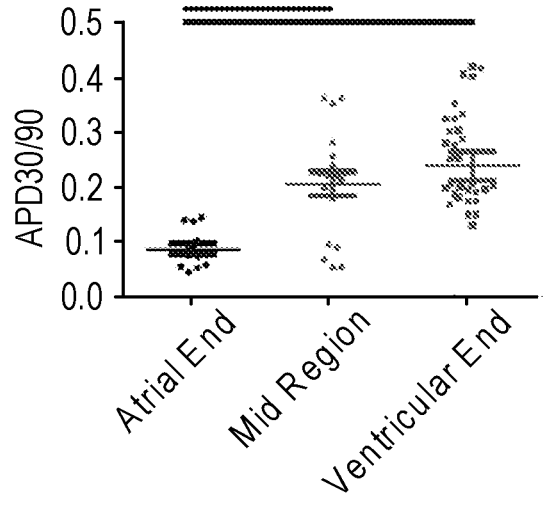
FIG. 7H  FIG. 7I
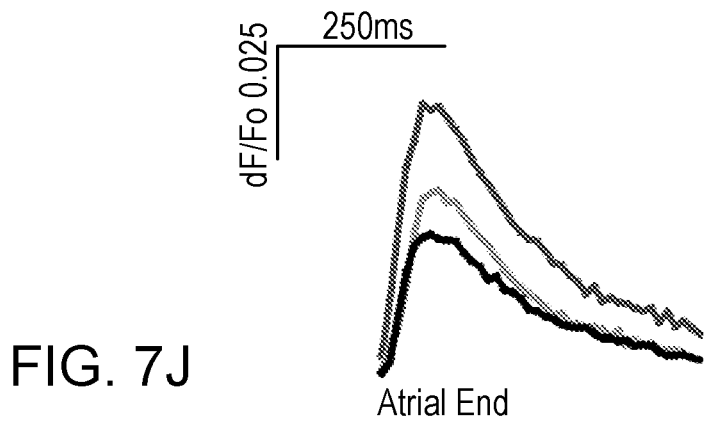
FIG. 7J
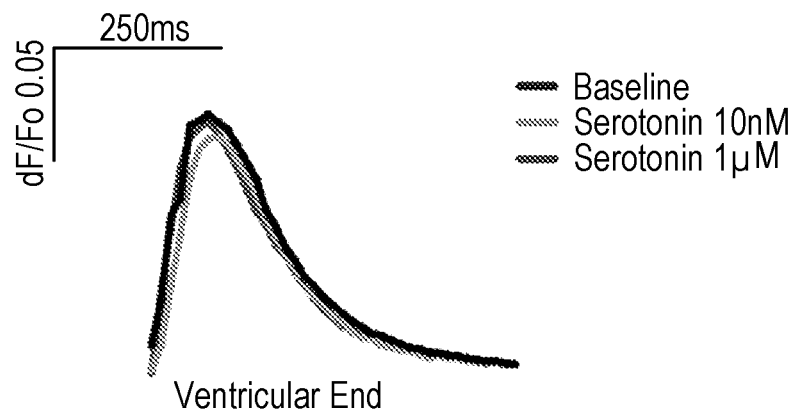
FIG. 7K

| Chamber Specification (Stimulation Protocol) | Source of Cardiomyocytes |
|---|---|
| Ventricular (1Hz/week) | BJ1D hiPSC |
| | HES3 hESC |
| | HES2 hESC |
| | iCell |
| | iCell² |
| | C2A iPSC |
| | Non-Affected A iPSC |
| | Non-Affected B iPSC |
| | Non-Affected C iPSC |
| | Affected D iPSC |
| | Affected E iPSC |
| | Affected F iPSC |
| Atrial (0.4Hz/day) | HES3 hESC* |
| | MSC-iPSC1* |
| Atrioventricular (1Hz/week) | HES3 hESC, HES3 hESC* |
| | BJ1D hiPSC, HES3 hESC* |

FIG. 8B

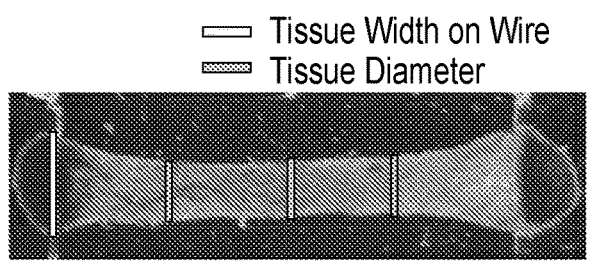

— Tissue Width on Wire
▬ Tissue Diameter

FIG. 8C

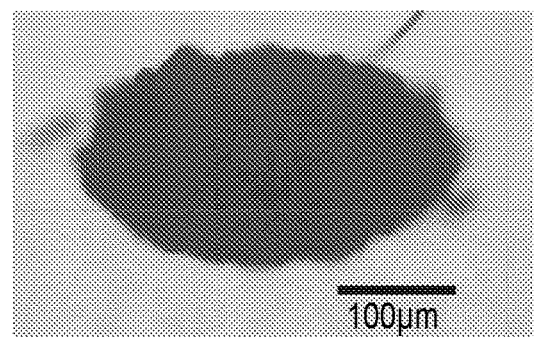

| Input Number of CMs | Active Force (mN) | Active Force (mN/mm²) | Active Force/Input CM nN/Cell | Pacing Frequency | Reference |
|---|---|---|---|---|---|
| 2.5x10⁶ | 0.35±0.11* | | 0.14±0.044 | 1Hz | (Riegler et al., 2015) |
| 1.0x10⁶ | 0.152±0.006* | | 0.152±0.006 | ~1Hz | (Mannhardt et al., 2016) |
| 3.75x10⁵ | 1.3±0.051* | 23.2±1.6* | 3.46±0.14 | 1.5Hz | (Jackman et al., 2016) |
| 1.5x10⁶ | 2.635±0.34 | 6.2±0.8* | 1.12±0.23 | 1.5Hz | (Tiburcy et al., 2017) |
| 2x10⁶ | | ~2.5* | ~1.25 | 1Hz | (Ronaldson-Bouchard et al., 2018) |
| 7.46x10⁴ | 0.0025±0.0012 | 0.051±0.025 | 0.034±0.017 | 1Hz | (Biowire II Platform) |
| 7.46x10⁴ | 0.062±0.04 | 1.2±0.8 | 0.83±0.53 | PRP | (Biowire II Platform) |

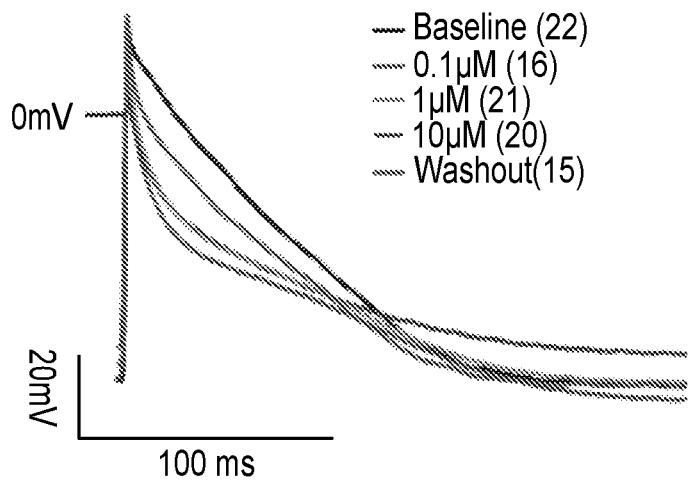 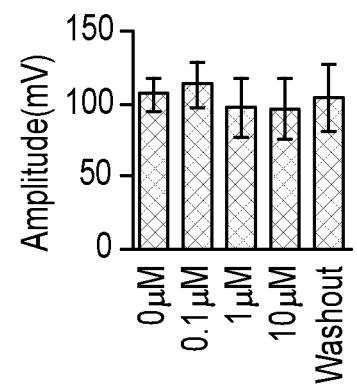
FIG. 12E
FIG. 12F
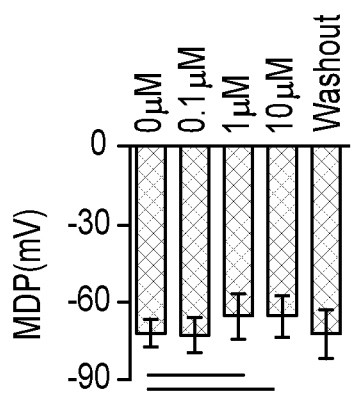 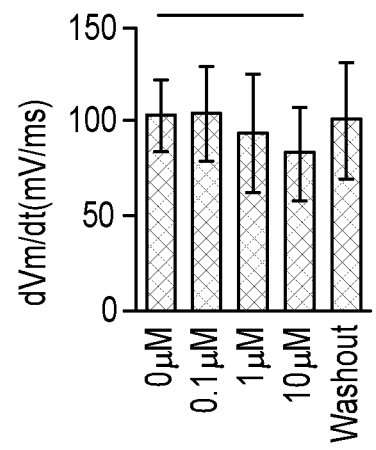
FIG. 12G
FIG. 12H
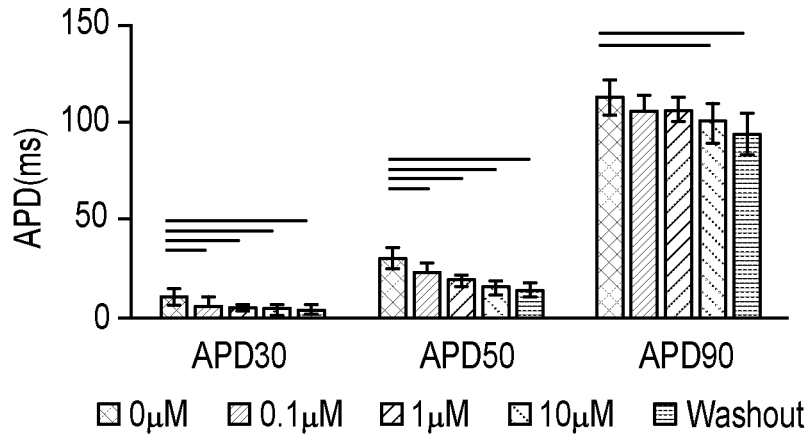
FIG. 12I

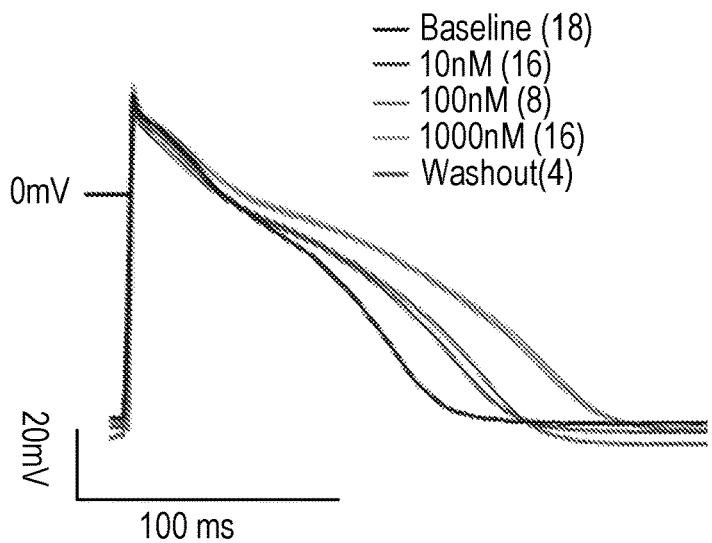
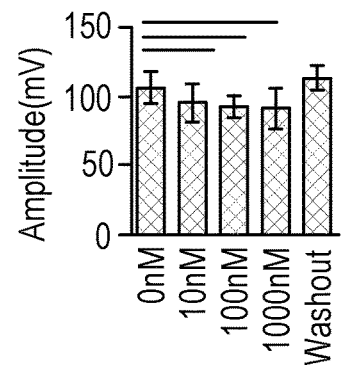
FIG. 12J
FIG. 12K
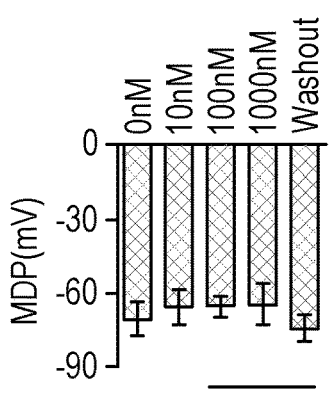
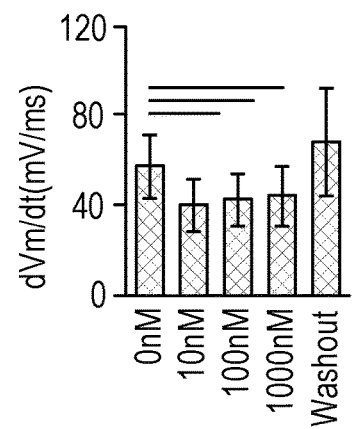
FIG. 12L
FIG. 12M
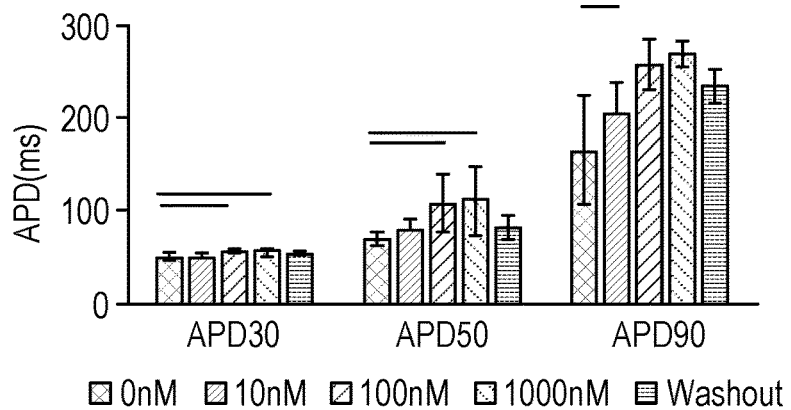
FIG. 12N

METHODS FOR TISSUE GENERATION

RELATED APPLICATIONS

This application is a national stage application, filed under 35 U.S.C. 371, of International Application No. PCT/US2019/063637, filed on Nov. 27, 2019, which claims priority to and the benefit of U.S. Provisional Application No. 62/772,515, filed Nov. 28, 2018, the contents of each of which are incorporated herein by reference in their entireties.

FIELD OF THE INVENTION

The present invention relates to ex vivo tissues, methods of generating the tissues, and methods of using the tissues.

BACKGROUND OF THE INVENTION

Profound physiological differences among species, in action potentials, ion current profiles, and contractile rates, motivate the development of human cardiac tissues for evaluation of the structural and functional changes induced by pharmacological compounds and disease modelling.

Although ideal platforms for human cardiac studies should yield distinct atrial and ventricular tissues of high biological fidelity, most cardiac tissue engineering approaches using human pluripotent stem cells (hPSC) have focused on generating ventricular myocardium and assessing adverse ventricular events such as long QT syndrome and torsades de pointes. This has in part been due to the lag in developing reliable chamber-specific hPSC differentiation protocols. Additionally, screening for atrial toxicity is important, given that atrial and ventricular cardiomyocytes (CMs) have distinct mechanical, electrophysiological and cellular properties. For example, the ultrarapid $K^+$ current, $I_{kur}$, is a major and unique repolarizing current in atrial CMs whereas the rapid ($I_{Kr}$) and slow ($I_{Ks}$) potassium currents are the predominant determinants of ventricular repolarization. Moreover, the ventricles and atria have unique chamber-specific defects and drug-induced myopathies, making human ventricular myocardium an inadequate platform for discovery of atrial drugs. The atrial-specific platforms for drug screening are especially important, given that atrial fibrillation is the most common cardiac arrhythmia which is reaching epidemic levels in our aging population, and for which current treatment approaches have limited success. Indeed, currently used pharmacological agents for treating atrial fibrillation have deadly unwanted side-effects on ventricular CMs which predispose to sudden cardiac death.

Induced pluripotent stem cells (iPSC) offer the possibility to determine the pathogenesis of cardiac disease as powerfully demonstrated with cardiac microtissues used to model cardiomyopathy as a result of sarcomeric protein titin truncations or mitochondrial protein taffazin mutations. Yet, some of the most common cardiac diseases are complex, polygenic conditions that are strongly influenced by environmental factors. For example, hypertensive heart disease arises from cardiac changes induced by prolonged hypertension leading to cardiac hypertrophy, left ventricular dysfunction and ultimately heart failure. Thus, to model polygenic disease, it is important to provide a chronic increased workload to the cardiac tissue over a prolonged time period.

There is a need for a platform that can enable creation of electrophysiologically distinct atrial and ventricular tissues, and that is capable of providing month-long biophysical stimulation of 3D tissues to model a polygenic disease.

SUMMARY OF THE INVENTION

One aspect of the present disclosure relates to a chamber-specific cardiac tissue comprising a chamber-specific cardiac tissue comprising a hydrogel and a plurality of cells including cardiomyocytes and cardiac fibroblasts, wherein at least a portion of the cells are encapsulated inside the hydrogel.

In some embodiments, at least 30% of the cells are substantially aligned in the same direction.

In some embodiments, at least 60% of the cells are substantially aligned in the same direction.

In some embodiments, the cardiac tissue is an atrial, a ventricular tissue, or a combination thereof.

In some embodiments, the cardiomyocytes and cardiac fibroblasts are present in a ratio of about 1:2 to 50:1.

In some embodiments, the chamber-specific cardiac tissue further comprises mesenchymal stem cells, CD90+ cells, mesodermal cells, or a combination thereof.

In some embodiments, the hydrogel comprises collagen or a collagen derivative, intestinal submucosa or a derivative thereof, cellulose or a cellulose derivative, a proteoglycan, heparin sulfate, chondroitin sulfate, keratin sulfate, hyaluronic acid, elastin, fibronectin, thrombin, laminin, fibrin, chitosan, alginate, Matrigel®, Geltrex®, agarose, decellularized extracellular matrix, polyethylene glycol or a derivative thereof, silicone or a derivative thereof, or a combination thereof.

In some embodiments, the hydrogel comprises collagen and fibrin.

In some embodiments, the cardiac tissue has a volume of about 0.1-2.5 $mm^3$.

In some embodiments, the cardiac tissue has a length of at least about 1 mm.

One aspect of the present disclosure relates to an ex vivo tissue comprising an atrial tissue and a ventricular tissue, wherein the atrial tissue is connected to the ventricular tissue.

In some embodiments, the ex vivo tissue has at least about 30% of cells substantially aligned in the same direction.

In some embodiments, the ex vivo tissue has at least about 60% of cells substantially aligned in the same direction.

In some embodiments, at least a portion of the cells are encapsulated inside the hydrogel.

In some embodiments, the hydrogel comprises collagen or a collagen derivative, intestinal submucosa or a derivative thereof, cellulose or a cellulose derivative, a proteoglycan, heparin sulfate, chondroitin sulfate, keratin sulfate, hyaluronic acid, elastin, fibronectin, thrombin, laminin, fibrin, chitosan, alginate, Matrigel®, Geltrex®, agarose, decellularized extracellular matrix, polyethylene glycol or a derivative thereof, silicone or a derivative thereof, or a combination thereof.

In some embodiments, the hydrogel comprises collagen and fibrin.

In some embodiments, an atrial-enriched biomarker is expressed at a higher level in the atrial tissue than the ventricular tissue.

In some embodiments, the atrial-enriched biomarker is selected from the group consisting of NPPA, GJA5, KCNJ12, MYH6, MYL4, MYL7, CACNA1G, KCNA5, GATA4, KCNJ3, HCN4, TBX5, and ATP2A2.

One aspect of the present disclosure relates to an ex vivo tissue system comprising a chamber-specific cardiac tissue and a bioreactor, wherein the bioreactor includes at least two elastic sensing elements configured to support the chamber-specific cardiac tissue.

In some embodiments, the chamber-specific cardiac tissue comprises a plurality of cells including cardiomyocytes and cardiac fibroblasts.

In some embodiments, at least about 30% of the cells are substantially aligned in the same direction.

In some embodiments, at least about 60% of the cells are substantially aligned in the same direction.

In some embodiments, the cardiomyocytes and cardiac fibroblasts are present in a ratio of about 1:2 to 50:1.

In some embodiments, at least a portion of the cells are encapsulated inside the hydrogel.

In some embodiments, the hydrogel comprises collagen or a collagen derivative, intestinal submucosa or a derivative thereof, cellulose or a cellulose derivative, a proteoglycan, heparin sulfate, chondroitin sulfate, keratin sulfate, hyaluronic acid, elastin, fibronectin, thrombin, laminin, fibrin, chitosan, alginate, Matrigel®, Geltrex®, agarose, decellularized extracellular matrix, polyethylene glycol or a derivative thereof, silicone or a derivative thereof, or a combination thereof.

In some embodiments, the bioreactor further comprises a well having a bottom; and the at least two elastic sensing elements are disposed across the well such that there is a gap between the sensing elements and the bottom of the well.

In some embodiments, the bioreactor further comprises at least two electrodes configured to apply an electrical stimulation across the well of the bioreactor.

In some embodiments, the at least two elastic sensing elements comprise a polymer selected from the group consisting of polylactic acid, poly(lactic-co-glycolic) acid, poly(caprolactone), polyglycolide, polylactide, polyhydroxobutyrate, polyhydroxyalcanoic acid, chitosan, hyaluronic acid, poly(2-hydroxyethyl-methacrylate), poly(ethylene glycol), poly(L-lactide) (PLA), poly(dimethysiloxane) (PDMS), poly(methylmethacrylate) (PMMA), poly(glycerol sebacate), poly(octamethylene maleate (anhydride) citrate) (POMaC), POMaC without citric acid, poly($\varepsilon$-caprolactone), polyurethane, silk, and a combination thereof.

In some embodiments, the polymer is POMaC.

In some embodiments, the chamber-specific cardiac tissue has a volume of about 0.1-20 $mm^3$.

One aspect of the present disclosure relates to a method for producing an ex vivo atrial tissue, the method comprising: (a) applying an electrical stimulation at a first frequency to a plurality of atrial cardiomyocytes for a first period of time, the first frequency being equal to or greater than a suprathreshold frequency; (b) increasing the frequency of the electrical stimulation at a rate of at least about 0.05 Hz/day until the frequency is at a second frequency of no more than about 6 Hz; and (c) maintaining the electrical stimulation at the second frequency for a second period of time, thereby producing the ex vivo atrial tissue.

In some embodiments, the first frequency is about 1-3 Hz.

In some embodiments, the rate is no more than about 1 Hz/day.

In some embodiments, the first period of time is about 1-100 days.

In some embodiments, the second period of time is about 1-7 days.

In some embodiments, the plurality of atrial cardiomyocytes is encapsulated in a hydrogel.

In some embodiments, the hydrogel comprises collagen or a collagen derivative, intestinal submucosa or a derivative thereof, cellulose or a cellulose derivative, a proteoglycan, heparin sulfate, chondroitin sulfate, keratin sulfate, hyaluronic acid, elastin, fibronectin, thrombin, laminin, fibrin, chitosan, alginate, Matrigel®, Geltrex®, agarose, decellularized extracellular matrix, polyethylene glycol or a derivative thereof, silicone or a derivative thereof, or a combination thereof.

In some embodiments, the plurality of atrial cardiomyocytes is suspended on at least two elastic sensing elements in a bioreactor; and the at least two elastic sensing elements deform in response to the contractile force exerted by the plurality of atrial cardiomyocytes.

One aspect of the present disclosure relates to a method for producing an ex vivo ventricular tissue, the method comprising: (a) applying an electrical stimulation at a first frequency to a plurality of ventricular cardiomyocytes for a first period of time, the first frequency being equal to or greater than a suprathreshold frequency; (b) increasing the frequency of the electrical stimulation at a rate of at least about 0.1 Hz/day until the frequency is at a second frequency of no more than about 6 Hz; and (c) maintaining the electrical stimulation at the second frequency for a second period of time, thereby producing the ex vivo ventricular tissue.

In some embodiments, the first frequency is about 1-3 Hz.

In some embodiments, the rate is no more than about 1 Hz/day.

In some embodiments, the first period of time is about 1-100 days.

In some embodiments, the second period of time is about 1-7 days.

In some embodiments, the plurality of ventricular cardiomyocytes is encapsulated in a hydrogel.

In some embodiments, the hydrogel comprises collagen or a collagen derivative, intestinal submucosa or a derivative thereof, cellulose or a cellulose derivative, a proteoglycan, heparin sulfate, chondroitin sulfate, keratin sulfate, hyaluronic acid, elastin, fibronectin, thrombin, laminin, fibrin, chitosan, alginate, Matrigel®, Geltrex®, agarose, decellularized extracellular matrix, polyethylene glycol or a derivative thereof, silicone or a derivative thereof, or a combination thereof.

In some embodiments, the plurality of ventricular cardiomyocytes is suspended on at least two elastic sensing elements in a bioreactor; and the at least two elastic sensing elements deform in response to the contractile force exerted by the plurality of ventricular cardiomyocytes.

One aspect of the present disclosure relates to an ex vivo atrial tissue produced by the methods described herein.

One aspect of the present disclosure relates to an ex vivo ventricular tissue produced by the methods described herein.

BRIEF DESCRIPTION OF THE DRAWINGS

FIG. 1A is a schematic of the Biowire II platform design and tissue generation.

FIGS. 1B-1D are images of representative tissues in the Biowire II platform. (FIG. 1B) shown with a bright field imaging (Scale bar=1 mm); (FIG. 1C) confocal imaging of F-actin and DAPI staining (Scale bar=1 mm); and (FIG. 1D) confocal imaging of troponin-T and DAPI staining (Scale bar=30 µm).

FIG. 1E is a series of representative bright field images of tissues generated from several different CM sources, where * denotes atrial-specific tissues. (Scale bar=1 mm).

FIG. 1F is a graph showing that for long-term absorption test, rhodamine B levels were assessed after incubation in Biowire II or PDMS chips for 6 h, 24 h, 48 h and 1 week. # indicates p<0.05 vs. control at each time point. Solid line indicates significant difference between the two groups. Dashed areas represent levels (avg±stdev) of rhodamine B in control polystyrene tissue culture wells. (Data are shown as avg±stdev, n=3, Two-way ANOVA followed by Tukey's test).

FIG. 1G is a series of bright field and fluorescence images of chips without rhodamine B incubation (No Treatment), incubated with rhodamine B for 1 wk (With Rhodamine) and incubated with Rhodamine B for 1 wk followed by washout for 2 h (After 2 h Wash). Scale bar=5 mm.

FIGS. 2A-2G show that the Biowire II platform enables non-invasive assessment of passive tension and active force.

FIG. 2A is a schematic of the apparatus used to calibrate POMaC wires using a "MicroSquisher" displacement test.

FIG. 2B is a set of images showing POMaC wire configuration prior to contact and after displacement by a 0.5 mm custom probe attached to the MicroSquisher.

FIG. 2C is a series of plots showing that mechanical testing of polymer wires revealed no differences in mechanical properties of the POMaC wires before and 6 weeks after cell cultivation.

FIG. 2D is a graph showing that the Young's Modulus of POMaC testing strips did not change measurably during 3 months of culture with cells and media. (avg±stdev, n≥3, one-way ANOVA).

FIG. 2E is a series of time lapse images showing the bending of POMaC wires due to tissue contraction (electrically paced at 1 Hz). Scale bar=200 μm. Wire bending due to passive tension and the maximum active force development generated by the tissues are illustrated with the red bars.

FIG. 2F is a graph showing typical forces dynamically estimated from video images using the force-displacement calibration curves allowing passive tension and the time course of active force development.

FIG. 2G is a series of representative traces of changes in the active forces and beat patterns of Biowire II tissues under stimulation in response to the application of several compounds with well-known cardiac actions. Tissues were generated from ventricular Hes3 hESC-CM and BJ1D iPSC-CM.

FIG. 3A is a graph showing the protocols used to electrically condition tissues in order to promote tissue organization and maturation.

FIG. 3B is a set of graphs showing that principal component analyses indicate distinct clustering of atrial versus ventricular tissues with (St) and without (UnSt) electrical conditioning (n=3-4/group).

FIG. 3C is a heat map illustrating differences in expression levels of selected atrial and ventricular functional markers between atrial and ventricular Biowires, with and without electrical conditioning.

FIG. 3D is a graph showing gene set enrichments based on custom cardiac ontologies for adult ventricle and atrial chambers. Electrically conditioned ventricular Biowires are significantly enriched for human ventricular genes, while conditioned atrial Biowires are statistically enriched for human atrial genes. In FIGS. 3A-3D, all tissues were derived from Hes3 cells.

FIGS. 3E and 3F are a series of confocal images of representative atrial (FIG. 3E) and ventricular (FIG. 3F) tissues immunostained for sarcomeric α-actinin and F-actin (first row); connexin-43 (Cx43, only for ventricular tissues) and cardiac troponin-T (second row) and Myosin light chain 2v (MLC2v) (third row). All samples were counterstained with DAPI. Atrial tissues were derived from Hes3 hESC-CM and ventricular from BJ1D iPSC-CM.

FIGS. 4A-4M show that atrial and ventricular tissues exhibit distinct functional responses after chronic electrical stimulation.

FIG. 4A is a series of representative force traces recorded in atrial and ventricular tissues. Atrial Biowires typically show a flat force-frequency relationship (FFR) and little post-rest potentiation (PRP) while ventricular Biowires showed positive FFRs and pronounced PRP.

FIGS. 4B-4C are graphs showing summary of data for active force of (FIG. 4B) atrial and (FIG. 4C) ventricular tissues. Data are presented as avg±stdev with two way ANOVA (P<0.05) between stimulated and unstimulated Biowires (n≥7 for atrial and n≥10 for ventricular Biowires).

FIG. 4D is a graph showing summary results for PRP normalized to the last pacing frequency (n≥6).

FIG. 4E is a set of conduction velocity maps for atrial and ventricular tissues. Scale bars=500 μm for atrial and 200 μm for ventricular tissue.

FIG. 4F is a graph showing summary of propagation velocity results for unstimulated and stimulated atrial and ventricular tissues. (Avg±stdev, n≥4; two way ANOVA).

FIGS. 4G-4H are chamber-specific action potential profiles of unstimulated and stimulated (FIG. 4G) atrial and (FIG. 4H) ventricular tissues.

FIGS. 4I-4M show summary of comparisons between atrial and ventricular tissues for: (FIG. 4I) action potential amplitudes, (FIG. 4J) maximum diastolic potentials (MDP), (FIG. 4K) upstroke velocities, (FIG. 4L) action potential duration measure at 30% ($APD_{30}$), 50% ($APD_{50}$) and 90% ($APD_{90}$) repolarization. (Avg±stdev, n≥3; two way ANOVA). (FIG. 4M) Summary of $APD_{30}/APD_{90}$ ratios (APD30/90). Atrial tissues were created from Hes3 hESC-CM and ventricular from BJ1D iPSC-CM.

FIG. 5A is a set of representative images of a tissue labelled with the calcium dye Fluo-4 under relaxation (left panel) and contraction (right panel) and the regions of interest used to measure the change in active force and calcium transients.

FIG. 5B is a graph showing representative force and calcium transients.

FIGS. 5C and 5E are graphs showing representative active force (top) and calcium transient (bottom) traces of an atrial tissue treated with increasing concentrations of (FIG. 5C) Nifedipine or (FIG. 5E) Thapsigargin under stimulation and the corresponding quantification. (Avg±stdev, n=3).

FIGS. 5D and 5F are graphs showing Representative active force (top) and calcium transient (bottom) traces of a ventricular tissue treated with increasing concentrations of (FIG. 5D) Nifedipine or (FIG. 5F) Thapsigargin under stimulation and the corresponding quantification. (Avg±stdev, n=3). Differences in the baseline represent variation in active forces of different tissues. Atrial tissues were derived from Hes3 hESC-CM and ventricular from BJ1D iPSC-CM.

FIGS. 6A-6I show that Biowire II platform enables cardiac disease modelling.

FIG. 6A is a summary of clinical features, hypertrophy index (lvmht27) and ejection fraction (EF) of hypertensive patients contributing iPSCs.

FIG. 6B is a graph showing the long-term electrical conditioning protocol used to mimic chronic increased workload in ventricular tissues created from patient iPSC-CMs. Tissues were first subjected to a ventricular 1 Hz step-up electrical conditioning protocol. Once the stimulation frequency of 6 Hz was reached and applied for a week, it was decreased to 3 Hz and maintained at that level for up to 6 months. The comparison between Biowires generated with iPSCs derived from hypertensive patients with evidence of heart disease (Affected D, E and F) and no evidence of heart disease (Non-Affected A, B and C). The results from two independent experiment, Non-affected A, B vs. Affected D, E and Non-affected C vs. Affected F, were analyzed by Gene Set Enrichment Analysis (GSEAs).

FIGS. 6C-6D show results from GSEAs for Biowires reveal enrichment in Affected patients for cardiac genes associated with (FIG. 6C) Cardio-functional categories and cardiac related canonical pathways, determined by IPA Tox List analysis; (FIG. 6D) Venn diagram indicates the overlap of enriched signaling pathways related to cardiotoxicity from both experiments. The functional categories shown are ones with Benjamini-Hochberg multiple correction p-value ≤0.05.

FIG. 6E is a heat map showing a sub-set of gene related to cardiac hypertrophy.

FIG. 6F is a graph showing that active force was significantly reduced in the tissues derived from the patients that exhibited a higher level of left ventricular hypertrophy in response to a prolonged hypertension (Affected D vs. Affected E, p=0.0387) compared to the Non-Affected patient (non-affected A vs. Affected D, p=0.0006; non-affected A vs. Affected F, p=0.0023; Non-affected B vs. Affected D, p=0.0382) at the 6 weeks culture period. One way ANOVA with Tukey's multiple comparisons test.

FIG. 6G is a graph showing that active force was absent in all tissues from Affected patients (Affected D, E and F) compared to the Non-Affected patients (non-affected A, B, and C) after 8 months culture period.

FIG. 6H shows live and dead staining of tissues at the end of 8 month culture period, where the live tissues appear brighter in the figure. Viability was quantified with no significant differences among the groups. Scale bar=100 μm.

FIG. 6I is a series of confocal images and quantification of the presence of sarcomeric α-actinin counterstained with DAPI, where the sarcomeric α-actinin staining appears brighter in the figure. Scale bar=30 μm (One way ANOVA with Tukey's multiple comparisons test).

FIG. 7A is a schematics of the experimental set-up.

FIG. 7E shows quantification of $Ca^{2+}$ transients.

FIGS. 7F-7I are graphs where action potential (FIG. 7F), profiles (FIG. 7G) amplitude (FIG. 7H) APD30 and (FIG. 7I) APD30/90 from atrial, mid and ventricular regions were compared.

FIGS. 7J-7K are graphs showing representative traces of calcium transients in response serotonin at (FIG. 7J) the atrial end and (FIG. 7K) the ventricular end on the tissue.

FIG. 7N is a graph showing quantification of the conduction velocity upon ranolazine application after normalization to the baseline (avg±stdev, n=4, p=0.0007, Student's t test). In FIGS. 7J-7N, both ends of the tissue were derived from Hes3 hESC.

FIGS. 8A-8J show experimental set-up and force-displacement curves for POMaC wires.

FIG. 8A is a series of images showing a petri-dish is fitted with a pair of carbon electrodes and a poly-styrene strip for cultivation of eight cardiac tissues. Position of tissues and polymer wires with respect to carbon electrodes is indicated in the zoomed-in images.

FIG. 8B shows summary of experimental conditions, *denotes the preparation for atrial differentiation.

FIG. 8C shows measurements of tissue width on the POMaC wire and the tissue diameter. Average tissue diameter is determined from multiple locations.

FIG. 8D is a representative image of cross-section from a tissue, scale bar=100 μm.

FIGS. 8E-8G are graphs showing force-displacement curves for the POMaC wire obtained by microscale mechanical testing using custom (FIG. 8E) 0.5 mm, (FIG. 8F) 0.7 mm and (FIG. 8G) 0.8 mm diameter probes. FIGS. 8E-8G show the polynomial equation fit and $R^2$ to the experimental data (data presented as mean±stdev, n≥55).

FIGS. 8H-8J are graphs showing the finite element model of the polymer wire force-displacement behavior using a neo-Hookean model compared to the experimental data illustrated by the average values and 95% confidence intervals

FIG. 9A is a graph showing that atrial and ventricular tissues compact in a similar fashion in the first week after seeding. (n≥8).

FIG. 9B is a graph showing excitation Threshold (ET).

FIG. 9C is a graph showing Maximum Capture Rate (MCR), for unstimulated and stimulated atrial and ventricular tissues. All data presented as mean±stdev, n>8. Dashed lines represent the average ET and MCR at day 7 after tissue compaction. Atrial tissues were derived from Hes3 ESC-CM and ventricular from BJ1D iPSC-CM.

FIG. 9D is a representative TEM image of a stimulated ventricular tissue generated from BJ1D hiPSC-CMs; Scale bar=500 nm.

FIGS. 9E-9F are representative confocal images of (FIG. 9E) a stimulated ventricular tissue generated from C2A hiPSC-CMs immunostained for caveolin 3 and counterstained with the nuclear stain DAPI, and (FIG. 9F) a stimulated ventricular tissue generated from BJ1D hiPSC- CMs immunostained for vimentin, F-actin and counterstained with DAPI; Scale bar=30 µm.

FIG. 10A is a heat map showing differential expressions of selected ventricular maturation markers.

FIG. 10B is a heat map showing that electrical conditioning significantly enhances expression of genes related to high density lipoprotein (HDL) metabolism in ventricular tissues. Network graph representation of enriched ontologies annotated for sub-networks.

FIG. 10C is a graph showing gene ontologies (biological process) that were significantly upregulated with electrical conditioning in atrial Biowires.

FIG. 10D is a graph showing gene ontologies (biological process) that were significantly upregulated with electrical conditioning in ventricular Biowires. Atrial and ventricular tissues were created from Hes3 hESC-CM.

FIG. 11A is a representative trace of an FFR and PRP test.

After applying maturation protocol, electrical function was improved for ventricular tissues derived from Hes2 and Hes3 cell lines in terms of (FIGS. 11G, 11H) Active force from 1 to 3 Hz.

FIG. 11O shows summary of active forces achieved by engineered cardiac tissues derived from human CMs in other publications.

FIG. 14A is a graph showing representative action potential of an atrial tissue treated with carbachol.

Figure 14A:
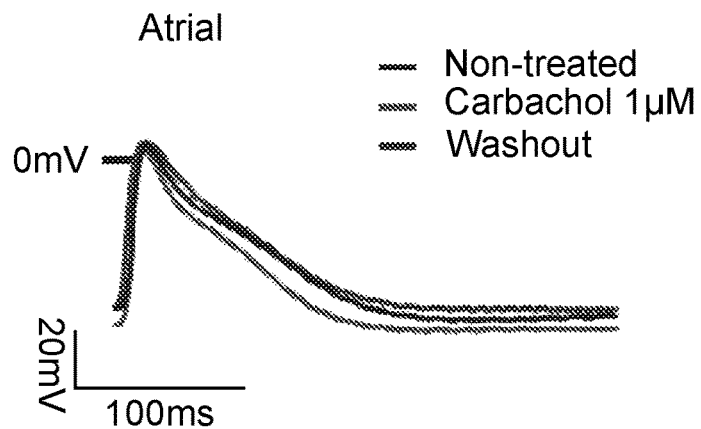
FIGS. 14A-14P show atrial and ventricular tissues exhibit chamber specific electrophysiological responses to drugs.
Figure 14B:
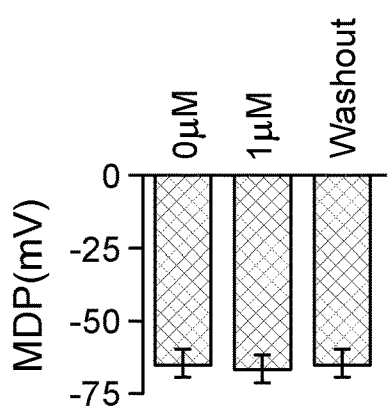
Figure 14C:
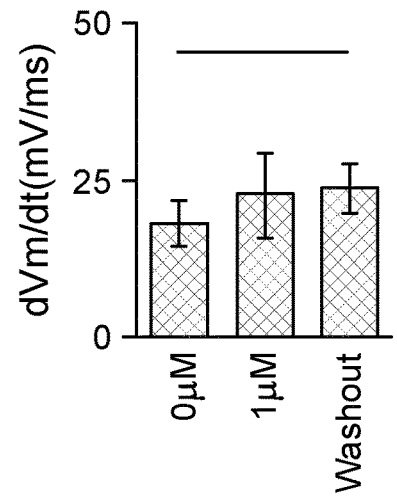
Figure 14D:
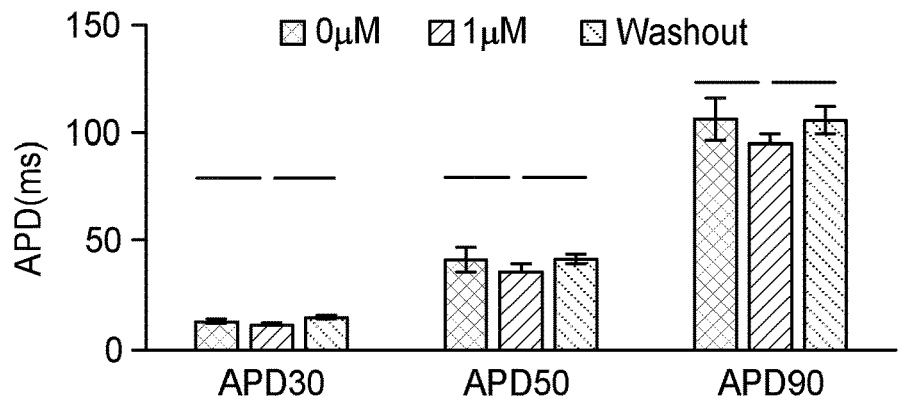

Quantification of (FIG. 14B) minimum diastolic potential, (FIG. 14C) upstroke velocity, (FIG. 14D) duration to 30% repolarization ($APD_{30}$), to 50% repolarization ($APD_{50}$) and to 90% repolarization ($APD_{90}$), for atrial tissues treated with carbachol. (mean±stdev, n≥3, one way ANOVA).

Figure 14E:
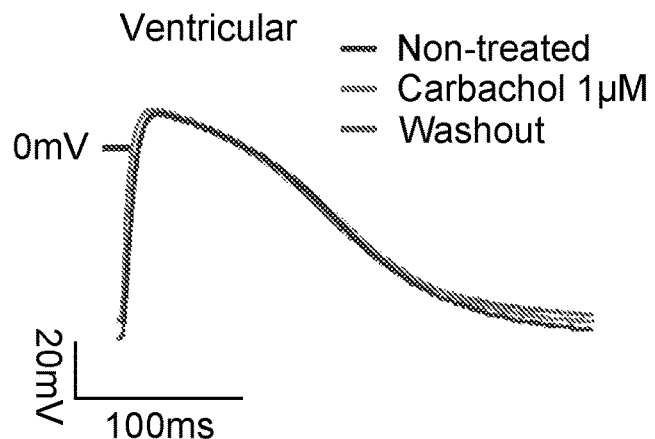

FIG. 14E is a graph showing representative action potential of a ventricular tissue treated with carbachol.

Figure 14F:
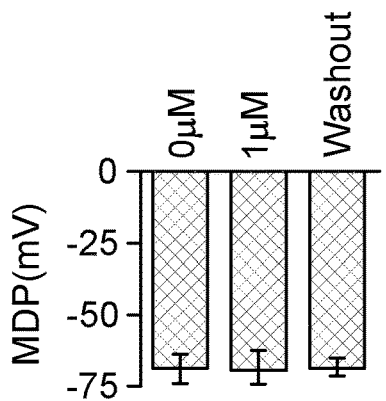
Figure 14G:
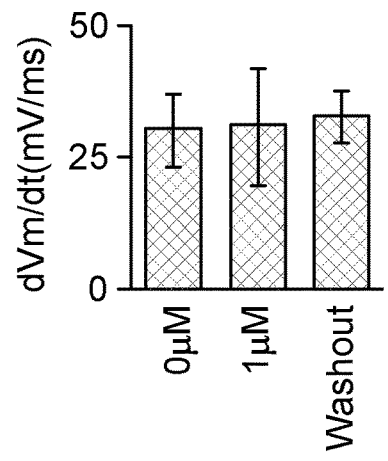
Figure 14H:
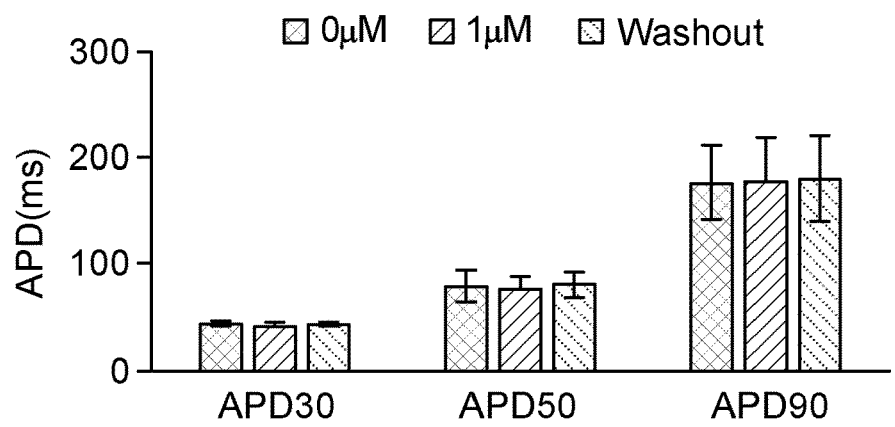

Quantification of the (FIG. 14F) minimum diastolic potential, (FIG. 14G) upstroke velocity, (FIG. 14H) $APD_{30}$, $APD_{50}$ and $APD_{90}$, for ventricular tissues treated with carbachol. (mean±stdev, n≥3, one way ANOVA).

Figure 14I:
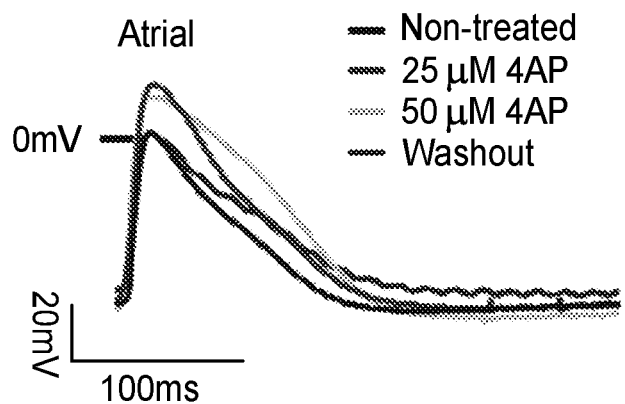

FIG. 14I is a graph showing representative action potential of an atrial tissue treated with 4-aminopyridine (4AP).

Figure 14J:
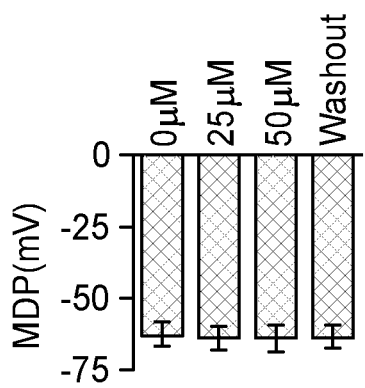
Figure 14K:
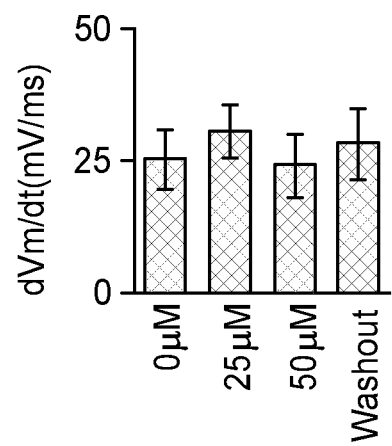
Figure 14L:
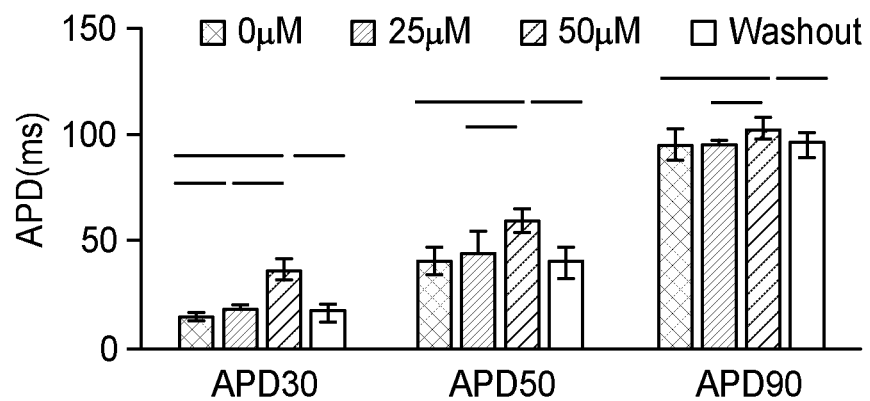

Quantification of the (FIG. 14J) minimum diastolic potential, (FIG. 14K) upstroke velocity, (FIG. 14L) $APD_{30}$, $APD_{50}$ and $APD_{90}$, for atrial tissues treated with 4AP. (mean±stdev, n≥3, one way ANOVA).

Figure 14M:
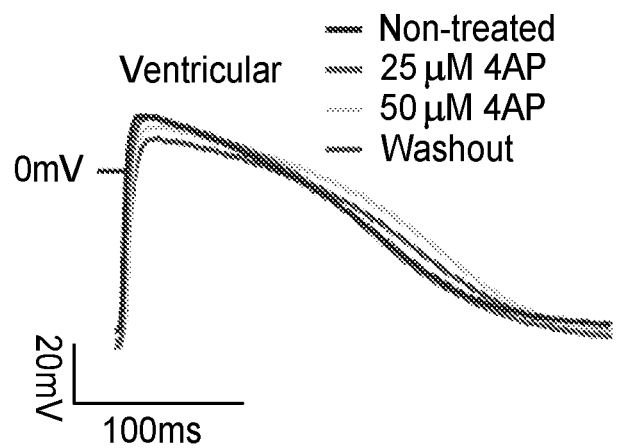

FIG. 14M is a graph showing representative action potential of a ventricular tissue treated with 4AP.

Figure 14N:
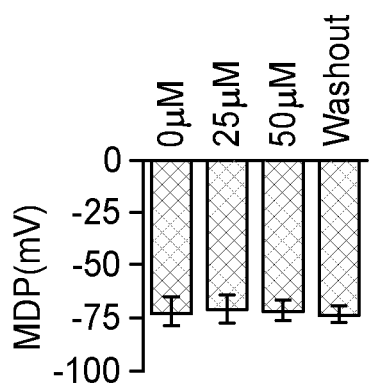
Figure 14O:
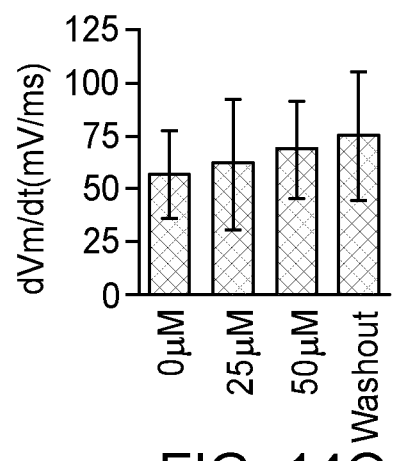
Figure 14P:
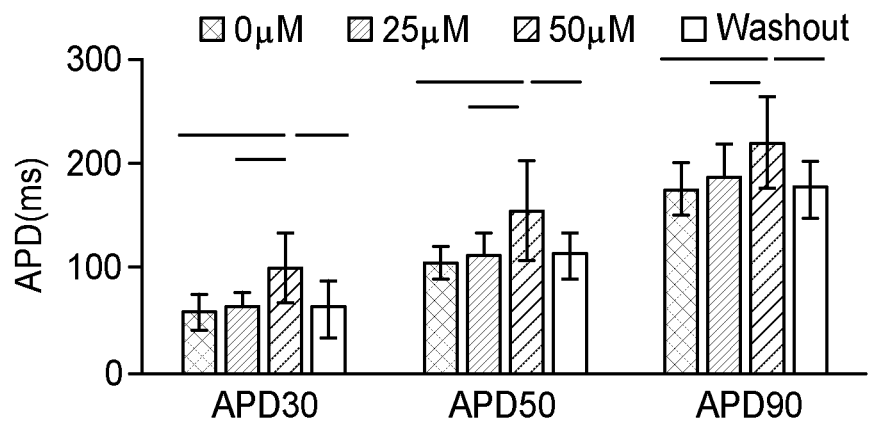

Quantification of the (FIG. 14N) minimum diastolic potential, (FIG. 14O) upstroke velocity, (FIG. 14P) $APD_{30}$, $APD_{50}$ and $APD_{90}$, for ventricular tissues treated with 4AP. (mean±stdev, n≥3, one way ANOVA). Atrial tissues were derived from Hes3 hESC-CM and ventricular from BJ1D iPSC-CM.

Figure 15A:
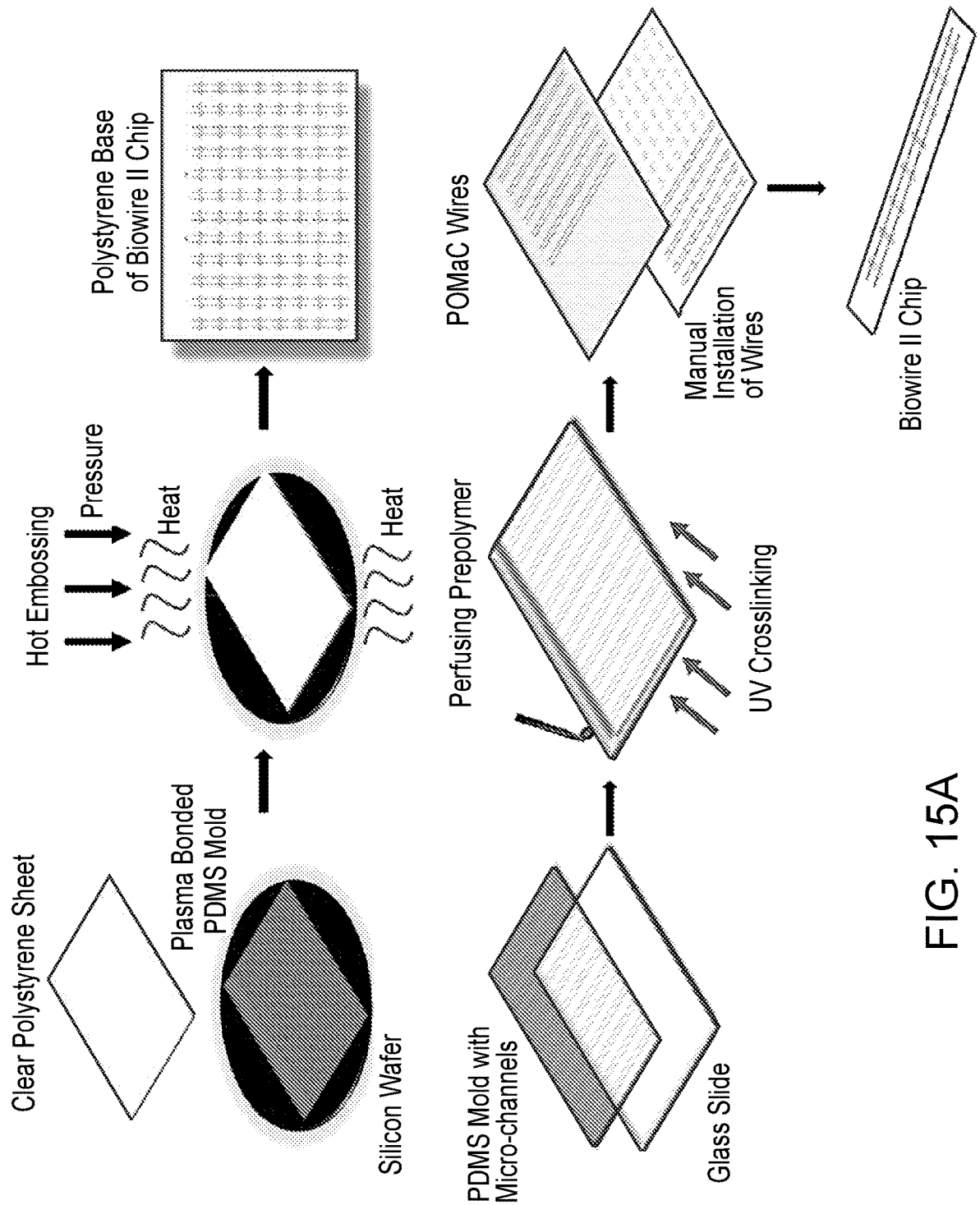
Figure 15B:
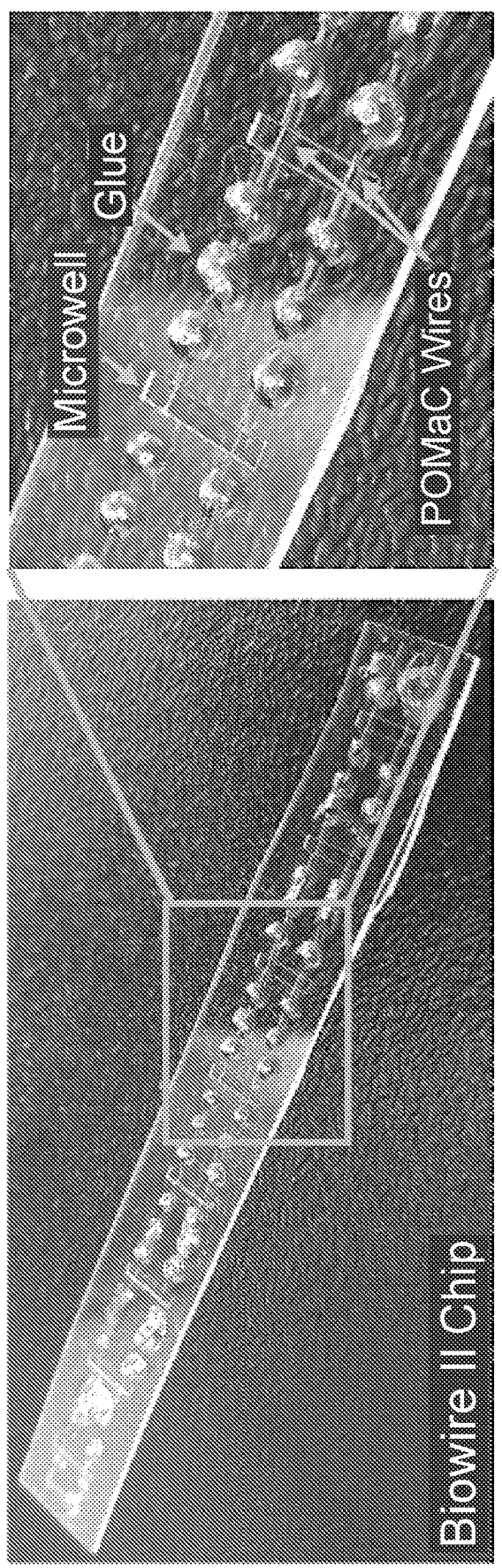

FIGS. 15A-15B show a schematic of the fabrication of the Biowire II Platform.

FIG. 15A shows that a polydimethylsiloxane (PDMS) mold was cast from an SU-8 master mold prepared with the desired microwell and groove topography. The PDMS mold was plasma bonded to a silicon wafer. A clear polystyrene sheet was placed on top of the bonded wafer and hot embossed using optimized heat and pressure under vacuum. After cooling, the polystyrene sheet imprinted with microwells and grooves, was separated from the PDMS mold. A second PDMS mold with a series of parallel microchannels was cast and perfused with POMaC prepolymer to form the polymer wires. After crosslinking under UV light, the POMaC wires were manually placed into the grooves on the polystyrene base. Polyurethane glue was used to fix the POMaC wires in place. The polystyrene sheet was then cut into columns of 8 microwells.

FIG. 15B is a representative photograph of a single Biowire II strip after fabrication.

FIGS. 16A-16I show how cell seeding density influences cardiac tissue structure and function in the Biowire II platform. HES3 ESC derived ventricular tissues were seeded using collagen hydrogel at the concentration of 25, 50, 100, 150 million cells per mL. (FIG. 16A) Tissue compaction; (FIG. 16B) Excitation threshold (ET) and (FIG. 16C) Maximum capture rate (MCR) at day 7. (n≥8) Active force and passive tension, at (FIG. 16D) day 7 (n≥6) and (FIG. 16E) day 30 (n≥5) of culture were examined. (FIG. 16F) Confocal images of NKX2.5-GFP (green) and Vimentin (red) with DAPI (blue) nuclear counterstaining at day 7, (n≥3), scale bar=100 µm. (FIG. 16G) Quantification of CM alignment based on the GFP signal. (FIG. 16H) Bright field images of tissues stained by Masson's Trichrome after 30 days of culture, scale bar=200 µm. (FIG. 16I) Quantification of collagen area, (n≥3). Data are presented as mean±stdev, one-way ANOVA with Holm-Sidak's multiple comparison test or ANOVA on ranks with Dunn's method.

FIGS. 17A-17K are a comparison of non-myocyte populations, mesenchymal stem cells (MSC) and cardiac fibroblasts (cFB), in Biowire II platform. (FIG. 17A) HES3 ESC derived atrial tissues compacted during the first week of culture. (n≥10) (FIG. 17B) Atrial specific electrical conditioning protocol. (FIG. 17C) Tissue appearance at the endpoint of culture after electrical conditioning. (FIG. 17D) Force-frequency relationship (FFR) (n≥15). (FIG. 17E) Excitation threshold (ET) and (FIG. 17F) Maximum capture rate (MCR) were significantly improved after electrical conditioning in both groups. (n≥10) (FIG. 17G) Action potential profiles, (FIG. 17H) action potential duration, (FIG. 17I) action potential amplitude, (FIG. 17J) minimum diastolic potential and (FIG. 17K) upstroke velocity were compared between the tissues with the two cell types. For electrophysiological assessment, the AP parameters were multiple pokes from at least three tissues. Data presented as mean±stdev, Student's t-test or Mann-Whitney test or ANOVA on ranks with Dunn's multiple comparisons test.

FIGS. 18A-18H show how cardiac fibroblast percentage influences tissue function. HES3 ESC derived ventricular tissues were seeded in collagen hydrogel with an additional 10% (low cFB group) or 25% (high cFB group) of cardiac fibroblasts. (FIG. 18A) Brightfield images of the tissue structure. (FIG. 18B) Tissue compaction (n≥10) in the first week. Electrical stimulation was initiated on day 7 after seeding and the protocol shown in (FIG. 18C) was used. (FIG. 18D) Excitation threshold (ET) and (FIG. 18E) Maximum capture rate (MCR) (n=7-14) were compared before and after electrical conditioning. Positive Force-frequency relationship (FFR) (n=7 for high cFB group and n=13 for the low cFB group) was shown with (FIG. 18F) active forces normalized to 1 Hz. Differences between two groups were demonstrated by (FIG. 18G) active forces stimulated at 1-3 Hz at the endpoint of cultivation. (FIG. 18H) Active force and passive tension were also compared for both groups. Data are presented as mean±stdev, Student's t-test or Mann-Whitney test or ANOVA on ranks with Dunn's multiple comparisons test.

FIGS. 19A-19H show how the Biowire II platform can generate high fidelity tissues using different stimulation schemes. (FIG. 19A) BJ1D iPSC derived ventricular tissues were conditioned with 1 Hz weekly stimulation regimen or 0.2 Hz daily stimulation regimen. Quantitative comparison of (FIG. 19B) Excitation Threshold (ET), (n≥8) and (FIG. 19C) Maximum Capture Rate (MCR), (n≥8). (FIG. 19D) Percent of tissues successfully reaching a positive FFR at the end of cultivation (n≥6 for two batches of tissues). (FIG. 19E) Force-Frequency Relationship (FFR), (n≥8), (FIG. 19F) Post-Rest Potentiation (PRP), (n≥4). Data presented as mean±stdev, Student's t-test or two-way ANOVA with Tukey's multiple comparisons test. (FIG. 19G) Confocal images of tissues stained for α-actinin, myosin light chain-2v (MLC2v) and F-actin and counterstained with the nuclear stain DAPI (left panels); and stained for connexin-43 (Cx43) and cardiac troponin-T, counterstained with DAPI (right panels). Scale bar=30 µm. (FIG. 19H) Quantification of myofiber alignment using cTNT staining. (n=3) Data presented as mean±stdev, Student's t-test or Mann-Whitney test or One-way ANOVA with Tukey's multiple comparisons test.

Figure 20A:
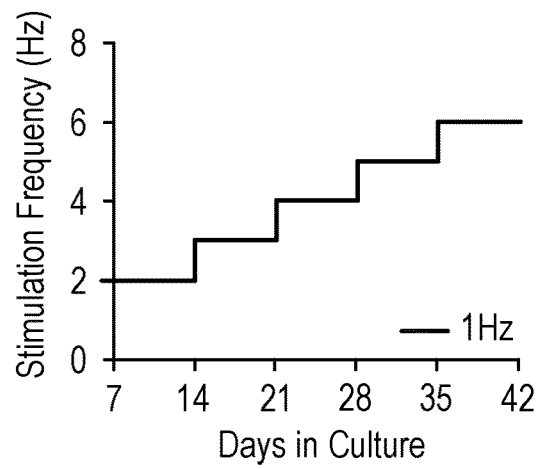

FIGS. 20A-20H show how the Biowire II platform can generate high fidelity tissues using different hydrogels. BJ1D iPSC derived ventricular tissues were electrically stimulated as shown in panel (FIG. 20A). Quantitative comparison of (FIG. 20B) Excitation Threshold (ET), (n≥8), (FIG. 20C) Maximum Capture Rate (MCR), (n≥8), (FIG. 20D) Percent of tissues successfully reaching a positive Force-Frequency Relationship (FFR) by the end of cultivation (two batches of tissues), (FIG. 20E) FFR, (FIG. 20F) Post-Rest Potentiation (PRP) for tissues generated using Collagen vs. Collagen/Fibrin hydrogel (n≥7). Data presented as mean±stdev, Student's t-test or two-way ANOVA with Tukey's multiple comparisons test. (FIG. 20G) Confocal images of tissues generated from Collagen vs. Collagen/Fibrin hydrogel stained with for α-actinin, myosin light chain-2v (MLC2v) and F-actin stain, and counterstained with the nuclear stain DAPI (left panels); and stained for connexin-43 (Cx43) and cardiac troponin T (cTNT), counterstained with DAPI (right panels). Scale bar=30 µm. (FIG. 20H) Quantification of myofiber alignment using cTNT staining. (n=3). Data presented as mean±stdev, Student's t-test or Mann-Whitney test or ANOVA on ranks with Dunn's multiple comparisons test.

Figure 21:
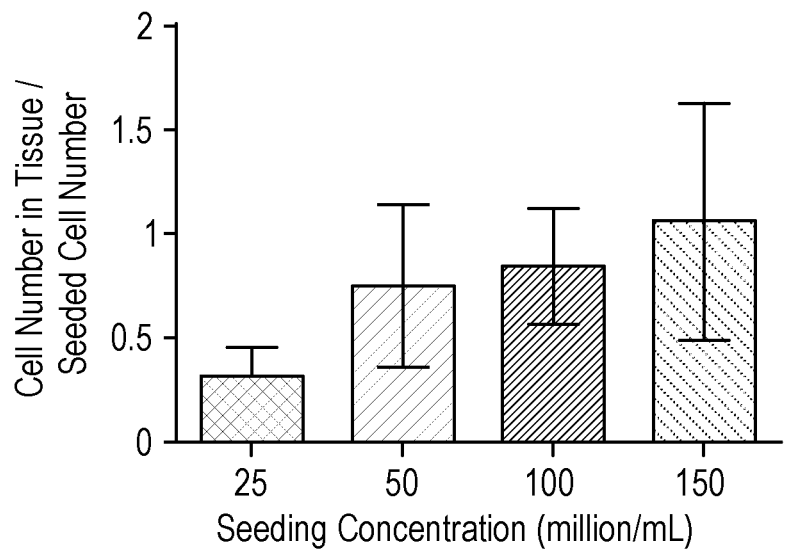

FIG. 21 is a graph showing the yield of cells in the tissues after 30 days in culture. HES3 derived ventricular cardiac tissues, n=3-5.

Figure 22A:
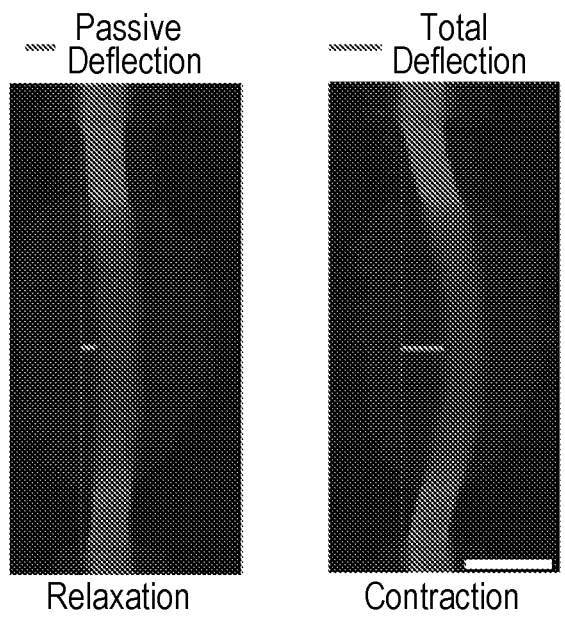
Figure 22B:
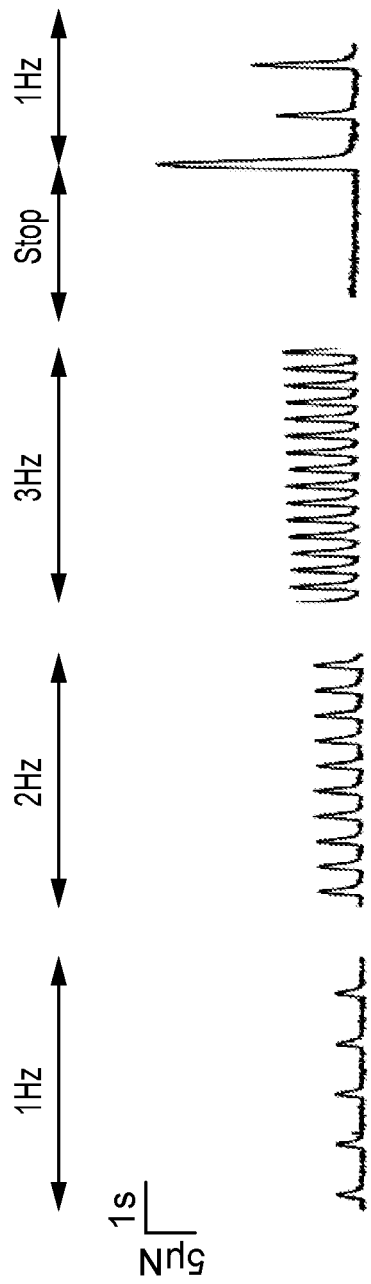

FIGS. 22A-22B show active and passive force detection.

FIG. 22A shows a polymer wire displacement during contraction and relaxation from BJ1D derived ventricular cardiac tissue.

FIG. 22B Shows representative traces of changes in the active forces and beat patterns of Biowire II tissues under stimulation in response to a routine force-frequency relationship (FFR) and post-rest potentiation (PRP) test.

Figure 23:
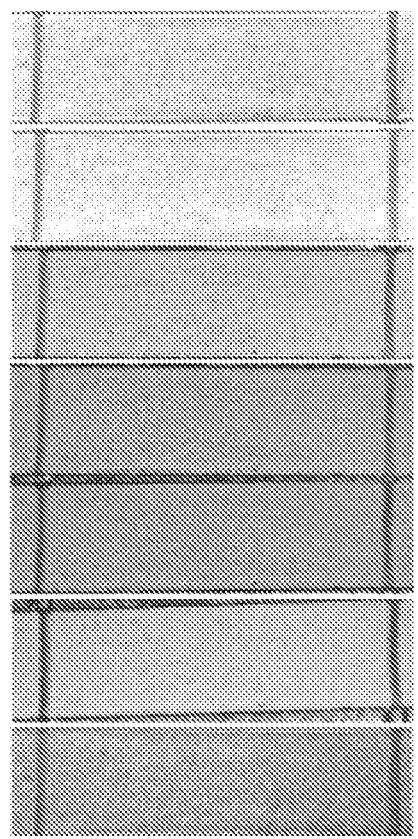

FIG. 23 shows the compaction of HES3-CM derived ventricular cardiac tissues is inhibited in the absence of a supporting non-myocyte population. Scale bar=1 mm.

DETAILED DESCRIPTION OF THE INVENTION

The heart has four chambers: two atria and two ventricles. As described herein, the Biowire II platform enables the production of high fidelity 3D human cardiac tissues from many different cells sources. In some embodiments, the POMaC polymer wires in the platform are used as both a mechanical stimulus attachment point for the tissue and a force sensor, enabling simultaneous assessments of intracellular calcium fluctuations and contractile force. Using heart chamber-specific directed differentiation and electrical conditioning protocols, cardiac tissues with distinct atrial or ventricular phenotypes as well as a combined heteropolar atrio-ventricular tissues are produced, demonstrating the utility of these preparations for drug testing. The platform is robust enough to enable months long electrical conditioning required to reach heart-failure like conditions in ventricular tissues derived from patients with LVH as a result of prolonged hypertension. These features prove that the Biowire II platform is well positioned for modelling polygenic cardiac disease that affects the majority of heart disease patients.

Accordingly, one aspect of the present disclosure relates to a chamber-specific cardiac tissue comprising a hydrogel and a plurality of cells including cardiomyocytes and cardiac fibroblasts, wherein at least a portion of the cells are encapsulated inside the hydrogel. Such chamber-specific cardiac tissue can be artificially engineered in a bioreactor, such as the one in the Biowire II platform. Thus, the chamber-specific cardiac tissue is generated ex vivo. In some embodiments, the cardiac tissue is an atrial tissue, a ventricular tissue, or a combination thereof. In some embodiments, the cardiac tissue is a composite tissue having an atrial tissue connected to a ventricular tissue.

A related aspect of the present disclosure relates to an ex vivo cardiac tissue comprising an atrial tissue and a ventricular tissue, wherein the atrial tissue is connected to the ventricular tissue. There can be a transition zone between the atrial tissue and the ventricular tissue. The transition zone can have mixed atrial and ventricular properties. Such ex vivo cardiac tissue can be artificially engineered in a bioreactor, such as the one in the Biowire II platform.

The ex vivo cardiac tissue can comprise 2, 3, 4, 5, 6, or more atrial tissues. The ex vivo cardiac tissue can comprise 2, 3, 4, 5, 6, or more ventricular tissues. In some embodiments, the ex vivo cardiac tissue comprises two atrial tissues and one ventricular tissue. In some embodiments, the ex vivo cardiac tissue comprises two atrial tissues and two ventricular tissues. In some embodiments, the ex vivo cardiac tissue comprises one atrial tissue and two ventricular tissues.

Methods for determining whether a cardiac tissue is atrial or ventricular are known in the art. For example, because an atrial-enriched biomarker is expressed at a higher level in an atrial tissue than a ventricular tissue, such atrial-enriched biomarker can be relied upon to differentiate an atrial tissue from a ventricular tissue. The atrial-enriched biomarker can be selected from the group consisting of NPPA, GJA5, KCNJ12, MYH6, MYL4, MYL7, CACNA1G, KCNA5, GATA4, KCNJ3, HCN4, TBX5, and ATP2A2.

In some embodiments, the cardiomyocytes and cardiac fibroblasts can be present at a ratio of at least about 1:4, at least about 1:3.5, at least about 1:3, at least about 1:2.5, at least about 1:2, at least about 1:1.8, at least about 1:1.6, at least about 1:1.4, at least about 1:1.2, or at least about 1:1. In some embodiments, the cardiomyocytes and cardiac fibroblasts can be present at a ratio of no more than about 100:1, no more than about 90:1, no more than about 80:1, no more than about 70:1, no more than about 60:1, no more than about 55:1, no more than about 50:1, no more than about 45:1, or no more than about 40:1.

Combinations of the above-referenced ranges for the ratio of cardiomyocytes over cardiac fibroblasts are also possible (e.g., at least about 1:4 to no more than about 100:1, or at least about 1:2 to no more than about 5:1), inclusive of all values and ranges therebetween.

In some embodiments, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, or at least about 25% of the cells in the cardiac tissue are cardiomyocytes. In some embodiments, about 100% of the cells in the cardiac tissue are cardiomyocytes. In some embodiments, no more than about 99%, no more than about 95%, no more than about 90%, no more than about 89%, no more than about 88%, no more than about 87%, no more than about 86%, no more than about 85%, no more than about 84%, no more than about 83%, no more than about 82%, no more than about 81%, or no more than about 80% of the cells in the cardiac tissue are cardiomyocytes.

Combinations of the above-referenced ranges for the ratio of cells that are cardiomyocytes are also possible (e.g., at least about 25% to no more than about 100%, or at least about 35% to no more than about 90%), inclusive of all values and ranges therebetween.

In some embodiments, at least about 1%, at least about 5%, at least about 10%, at least about 15%, at least about 20%, at least about 25%, at least about 30%, at least about 35%, at least about 40%, at least about 45%, or at least about 50% of the cells in the cardiac tissue are cardiac fibroblasts. In some embodiments, no more than about 75%, no more than about 70%, no more than about 65%, no more than about 60%, no more than about 55%, no more than about 50%, no more than about 45%, no more than about 40%, no more than about 35%, no more than about 30%, no more than about 25%, no more than about 20%, more than about 15%, no more than about 10%, or no more than about 5% of the cells in the cardiac tissue are cardiac fibroblasts. In some embodiments, the cardiac tissue does not include cardiac fibroblasts.

Combinations of the above-referenced ranges for the ratio of cells that are cardiac fibroblasts are also possible (e.g., about 0% to no more than about 75%, or at least about 10% to no more than about 60%), inclusive of all values and ranges therebetween.

In some embodiments, the plurality of cells can further comprise mesenchymal stem cells, CD90+ cells, mesodermal cells, or a combination thereof. The cells can be derived from any animal including human or non-human animals. In some embodiments, the cells are human cells.

Both cardiomyocytes and cardiac fibroblasts can be elongated. In some embodiments, at least about 30% of the cells are substantially aligned in the same direction, e.g., at least about 30%, at least about 35%, at least about 40%, at least about 45%, at least about 50%, at least about 55%, at least about 60%, at least about 65%, at least about 70%, at least about 75%, or at least about 80% of the cells are substantially aligned in the same direction. In some embodiments, about 100% of the cells are substantially aligned in the same direction. In some embodiments, no more than about 99% of the cells are substantially aligned in the same direction, e.g., no more than about 95%, no more than about 90%, no more than about 85%, no more than about 80%, no more than about 75%, or no more than about 70% of the cells are substantially aligned in the same direction.

Combinations of the above-referenced ranges for the ratio of cells substantially aligned in the same direction are also possible (e.g., at least about 30% to about 100%, or at least about 40% to no more than about 90%), inclusive of all values and ranges therebetween.

Methods for determining cell alignment are known in the art. For example, optical microscopy based on GFP signals can be used for determining cell alignment.

The hydrogel can include collagen or a collagen derivative, intestinal submucosa or a derivative thereof, cellulose or a cellulose derivative, a proteoglycan, heparin sulfate, chondroitin sulfate, keratin sulfate, hyaluronic acid, elastin, fibronectin, thrombin, laminin, fibrin, chitosan, alginate, Matrigel®, Geltrex®, agarose, decellularized extracellular matrix, polyethylene glycol or a derivative thereof, silicone or a derivative thereof, or a combination thereof. In some embodiments, the hydrogel can include Matrigel® or Geltrex®. In some embodiments, the hydrogel can include collagen and fibrin.

In some embodiments, the hydrogel can include at least about 1 wt % collagen or a collagen derivative, at least about 2 wt % collagen or a collagen derivative, at least about 3 wt % collagen or a collagen derivative, at least about 4 wt % collagen or a collagen derivative, at least about 5 wt % collagen or a collagen derivative, at least about 6 wt % collagen or a collagen derivative, at least about 7 wt % collagen or a collagen derivative, at least about 8 wt % collagen or a collagen derivative, at least about 9 wt % collagen or a collagen derivative, or at least about 10 wt % collagen or a collagen derivative. In some embodiments, the hydrogel can include about 100 wt % collagen or a collagen derivative. In some embodiments, the hydrogel can include no more than about 95 wt % collagen or a collagen derivative, no more than about 90 wt % collagen or a collagen derivative, no more than about 85 wt % collagen or a collagen derivative, no more than about 80 wt % collagen or a collagen derivative, no more than about 75 wt % collagen or a collagen derivative, no more than about 70 wt % collagen or a collagen derivative, no more than about 65 wt % collagen or a collagen derivative, no more than about 60 wt % collagen or a collagen derivative, no more than about 55 wt % collagen or a collagen derivative, no more than about 50 wt % collagen or a collagen derivative, no more than about 45 wt % collagen or a collagen derivative, no more than about 40 wt % collagen or a collagen derivative, no more than about 35 wt % collagen or a collagen derivative, no more than about 30 wt % collagen or a collagen derivative, or no more than about 25 wt % collagen or a collagen derivative.

Combinations of the above-referenced ranges for the weight ratio of collagen or a collagen derivative in the hydrogel are also possible (e.g., at least about 1 wt % to about 100 wt %, or at least about 5 wt % to no more than about 90 wt %), inclusive of all values and ranges therebetween.

In some embodiments, the collagen comprises of Type I collagen, Type III collagen, Type IV collagen, Type V collagen, Type XI collagen, Type XII collagen or a combination thereof.

In some embodiments, at least about 40% of the cells are encapsulated inside the hydrogel. In some embodiments, at least about 45% of the cells are encapsulated inside the hydrogel. In some embodiments, at least about 50% of the cells are encapsulated inside the hydrogel. In some embodiments, at least about 55% of the cells are encapsulated inside the hydrogel. In some embodiments, at least about 60% of the cells are encapsulated inside the hydrogel. In some embodiments, at least about 65% of the cells are encapsulated inside the hydrogel. In some embodiments, at least about 70% of the cells are encapsulated inside the hydrogel. In some embodiments, about 100% of the cells are encapsulated inside the hydrogel. In some embodiments, no more than about 99% of the cells are encapsulated inside the hydrogel. In some embodiments, no more than about 95% of the cells are encapsulated inside the hydrogel. In some embodiments, no more than about 90% of the cells are encapsulated inside the hydrogel. In some embodiments, no more than about 85% of the cells are encapsulated inside the hydrogel. In some embodiments, no more than about 80% of the cells are encapsulated inside the hydrogel.

Combinations of the above-referenced ranges for the percentage of cells encapsulated in the hydrogel are also possible (e.g., at least about 40% to about 100%, or at least about 50% to no more than about 99%), inclusive of all values and ranges therebetween.

In some embodiments, the volume of the cardiac tissue can be at least about 0.1 mm$^3$, at least about 0.5 mm$^3$, at least about 1 mm$^3$, at least about 1.5 mm$^3$, at least about 2 mm$^3$, or at least about 2.5 mm$^3$. In some embodiments, the volume of the cardiac tissue can be no more than about 20 mm$^3$, no more than about 15 mm$^3$, no more than about 10 mm$^3$, no more than about 9 mm$^3$, no more than about 8 mm$^3$, no more than about 7 mm$^3$, no more than about 6 mm$^3$, no more than about 5 mm$^3$, no more than about 4 mm$^3$, no more than about 3 mm$^3$, or no more than about 2.5 mm$^3$.

Combinations of the above-referenced ranges for the volume of the cardiac tissue are also possible (e.g., at least about 0.1 mm$^3$ to no more than about 20 mm$^3$, or at least about 0.1 mm$^3$ to no more than about 2.5 mm$^3$), inclusive of all values and ranges therebetween.

The number of cells in the cardiac tissue depends on the volume of the tissue. In some embodiments, the number of cells can be at least about 20,000, at least about 25,000, at least about 30,000, at least about 35,000, at least about 40,000, at least about 45,000, at least about 50,000. In some embodiments, the number of cells can be no more than about 50,000,000, no more than about 25,000,000, no more than about 10,000,000, no more than about 5,000,000, no more than about 2,000,000, no more than about 1,000,000, no more than about 900,000, no more than 800,000, no more than about 700,000, no more than 600,000, no more than about 500,000, no more than 400,000, no more than about 300,000, no more than 200,000, or no more than 100,000.

Combinations of the above-referenced ranges for the number of cells in the cardiac tissue are also possible (e.g., at least about 20,000 to no more than about 50,000,000, or at least about 30,000 to no more than about 1,000,000), inclusive of all values and ranges therebetween.

The cardiac tissue is three-dimensional. In some embodiments, the longest dimension of the cardiac tissue can have a length of at least about 1 mm, at least about 1.5 mm, at least about 2 mm, at least about 2.5 mm, at least about 3 mm, at least about 3.5 mm, at least about 4 mm, at least about 4.5 mm, or at least about 5 mm. In some embodiments, the longest dimension of the cardiac tissue can have a length of no more than about 20 mm, no more than about 15 mm, no more than about 10 mm, no more than about 9 mm, or no more than about 8 mm.

Combinations of the above-referenced ranges for the length of the longest dimension are also possible (e.g., at least about 3 mm and no more than about 20 mm, or at least about 5 mm to no more than about 10 mm), inclusive of all values and ranges therebetween.

In some embodiments, the cardiac tissue can be in the form of a wire.

In some embodiments, the ex vivo cardiac tissue can have one or more features substantially the same as a healthy native human cardiac tissue. In some embodiments, the ex vivo cardiac tissue can substantially recapitulate the organization and function of native cardiac tissues, e.g., mature human cardiac tissues.

Similar to the differences in native tissues, the ex vivo ventricular tissue can differ from the ex vivo atrial tissue in a few different ways. For example, calcium transients are larger and rise more rapidly in the ex vivo ventricular tissue than the atrial tissue.

In some embodiments, the ex vivo ventricular tissues are quiescent at the end of cultivation in the absence of external stimulation and display a robust positive FFR, PRP and a fast conduction velocity, which are the hallmarks of adult human myocardium that allow for enhanced pumping during periods of increased blood flow demand. In addition, the ex vivo ventricular tissues display notches in the action potential profile which are associated with the presence of the rapidly activating and inactivating transient outward potassium currents, which are also hallmarks of the adult myocardium. In contrast, consistent with the native adult atrial muscle physiology, the ex vivo atrial tissues display a relatively flat FFR, minimal PRP and a slower conduction velocity.

Consistent with the electrical differences between atrial and ventricular myocardium, the action potential (AP) profiles in the ex vivo ventricular tissues are distinctly different from the atrial tissues. Specifically, compared to the ex vivo atrial tissues, the ex vivo ventricular tissues show higher AP amplitudes and upstroke velocity, more negative MDPs, and longer APDs.

$APD_{30}/APD_{90}$ ratio is a distinguishing feature between atrial and ventricular CMs. In human myocardium, the $APD_{30}/APD_{90}$ ratio is about 0.75 for ventricular CMs, and about 0.1 for atrial CMs.

In some embodiments, the $APD_{30}/APD_{90}$ ratio is in the range of 0.2-0.9 for the CMs in the ex vivo ventricular tissues. In some embodiments, the $APD_{30}/APD_{90}$ ratio is about 0.45, about 0.5, about 0.55, about 0.6, about 0.65, about 0.7, about 0.75, or about 0.8 for the CMs in the ex vivo ventricular tissues.

In some embodiments, the $APD_{30}/APD_{90}$ ratio is in the range of 0.01-0.5 for the CMs in the ex vivo atrial tissues. In some embodiments, the $APD_{30}/APD_{90}$ ratio is about 0.08, about 0.09, about 0.1, about 0.11, or about 0.12 for the CMs in the ex vivo atrial tissues.

Biowire II Platform

Another aspect of the present disclosure relates to an ex vivo tissue system comprising a chamber-specific cardiac tissue and a bioreactor, wherein the bioreactor includes at least two elastic sensing elements configured to support the cardiac tissue. In some embodiments, the cardiac tissue is an atrial tissue. In some embodiments, the cardiac tissue is a ventricular tissue. In some embodiments, the cardiac tissue is a composite tissue including an atrial tissue and a ventricular tissue, wherein the atrial tissue is connected to the ventricular tissue.

Details about the Biowire II platform can be found at US20160282338, the contents of which are incorporated by reference in its entirety.

The Biowire II platform can include a bioreactor for growing a tissue. The bioreactor can include a well having a bottom and at least two elastic sensing elements that are disposed across the well. The at least two sensing elements can function as anchor points for a tissue formed therebetween. There is a gap between the bottom of the well and the at least two sensing elements. There is also a gap between the bottom of the well and the tissue suspended on the at least two sensing elements. The bioreactor is not limited to having two such sensing elements, but may include more than two, such as 2-30 sensing elements per well, e.g., 2-25, 2-20, 2-15, or 2-10 sensing elements. In some embodiments, the bioreactor can include 2, 3, 4, 5, 6, 7, 8, 9, or more elastic sensing elements per well. Any number of elements per well may be provided so long as there is the ability to form a tissue that forms around each of the sensing elements and becomes joined therebetween such that the tissue is suspended above the bottom of the well.

In some embodiments, the sensing elements are deflectable, deformable, bendable, or the like, which are further configured to allow the measurement of contractile forces exerted by the tissue on the sensing elements.

In some embodiments, the well has a longitudinal axis. The sensing elements can have an orientation that is perpendicular, parallel, diagonal, or at any angle in between to the longitudinal axis of the well. The cells can be aligned in the same direction as the longitudinal axis of the well.

The sensing elements can comprise a polymer, which can be synthetic or biologic, degradable or nondegradable.

The sensing elements can comprise a polymer having a Young's modulus similar to that of the tissue supported thereon. For example, the Young's modulus of the polymer can be within ±2000% of the Young's modulus of the tissue; the Young's modulus of the polymer can be within ±1000% of the Young's modulus of the tissue; the Young's modulus of the polymer can be within ±500% of the Young's modulus of the tissue; the Young's modulus of the polymer can be within ±250% of the Young's modulus of the tissue; the Young's modulus of the polymer can be within ±100% of the Young's modulus of the tissue; the Young's modulus of the polymer can be within ±50% of the Young's modulus of the tissue; the Young's modulus of the polymer can be within ±30% of the Young's modulus of the tissue; the Young's modulus of the polymer can be within ±25% of the Young's modulus of the tissue; the Young's modulus of the polymer can be within ±20% of the Young's modulus of the tissue; the Young's modulus of the polymer can be within ±15% of the Young's modulus of the tissue; or the Young's modulus of the polymer can be within ±10% of the Young's modulus of the tissue.

A relaxed cardiac tissue can have a Young's modulus of about 10 kPa to about 50 kPa, and a contracted cardiac tissue can have a Young's modulus of about 500 kPa. In some embodiments, the sensing elements can comprise a polymer having a Young's modulus in the range of about 10 kPa to 800 kPa. For example, the polymer can have a Young's modulus in the range of about 20 kPa to 700 kPa, about 20 kPa to 600 kPa, about 20 kPa to 500 kPa, about 50 kPa to 500 kPa, or about 100 kPa to 500 kPa. In some embodiments, the polymer can have a Young's modulus of about 150 kPa, about 200 kPa, about 250 kPa, about 300 kPa, about 350 kPa, about 400 kPa, about 450 kPa, about 500 kPa, or about 550 kPa.

In some embodiments, the sensing elements can comprise a polymer whose mechanical properties are tunable by controlling the polymerization using different crosslinking energy. Tunability can also be controlled by the ratio of the mixtures of polymer units during the polymerization reaction.

The polymer can be selected from the group consisting of polylactic acid, poly(lactic-co-glycolic) acid, poly(caprolactone), polyglycolide, polylactide, polyhydroxybutyrate, polyhydroxyalcanoic acid, chitosan, hyaluronic acid, poly (2-hydroxyethyl-methacrylate), poly(ethylene glycol), poly (L-lactide) (PLA), poly(dimethysiloxane) (PDMS), poly(methylmethacrylate) (PMMA), poly(glycerol sebacate), poly (octamethylene maleate (anhydride) citrate) (POMaC), POMaC without citric acid, poly(ε-caprolactone), polyurethane, silk, and a combination thereof.

The shape, thickness, length, orientation, and surface topographical properties of the sensing elements can vary any number of suitable ways so long as the sensing elements are capable of deforming, bending, or otherwise changing shape in response to the contractile action or activity of the tissue connected therebetween, and that such deforming, bending, or otherwise shape changing can be reliably measured. In some embodiments, the sensing elements are in the form of wires, e.g., polymer wires.

In some embodiments, the sensing elements are porous, thereby permitting delivery of nutrients and growth factors to the cardiac tissue.

The shape of the well is not limited in any particular manner and can be square, rectangular, circular, oval, oblong, triangular, or any combination of shapes. The other dimensions of the well also may vary in any suitable manner. For example, the depth of the well, height of the well, and length of the well, and the overall volume of the well may be varied in any suitable way.

For example, the length, height, or width of the well can be about 0.1-1 mm, about 0.2-2 mm, about 0.3-3 mm, about 0.4-4 mm, about 0.5-5 mm, about 0.6-6 mm, about 0.7-7 mm, about 0.8-8 mm, about 0.9-9 mm, about 1-10 mm, about 1-100 mm, or about 10-100 mm.

The surface of the well may also be modified with any suitable surface treatments, including chemical modifications (such as, for example, ligands, charged substances, bind agents, growth factors, antibiotics, antifungal agents), or physical modifications (such as, for example, spikes, curved portions, folds, pores, uneven portions, or various shapes and topographies) which may facilitate the tissue culture process.

In some embodiments, the bioreactor described herein can further include electrodes configured to generate an electric field across the well of the bioreactor. The direction of the electric field can be in any direction, e.g., in a direction that is generally parallel to the longitudinal axis of the well, or which is generally perpendicular to the longitudinal axis of the well. In certain embodiments, the electric field facilitates that maturation of the cells to form tissue that more closely mimics the physiological and electrical properties of actual tissue, e.g., an atrial tissue, a ventricular tissue, or a combination thereof.

The Biowire II platform can include a plurality of individual bioreactors, e.g., in the format of multi-well plates, such as 6-well, 8-well, 12-well, 24-well, 96-well, 384-well, and 1536-well plates, such that a plurality of tissues may be grown, tested, measured, and evaluated, etc., in a simultaneous manner.

Methods of Tissue Generation

Cells can be obtained by biopsy or harvested from a living donor, cell culture, or autopsy, all techniques well known in the art. In some embodiments, the cells are autologous. Cells to be implanted can be dissociated using standard techniques such as digestion with a collagenase, trypsin or other protease solution and are then seeded into the mold or polymer scaffold immediately or after being maintained in culture. Cells can be normal or genetically engineered to provide additional or normal function. Immunologically inert cells, such as embryonic or fetal cells, stem cells, and cells genetically engineered to avoid the need for immunosuppression can also be used.

Undifferentiated or partially differentiated precursor cells may also be used. For example, the invention may use embryonic germ cells (Gearhart, et al., U.S. Pat. No. 6,245, 566), embryonic stem cells (Thomson, U.S. Pat. Nos. 5,843, 780 and 6,200,802), mesenchymal stem cells (Caplan, et al. U.S. Pat. No. 5,486,359), neural stem cells (Anderson, et al., U.S. Pat. No. 5,849,553), hematopoietic stem cells (Tsukamoto, U.S. Pat. No. 5,061,620), multipotent adult stem cells (Furcht, et al., WO 01/11011), the contents of each of which are incorporated by reference. Cells can be kept in an undifferentiated state by co-culture with a fibroblast feeder layer (Thomson, U.S. Pat. Nos. 5,843,780 and 6,200,802), or by feeder-free culture with fibroblast conditioned media (Xu, et al. Nat. Biotechnol., 19, 971 (2001)). Undifferentiated or partially differentiated precursor cells can be induced down a particular developmental pathway by culture in medium containing growth factors or other cell-type specific induction factors or agents known in the art. Some examples of such factors include: vascular endothelial growth factor; Sonic Hedgehog; insulin-like growth factor II; osteogenin; cytotoxic T cell differentiation factor; beta-catenin; bone morphogenic protein 2; interleukin 2; transforming growth factor beta; nerve growth factor; interleukin I; fibroblast growth factor 2; retinoic acid; and Wnt3.

The cells can be seeded and cultivated in the bioreactor. The cells can be encapsulated in a hydrogel to create a cell-hydrogel suspension. The cell-hydrogel suspension can then be placed in a well of a bioreactor, e.g., on at least two elastic sensing elements that are disposed across the well. Electrical stimulations can be applied to the cell-hydrogel suspension to facilitate tissue maturation.

In some embodiments, the cells can be seeded at a density of at least about 10 million/mL, at least about 15 million/mL, at least about 20 million/mL, at least about 30 million/mL, at least about 35 million/mL, at least about 40 million/mL, at least about 45 million/mL, or at least about 50 million/mL. In some embodiments, the cells can be seeded at a density of no more than about 300 million/mL, no more than about 250 million/mL, no more than about 200 million/mL, no more than about 150 million/mL, no more than about 100 million/mL, no more than about 95 million/mL, no more than about 90 million/mL, no more than about 85 million/mL, no more than about 80 million/mL, or no more than about 75 million/mL.

Combinations of the above-referenced ranges for the number of cells in the cardiac tissue are also possible (e.g., at least about 10 million/mL to no more than about 300 million/mL, or at least about 30 million/mL to no more than about 200 million/mL), inclusive of all values and ranges therebetween.

In some embodiments, the cells can be seeded at a density of about 40 million/mL, about 50 million/mL, about 60 million/mL, about 80 million/mL, about 100 million/mL, or about 200 million/mL.

One aspect of the present disclosure relates to a method for producing an ex vivo atrial tissue, the method comprising: (a) applying an electrical stimulation at a first frequency to a plurality of atrial cardiomyocytes for a first period of time, the first frequency being equal to or greater than a suprathreshold frequency; (b) increasing the frequency of the electrical stimulation at a rate of at least about 0.05 Hz/day until the frequency is at a second frequency of no more than about 6 Hz; and (c) maintaining the electrical stimulation at the second frequency for a second period of time, thereby producing the ex vivo atrial tissue.

In some embodiments of the methods for producing an ex vivo atrial tissue, the plurality of atrial cardiomyocytes is encapsulated in a hydrogel, such as a collagen hydrogel. The hydrogel can further include cardiac fibroblasts.

In some embodiments of the methods for producing an ex vivo atrial tissue, the first frequency can be about 1-3 Hz, e.g., about 1 Hz, about 1.5 Hz, about 2 Hz, about 2.5 Hz, or about 3 Hz.

In some embodiments of the methods for producing an ex vivo atrial tissue, the frequency of the electrical stimulation is increased at a rate of at least about 0.1 Hz/day, at least about 0.15 Hz/day, at least about 0.2 Hz/day, at least about 0.25 Hz/day, or at least about 0.3 Hz/day. In some embodiments of the methods for producing an ex vivo atrial tissue, the frequency of the electrical stimulation is increased at a rate of no more than about 1 Hz/day, no more than about 0.9 Hz/day, no more than about 0.8 Hz/day, no more than about 0.7 Hz/day, no more than about 0.6 Hz/day, or no more than about 0.5 Hz/day.

In some embodiments of the methods for producing an ex vivo atrial tissue, the first period of time is about 1-100 days, e.g., about 1-50 days, about 1-14 days, 1 day, 2 days, 3 days, 4 days, 5 days, 6 days, or 7 days. In some embodiments of the methods for producing an ex vivo atrial tissue, the second period of time is about 1-7 days, e.g., 1, day, 2 days, 3 days, 4 days, 5 days, 6 days, or 7 days.

In some embodiments of the methods for producing an ex vivo atrial tissue, the plurality of atrial cardiomyocytes is suspended on at least two elastic sensing elements in a bioreactor, wherein the at least two elastic sensing elements deform in response to the contractile force exerted by the plurality of atrial cardiomyocytes.

Another aspect of the present disclosure relates to a method for producing an ex vivo ventricular tissue, the method comprising: (a) applying an electrical stimulation at a first frequency to a plurality of ventricular cardiomyocytes for a first period of time, the first frequency being equal to or greater than a suprathreshold frequency; (b) increasing the frequency of the electrical stimulation at a rate of at least about 0.1 Hz/day until the frequency is at a second frequency of no more than about 6 Hz; and (c) maintaining the electrical stimulation at the second frequency for a second period of time, thereby producing the ex vivo ventricular tissue.

In some embodiments of the methods for producing an ex vivo ventricular tissue, the plurality of ventricular cardiomyocytes is encapsulated in a hydrogel, such as a collagen hydrogel. The hydrogel can further include cardiac fibroblasts.

In some embodiments of the methods for producing an ex vivo ventricular tissue, the first frequency is about 1-3 Hz, e.g., about 1 Hz, about 1.5 Hz, about 2 Hz, about 2.5 Hz, or about 3 Hz.

In some embodiments of the methods for producing an ex vivo ventricular tissue, the frequency of the electrical stimulation is increased at a rate of at least about 0.15 Hz/day, at least about 0.2 Hz/day, at least about 0.25 Hz/day, or at least about 0.3 Hz/day. In some embodiments of the methods for producing an ex vivo ventricular tissue, the frequency of the electrical stimulation is increased at a rate of no more than about 1 Hz/day, no more than about 0.9 Hz/day, no more than about 0.8 Hz/day, no more than about 0.7 Hz/day, no more than about 0.6 Hz/day, or no more than about 0.5 Hz/day.

In some embodiments of the methods for producing an ex vivo ventricular tissue, the first period of time is 1-100 days, e.g., about 1-50 days, about 1-14 days, 1 day, 2 days, 3 days, 4 days, 5 days, 6 days, or 7 days. In some embodiments of the methods for producing an ex vivo ventricular tissue, the second period of time is about 1-7 days, e.g., 1 day, 2 days, 3 days, 4 days, 5 days, 6 days, or 7 days. In some embodiments of the methods for producing an ex vivo ventricular tissue, the plurality of ventricular cardiomyocytes is suspended on at least two elastic sensing elements in a bioreactor, wherein the at least two elastic sensing elements deform in response to the contractile force exerted by the plurality of ventricular cardiomyocytes.

The methods described herein can be used for producing an ex vivo composite tissue. In some embodiments, the composition tissue includes an atrial tissue and a ventricular tissue.

Applications of the Cardiac Tissues

The tissues and/or tissue systems described herein permit testing on an atrial tissue, a ventricular tissue, or both atrial and ventricular tissues in a single pass, thereby doubling the throughput. The tissues and/or tissue systems described herein also permit comparing drug response in a ventricular tissue versus an atrial tissue.

In some embodiments, the tissue system described herein can be used for measuring the effect on contraction of the cardiac tissue formed therein resulting from exposure to a test agent of interest.

In some embodiments, the tissue system can be used for (a) testing of the efficacy and safety (including toxicity) of a test agent (e.g., an experimental pharmacologic agent), (b) defining the pharmacokinetics and/or pharmacodynamics of a pharmacologic agent, (c) characterizing the properties and therapeutic effects of a pharmacologic agent on a subject, (d) screening an experimental pharmacologic agents, and/or (e) providing implantable engineered tissues for use in regenerative medicine for treating damaged and/or diseased tissues.

Accordingly, one aspect of the present disclosure provides a method for measuring an effect of a test agent on contraction using the tissue system described herein, comprising: measuring a first value of a contraction characteristic of the cardiac tissue in the bioreactor before exposure to the test agent; contacting the cardiac tissue with the test agent under conditions sufficient for the test agent to modulate the contraction; measuring a second value of the contraction characteristic of the cardiac tissue after exposure to the test agent; and determining whether the test agent modulates the contraction by comparing the first value with the second value.

The contraction characteristic can be a contractile force, passive tensions, a contraction slope, a relaxation slope, total duration, time to peak, time from peak or a combination thereof.

In some embodiments, the test agent modulates the contraction when there is a significant difference between the first value and the second value, e.g., a difference of at least about 10%, a difference of at least about 15%, a difference of at least about 20%, a difference of at least about 25%, a difference of at least about 30%, a difference of at least about 35%, a difference of at least about 40%, a difference of at least about 45%, or a difference of at least about 50%.

In some embodiments, the measurement of a contractile force comprises measuring an amount of movement imposed by the cardiac tissue on the sensing elements from a first position to a second position.

In some embodiments, the test agent modulates the contractile force when there is a significant difference between the first contractile force and the second contractile force, e.g., a difference of at least about 10%, a difference of at least about 15%, a difference of at least about 20%, a difference of at least about 25%, a difference of at least about 30%, a difference of at least about 35%, a difference of at least about 40%, a difference of at least about 45%, or a difference of at least about 50%.

In some embodiments, the contractile force can be measured by optical microscopy as disclosed by US20160282338.

Another aspect of the present disclosure relates to a method for measuring an effect of a test agent on a calcium transient using the tissue system described herein, comprising: measuring a first value of a calcium transient characteristic of the cardiac tissue in the bioreactor before exposure to the test agent; contacting the cardiac tissue with the test agent under conditions sufficient for the test agent to modulate the calcium transient; measuring a second value of the calcium transient characteristic of the cardiac tissue after exposure to the test agent; and determining whether the test agent modulates the calcium transient by comparing the first value with the second value.

The calcium transient characteristic can be magnitude of calcium transient, time constant of calcium transient, rate of calcium transient, or a combination thereof.

In some embodiments, the test agent modulates the calcium transient when there is a significant difference between the first value and the second value, e.g., a difference of at least about 10%, a difference of at least about 15%, a difference of at least about 20%, a difference of at least about 25%, a difference of at least about 30%, a difference of at least about 35%, a difference of at least about 40%, a difference of at least about 45%, or a difference of at least about 50%.

In some embodiments, the measurement of a calcium transient characteristic comprises measuring a fluorescence signal of an intracellular calcium indicator in the cardiac tissue.

In some embodiments, the intracellular calcium indicator is selected from Fura-4F AM, Fura-2, Fluo-3, Fluo-4, and Indo-1, Mag-Fura-5, and Mag-Fura-red.

Another aspect of the present disclosure relates to a method for evaluating the safety of a test agent using the tissue system described herein, comprising: (a) contacting the cardiac tissue with the test agent; (b) measuring the effect on one or more physiological parameters indicative of safety; (c) comparing the physiological parameters in (b) to the same physiological parameters measured from a control bioreactor not exposed to the test agent, wherein a statistically significant change in the physiological parameters in (b) as compared to the same physiological parameters measured from the control bioreactor indicates that the test agent lacks safety.

The undesired effects of toxicity caused by administration of a test agent can be screened in several ways. The tissue system described herein can be used to determine the range of toxic dosimetry of a test agent in a chamber-specific manner. The effect of increasing concentrations of the test agent (i.e., dose) on cardiac tissue can be monitored to detect toxicity. A toxic effect, when observed, can be equated with a measurement of test agent concentration/cells $cm^2$. By calculating the toxic concentration according to the distribution of cells in the cardiac tissue, one of skill in the art can extrapolate to the living system, to estimate toxic doses in subjects of various weights and stages in development.

The tissue system described herein can also be used to evaluate a test agent's efficacy. Efficacy can be detected by measuring individual parameters associated with the repair, enhancement, improvement and/or regeneration of a disease model comprising a diseased cardiac tissue. The diseased state can be induced or can be the result of a pre-existing condition in the tissue donor, including conditions relating to inherited genetic abnormalities. Either the induced or pre-existing condition can comprise a weakened state resulting from a previous drug exposure. Test agents can be analyzed for efficacy in disease models of the present disclosure.

Using methods of the invention, various doses of individual test agents and combinations of test agents can be screened in panels comprised of tissues having diverse genetic backgrounds to determine the pharmacogenetic efficacy profile of the test agents. For example, multiple doses of, or combinations with, test agents will be screened for efficacy, or the lack thereof, specific to one or more genetic backgrounds.

In general, test agents can be incubated with the cardiac tissue in a dosage range estimated to be therapeutic and for a duration sufficient to produce an effect (e.g., metabolic effects or effects indicating to toxicity or efficacy). The incubation time can range from about one minute to 24 hours, or can be extended as necessary for several days or even weeks. The incubation conditions typically involve standard culture conditions known in the art, including culture temperatures of about 37 degrees Celsius, and culture mediums compatible with the cardiac tissue.

In some embodiments, the test agent is selected from the group consisting of a small molecule, an antibody, an ion, a protein, a peptide, a lipid, DNA, RNA, a virus, bacteria, a microparticle, a nanoparticle, a therapeutic agent, and a toxin.

Examples of test agents include, but are not limited to, opioid analgesics, anti-inflammatory drugs such as antihistamines and non-steroidal anti-inflammatory drugs (NSAIDs), diuretics such as carbonic anhydrase inhibitors, loop diuretics, high-ceiling diuretics, thiazide and thiazide-like agents, and potassium-sparing diuretics, agents that impinge on the renal and cardiovascular systems such as angiotensin converting enzyme (ACE) inhibitors, cardiac drugs such as organic nitrates, calcium channel blockers, sympatholytic agents, vasodilators, β-adrenergic receptor agonists and antagonists, α-adrenergic receptor agonists and antagonists, cardiac glycosides, anti-arrhythmic drugs, agents that affect hyperlipoproteinemias such as 3-hydroxymethylglutaryl-coenzyme A (HMG-CoA) inhibitors, anti-neoplastic agents such as alkylating agents, antimetabolites, natural products, antibiotics, and other drugs, immunomodulators, anti-diabetic agents, and anti-microbial agents such as antibacterial agents, antiviral agents, antifungal agents, antiprotozoal agents, and antihelminthic agents.

Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Definitions

All definitions, as defined and used herein, should be understood to control over dictionary definitions, definitions in documents incorporated by reference, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "about" refer to a range of values that are similar to the stated reference value. In certain embodiments, the term "about" refers to a range of values that fall within 10 percent or less (e.g., 10%, 9%, 8%, 7%, 6%, 5%, 4%, 3%, 2%, or 1%) of the stated reference value.

The term "substantially" when used to describe cell alignment, refers to an angle difference of 20% or less (e.g., 20%, 15%, 10%, 9%, 8%, 7%, 6%, 5%, 4%, 3%, 2%, 1% or less) in the direction of cell alignment.

As used herein, the term "POMaC" refers to poly(octamethylene maleate (anhydride) citrate) (POMaC) or the POMaC prepolymer which comprises a mixture of 1,8-octandiol, citrate acid, and maleic anhydride. Reference can be made to Tran et al., "Synthesis and characterization of a biodegradable elastomer featuring a dual crosslinking mechanism," Soft Matter, Jan. 1, 2010; 6(11): 2449-2461, which is incorporated herein by reference in its entirety.

As used herein, the term "tunability" as it is used in reference to a "tunable" polymer, e.g., POMac, refers to the capability of adjusting the process of polymerization of a polymer in a manner that allows for the formation of a resultant polymer product to have different mechanical and/or physical properties, such as elasticity, stiffness, and/or reactivity, or other properties. This concept is referred to in the context of certain polymers, such as POMac, that may be advantageously used in various embodiments/devices of the present disclosure to form the various components of the devices of the present disclosure, e.g., polymer wires, scaffolds, scaffold layers, and other components. Tunable polymers, such as POMac, may have adjustable or "tunable" properties by adjusting, for example, (a) the degree or quantity of UV crosslinking or (b) the ratio of pre-polymer units that form the polymer, e.g., the ratio of 1,8-octanediol, citric acid, and maleic anhydride in the case of POMac. The controlled formation of pores in the polymer can also be regarded as an aspect of tunability, and in particular, pore size may be controlled as exemplified herein by the inclusion of different amounts of polyethylene glycol dimethyl ether (PEGDME) or an equivalent during the UV crosslinking stage.

As used herein, the term "biowire" refers to a tissue having the shape of a wire. The biowire can have an aspect ratio of at least about 2:1, about least about 3:1, about least about 4:1, at least about 5:1, at least about 6:1, at least about 7:1, at least about 8:1, at least about 9:1, or at least about 10:1.

As used herein, the term "test agent" is any substance that is evaluated for its ability to diagnose, cure, mitigate, treat, or prevent disease in a subject, or is intended to alter the structure or function of the body of a subject. A test agent in an embodiment can be a "drug" as that term is defined under the Food Drug and Cosmetic Act, Section 321(g)(1). Test agents can include, but are not limited to, chemical compounds, biologic agents, proteins, peptides, antibodies, nucleic acids, lipids, polysaccharides, supplements, diagnostic agents and immune modulators and may also be referred to as "pharmacologic agents."

As used herein, the term "toxicity" is defined as any unwanted effect on human cells or tissue caused by a test agent, or test agent used in combination with other pharmaceuticals, including unwanted or overly exaggerated pharmacological effects. An analogous term used in this context is "adverse reaction."

As used herein, the term "suprathreshold frequency" means the frequency right above the spontaneous beating frequency of a cardiac tissue or cell. Generally, the suprathreshold frequency is between about 1 Hz and about 3 Hz. In some embodiments, the suprathreshold frequency is about 1 Hz, about 1.2 Hz, about 1.4 Hz, about 1.6 Hz, about 1.8 Hz, about 2 Hz, about 2.2 Hz, about 2.4 Hz, about 2.6 Hz, about 2.8 Hz, or about 3 Hz.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1. Materials and Methods

Predominantly ventricular cardiomyocytes (CMs) were derived from the human embryonic stem cell (hESC) lines Hes2 and HES3-NKX2-5gfp/w using the using embryoid body (EB) differentiation protocol and the human induced pluripotent stem cell (hiPSC) line BJ1D using the monolayer differentiation protocols as previously described. Ventricular cell populations contained 74.7±6.3% (n=9) of CMs on average, based on cardiac troponin T expression analysis using flow cytometry, at the end of directed differentiation protocols.

C2A hiPSC derived cardiomyocytes were differentiated with EB protocol as previously described.

iCell™ and iCell2™ cardiomyocytes were purchased from CDI and used according to the manufacturer's instructions.

Cardiomyocytes of Non-affected A, Non-affected B, Non-Affected C, affected D, affected E, and affected F were provided by Cellular Dynamics Inc, Madison, Wisconsin Predominantly atrial cardiomyocytes were derived from Hes3-NKX2-5gfp/w hESCs and MSC-iPSC1 using an atrial-specific EB differentiation protocol as described. Briefly, all trans retinoic acid (0.5 µM, Sigma) was added during the cardiac mesoderm specification stage (days 3-5 of differentiation) to promote atrial cardiogenesis. At day 20 of differentiation, atrial cardiomyocytes from Hes3-NKX2-5gfp/w hESCs were analyzed and defined based on the proportion of NKX2.5+, cTNT+ and MLC2v− cells using flow cytometry, 79.1±8.0%, n=10. For predominantly atrial CMs from MSC-IPS1 cell lines, 73.2%±7.7% of total cells were atrial CMs (cTNT+ and MLC2V−), n=2 batches. Differentiation cultures were dissociated to single cells for subsequent tissue seeding.

Rat CMs were isolated from neonatal rat (Sprague Dawley) hearts three days after birth.

Device Fabrication

Figure 8A:
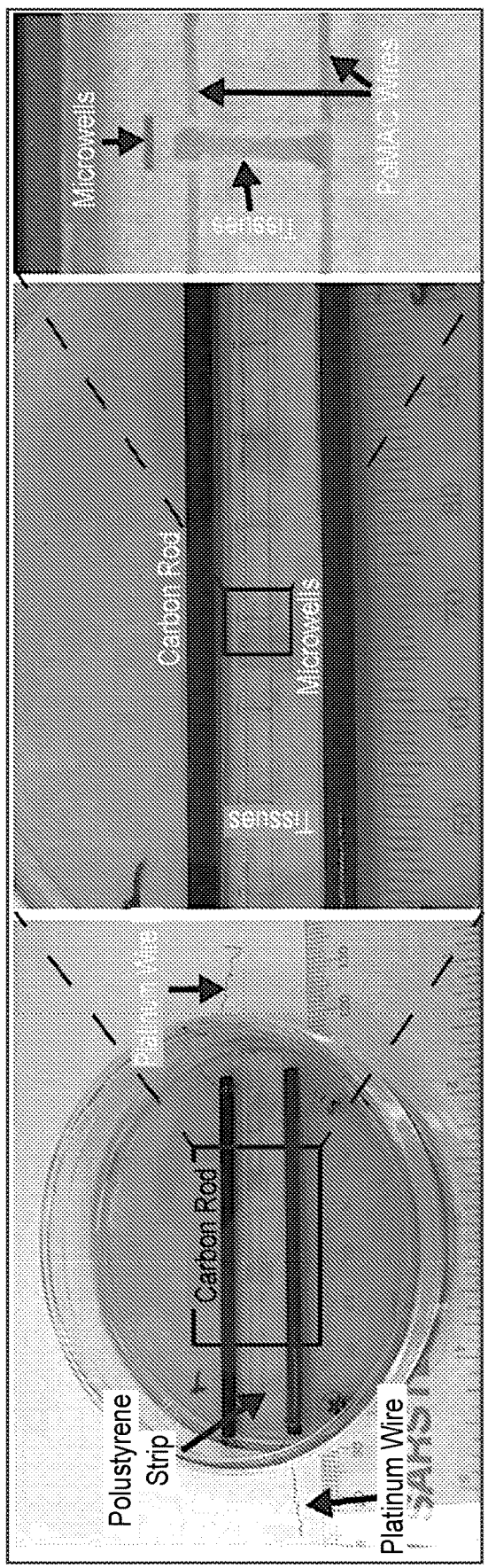

Polystyrene sheet patterned with microwells: A repeating pattern consisting of rectangular microwells (5 mm×1 mm×300 µm, L×W×H) interconnected by two parallel grooves (200 µm×100 µm, W×H) was designed using AutoCAD. An SU-8 photoresist master mold, fabricated as previously described, was used to produce a negative polydimethylsiloxane (PDMS) master mold. The PDMS master was used to hot emboss the microwells into a polystyrene sheet (FIG. 8A).

Polymer wires: Poly(octamethylene maleate (anhydride) citrate) (POMaC) polymer wires (100 µm×100 µm, W×H) were prepared from a pre-polymer as previously described. To fabricate the POMaC wires, a PDMS mold with parallel microchannels of the desired dimensions was fabricated from an SU-8 master, as previously described. The PDMS mold was lightly pressed onto a glass slide and the POMaC pre-polymer solution was perfused through the microchannels by capillary action. The pre-polymer solution was then cured by UV exposure (5100 mJ/cm$^2$). Due to the stronger adhesion of the POMaC wires to glass than PDMS, the POMaC wires remained adherent to the glass when the PDMS mold was carefully peeled off the glass slide. The POMaC wires were soaked in phosphate buffered saline (PBS) to release them from the glass slide and manually placed into the two parallel grooves patterned into the polystyrene sheet (FIG. 8A). In some configurations, clear polyurethane 2-part adhesive (SP 1552-2, GS Polymers, Inc.) was used in a minimal quantity to fix the POMaC wires in place.

Hydrogel Preparation

A collagen hydrogel was prepared by combining 3.0 mg/mL rat tail collagen (Corning) with 10% (v/v) Matrigel (BD Biosciences), 0.2 mg/mL NaHCO$_3$, 10 mM NaOH, and 1×M199 (Sigma).

Electrical Stimulation Chamber Fabrication

Two ⅛ inch-diameter carbon rods (Ladd Research Industries) were fixed 1 cm apart (inner edge-to-inner edge) to the bottom of a 10 cm tissue culture dish using polyurethane 2-part adhesive (FIG. 8A). The carbon rods were connected to the lead wires of an external electrical stimulator (Grass Technology S88X Square Pulse Stimulator) with platinum wires (Ladd Research Industries).

Generation of Engineered Cardiac Tissues

Strips of polystyrene containing eight microwells were transferred to a 10 cm tissue culture dish (FIG. 8A). The strip surface was rinsed with 5% (w/v) Pluronic Acid (Sigma-Aldrich) and then air dried in the biosafety cabinet. Dissociated cardiac cells and cardiac fibroblasts (LONZA, Clonetics™ NHCF-V) were mixed in a 10:1 (ventricular cardiac cells:fibroblasts) or 10:1.5 (atrial cardiac cells:fibroblasts) cell number ratio, pelleted and resuspended at a concentration of 5.5×10$^7$ cells/mL (unless otherwise specified) in a hydrogel. This results in a 74,700 CMs per tissue on average. The cell-hydrogel suspension (2 µl per well) was seeded into the polystyrene microwells, to give a final seeding concentration of 1.1×10$^5$ cells/microwell or 7.47×10$^4$ CMs/microwell. The tissues were cultured for 7 days to allow for remodeling and compaction around the POMaC wires. Daily bright field images of the tissues were taken using an Olympus CKX41 inverted microscope and CellSens software (Olympus Corporation). By Day 7, the tissues synchronously contracted and deflected the POMaC wire with each contraction.

To generate atrioventricular tissues, dissociated atrial cardiac cells and cardiac fibroblasts were mixed in a 10:1.5 cell number ratio. Dissociated ventricular cells and cardiac fibroblasts were mixed in a 10:1.5 cell number ratio. The mixed cells were pelleted and resuspended at a concentration of 5.75×10$^7$ cells/mL in collagen hydrogel. When seeding, cell-hydrogel mixture containing atrial CMs (1 µL) were seeded on one side of the Biowire II well first, followed by mixture containing ventricular CMs (1 µL) seeded on the other side. After seeding, tissues were cultured for 7 days to allow for remodeling and compaction around the POMaC wires.

Electrical Stimulation Protocols

On Day 7, each strip of 8 tissues was transferred to an electrical stimulation chamber, such that the tissues were positioned between the carbon rods. On Day 7 and weekly thereafter, 4× bright field movies were taken of beating under stimulation at 1 Hz. The minimum voltage per cm required to stimulate the synchronized contraction of the tissue (excitation threshold, ET) and the maximum frequency the tissue could contract in response to the stimulation pulse at twice the ET (maximum capture rate, MCR) were measured and recorded. POMaC is intrinsically fluorescent, hence the deflection of the polymer wire due to tissue contraction was isolated and tracked under the blue fluorescent light. Blue channel movies (10× objective; $\lambda_{ex}=350$ nm, $\lambda_{em}=470$ nm; 100 frames/s, 5 ms exposure) were taken to record the bending movement of the POMaC wire during tissue contraction from 1-3 Hz (1 Hz increase every 20 sec) to measure the force-frequency relationship (FFR). After FFR, the tissue had been stimulated at high frequency (6 Hz) for 20 sec, stimulation was turned off and re-initiated at 1 Hz to measure the post-rest potentiation (PRP) of the tissue. To quantify the FFR and PRP, all measurements were normalized to the 1 Hz baseline values. All imaging was performed using an Olympus IX81 inverted fluorescent microscope and CellSens software (Olympus Corporation).

The Day 7 electrical excitability assessments were used to determine the long-term stimulation conditions, specifically stimulation voltage (1.5-times the $ET_{avg}$). Electrical stimulation was continued with weekly monitoring of ET, MCR, FFR, and PRP. Culture media was changed every week.

Electrical stimulation protocol of weekly 1 Hz increase in frequency was implemented for ventricular maturation. If average MCR exceeds 4 Hz after one week of 2 Hz stimulation or exceeded 5 Hz after one week of 3 Hz stimulation, stimulation frequency can be changed directly from 2 Hz to 4 Hz or 3 Hz to 5 Hz to accelerate the process. End point assessments were performed when a positive FFR in the range from 1 to 3 Hz was achieved. If a positive FFR was not observed once the frequency reached 6 Hz, stimulation continued at 6 Hz, until a positive FFR was observed. The stimulation voltage was adjusted weekly to 1.5-times the average ET, down to a minimum voltage of 3.5V/cm. For atrial preparations, a similar procedure was applied with the daily increase of the stimulation frequency by 0.4 Hz, from 2 Hz to 6 Hz, then retaining the stimulation frequency at 6 Hz for 1 week.

For the ventricular disease model preparation, tissues were generated from non-affected A, non-affected B, non-affected C, affected D, affected E, and affected F cardiomyocytes. Electrical stimulation started at 2 Hz on day 7 post cell seeding and the protocol of 1 Hz weekly step-up was used until the frequency reached 6 Hz, at which point it was maintained at 6 Hz for one week. Subsequently, the frequency was decreased to 3 Hz and maintained at that level for the remainder of the cultivation period, up to 6 months. Tissues were assessed after 6 weeks and 8 months.

For atrioventricular preparations, electrical stimulation started at 2 Hz on day 7 and the protocol of 1 Hz weekly step-up was used until the frequency reached 6 Hz. If average MCR exceeded 4 Hz after one week of 2 Hz stimulation, or exceeded 5 Hz after one week of 3 Hz stimulation, stimulation frequency could be changed directly from 2 Hz to 4 Hz or 3 Hz to 5 Hz to accelerate the process. The stimulation at 6 Hz was maintained for 1 week, at which point it was decreased to 3 Hz and maintained for a period of several days until the tissues were used for drug testing.

Atrial and Ventricular Tissue RNA Sequencing

RNA was isolated using a commercially available kit: PicoPure™ RNA Isolation Kit (Thermo Fisher, KIT0204) and RNase-Free DNase Set (Qiagen #79254). RNA sequencing was performed at the Illumina CSPro Next Generation Sequencing facility of the Donnelly Sequencing Centre at the University of Toronto. Alignments were made using the pseudo alignment method from Kallisto. The transcriptome used was obtained from ESEMBL, human genome build GRCh38.p10, yielding 63967 genes and over 200,000 spliced transcripts. Single end mode with a mean fragment insert size of 270 and SD of 40 bases was used. Counts were quantified from Kallisto output files using Sleuth. Technical and biological variance was calculated using Sleuth to yield test statistics based on a linear model, where the treatment was corrected against the intercept. No batch was present in the dataset as all samples were sequenced across 4 flow cells to generate approximately 20 million reads per sample. Log fold changes were calculated using DESeq2. Heat maps were generated using the R function pheatmap.

Gene Set Enrichment Analysis

Normalized counts of RNA-sequencing data were processed using the R function voom to transform counts into Gaussian distributions. The R function camera was used to calculate gene set enrichments to the Gene Ontology Biological Process gene sets obtained from the Broad Institute and custom ontology files generated from differential expression analysis using the R library limma of deposited human atrial and ventricle gene expression data (GSE2240). The gene matrix table file for gene set enrichment of atria and ventricle gene expression data was generated using custom R scripts. Output from camera gene set enrichment analysis was formatted as a generic table format for graphing and analysis in Cytoscape using custom R scripts. Network graphs of gene set enrichments were generated in Cytoscape using enrichmentmap. Sub-networks were named using clustermaker and word cloud annotating for enrich words with a bonus for adjacent words.

Gene Expression for Patient Derived Cells

Gene expression of ventricular tissues based on two individual hiPSC-CM cell lines (Affected D, E, and F and non-affected A, B, and C) at the end of 8 month cultivation with electrical conditioning, was assessed as previously described. Whole transcriptome sequencing was done utilizing the Ion Total RNA-Seq Kit and the Ion Torrent Proton System (Thermofisher Scientific) following manufacturer's recommendations. Data analysis was performed using Qiagen's Ingenuity Pathway Analysis (IPA) software with the overlay tool IPA-Tox. The feature "Tox List" was set at default parameters to analyze genes contributing to principle component analysis between Affected D, E, and F and Non-affected A, B, and C, focusing on cardiotoxicity.

Elastic Modulus of Polymer Wires

To determine the elastic modulus of the POMaC wires, testing strips (1.5 mm×10 mm×0.1 mm) were cured at 5100 mJ/mm², the same condition as used for preparation Biowire II platform. The tensile test was conducted with a Myograph (Kent Scientific) in the longitudinal direction of strips (n≥5), using a modified ASTM D638-10 Standard Test Method for Tensile Properties of Plastics as described.

To test the long-term POMaC wire stability, the testing strips were placed in a 12-well plate in media (DMEM, 10% fetal bovine serum (FBS), 1% Penicillin-Streptomycin). A transwell insert (Corning) seeded with 1×10⁵ neonatal rat CMs, isolated as described above, was added to each well. Media was changed twice a week and mechanical tests were performed on Day 0, 15, 30, 60 and 90.

Polymer Wire Force-Displacement Curves

Figure 8E:
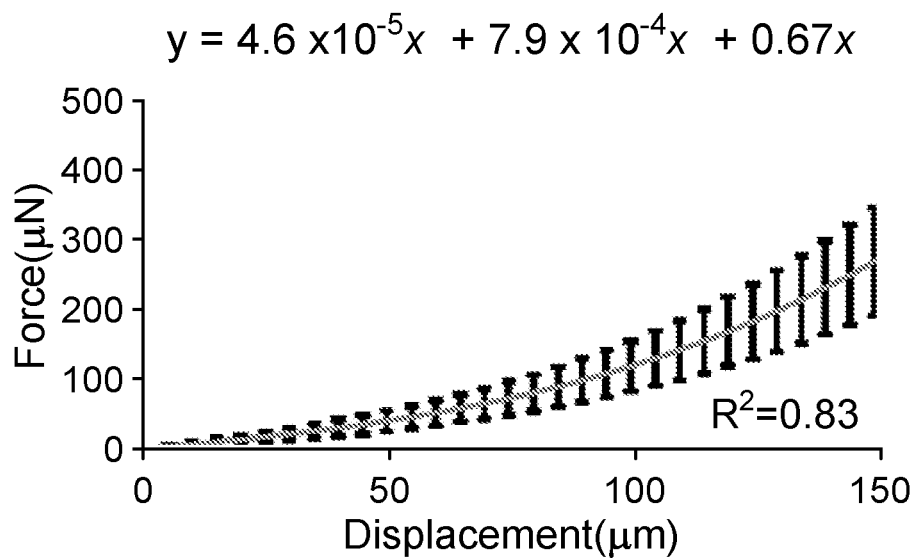
Figure 8F:
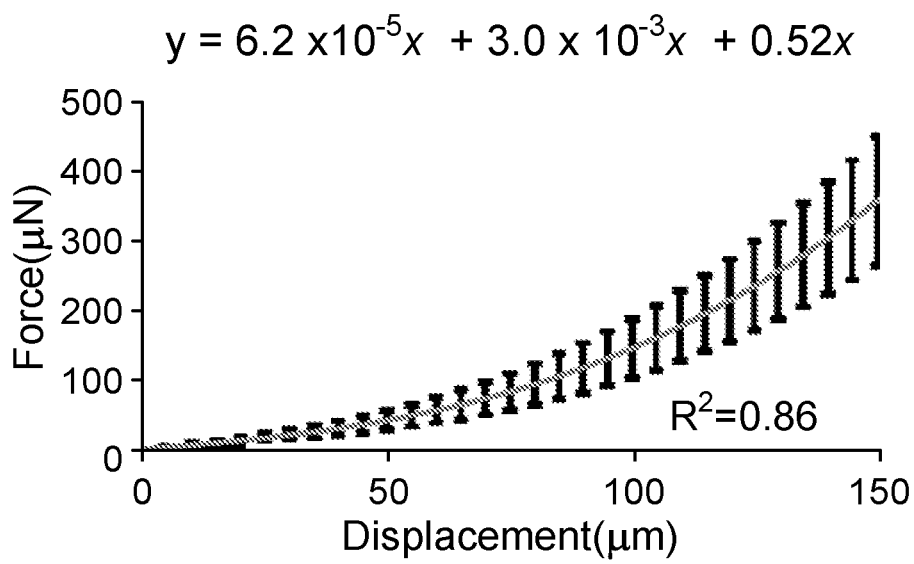
Figure 8G:
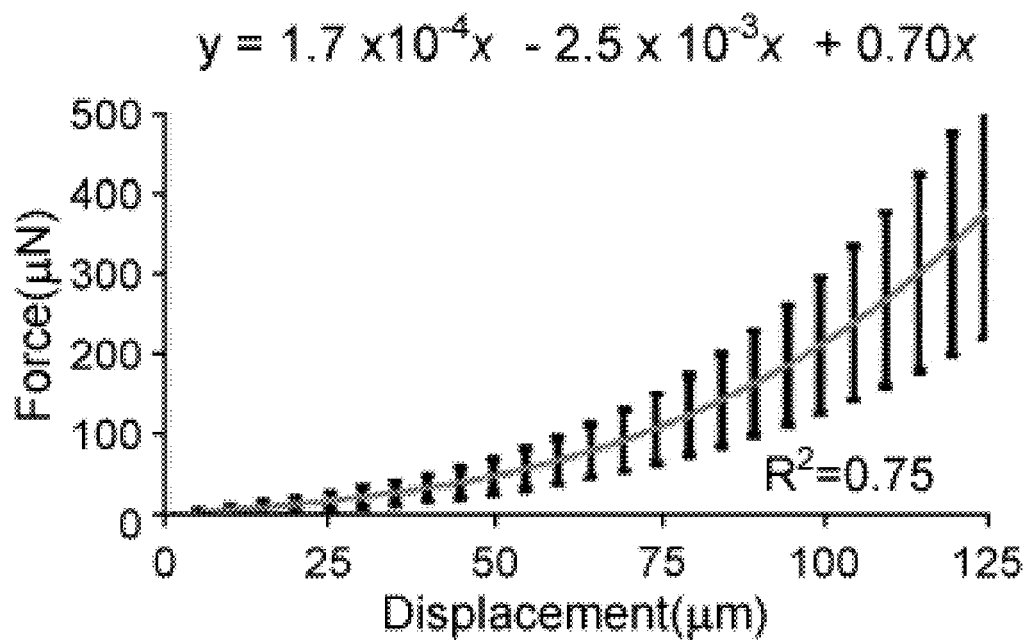

The force required to displace the POMaC wire was determined using a microscale mechanical tester, MicroSquisher (CellScale). The 0.1524 mm-diameter tungsten probe was modified with custom tips (0.5 mm-, 0.7 mm-, and 0.8 mm-diameter) to recapitulate the tissue diameter and curvature on the POMaC wire. The custom tips (half ellipse, 4:1 diameter ratio) were fabricated from an SU-8 master by soft lithography and attached to the tungsten probe using an adhesive (T-GSG-01 Titan Gel). Four separate 8-well polystyrene strips with POMaC wires were tested per probe tip. The polystyrene strips were soaked in media for 7 days prior to testing. During the test, the polystyrene strip was affixed to a 10 cm dish and testing was performed in culture media. The probe tip was placed at one end of microwell and moved towards the POMaC wire at a velocity of 2.5 μm/s. The tip displaced the wire at the midsection, applying the force perpendicular to the long axis of the POMaC wire. The force, probe displacement (0-150 μm) and time were recorded (n≥55). The experimental data, over the entire range, for each custom tip were fit to a third-degree polynomial equation, generating a force-displacement calibration curve for each custom probe tip (FIG. 8E).

To assess if cell cultivation around the polymer wire affects the force-displacement curve, a batch of polystyrene chips with POMaC wires were fabricated and divided into two groups. Both groups were incubated in media at 37° C. for a week before use. Group one was tested right after the incubation as described above, whereas group two was tested after cell seeding and two months of ventricular tissue conditioning. A probe tip of 0.5 mm was used during the tests. Fitted curves, 95% confidence interval curves, and $R^2$ values were calculated with Prism 6.0.

Finite Element Modeling (FEM)

The finite element model simulated the behaviour of the POMAC during mechanical testing. The model included the polymer wire and the indenter; the dimensions and material properties for the FEM components were set to match the conditions during experimental testing. The two ends were constrained by fixed supports and the load was applied to the polymer wire through the indenter. The mesh was made of solid elements, and the number of elements and mesh nodes in the model for the 0.5 mm indenter were 11448 and 52622, for the 0.7 mm indenter were 15702 and 71225, and for the 0.8 mm indenter were 18468 and 83232, respectively. A neo-Hookean, hyperelastic material model was used for the POMAC material to account for the non-linear behavior and the large deformations observed during physical testing. Poisson ratio was assumed to be 0.5.

Active and Passive Force for Cardiac Tissues

Blue channel image sequences were analyzed using a custom MatLab code that traced the maximum deflection of the POMaC wire. Average tissue width (diameter) and width of the tissue on the polymer wire (Tw) were measured from still frames of the 4× bright field video of the tissue in the relaxed position (FIGS. 8C-8D). Total (at peak contraction) and passive (at rest) POMaC wire deflections were converted to force measurements (μN) using the force calibration curves described in the previous section. The final readouts for the total and passive tension of tissue were then interpolated according to the Tw and custom tip sizes. The active force was calculated as the difference between the total and passive tension (FIG. 2C). The custom MatLab code was used to calculate the passive tension, active force, contraction and relaxation duration, and upstroke and relaxation velocity.

Absorption Testing

For the acute test, polystyrene strips containing microwells and POMaC wires, with and without the adhesive, were cut into chips (9 mm×9 mm×1 mm) containing a single microwell. Chips of the same geometry were also made with PDMS. The polystyrene and PDMS chips were incubated in 650 μL Rhodamine 6G (10 nM; Sigma-Aldrich) in closed round bottom polypropylene test tubes at room temperature for half an hour. Rhodamine 6G solution without any chip incubating at same condition was used as a control. 200 μL of the dye solution was transferred to a 96-well plate and the fluorescence was read using a SpectraMax i3 plate reader (Molecular Devices; $\lambda_{ex}$=526 nm, $\lambda_{em}$=555 nm), (n=12).

For the long-term absorption test, polystyrene strips containing microwells and POMaC wires, with and without the adhesive, were cut into chips (9 mm×9 mm×1 mm) containing a single microwell. Chips of the same geometry were also made using PDMS. The polystyrene and PDMS chips were incubated in 1 mL Rhodamine B (1 μM; Sigma-Aldrich) in a 24 well-plate at 37° C. for up to 1 wk. Tissue culture treated 24 well-plates were incubated with the dye in the absence of any chips as a control. At 6 h, 24 h, 48 h, and 1 wk, 100 μL of the dye solution was transferred to a 96-well plate and the fluorescence was read using a SpectraMax i3 plate reader (Molecular Devices; $\lambda_{ex}$=540 nm, $\lambda_{em}$=625 nm), (n=3). Additionally, fluorescent images of the chips were taken in the absence of treatment, after 1 wk of dye incubation, and after 2 h of washing following 1 wk of dye incubation.

Immunostaining and Confocal Microscopy

Tissues were fixed with 4% paraformaldehyde, permeabilized with 0.2% Tween20™, and blocked with 10% FBS. Immunostaining was performed using the following primary antibodies: mouse anti-cardiac Troponin T (cTnT) (ThermoFisher; 1:200), rabbit anti-Connexin 43 (Cx-43) (Abcam; 1:200), mouse anti-α-actinin (Abcam; 1:200), rabbit anti-myosin light chain-2v (Santa Cruz; 1:200), goat anti-caveolin3 (Santa Cruz; 1:100); and the following secondary antibodies: donkey anti-mouse-Alexa Fluor 488 (Abcam; 1:400), donkey anti-rabbit-Alexa Fluor 594 (Life Technologies; 1:200) and donkey anti-goat-Alexa Fluor 647 (Life Technologies; 1:200). Phalloidin-Alexa Fluor 660 (Invitrogen; 1:200) was used to stain F-actin fibers. Conjugated vimentin-Cy3 (Sigma; 1:200) was used to stain for vimentin. Confocal microscopy images were obtained using an Olympus FluoView 1000 laser scanning confocal microscope (Olympus Corporation).

Live and dead staining was performed with CFDA (1:1000, Life Technologies) and Propidium Iodide (75:1000, Life Technologies) in PBS. Viability was calculated as the average intensity of CFDA divided by the sum of average intensities of CFDA and PI. (n≥3).

Sarcomere presence was quantified by average intensity of α-actinin divided by the average intensity of DAPI counterstain. (n=3).

Transmission Electron Microscopy

The tissues were fixed with 4% paraformaldehyde, 1% glutaraldehyde in PBS for at least overnight and washed 3-times with PBS. Secondary-fixation was done with 1% osmium tetroxide in PBS for 1 hr. The tissues were dehydrated using an ethanol series from 50% to 100%. Tissues were infiltrated using Epoxy resin and polymerized in plastic dishes at 40° C. for 48 h. The tissues were stained with uranyl acetate and lead citrate after sectioning. Imaging was performed using a Hitachi H-7000 transmission electron microscope (Hitachi, Ltd.).

Contractile and Calcium Transients

To investigate the contractile effects of various compounds on the tissues, a custom testing chamber was fabricated in a 6-well plate modified with an extraction/injection port connected to a 5 mL syringe, a pair of carbon electrodes (set 1 cm apart) with platinum wire lead attachments and a custom 3D-printed holder for a polystyrene chip with a single microwell. Prior to testing, the tissue was transferred to the custom testing chamber and placed in the environmental chamber on the microscope stage (37° C., 5% $CO_2$), where it was allowed to equilibrate for 30 min in the presence of electrical field stimulation (1 Hz, at ET). A bright field video of the tissue was taken before testing to obtain all the necessary measurements for the force calculation. For testing, the voltage was increased to 10% above the ET, and videos were taken of one polymer wire (10× objective). Prior to the test compound injection, media were extracted and injected through the port twice at 10 min intervals to pre-condition the tissue to the testing process. Compounds were diluted in media at concentrations 1000-fold higher than the desired final concentration. For compound testing, $\frac{1}{3}^{rd}$ of the media was extracted from the chamber, the compound was added to the extracted media and then injected back into the testing chamber. After 10-15 min, videos in the blue channel were recorded. The procedure was repeated for sequential drug dosages. The videos were analyzed using the custom MatLab software, as indicated for the weekly FFR assessments.

To investigate the relative changes of intracellular calcium concentration, tissues were incubated with the calcium dye Fluo-4 NW (Thermo Fisher) for 30 min at 37° C. prior to testing. To obtain both calcium transients and contractility readouts consecutively and synchronously, the testing process was performed using both green light channel ($\lambda_{ex}$=490 nm, $\lambda_{em}$=525 nm) and/or blue channel at 10× or 4× magnification. The ImageJ software (NIH) Stacks plugin was used to determine the average intensity of a region of interest in the tissue located at a distance from the PoMaC wire, wherein the movement artifacts were minimal. The ratio of peak tissue fluorescence intensity to baseline intensity, $dF/F_0$ was calculated to determine the relative changes in intracellular calcium in the presence of the compound. For the consecutive force and calcium transient readouts, contractile measurements were extracted from the blue channel as described before. For the synchronous readouts, the contractile measurements were extracted from the green channel videos using modified version of the ImageJ SpotTracker plugin. Prism 6.0 was used to calculate the IC50.

Intracellular Recordings

Tissues were perfused with 35-37° C. Kreb's Solution (118 mM NaCl, 4.2 mM KCl, 1.2 mM $KH_2PO_4$, 1.2 mM $MgSO_4$, 1.8 mM $CaCl_2$, 23 mM $NaHCO_3$, 2 mM Na-pyruvate and 20 mM glucose, equilibrated with 95% 02 and 5% $CO_2$, pH 7.4) or DMEM medium. They were paced at twice the ET. The action potential was recorded with high impedance microelectrodes (60-90 MΩ) filled with 3M KCl, connected to an Axopatch 200B amplifier (Axon Instruments). Recordings were performed in current clamp mode at 2 kHz and signals were analyzed using the Clampfit 10 Data Analysis Module of the pCLAMP™ 10 Electrophysiology Data Acquisition & Analysis Software (Axon Instruments). The movement of the tissue was minimized by perfusing with 10 µM blebbistatin (Toronto Research Chemicals) for 20 min. The effect of various compounds on the action potential was assessed by preparing an appropriate dilution of the compound in Krebs's Solution or DMEM.

Optical Mapping

Tissues were perfused with 5 µM voltage sensitive dye, Di-4-ANEPPS (Invitrogen), in Kreb's Solution at 35-37° C. for 20 min. Dye fluorescence was recorded on an MVX-10 Olympus fluorescence microscope (Olympus Corporation) equipped with a charged coupled device (CCD) (Cascade 128, Photometrics). The 1 cm sensor had 128×128 pixel resolution. Recordings were performed at 500 frames/s with 0 exposure time. Biowires were paced at 1.5-2 Hz with a Pulsar 6i Stimulator (FHC, Inc.) at twice the ET.

Quantification and Statistical Analysis

Statistical analysis was performed using Prism 6.0. Differences between experimental groups were analyzed by Student's t-test (two groups) or one-way ANOVA (more than two groups). Experiments with two different variables were analyzed with two-way ANOVA. Normality test (Shapiro-Wilk) and pairwise multiple comparison procedures (Tukey's post hoc method or Holm-Sidak method or Sidak-Bonferroni method) were used for one-way ANOVA and two-way ANOVA tests. P<0.05 was considered significant for all statistical tests.

Example 2

Generating Heart Tissues From Multiple Cell Sources

Figure 1A:
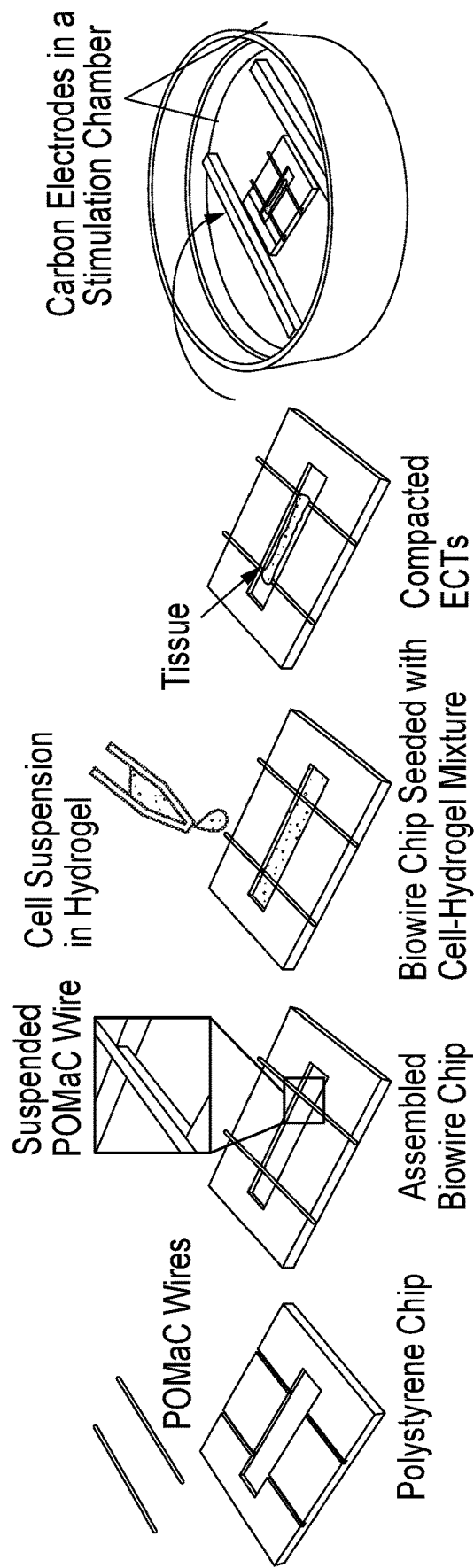
FIGS. 1A-1G show that the Biowire II platform generates micro-scale engineered cardiac tissues in a low-absorption environment.
Figure 1B:
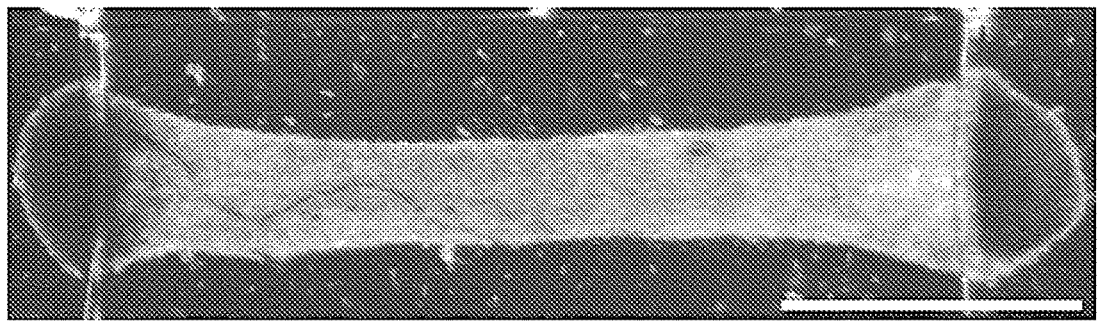

FIG. 1A and FIG. 8A illustrate the general features of our "Biowire" platform which consists of an array of microwells (5 mm×1 mm×0.3 mm) patterned onto polystyrene sheets. Two flexible wires manufactured from a POMaC polymer are secured with adhesive glue along either end of the microwells. Myocardial tissues are created by combining 100,000 CMs (either ventricular or atrial or both) and cardiac fibroblasts (usually at a 10:1 ratio) with hydrogel within the microwells. During the next ~7 days, cells undergo "compaction" thereby forming cylindrical trabecular strips (called Biowires II) that are suspended in the microwell but physically attached to the POMaC wires (FIGS. 8A, 8C, and 8D). Beginning at 1 week, the suspended Biowires are electrically conditioned for weeks with electrical field stimulation via a pair of carbon electrodes connected to a stimulator with platinum wires (FIG. 8A).

Figure 1C:
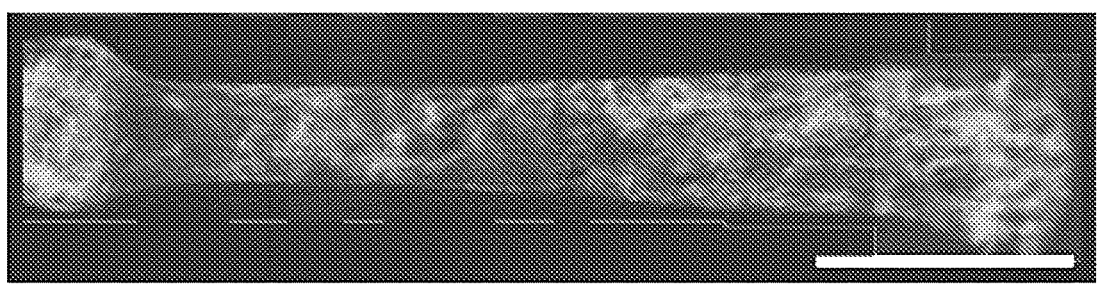
Figure 1D:
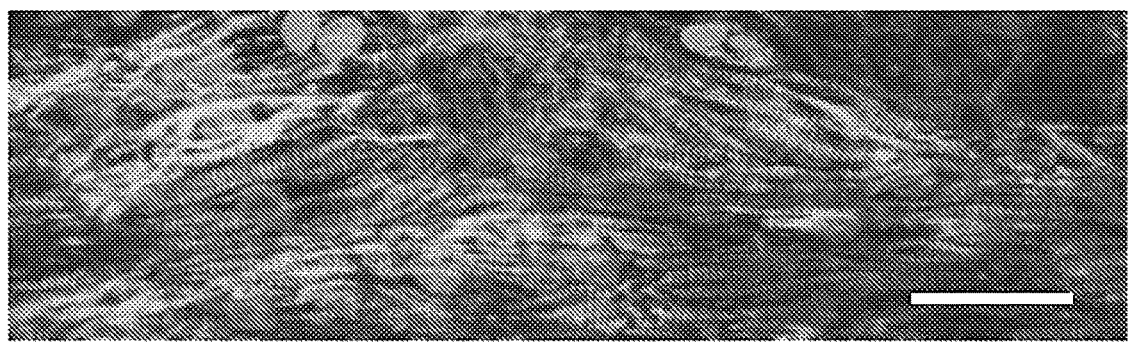
Figure 1E:
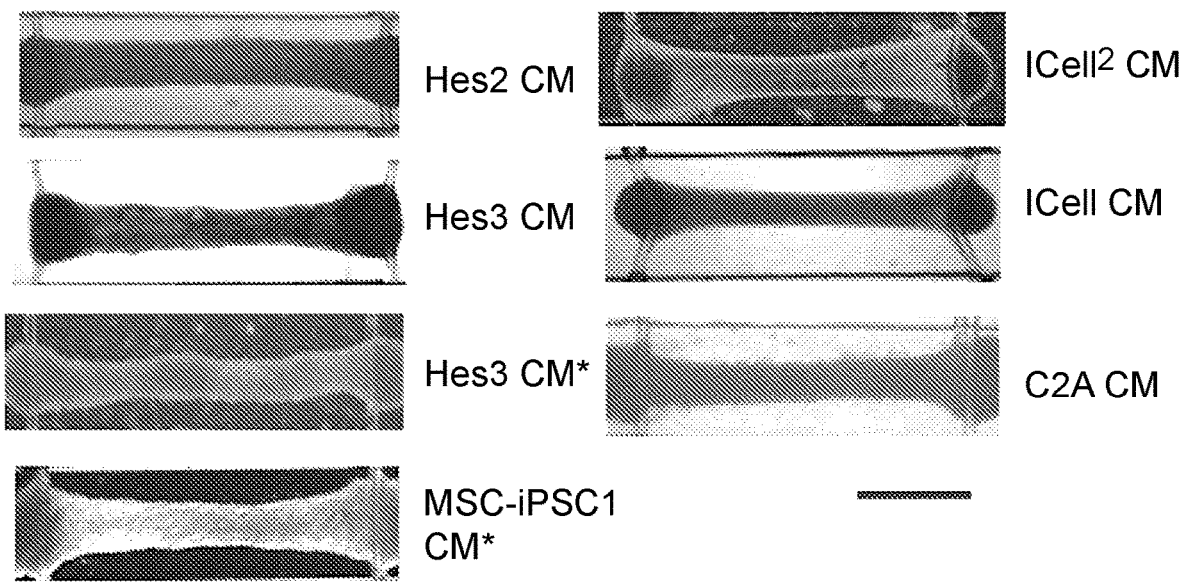

Details of the conditioning protocols used are described below. A typical Biowire created using ventricular CMs from BJ1D stem cells displays uniform longitudinal alignment of sarcomeric contractile proteins (FIGS. 1C-1D) after 6 weeks in culture. Additional examples of Biowires using CMs obtained from other stem cell sources are presented in FIG. 1E while FIG. 8B lists all the sources of cells used in the studies.

Biowire II Platform Exhibits Reduced Absorption of Hydrophobic Compounds

Figure 1F:
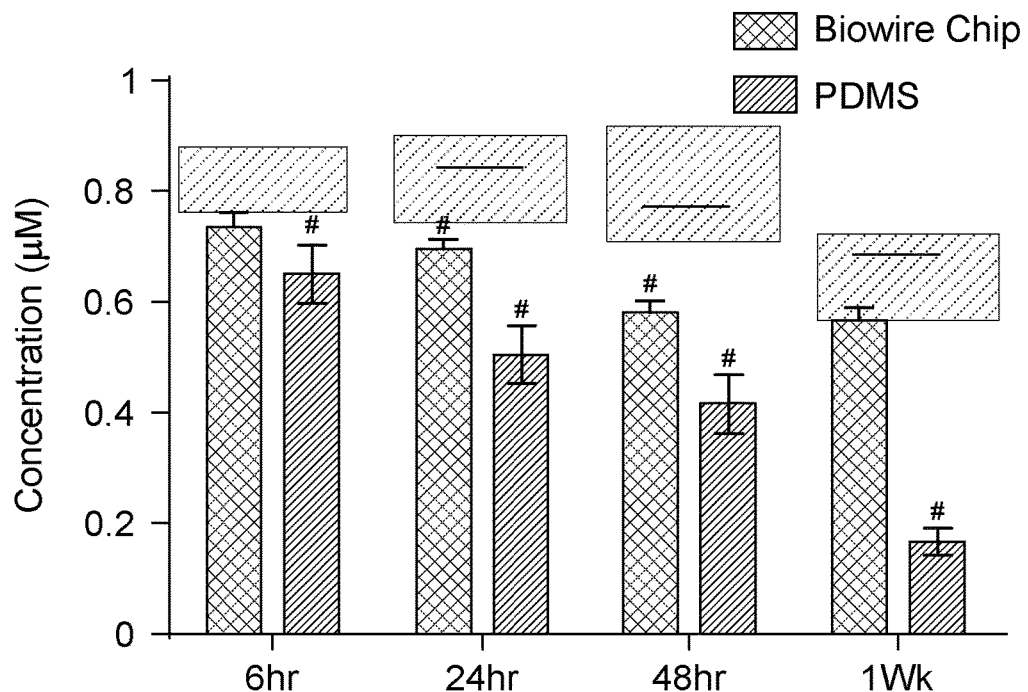
Figure 1G:
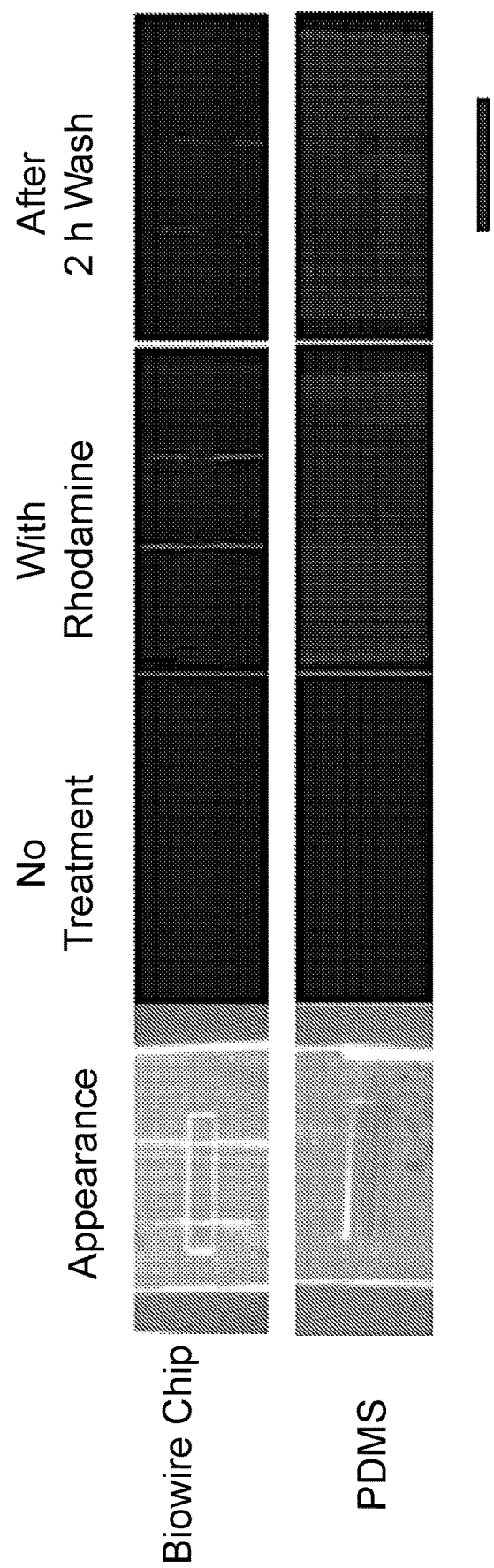

Most previous 3D cell cultivation platforms have used materials such as PDMS, which absorb hydrophobic drugs thereby complicating the interpretation of both long-term and short-term drug screening studies. Thus, we assessed the drug absorption properties of our platform by comparing the time-dependent changes in the levels of a moderately hydrophobic compound Rhodamine B (Sigma83689) in our Biowire chips with chips of identical geometry manufactured from commonly used PDMS. We found (FIG. 1F) that, although the fluorescence levels of Rhodamine B declined with time in our Biowire chips, they nevertheless remained higher than in PDMS chips when incubation times were 24 hours and longer. Moreover, after only 6 hours, the levels of Rhodamine B were not significantly different compared to the tissue plastic well controls. Similarly, the levels of a more hydrophobic compound (Rhodamine 6G) were also higher in our Biowire chips (6.8±0.9 nM) compared to PDMS chips (5.4±0.5 nM, p=0.0109) when incubation times were reduced to 30 minutes, indicating less absorption by the Biowire chip compared to the PDMS chip in an acute test. The time-dependent reductions in Rhodamine B were associated with the appearance of rhodamine fluorescence throughout the PDMS chips, whereas the fluorescence in our Biowire chips was limited to the POMaC wires. After extensive washout for 2 hours, the fluorescence remained widespread in the PDMS chips while being undetectable in the Biowire chips (FIG. 1G).

Stable Non-Invasive Force Recordings in Biowire Platform

Figure 2A:
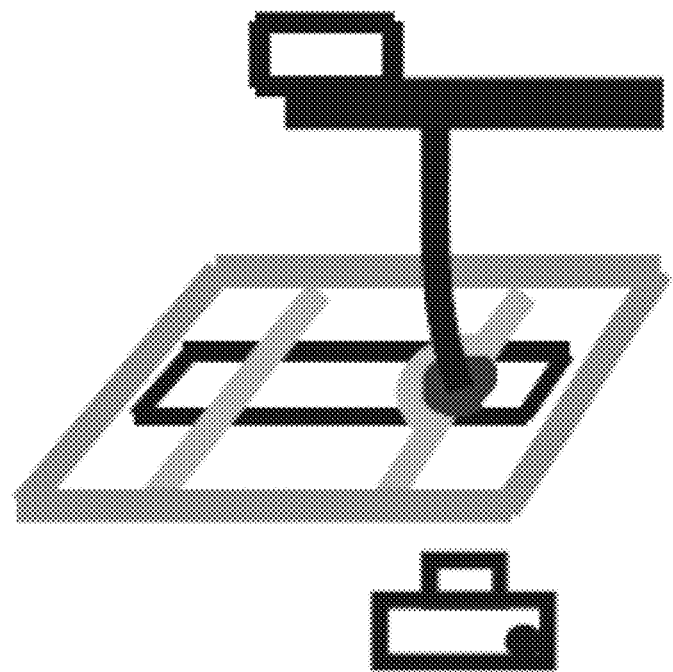
Figure 2B:
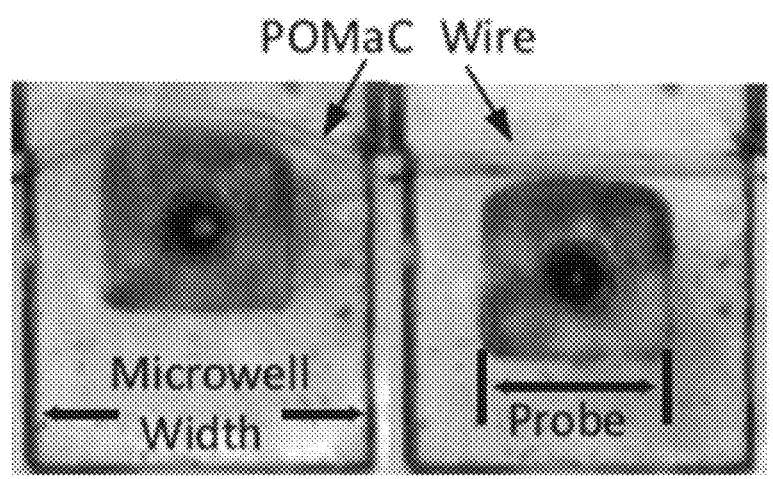
Figure 8H:
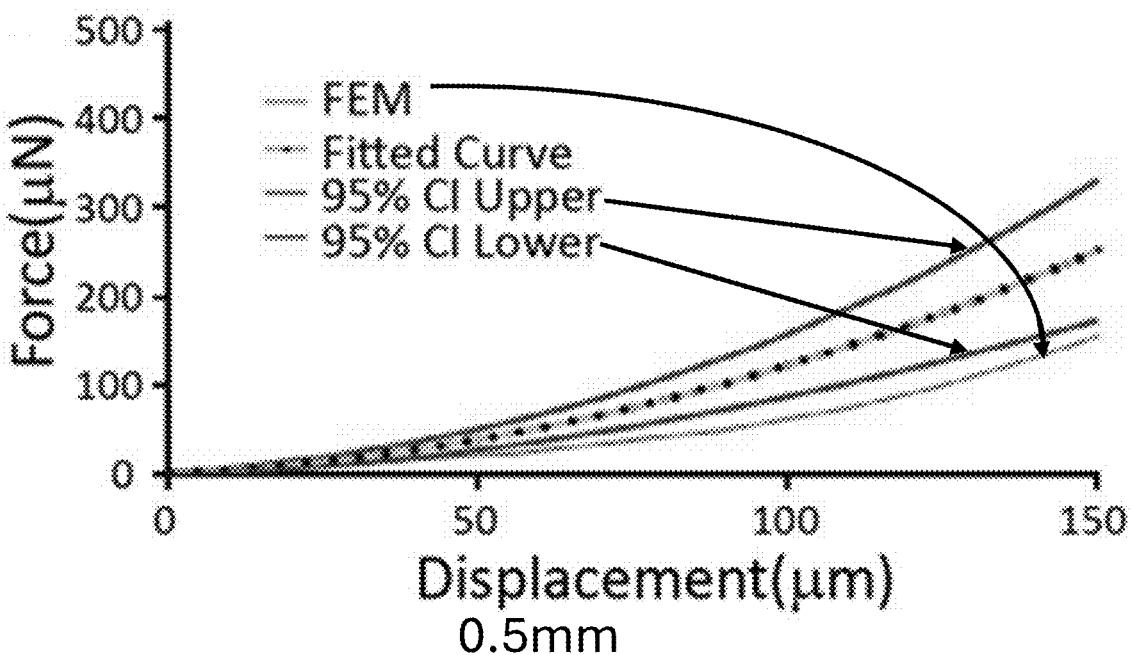
Figure 8I:
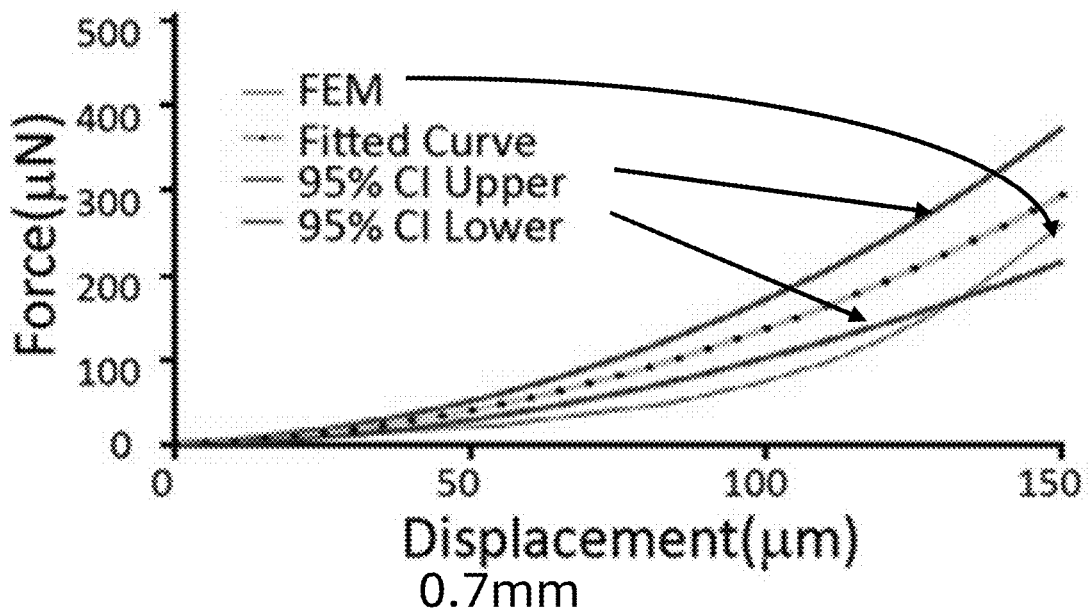
Figure 8J:
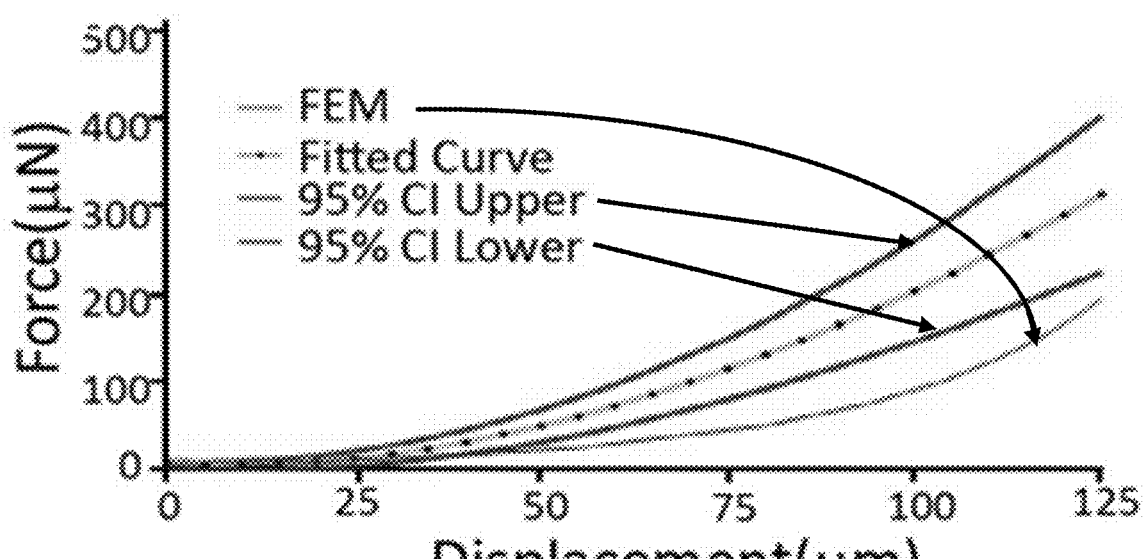

Since Biowires attach to the elastic POMaC wires at the ends of the microwells, it becomes possible to non-invasively estimate the forces generated by Biowires in response to contraction throughout the culture period by assessing the bending properties of the POMaC wires. To calibrate the forces produced by Biowires, we displaced POMaC wires at their centers with probes having known mechanical properties (FIGS. 2A, 2B). We found that, regardless of the probe cross-sectional area, POMaC wires reproducibly displayed non-linear elastic behavior over the range of wire displacements typically produced by Biowire tissues (FIGS. 8E-8J). These elastic properties of the POMaC wires could be readily modeled using finite element analysis (FIGS. 8H-8I). Importantly, the force-displacement curves were unaltered after 6 weeks in culture (FIG. 2C) and the Young's Modulus estimates of the POMaC wires remained unchanged for up to 3 months in culture (FIG. 2D).

Figure 2E:
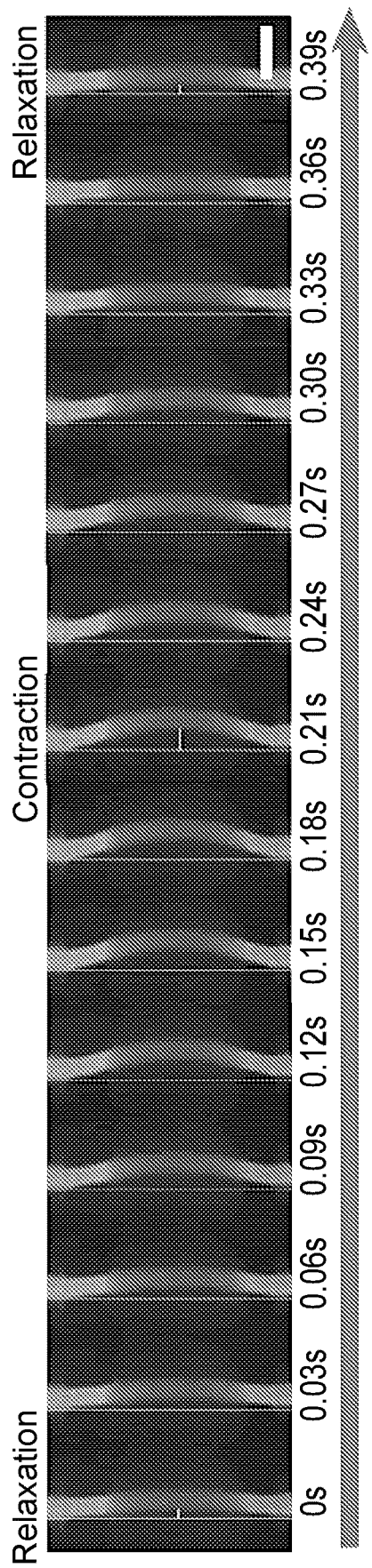
Figure 2F:
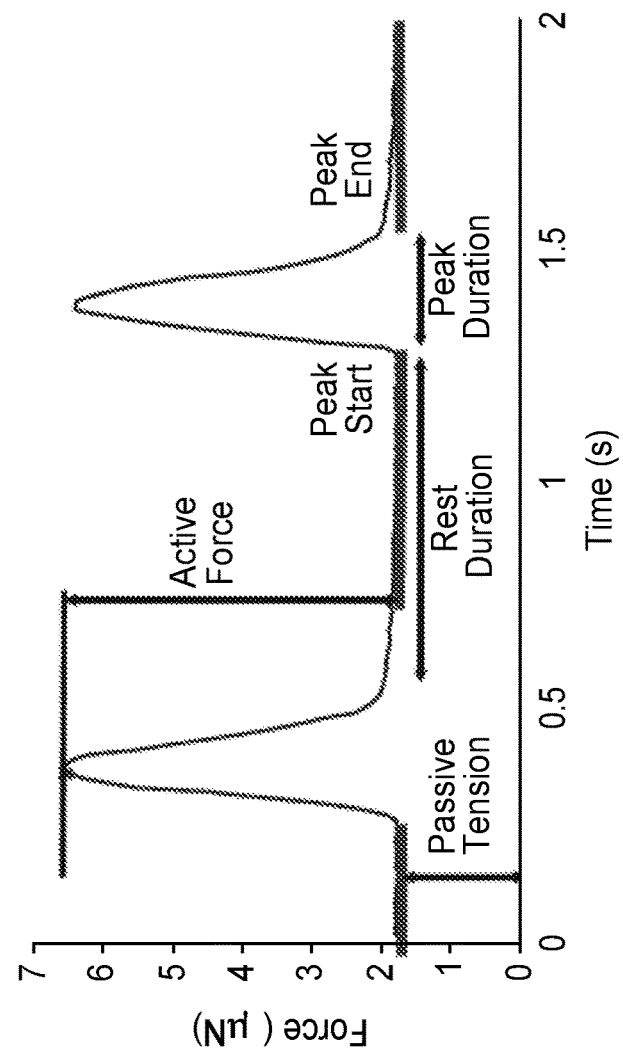

To assess the passive tension as well as dynamic active forces generated by the Biowires, we took advantage of the intrinsic fluorescence of POMaC wires when illuminated with blue light ($\lambda_{ex}$350 nm/$\lambda_{em}$ 470 nm). Fluorescence imaging of ventricular Biowires during electrical pacing (FIG. 2E) revealed that the POMaC wires are typically bent somewhat at baseline, indicating passive tension generation by the attached cardiac tissues, and undergo dynamic time-dependent deformations in response to electrical stimulation arising from active force generation. Conversion of the wire deformations force via our calibration curves allow passive and active force properties (i.e. resting tension, active force, rates of force development and relaxation) of our Biowires to be non-invasively estimated throughout the culture period (FIG. 2F).

Figure 2G:
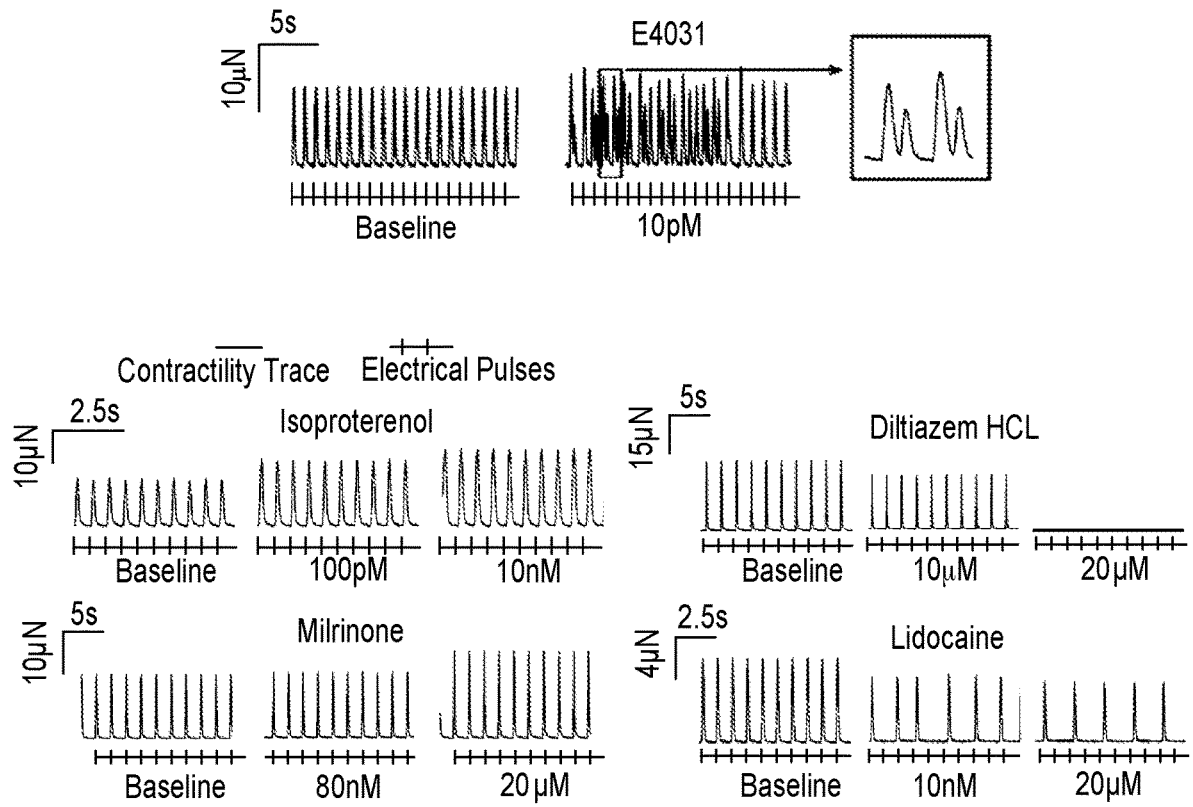

To illustrate the utility of dynamic force recordings, we examined the effects of several commonly used agents with cardiac effects for typical ventricular Biowires created from BJ1D iPSCs and HES3 ESCs (FIG. 2G). The results reveal that: the β-adrenoceptor agonist, isoproterenol, increases contractility; the L-type calcium channel blocker, diltiazem, produces negative inotropic effects; the sodium channel blocker, lidocaine, inhibits tissue electrical excitability; the cAMP phosphodiesterase 3 inhibitor, milrinone, enhances contractility and the human ether-a-go-go (hERG) channel blocker, E-4031, promotes spontaneous irregular beating patterns consistent with arrhythmias (FIG. 2G).

Generating Biowires from Atrial and Ventricular Cardiomyocytes

Figure 3A:
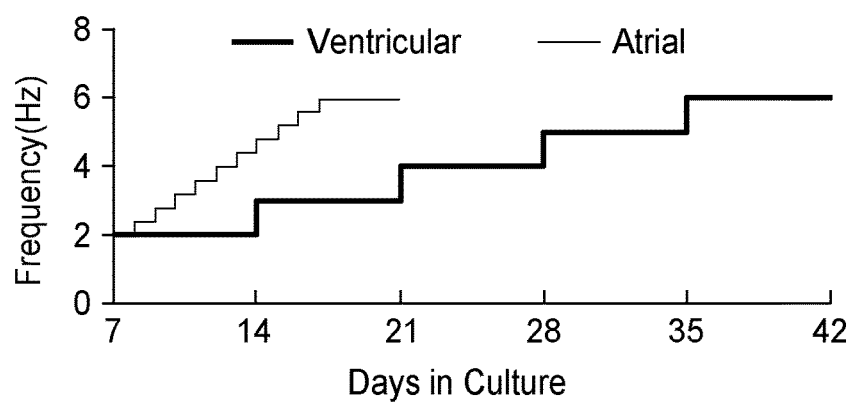
FIGS. 3A-3F show that atrial and ventricular tissues exhibit distinct patterns of gene expression and morphology upon chronic electrical conditioning.
Figure 9A:
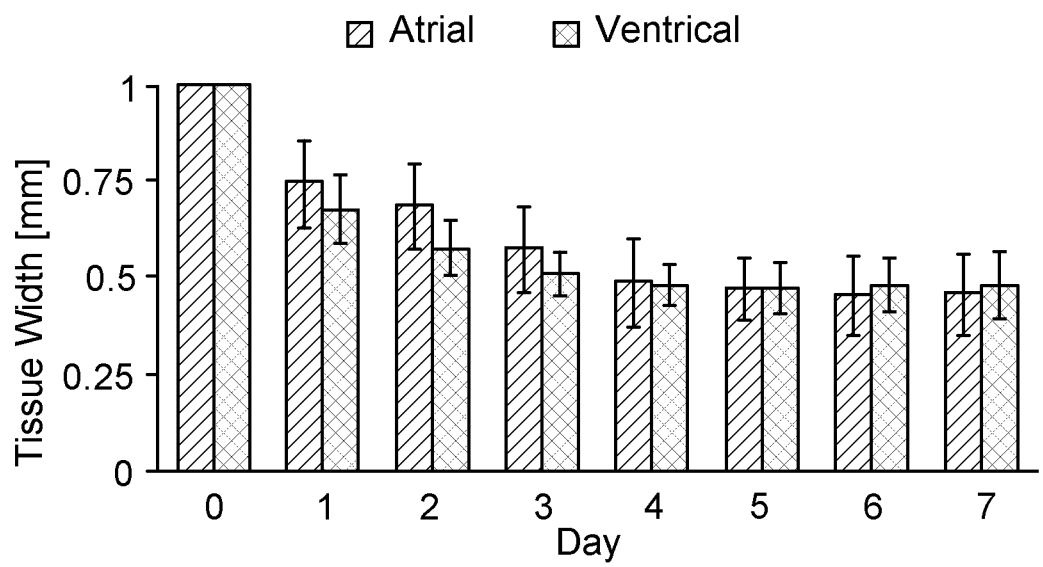
FIGS. 9A-9F show tissue compaction, electrical excitability properties and structural characterization.
Figure 9B:
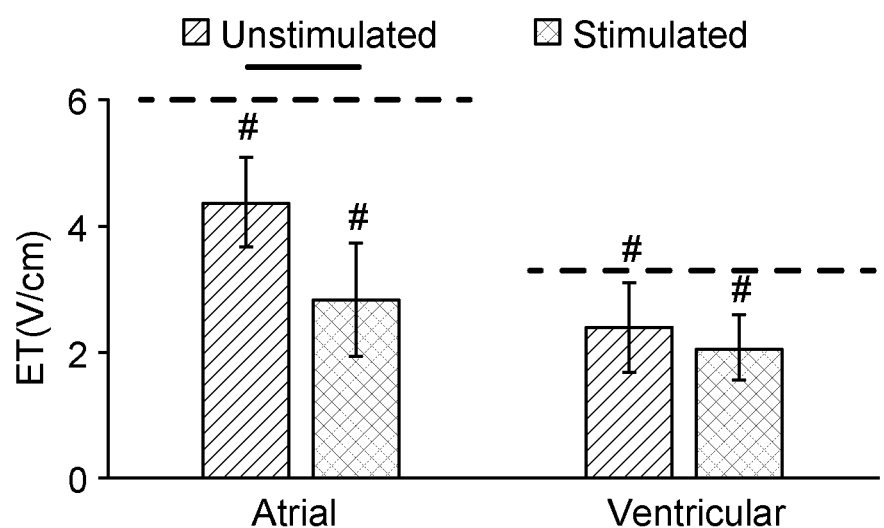
Figure 9C:
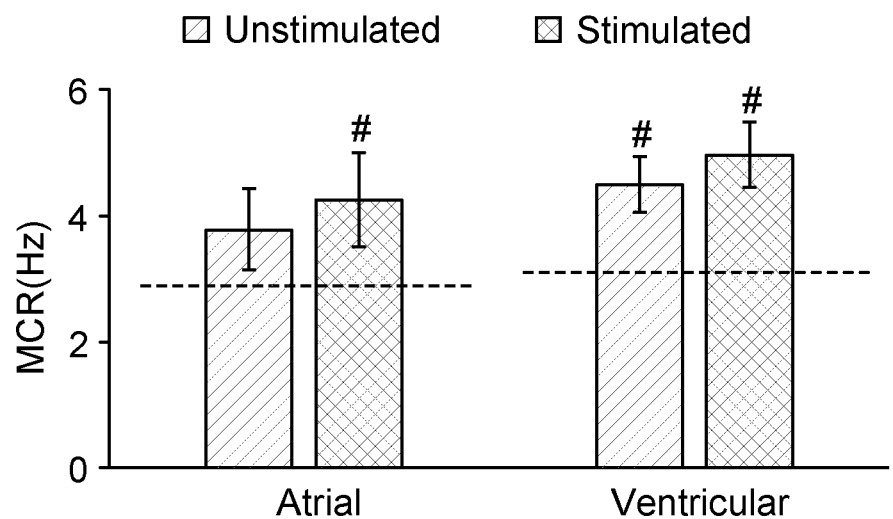
Figure 9D:
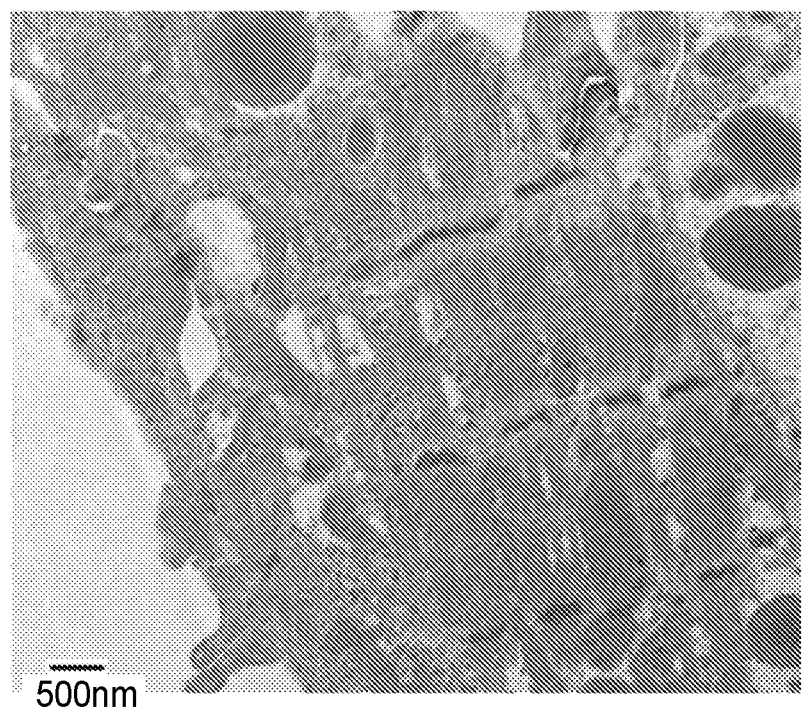
Figure 9E:
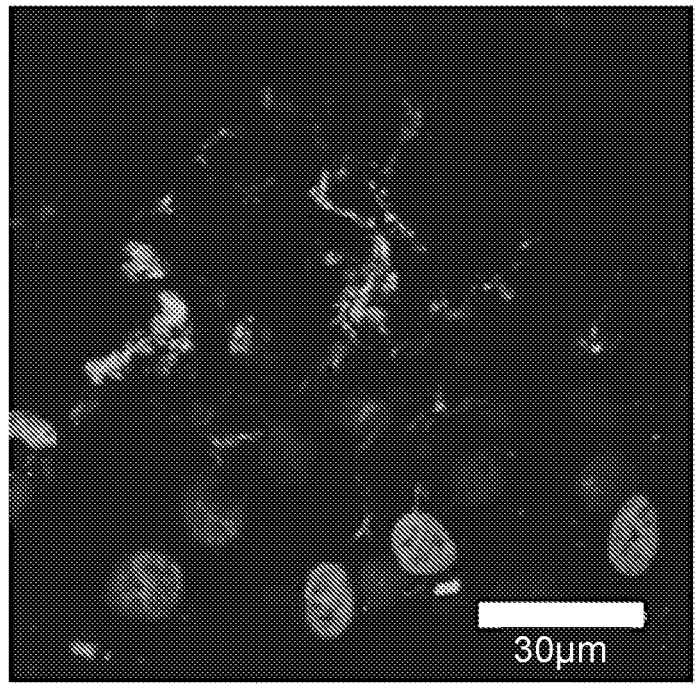
Figure 9F:
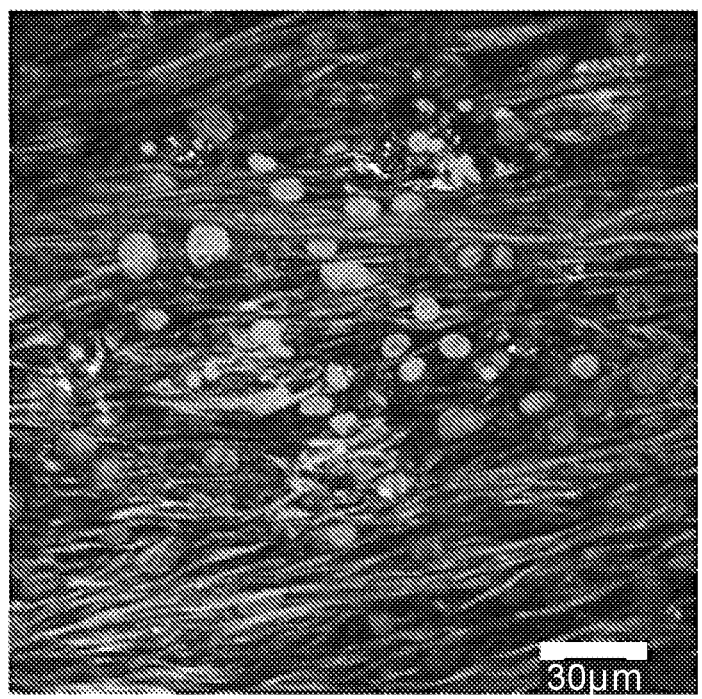

A major unmet need in current screening platforms for drug development and assessing disease mechanisms in human heart tissues derived from stem cells is the capability of comparing responses in atrial versus ventricular myocardium. With this in mind, we created Biowires using directed differentiation protocols designed to produce either atrial or ventricular CMs. Both atrial and ventricular Biowires underwent similar cellular compaction and tissue stabilization over the first 7 days in culture (FIG. 9A). Although non-myocytes were added to facilitate gel compaction, CMs appeared to occupy the majority of tissue volume (FIG. 9F) as in the native myocardium. Over the next 5 weeks, the Biowires were routinely conditioned using chronic electrical stimulation protocols (FIG. 3A) in which the stimulation rates were progressively increased, in order to mimic the working heart and promote cardiac maturation, as shown previously. Consistent with shorter refractiveness in atrial myocardium, we were able to ramp up the stimulation frequency more quickly when conditioning atrial vs. ventricular Biowires, allowing maximum stimulation rates to be achieved earlier in atrial Biowires (FIG. 3A).

Figure 3B:
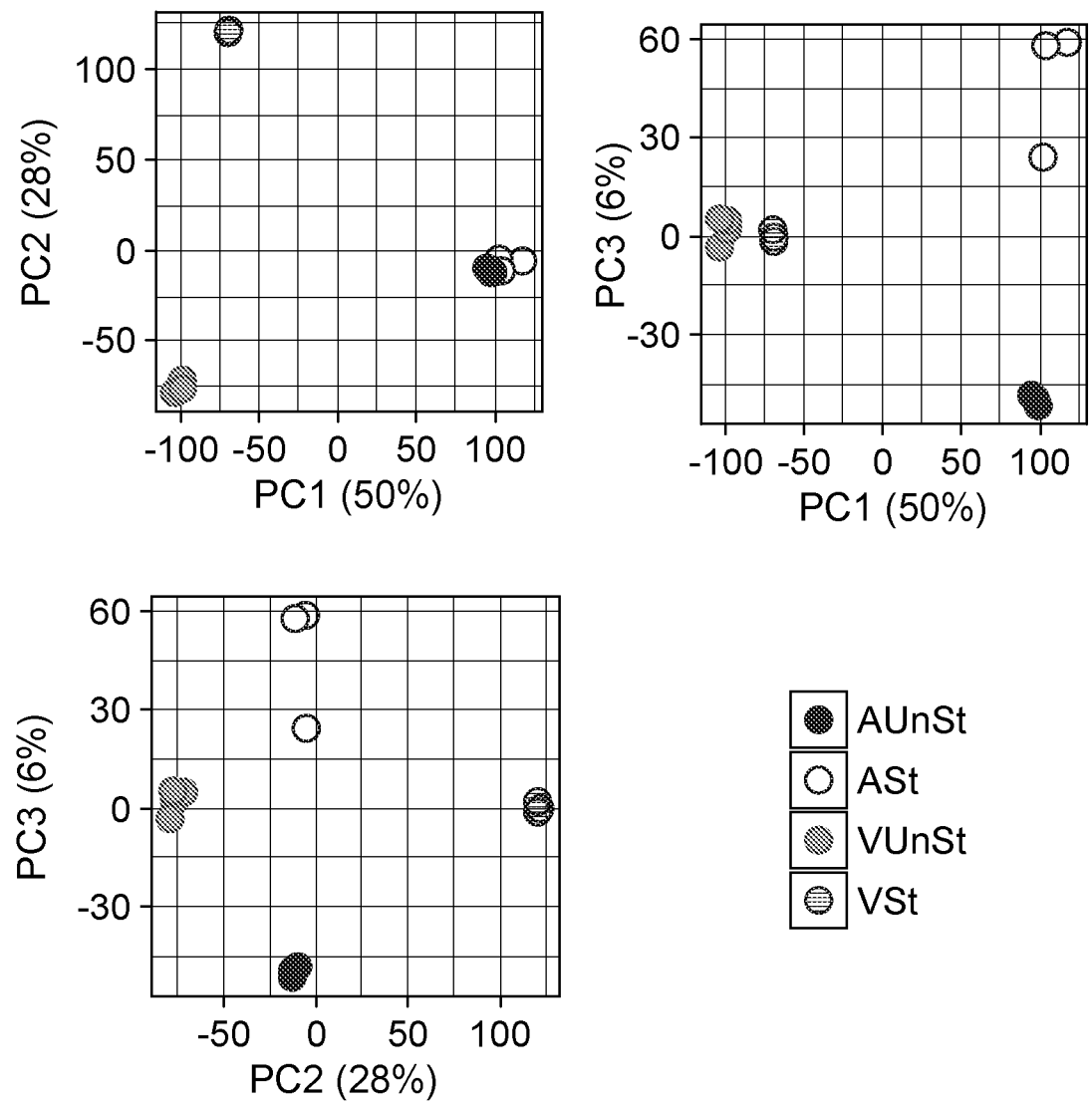

Importantly, the distinct electrical conditioning regimens strongly promoted atrial versus ventricular specification. Indeed, principal component analyses (PCA) of RNA sequencing data (63967 genes), after removal of low expressed genes (17620 genes), revealed that electrical conditioning induced gene expression changes that strongly enhanced atrial or ventricular identities of the seeded cells. Specifically, the first component of the PCA (FIG. 3B), which accounted for >50% of the variance in gene expression, segregated atrial from ventricular tissues. The second PCA component (28% of variance) separated stimulated and unstimulated ventricular tissues, while the third component (6% of variance) separated the stimulated and unstimulated atrial tissues. This indicates that the most profound changes in stimulation were to the ventricle samples and that the gene expression changes induced in the atrial and ventricular cells by stimulation were independent (FIG. 3B).

Figure 3C:
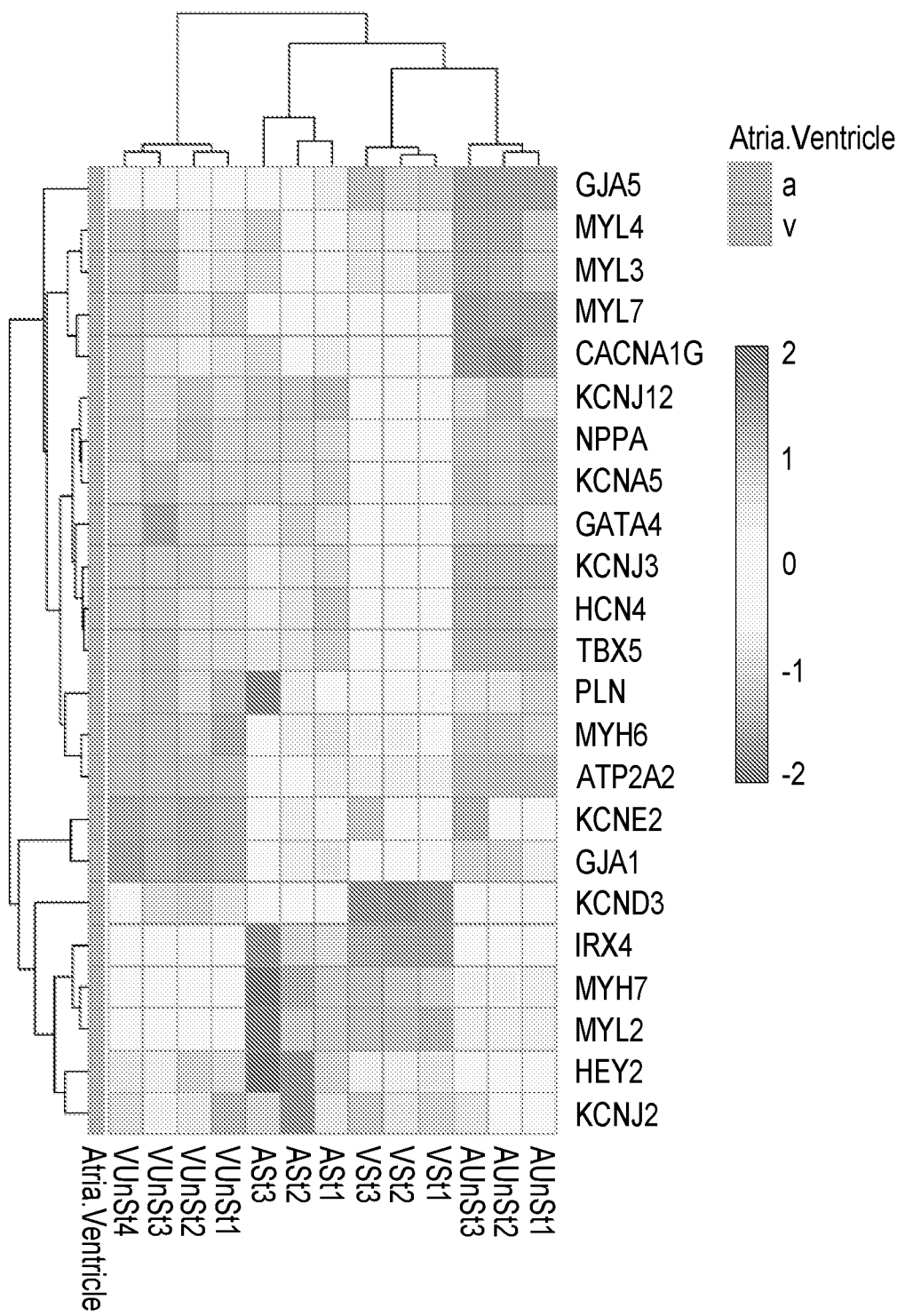

Gene Set Enrichment Analyses (GSEA) and manual curation of the clear transcriptional distinction between atrial and ventricular Biowires, with and without electrical conditioning, identified changes in known markers of cardiac chambers, metabolic and structural gene sets needed for adult heart function (FIGS. 10A-10D). Known atrial and atrial-enriched markers (FIG. 3C) such as NPPA, GJA5, KCNJ12, MYH6 and MYL4 were expressed at higher levels in atrial compared to the ventricular Biowires.

Figure 3D:
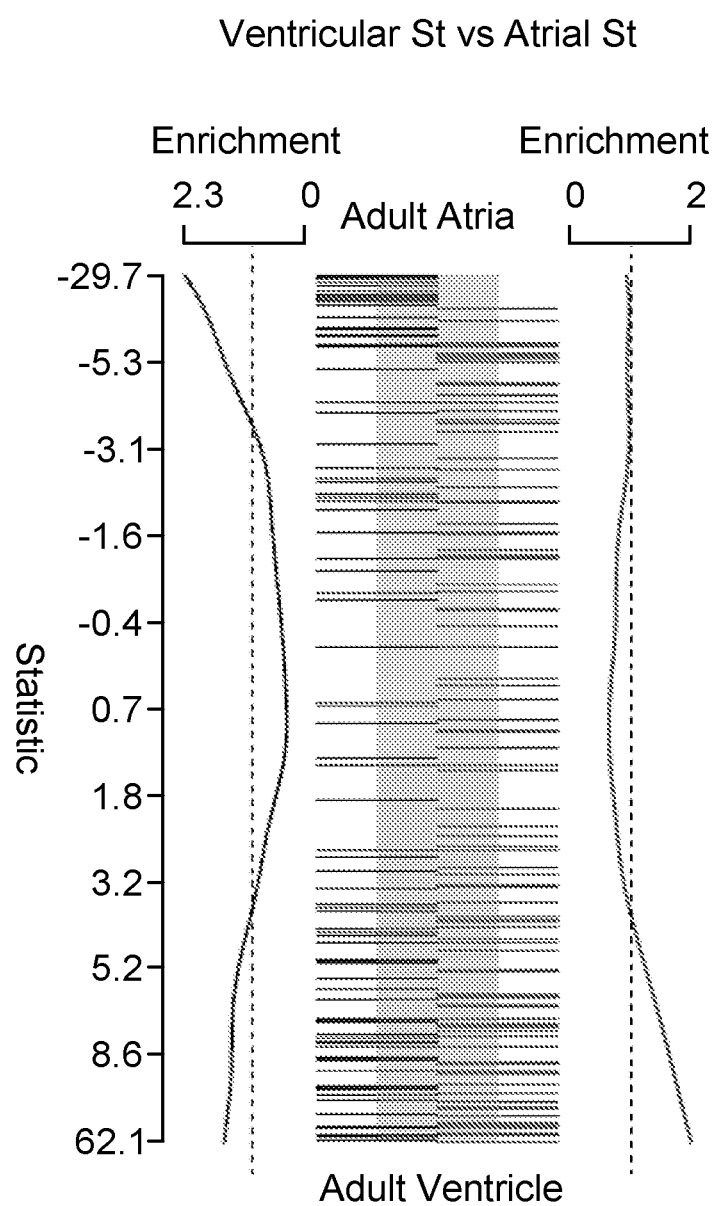

We next globally assessed if the stimulation induced gene changes and maturation of Biowires were reflective of the chamber specific in vivo expression of the adult human heart. Comparison of gene expression patterns of atrial and ventricular Biowires to in vivo cardiac regions demonstrated that electrically conditioned Biowires are enriched for gene expression patterns of the corresponding in vivo cardiac regions. (FIG. 3D).

Figure 10A:
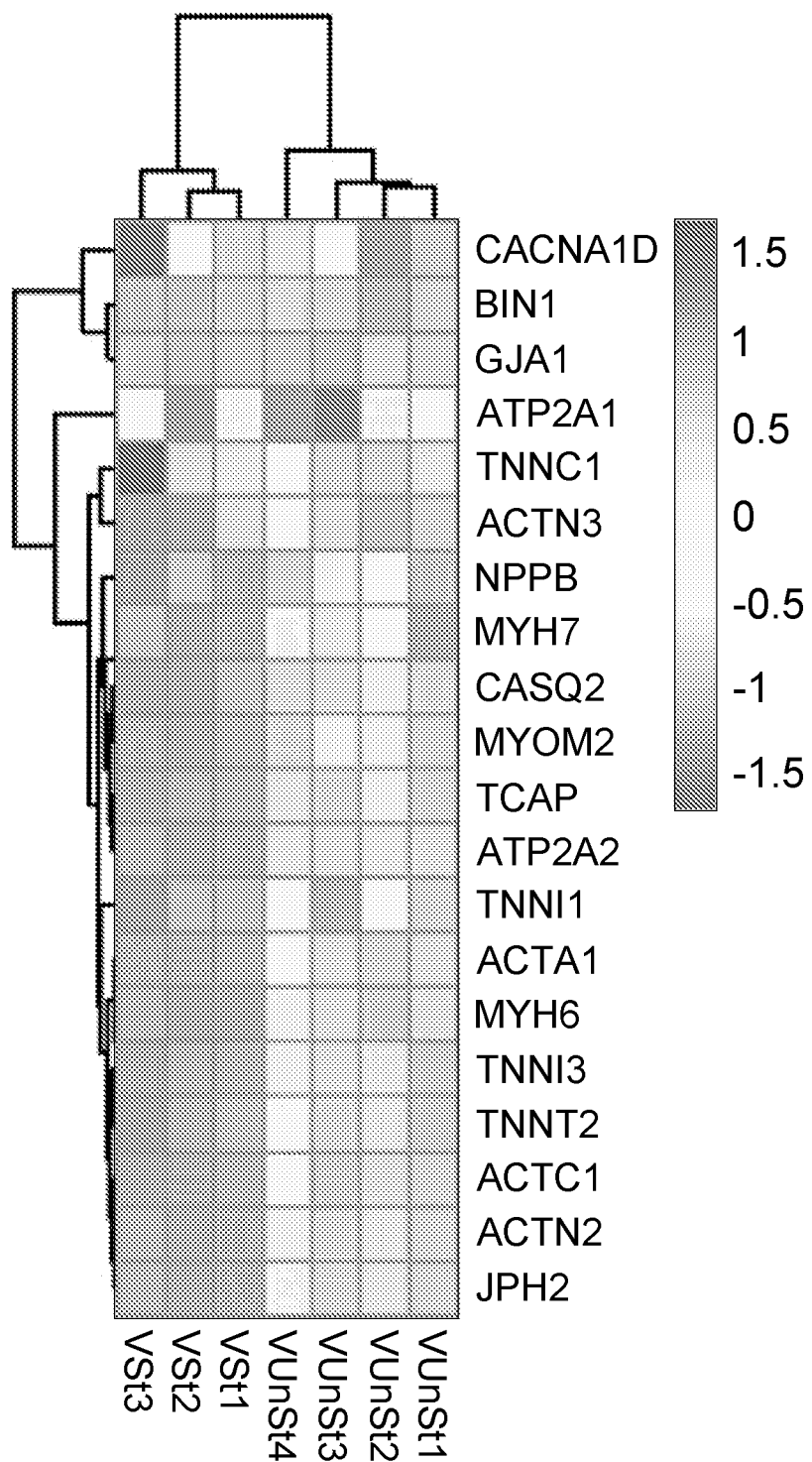
FIGS. 10A-10D show gene expression analysis of atrial and ventricular tissues with and without electrical conditioning.
Figure 10B:
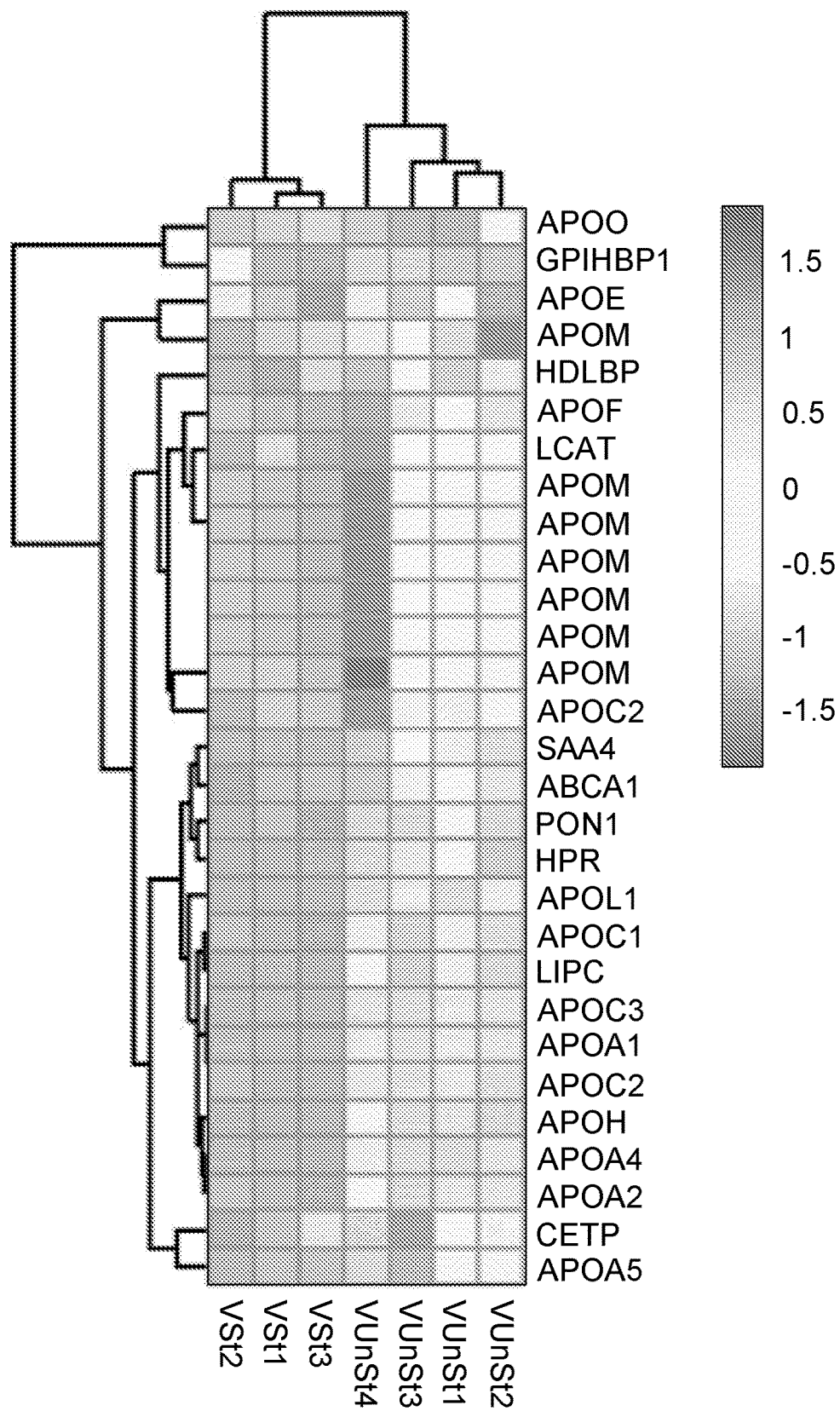
Figure 10C:
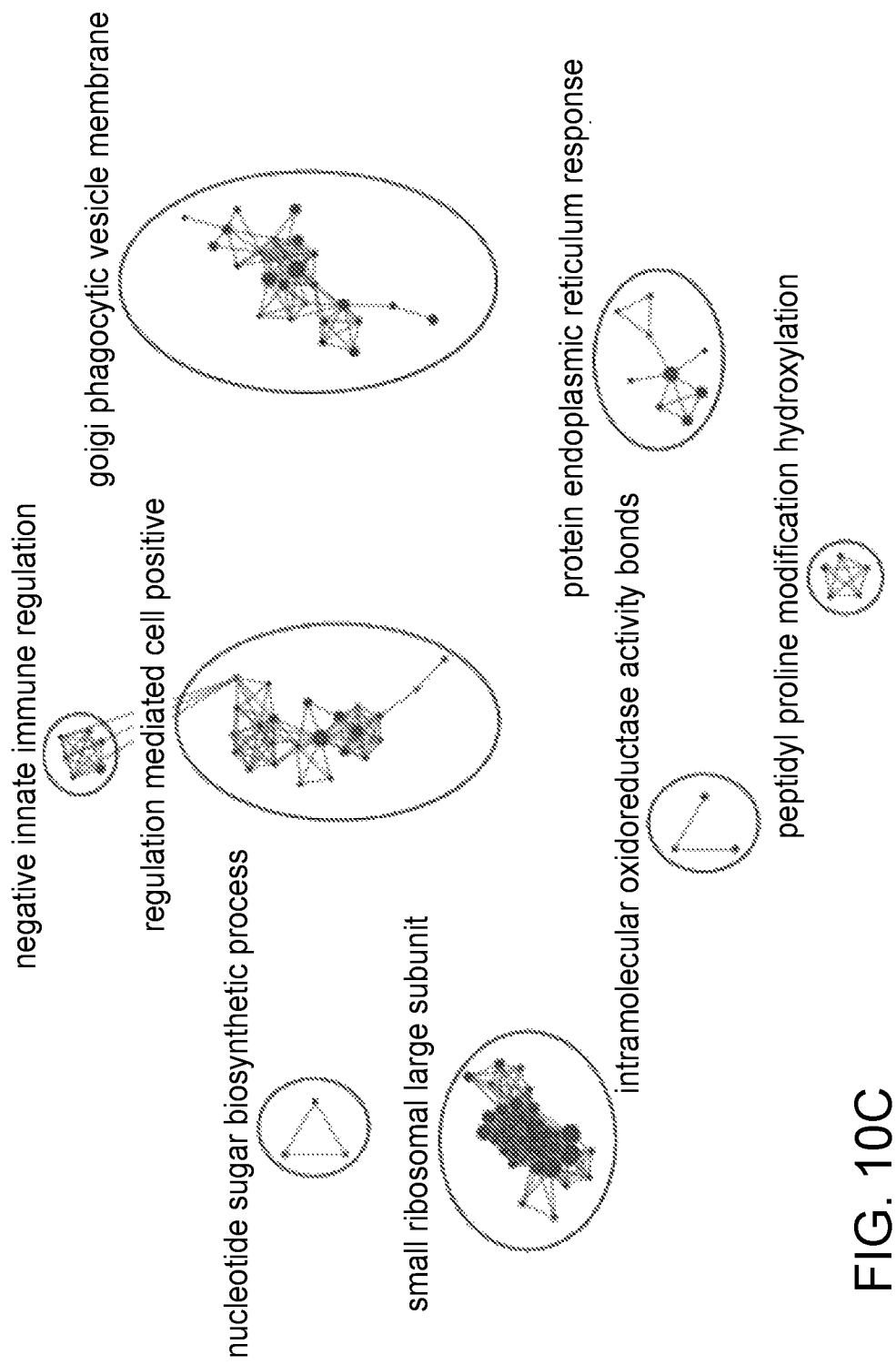
Figure 10D:
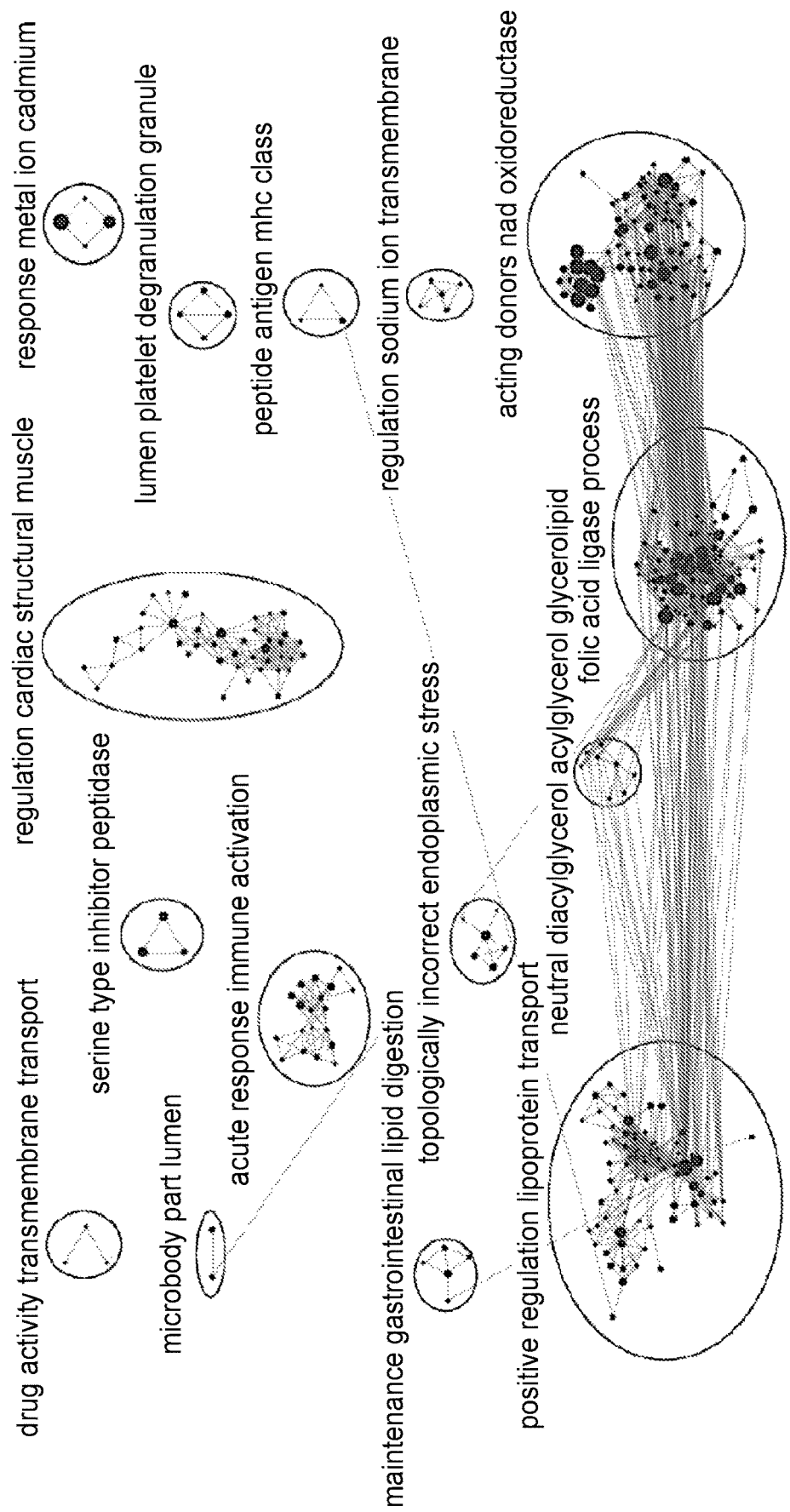

Consistent with our gene expression results, histological analyses demonstrate that electrical conditioning improves sarcomeric organization and alignment for both atrial and ventricular Biowires (FIGS. 3E, 3F, and 9D) while also clearly promoting the expression of maturation genes in ventricular Biowires associated with contraction, calcium handling and electrical properties (FIGS. 3C and 10A), and lipid metabolism (FIG. 10B).

Figure 3E:
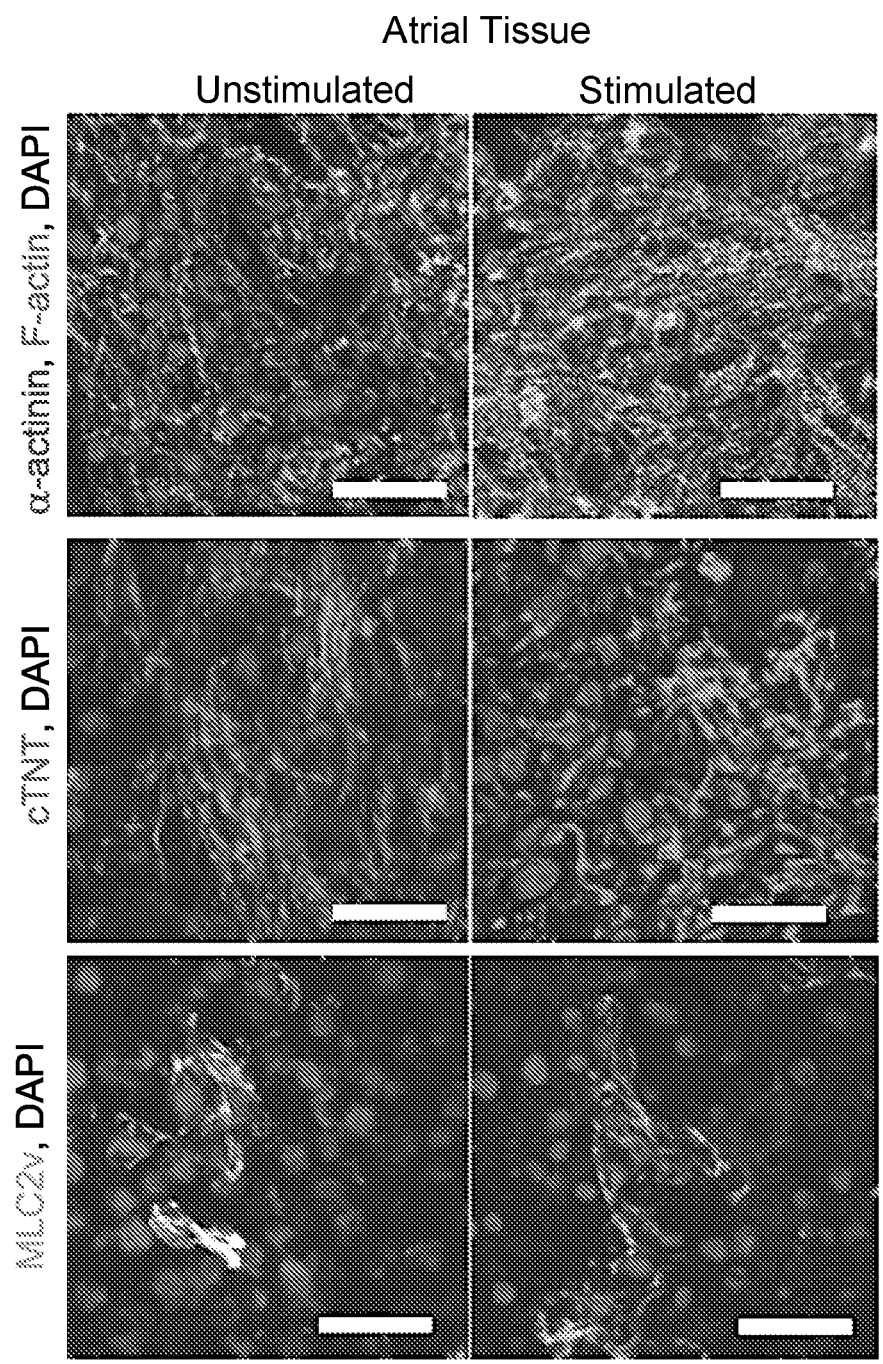
Figure 3F:
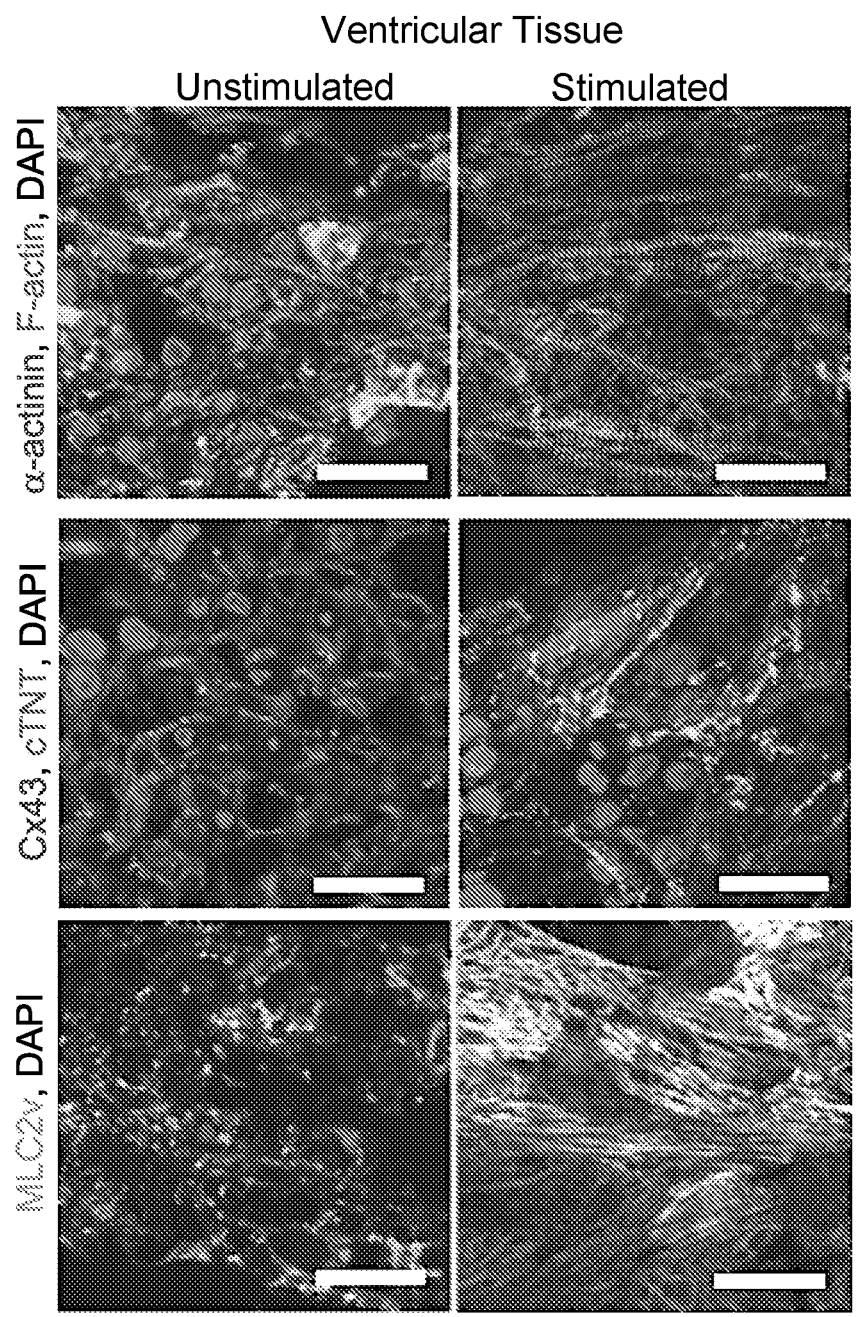
Figure 4C:
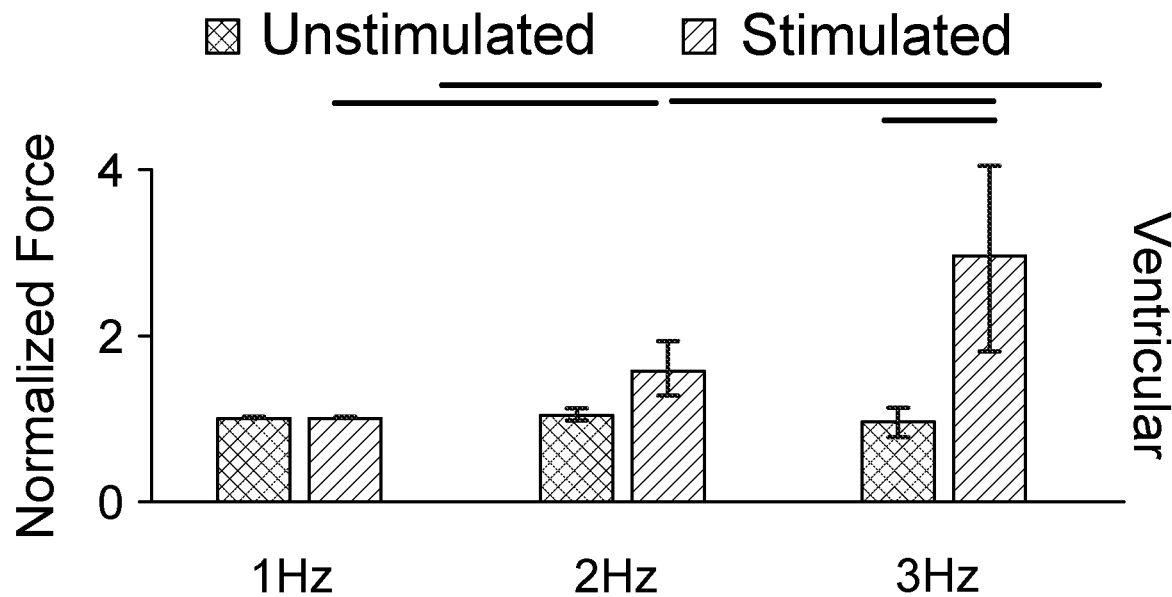
Figure 4D:
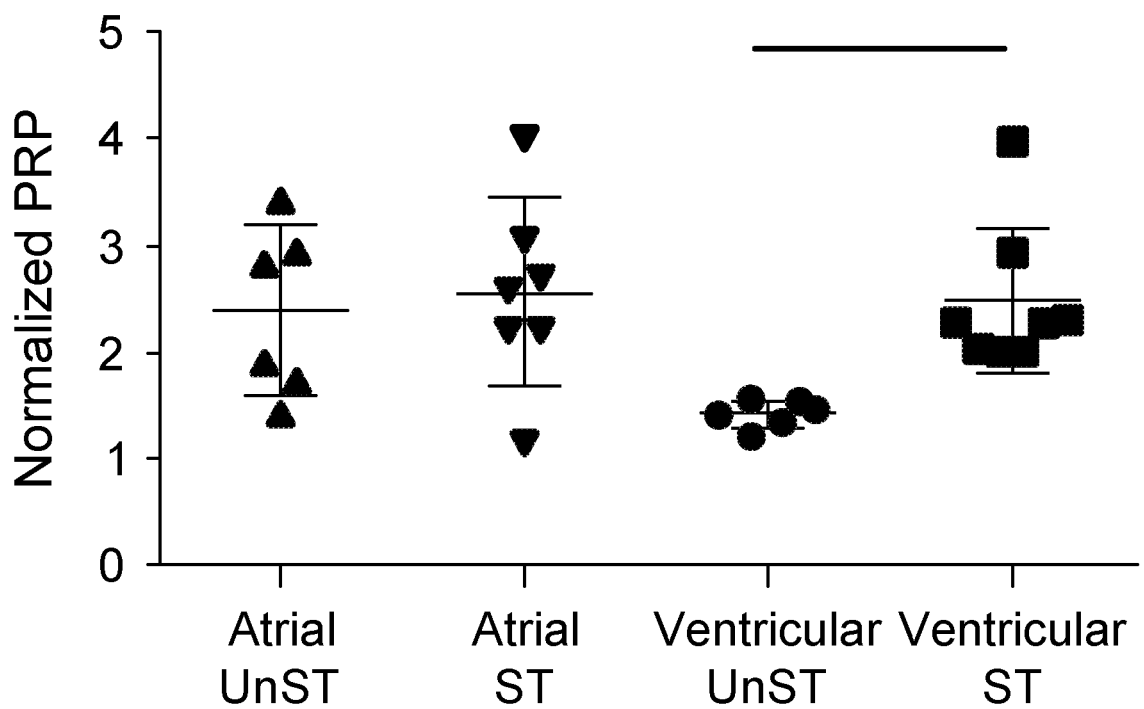
Figure 11A:
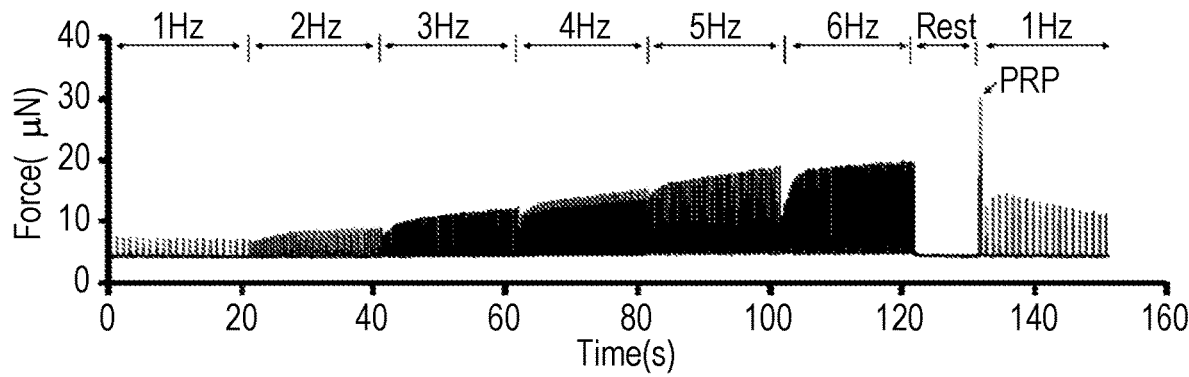
FIGS. 11A-11O show batch-to-batch variability, cell line variability and comparison of active forces achieved by ventricular tissues. Consistency of ventricular tissues generated from four batches of BJ1D hiPSC-CMs.
Figure 11B:
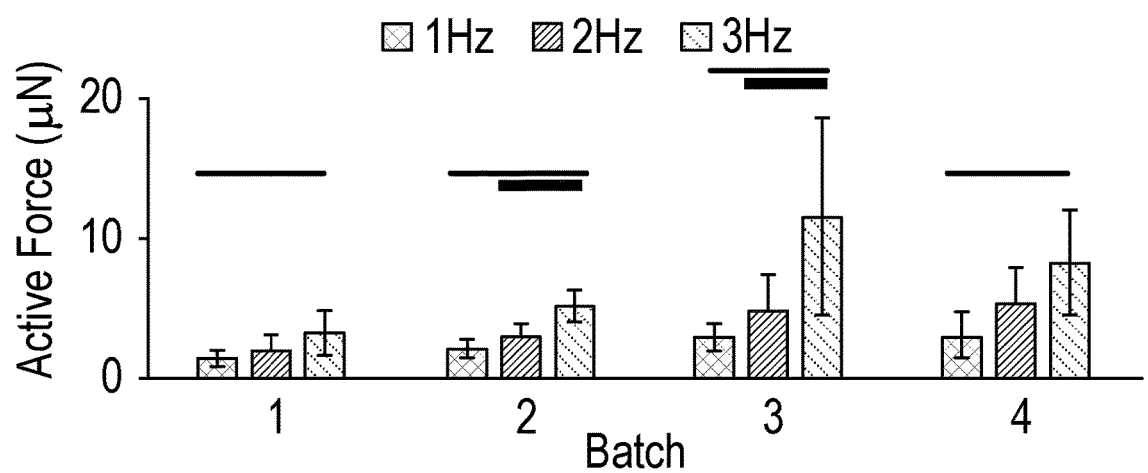
FIG. 11B is a graph of active force (one way ANOVA with Tukey's multiple comparisons test).
Figure 11C:
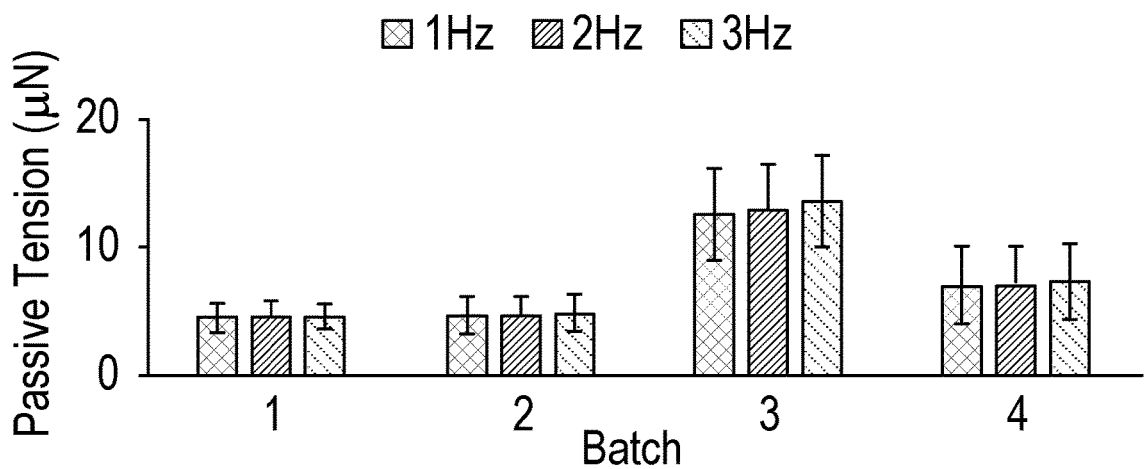
FIG. 11C is a graph of passive tension from 1 to 3 Hz.
Figure 11D:
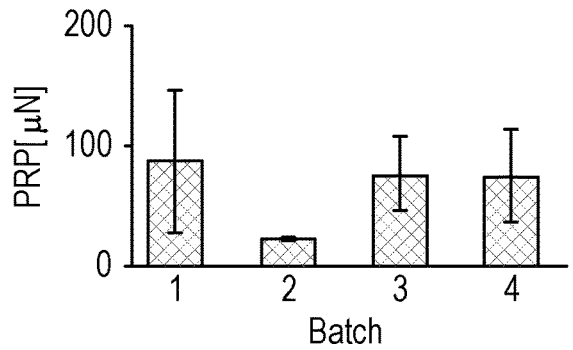
FIG. 11D is a graph of Post-Rest Potentiation (PRP).
Figure 11E:
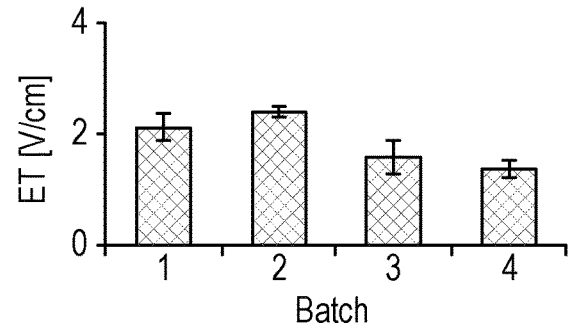
FIG. 11E is a graph of Excitation Threshold (ET).
Figure 11F:
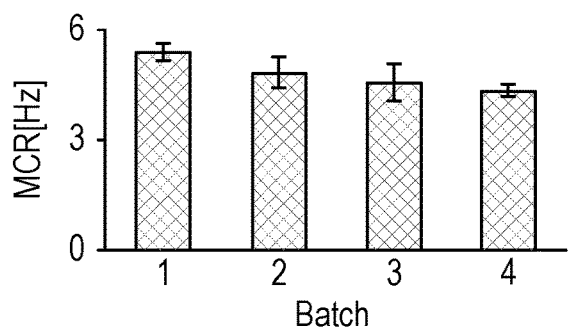
FIG. 11F is a graph of Maximum Capture Rate (MCR). Data presented as mean±stdev, (n≥4 tissues per experiment).
Figure 11G:
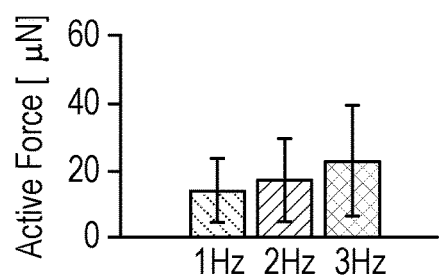
(FIGS. 11K, 11L) Normalized active force from 1 to 3 Hz; I, (FIGS. 11I, 11M) Excitation Threshold (ET) and (FIGS. 11J, 11N) Maximum Capture Rate (MCR); (Data presented as mean±stdev, n≥3, One-way ANOVA with Tukey's multiple comparisons test).
Figure 11H:
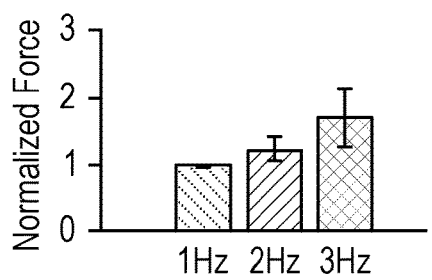
Figure 11I:
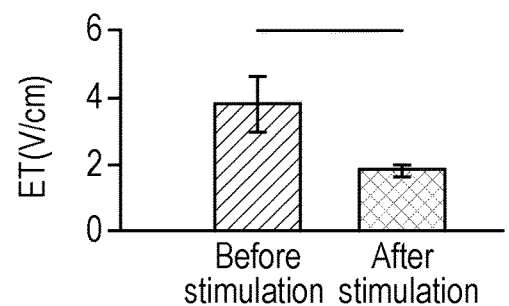
Figure 11J:
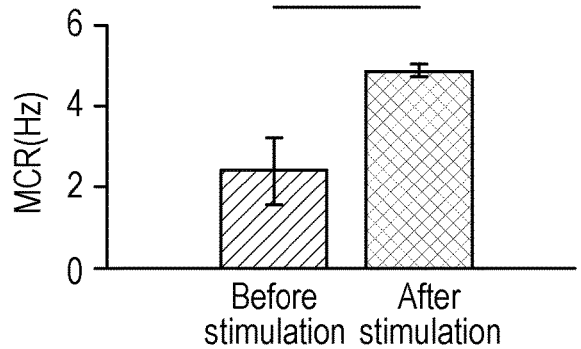
Figure 11K:
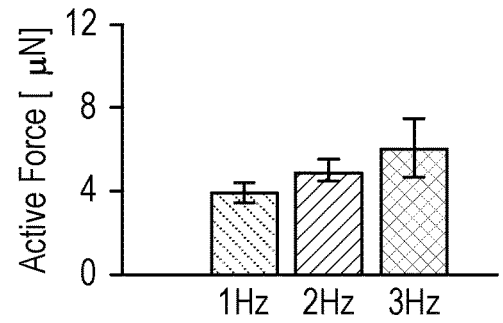
Figure 11L:
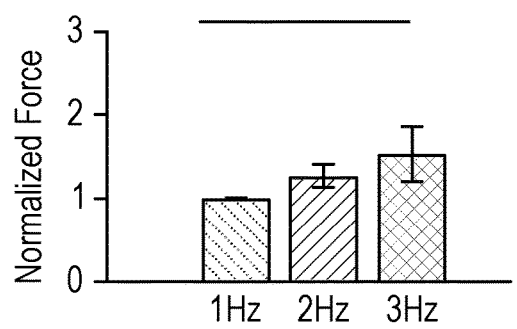
Figure 11M:
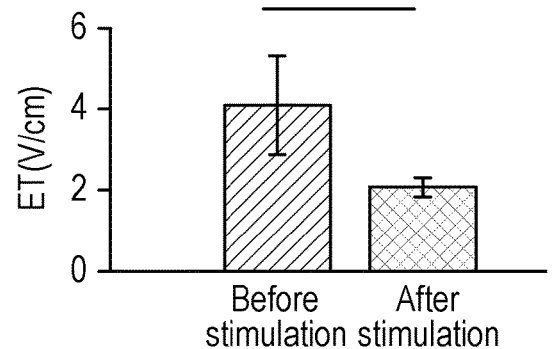
Figure 11N:
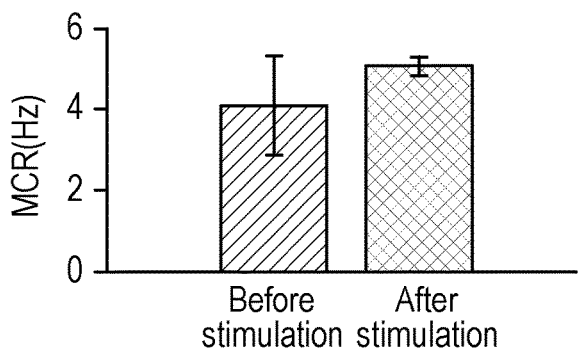

We next examined whether chamber-specific differences in gene expression correlate with contractile and electrical properties of Biowire tissues. Consistent with adult human atrial muscle, the atrial Biowires display a relatively flat force-frequency relationship (FFR) with no appreciable post-rest potentiation (PRP) of force, regardless of electrical conditioning, although normalized force amplitudes, measured with 3 Hz pacing, are about ~30% larger in conditioned atrial Biowires, compared to the control atrial Biowires (FIGS. 4A, 4B, and 4D). By contrast, electrical conditioning of ventricular Biowires during culture increases (p<0.0001) the contractile amplitudes, converts the profiles of the FFRs from flat to strongly positive (p<0.0001), FIG. 11A, and produces a PRP of force in the ventricular tissues all hallmarks of the adult human ventricular myocardium (FIGS. 4A, 4C, and 4D). Specifically, post-rest force after pacing at 6 Hz was ~21-fold higher (p<0.0001) than the force measured at 1 Hz pacing and was ~2.5 fold higher (p=0.044) than the force at 6 Hz pacing (FIG. 4D). It is notable that atrial Biowires generate less force than ventricular Biowires (FIG. 4A), as expected from the lower contractile protein densities in atrial vs. ventricular Biowires seen with histology (FIGS. 3E and 3F).

The electrical properties of Biowires also show distinct tissue specification. With time in culture the excitation threshold voltage (ET) needed to initiate contraction decreased, while the maximum capture rates (MCR) increased for both atrial and ventricular Biowires (FIGS.

Figure 4E:
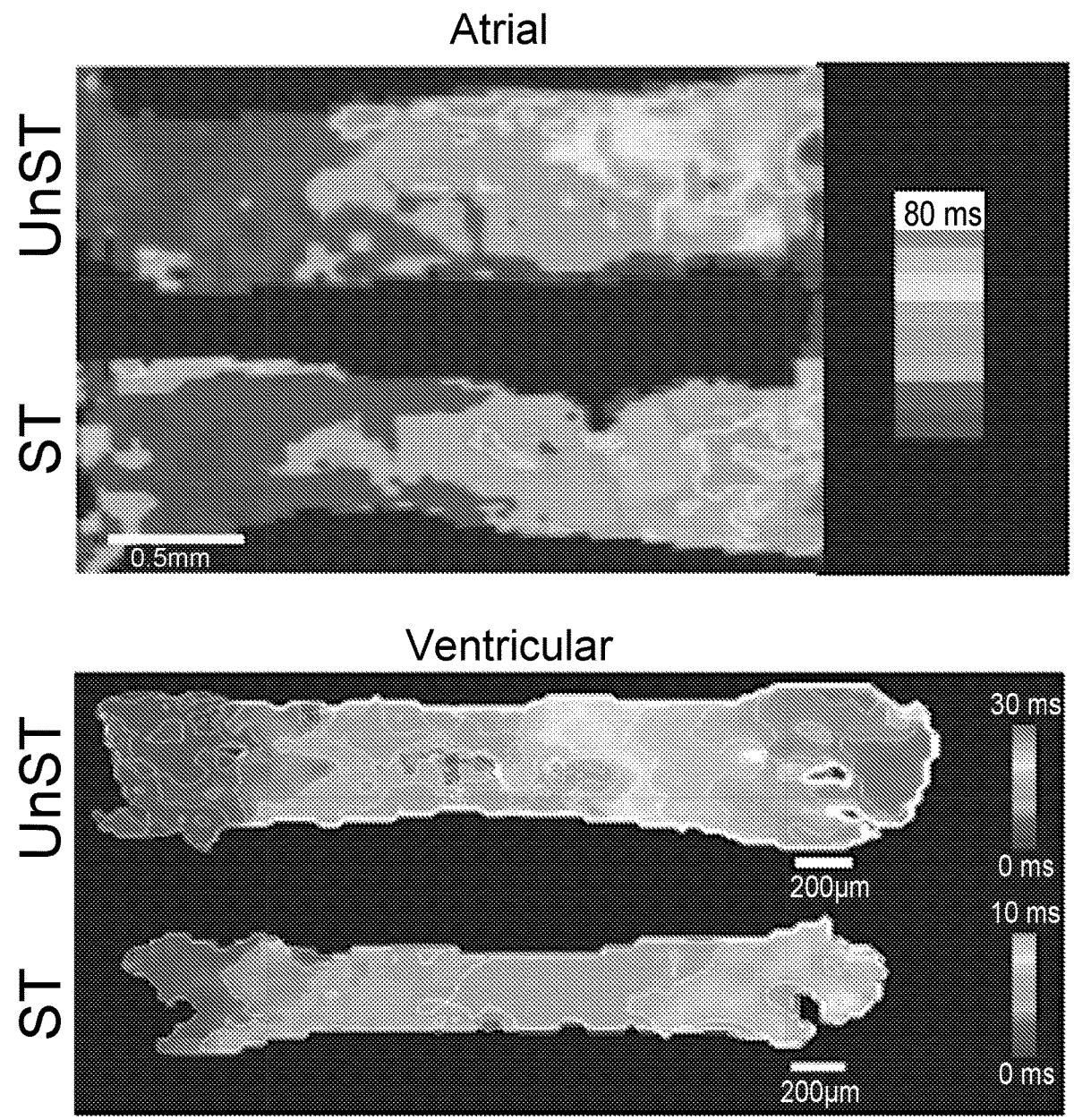
Figure 4F:
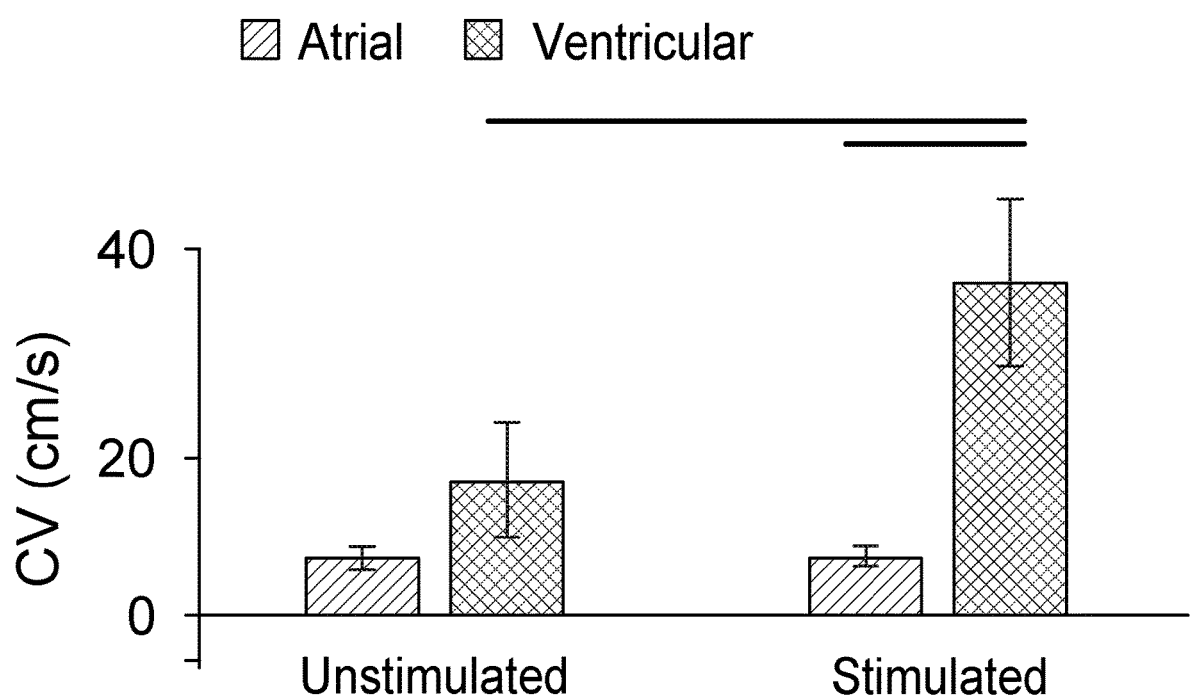
Figure 4G:
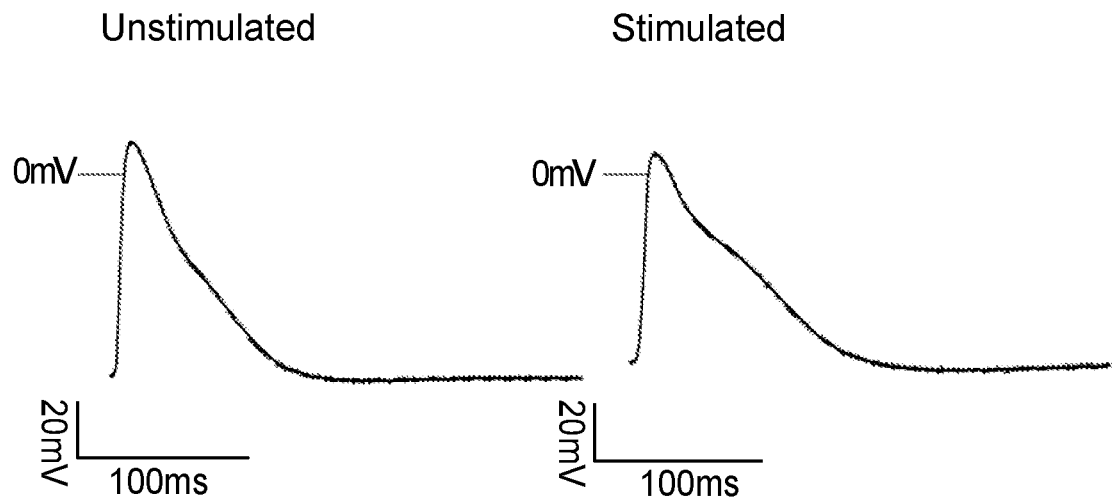
Figure 4H:
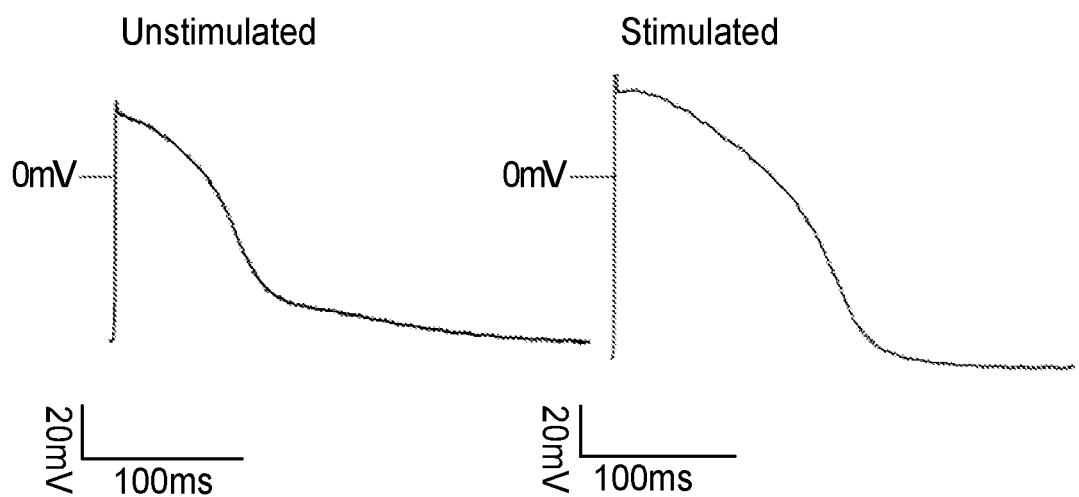
Figure 4I:
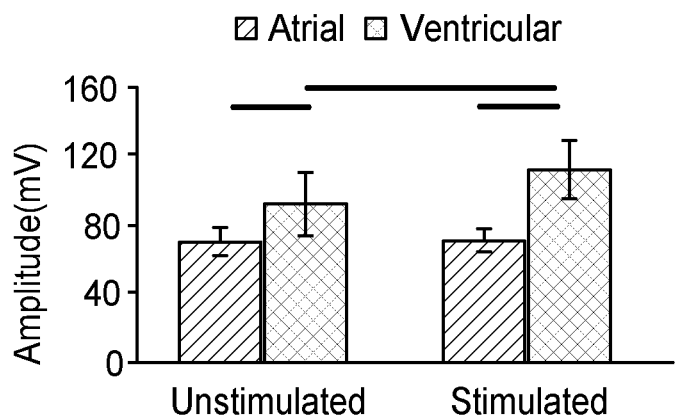
Figure 4J:
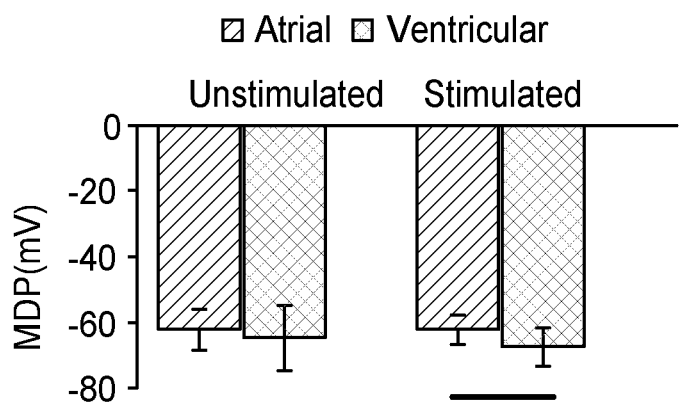
Figure 4K:
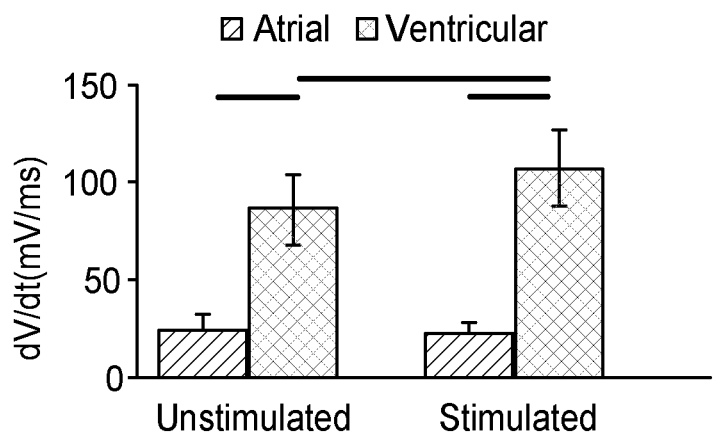

9B-9C). Moreover, although conduction velocities in atrial tissues (FIGS. 4E-4F) are unaffected (p=0.9830) by conditioning (5.6±1.0 cm/s without versus 5.7±0.9 cm/s with conditioning, HES3 hESC-CM), they increase (p=0.0077) markedly from 13.0±5.5 cm/s to 31.8±7.9 cm/s (BJ1D iPSC) in ventricular Biowires with electrical conditioning. Similarly, conditioning of atrial Biowires has minimal effects on action potential properties (i.e. amplitude, minimum diastolic potential (MDP), upstrokes (dV/dt), and durations (APD, APD30, APD30/APD90)), except for small increases in APD90, whereas most AP parameters, except MDP and APD90, are altered by conditioning in ventricular tissues (FIGS. 4G-4M). Of particular note, electrically conditioned ventricular tissues possess rapid upstroke velocities and display an early repolarization notch (FIG. 4H) as seen in adult human epimyocardium that is linked to developmentally regulated transient outward $K^+$ currents (FIGS. 4H and 4K).

Consistent with the electrical differences between atrial and ventricular myocardium, the AP profiles in atrial tissues are distinctly different from ventricular tissues (FIGS. 4I-4M). Specifically, compared to atrial Biowire, ventricular Biowires show higher AP amplitudes (111.7±16.9 vs 70.3±6.6 mV, p<0.0001) and upstroke velocity (108.8±19.6 vs 23.3±4.8 mV/ms, p<0.0001), more negative MDPs (−68.0±5.9 vs −62.7±4.5 mV, p=0.0020), and longer APDs (73.7±7.0 vs 13.4±3.6 ms for $APD_{30}$, p<0.0001; 119.0±9.0 vs 41.3±7.6 ms for $APD_{50}$, p<0.0001; 162.6±7.0 vs 97.9±9.6 ms for $APD_{90}$, p<0.0001). Accordingly, $APD_{30}/APD_{90}$ ratio, a distinguishing feature between atrial and ventricular CMs, was 0.45±0.04 for ventricular and 0.14±0.04 for atrial tissues, approaching the ratios reported in human myocardium, ~0.75 in ventricular CMs; ~0.1 for atrial CMs.

A major challenge for current platforms designed to study cardiac tissues derived from stem cells is the high degree of batch-to-batch variability. In this regard, we found a high degree of reproducibility in passive tension, active force amplitudes, PRP, maximum capture rates (MCRs) and electrical thresholds (ETs) between batches of conditioned ventricular Biowires generated from BJ1D cells (FIGS. 11B-11F), as well as when other stem cell sources are used to generate tissues. For example, while the genetic, structural and functional results described above were recorded in atrial Biowires generated from HES3 stem cells and in ventricular Biowires created from BJ1D cells, conditioned ventricular Biowires generated from HES3 and HES2 CMs exhibit similar positive FFR and undergo similar remodeling with electrical conditioning (FIGS. 11G-11N). However, some baseline variability in electrical properties exists between Biowires generated from different cell sources, HES3, iCell™ and BJ1D stem cells (FIGS. 12A-12D). For example, upstroke velocities and impulse propagation velocities were lower (p<0.0001) in HES3 derived Biowires (i.e. 25.3±14.0 mV/s and 5.7±0.9 cm/s) than in BJ1D-derived Biowires (108.8±19.6 mV/s and 31.8±7.9 cm/s), differences that can be explained by the higher minimum diastolic potential in the HES3 Biowires which is expected to lead to reduced $Na^+$ channel availability due to increased channel inactivation. Likewise, conditioned atrial Biowires derived from different stem cells source (i.e. HES3 and MSC-IPS1) also produced relatively similar electrical properties. Importantly, standard pharmaceutical agents such as blockers of L-type $Ca^{2+}$ channels (verapamil) and hERG channels (dofetilide) exhibited predictable responses on action potentials of ventricular Biowires (FIGS. 12E-12N), thus further establishing their utility in drug testing.

Figure 5A:
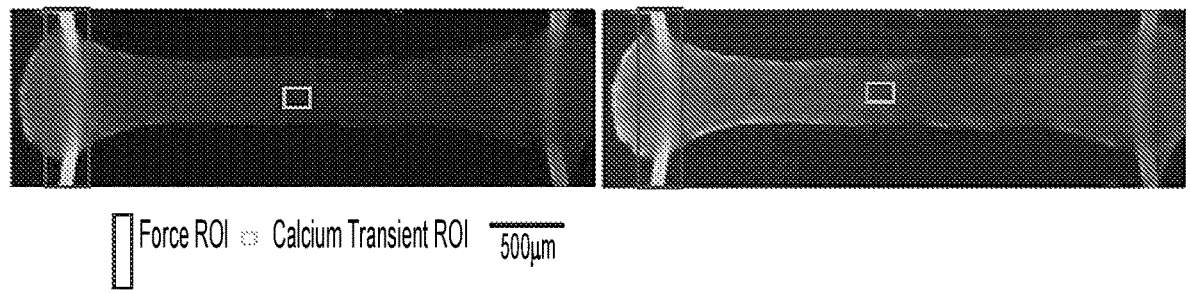
FIGS. 5A-5F show that Biowire II platform enables measurement of synchronous force and calcium transient responses to drugs in atrial and ventricular tissues.
Figure 5B:
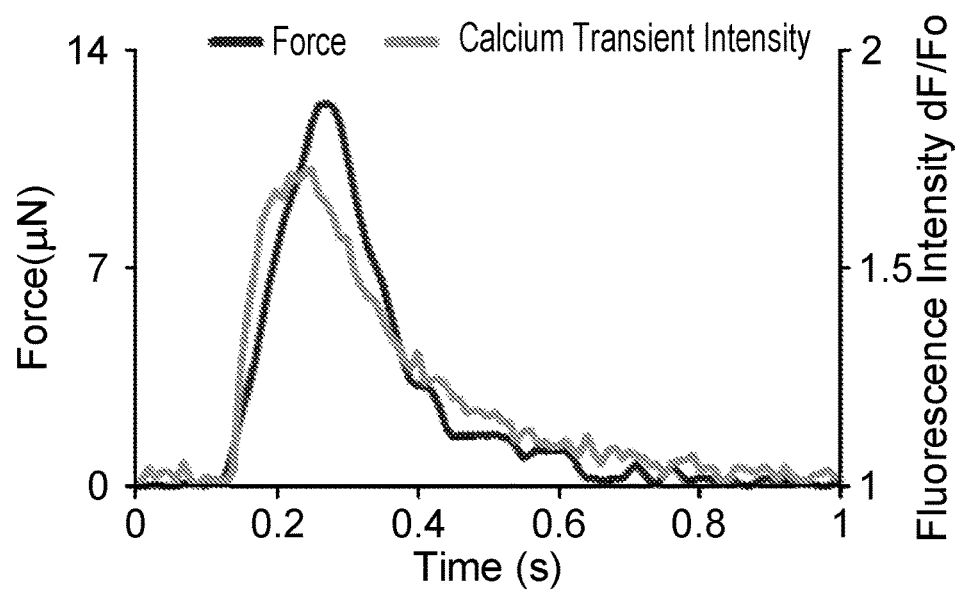
Figure 5C:
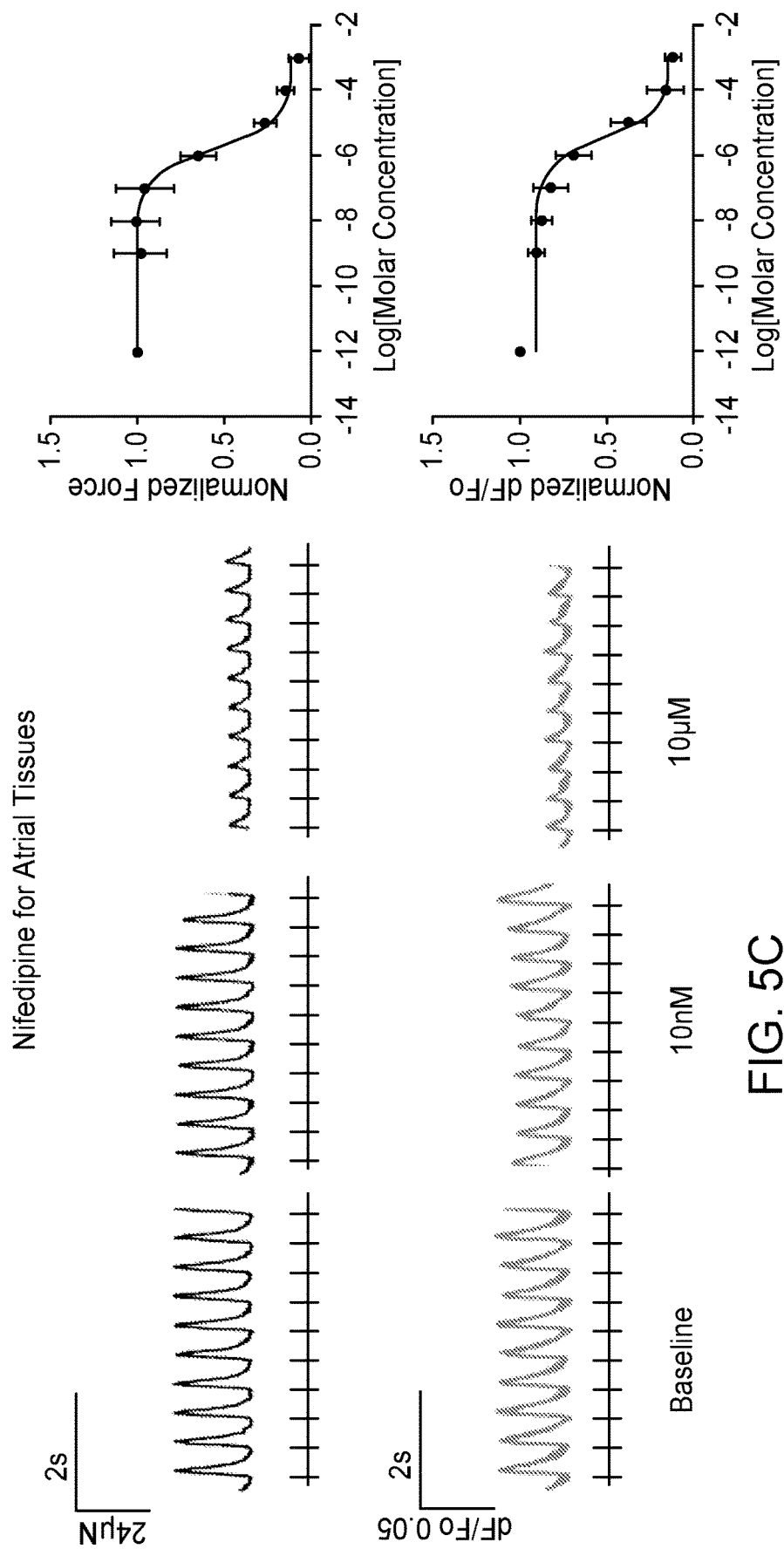
Figure 5D:
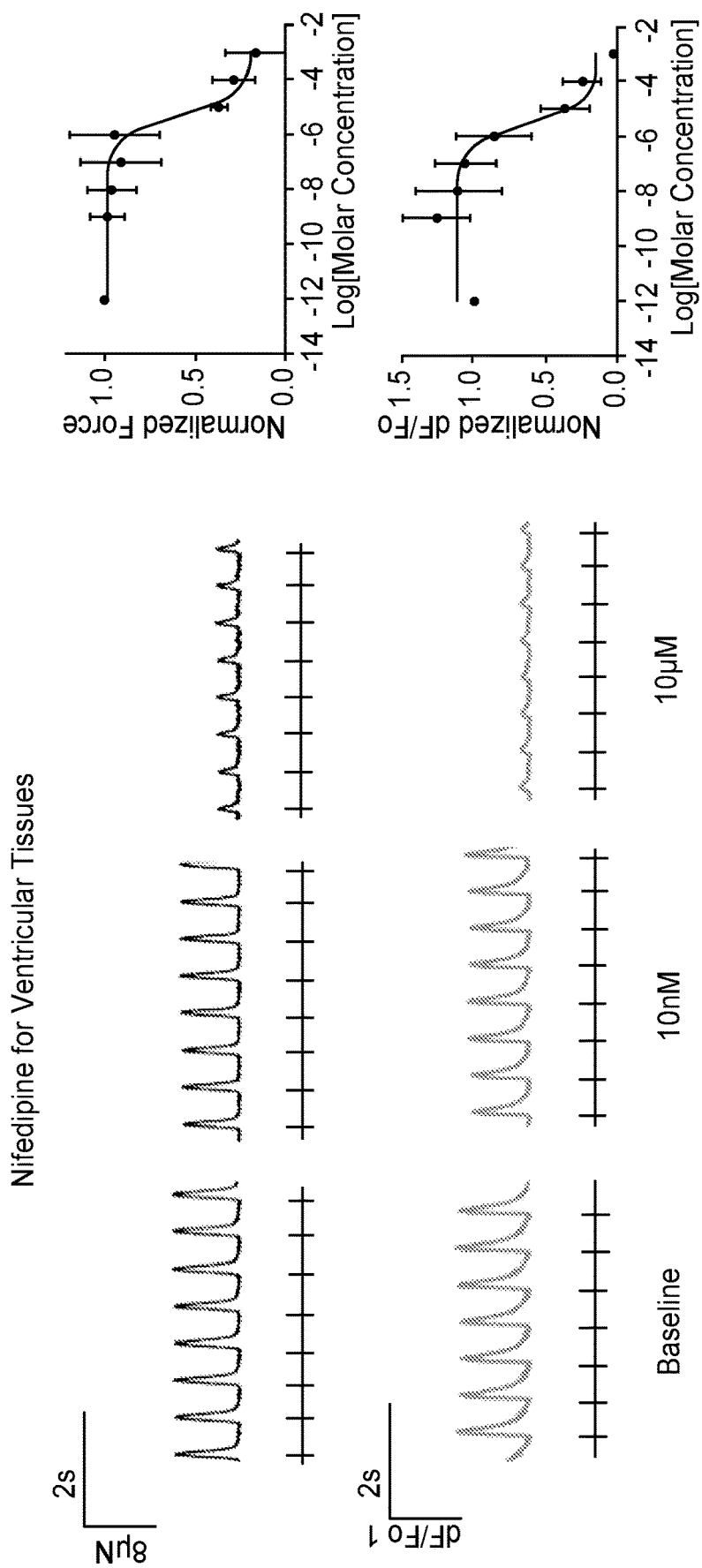
Figure 5E:
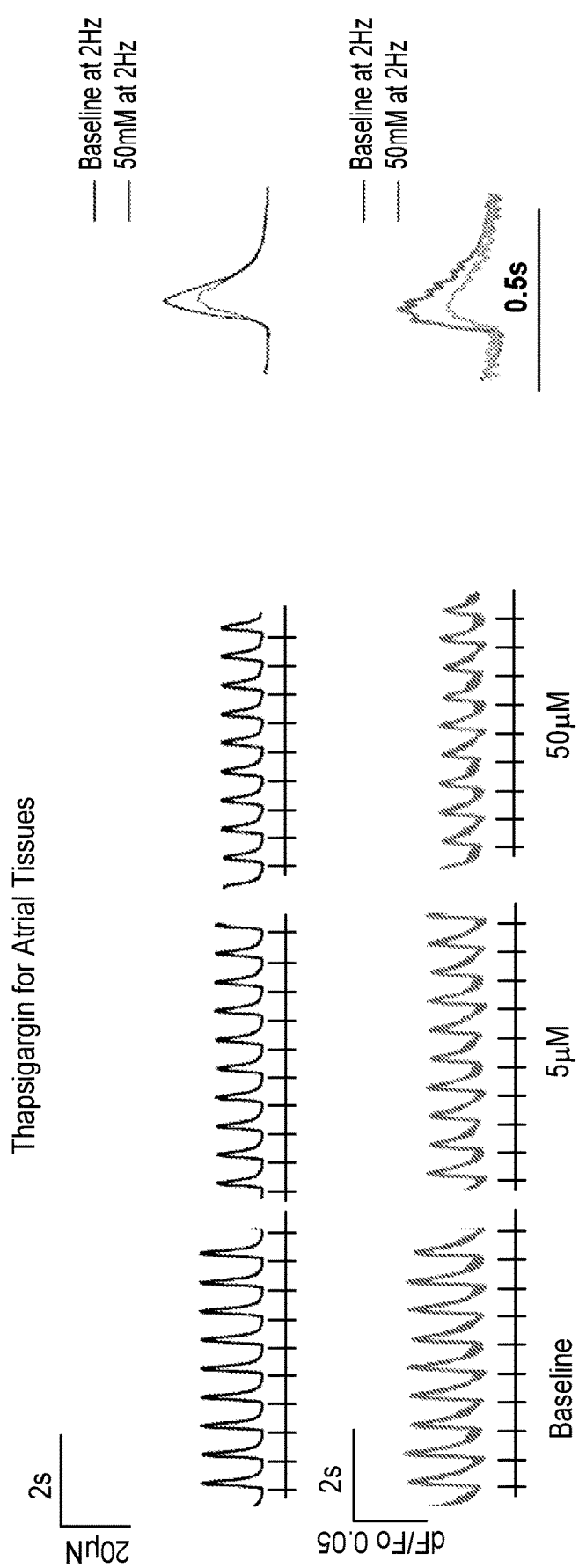
Figure 5F:
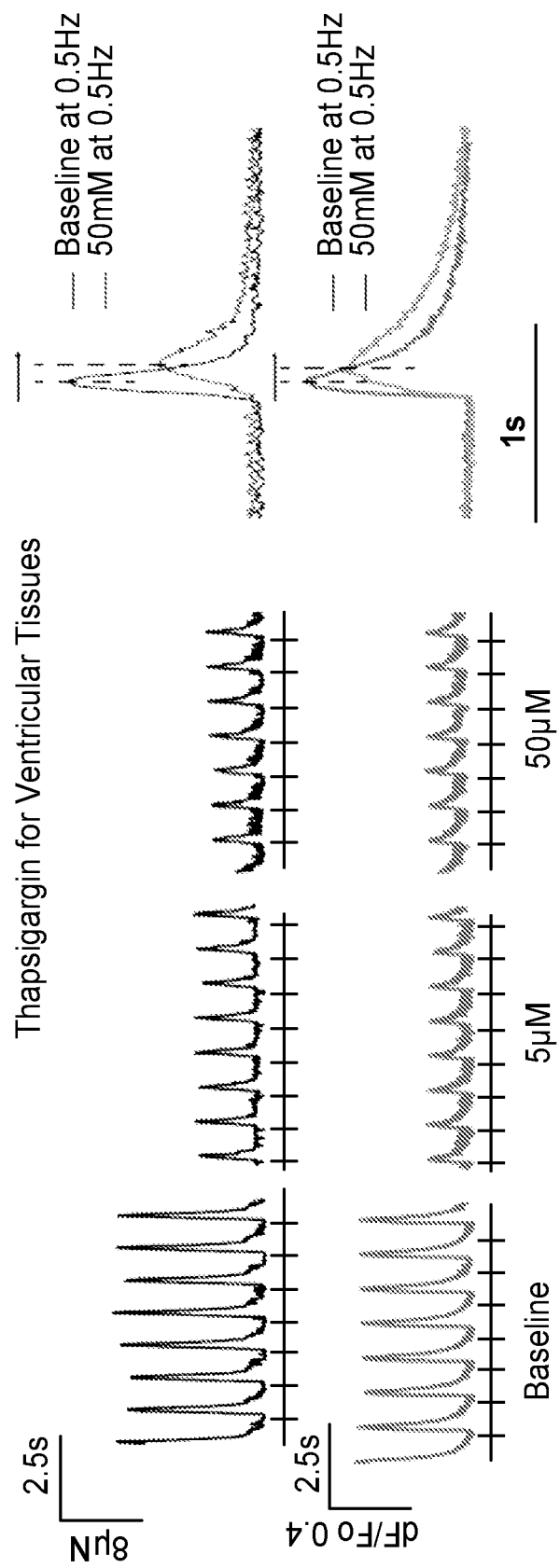

Responses of Atrial Vs Ventricular Tissues to Agents Affecting Functional Properties Upon incubation of Biowires with fluorescent $Ca^{2+}$ indicators, it becomes possible to measure simultaneously force and calcium in our platform (FIGS. 5A-5B), thereby providing opportunities for conveniently assessing some details of drug mechanisms. To illustrate this capability (FIGS. 5C-5D), we examined the actions of agents such as the L-type $Ca^+$ channel blocker, nifedipine, which dose-dependently reduced force and Ca' transients with similar IC50s for Biowires made from atrial CMs (IC50=2.0±1.2 μM for force and 3.6±1.5 μM for Ca' transients) versus ventricular CMs (IC50=4.5±1.4 μM for force and 3.1±1.9 μM for Ca' transients). Similarly, the sarco/endoplasmic reticulum calcium ATPase (SERCA) inhibitor, thapsigargin, dose-dependently decreased force and Ca' transient amplitudes (FIGS. 5E-5F) in both atrial and ventricular preparations with a higher potency in ventricle, as expected with SERCA2a inhibition. Moreover, at low pacing rates, thapsigargin prolonged the time-to-peak and decay rates of both force and $Ca^{2+}$ in ventricular, but not atrial Biowires, consistent with differences in sarcoplasmic reticular $Ca^{2+}$ handling between atrial and ventricular human myocardium.

As expected for large differences in acetylcholine-dependent $K^+$ currents (i.e. $I_{K,ACH}$) between atria and ventricles, the Type 2 muscarinic receptor agonist, carbachol, abbreviated APDs in atrial Biowires without affecting these parameters in ventricular tissues (FIGS. 14A-14H). Another notable difference between atrial and ventricular myocardium is the presence in atria of $K_V1.5$-dependent ultra-rapidly activated potassium currents, $I_{Kur}$, a current with a high sensitivity to block by 4-aminopyridine (4AP). Accordingly, 4AP at low doses (25 μM) increased action potential amplitudes and prolonged $APD_{30}$ in the atrial Biowires, without measurable effects on ventricular tissues (FIGS. 14I-14P), although higher doses of 4AP did prolong APD, which arise from blockade of the 4AP-sensitive $K_V1.4$-based transient outwards currents ($I_{to}$) found in ventricular myocardium.

In Vitro Disease Modeling Using the Biowire Platform

Figures 6A, 6B:
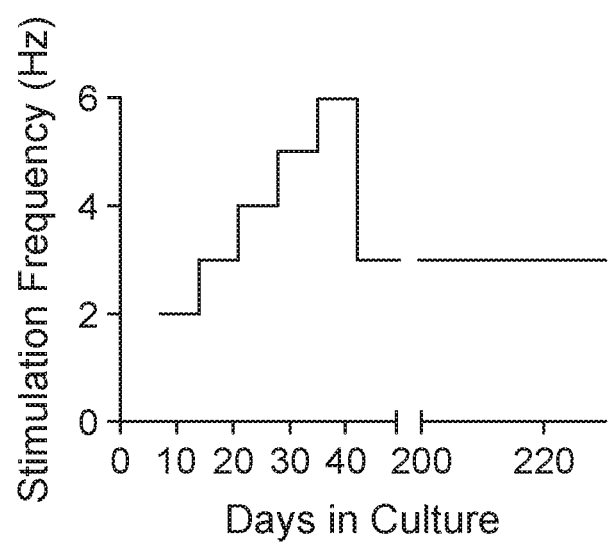

To demonstrate proof-of-concept for the utility of our Biowire platform in disease modeling (FIGS. 6A-6I), iPSCs were obtained from patients enrolled in the NHLBI Hyper-GEN study, one of the largest epidemiological studies focusing on left ventricular hypertrophy (LVH) in families with primary hypertension. Our strategy involved comparing ventricular tissues generated from iPSC-CMs obtained from hypertensive participants with clear echocardiographic evidence of left ventricular hypertrophy (Affected group) versus participants without ventricular hypertrophy (Non-Affected group), as summarized in FIG. 6A.

Although the underlying basis for the phenotypic differences between the Affected group and Non-Affected group is unknown, hypertension as well as the associated cardiac responses to the increased workloads generally represent a polygenic disorder. Thus, we hypothesized that chronic electrical conditioning protocols, designed to mimic the chronic increases in cardiac workloads arising from hypertension, will uncover differences between the patient groups. Accordingly, tissues were conditioned during the first 6 weeks using our standard ventricular conditioning protocols. Thereafter, electrical stimulation was continued at 6 Hz for 1 additional week, after which the stimulation frequency was reduced to 3 Hz and maintained for up to 6 months (FIG. 6B) to mimic chronic increased workload, resulting in a total cultivation time of 8 months.

Figure 6C:
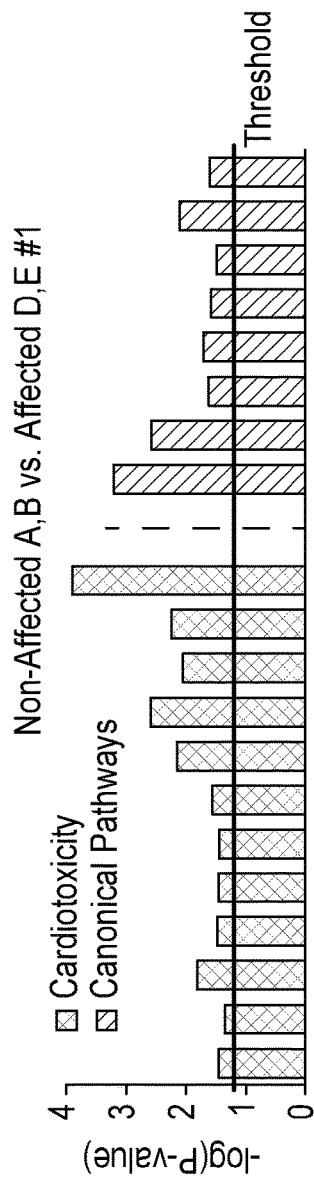
Figure 6D:
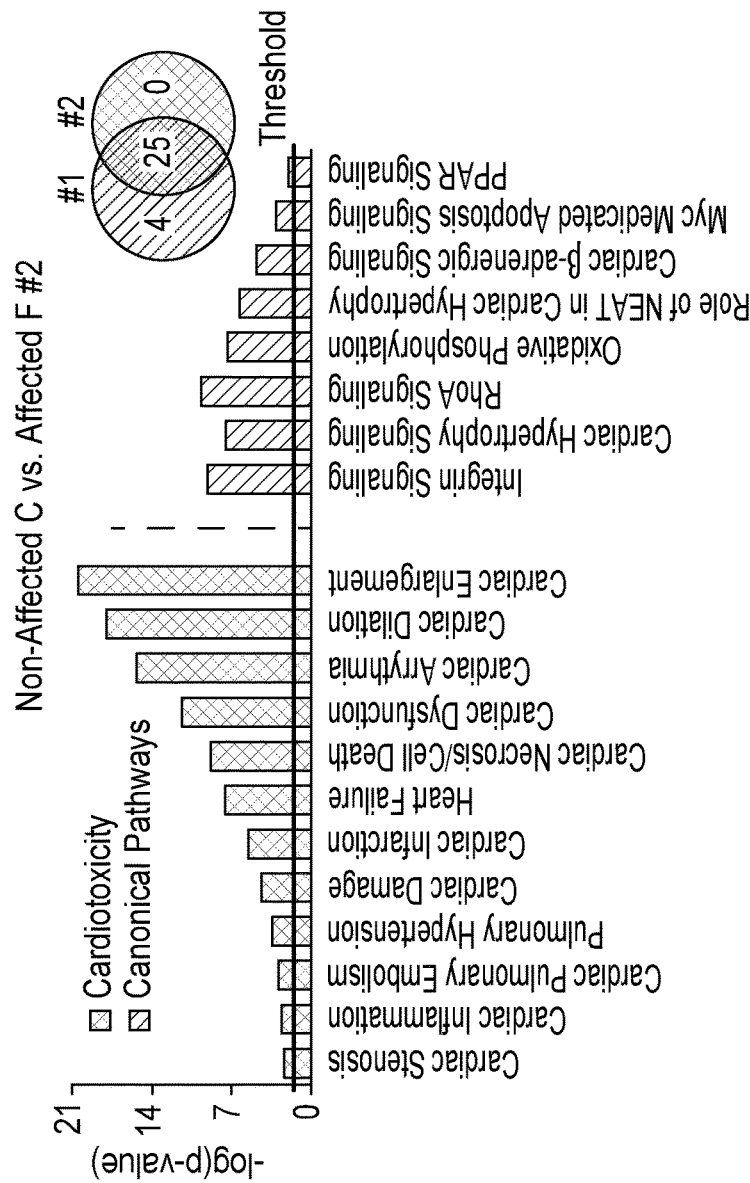
Figure 6H:
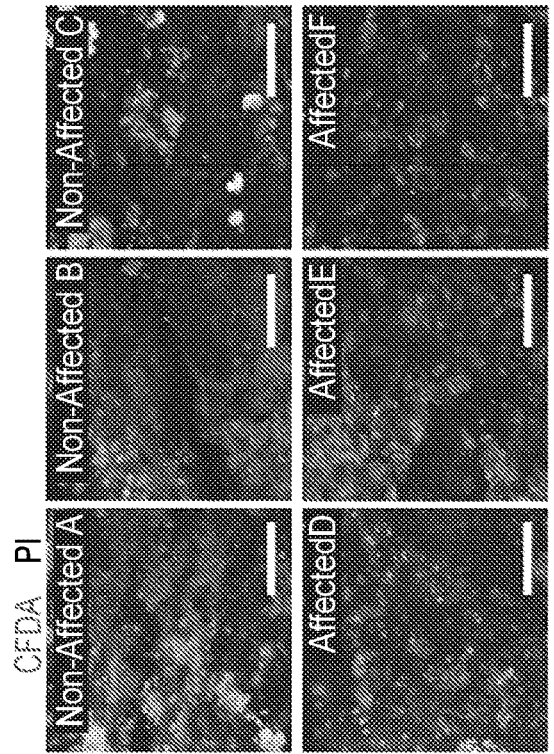
Figure 6H:
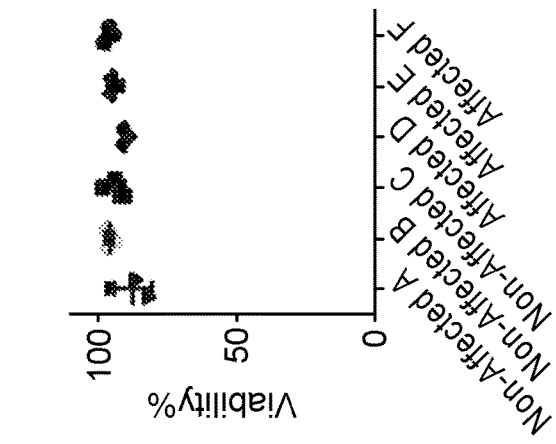
Figure 6I:
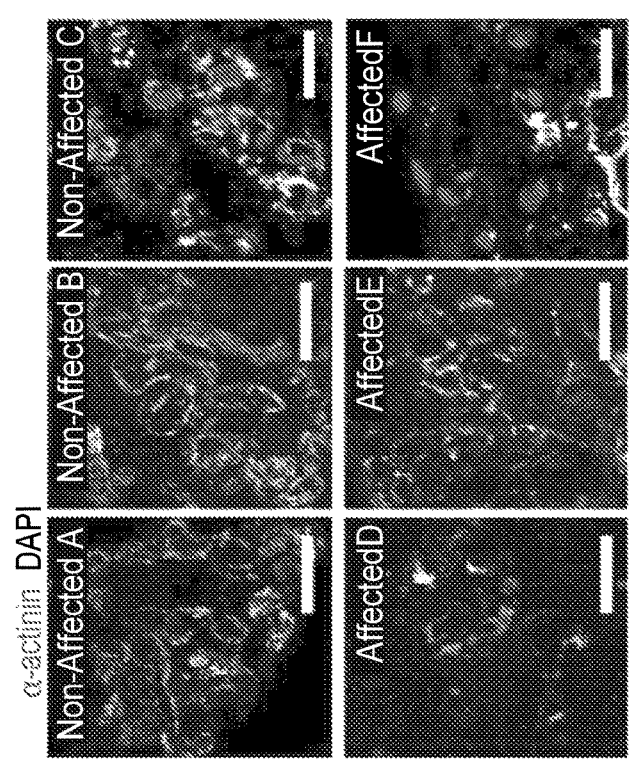
Figure 6I:
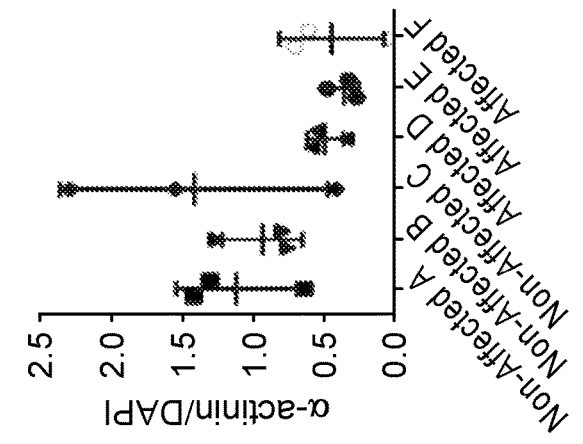

In contrast to previous modeling studies that focused on monogenic cardiac diseases, modeling of polygenic disease necessitates more comprehensive genetic profiling analysis. Interestingly, profiling of RNA expression in conditioned ventricular Biowires (FIG. 6C) after 8 months of culture demonstrates distinct gene expression profiles for Affected versus Non-Affected patients as revealed from gene set enrichment analyses. These studies were performed in two separate batches of Biowires generated from Affected and Non-Affected participants as summarized in FIG. 6C. In both batches, enrichment in 25 cardiac toxicity and canonical signaling pathways was consistently uncovered in Biowires from Affected vs Non-Affected patients (FIG. 6D), including many pathways broadly linked to pathological remodeling in cardiovascular disease such as cardiac enlargement, cardiac dilatation, cardiac dysfunction, heart failure and cardiac hypertrophy signaling (FIG. 6C). Analysis of the specific genes related to cardiac hypertrophy and heart failure within individual replicates of independent experimental groups, further indicates clear upregulation in all samples derived from the Affected participants (FIG. 6E), with only one of 3 replicates from one of the Non-Affected participants (Non-Affected A) exhibiting a relatively high expression of the hypertrophy associated genes (FIG. 6E).

Consistent with these differences in mRNA expression, long-term culturing for 8 months lead to profound differences in contractile function between Biowires from Affected participants compared to Non-Affected, with all 3 Affected samples generating virtually no force compared to the Non-Affected samples (FIGS. 6F-6G). Despite these profound differences in contractile function, no differences in cell viability (FIG. 6H) or cardiomyocyte content (FIG. 6I) were observed in the Biowires from the two groups of participants.

Engineering of Atrio-Ventricular Biowires

Figure 7A:
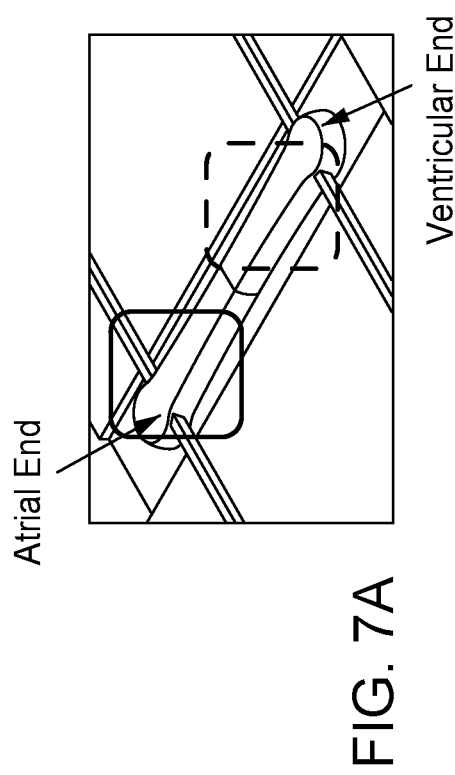
FIGS. 7A-7N show the engineering of atrioventricular tissues.
Figure 7B:
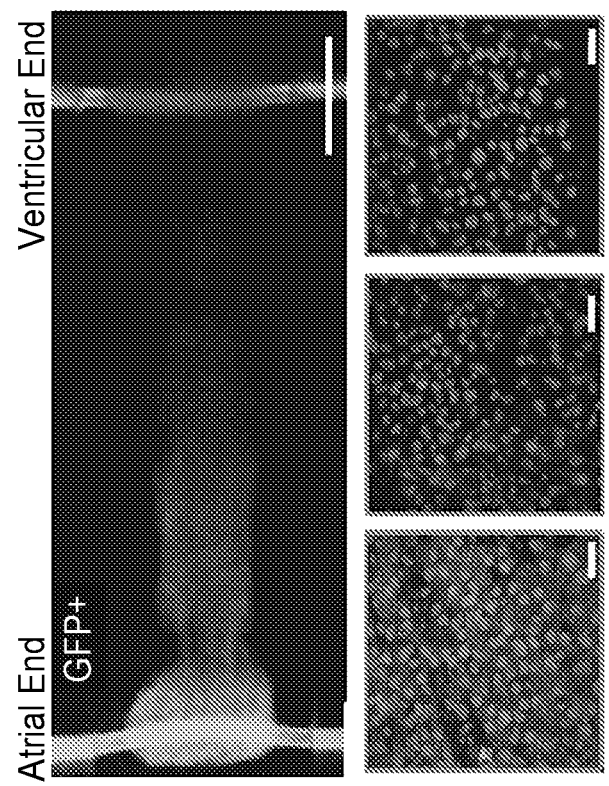
FIG. 7B is a series of images showing atrial cells (GFP+) are located at a distinct end of the cardiac tissue. POMaC polymer wires exhibit autofluorescence in the green channel. Zoomed-in images from the atrial, mid and ventricular region were presented as insets. (Scale bar=0.5 mm, Insets scale bar=30 μm).
Figure 7C:
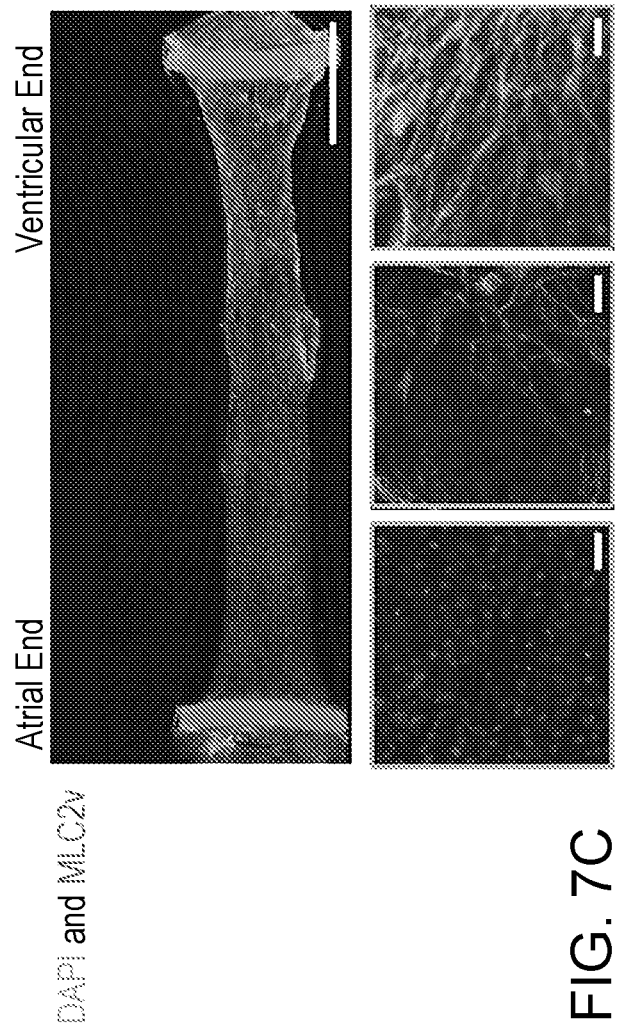
FIG. 7C is a series of images showing only ventricular end of the tissues stains positive for myosin light chain 2v (MLC2v). Zoomed-in insets from the atrial end, mid region and ventricular end were compared. Nuclei are counterstained with DAPI. POMaC polymer wires exhibit blue autofluorescence (Scale bar=0.5 mm).
Figure 7D:
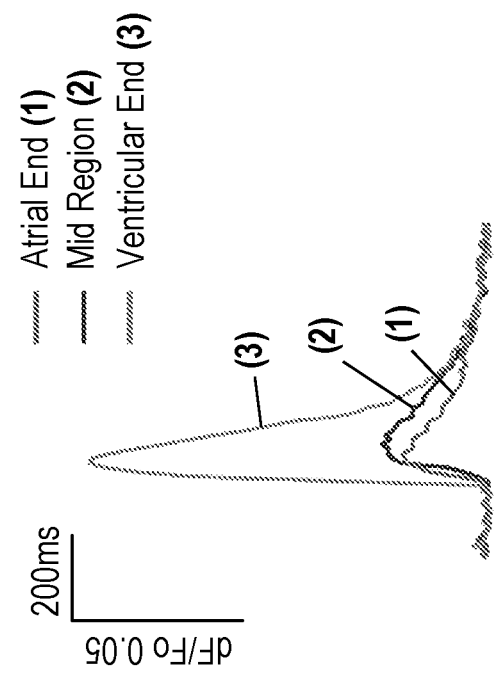
FIG. 7D is a graph showing representative traces of $Ca^{2+}$ transients from atrial, mid and ventricular region of atrioventricular tissues.

A major potential advantage of our Biowire platform is the ability to generate composite cardiac tissues containing both atrial and ventricular zones that would allow efficient screening of differential responses to agents with chamber-specific actions. With this in mind, we spatially patterned Biowires by adding atrial CMs to one end and ventricular CMs to the other end of the microwells (FIG. 7A) which resulted in heteropolar tissues with clearly atrial properties at one end and ventricular properties at the other end, as established with GFP fluorescence of atrial cells (FIG. 7B) and MLC2v staining (FIG. 7C). The transition zone between the atrial and ventricular ends was ~200 μm wide and showed mixed atrial and ventricular properties (FIGS. 7B-7C). Functionally, $Ca^{2+}$ transients were larger and rose more rapidly at the ventricular end compared to the atrial end, with intermediate properties in the transition zone (FIGS. 7D-7E). AP characteristics also showed distinct atrial versus ventricular properties at the ends of Hes3-derived Biowires, and intermediate APs in the transition zone (FIGS. 7F-7G).

Figure 7L:
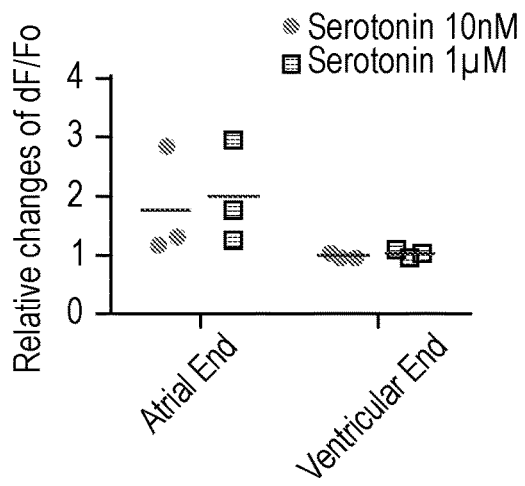
FIG. 7L is a graph showing change in calcium transient amplitude in response to serotonin normalized to the baseline. (n=3, two way ANOVA with Sidak's multiple comparisons test).
Figure 7M:
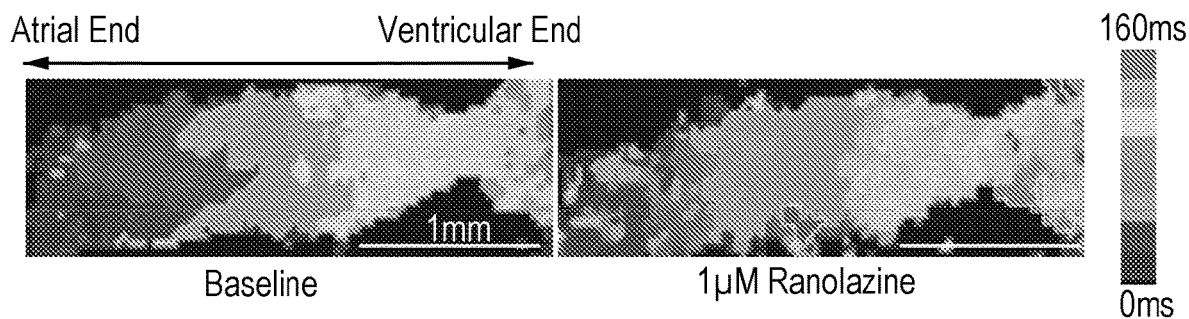
FIG. 7M is a set of optical mapping of impulse propagation before and after application of 1 μM ranolazine.
Figure 7N:
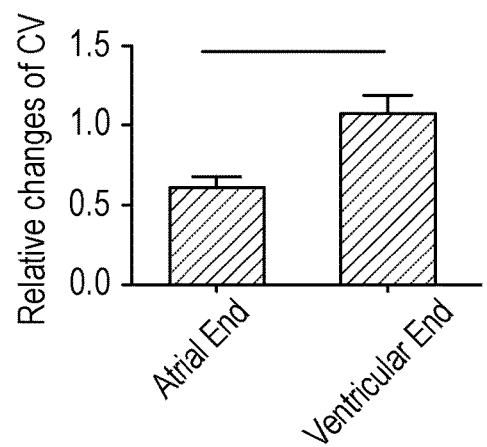

To illustrate the utility of such preparations, we examined the effects of the 5-HT agonist, serotonin and the rapid voltage-gated $Na^+$ channel blocker, ranolazine, which have both been shown to selectively affect atrial properties. Consistent with atrial selectivity, serotonin increased $Ca^{2+}$ transients in the atrial end but not the ventricular end of Biowires (FIGS. 7J-7L). Ranolazine decreased conduction velocity in the atrial region without affecting the ventricular portions of heteropolar Biowires, consistent with preferential blockade of $Na^+$ in atrial CMs (FIG. 7M-7N).

The results described herein show that the Biowire II platform is a novel resource and a significant technical advance for 3D cardiac cell cultivation. The platform uniquely combines the benefits of organ-on-a-chip engineering and organoid self-assembly to enable non-invasive, multi-parametric readouts of physiological responses thereby allowing important biomedical questions to be addressed.

These capabilities are made possible by the self-assembly of tissues between two parallel POMaC wires, matching the mechanical properties of the native cardiac tissue (10-500 kPa) and allowing the force to be routinely and continuously measured. This configuration enables cultivation of multiple tissues suspended on only 2 parallel polymer wires, in contrast to the microcantilever approach that requires a pair of silicone posts for a cultivation of a single tissue.

Common platforms for cultivation of 3D cardiac microtissues incorporate PDMS because of its biocompatibility and ease of use but at the expense of absorption of small hydrophobic molecules. Although the plastic Biowire II platform does not completely eliminate absorption of small molecules, it does significantly reduce absorption in comparison to PDMS. Moreover, the small amount of drug absorption is associated with the POMaC wires as well as some absorption arising from the use of low absorption polyurethane adhesive used to secure the POMaC wires to the plastic. Fortunately, functional Biowire II devices can also be constructed without the adhesive. The absorbed molecules are easily washed out of Biowire II devices, in contrast to the molecules absorbed into PDMS devices that remain present even after a washout step, which may hinder drug dose response testing.

A major advantage of the platform described herein is the ability to continuously and non-invasively measure $Ca^{2+}$ transients and active force, in combination with other end-point measurements such as conduction velocity and action potentials.

Figures 11O, 12A:
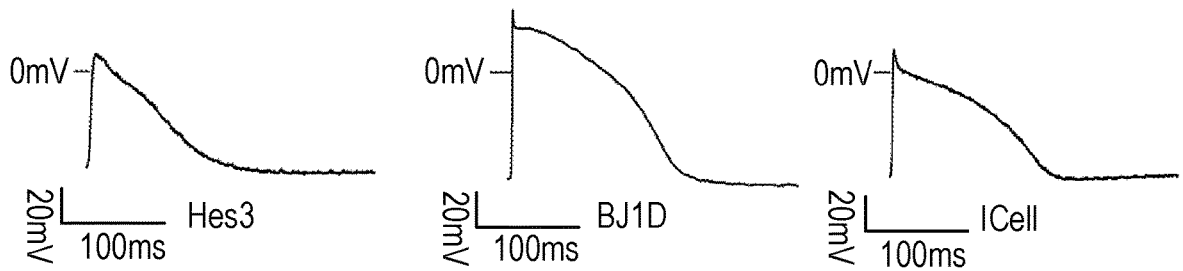
FIGS. 12A-12N show action potential characterization of ventricular tissues generated from different cell lines and responses of BJ1D ventricular tissues to verapamil and dofetilide. Hes3, BJ1D and iCell™ cell lines were assessed with sharp microelectrode recordings performed at the end of cultivation and exhibited some differences in (FIG. 12A) Action potential profiles of Hes3, BJ1D and iCell™ derived CMs respectively. 90% of BJ1D CMs and 39% of iCells™ had notch in their AP profiles.
Figure 12B:
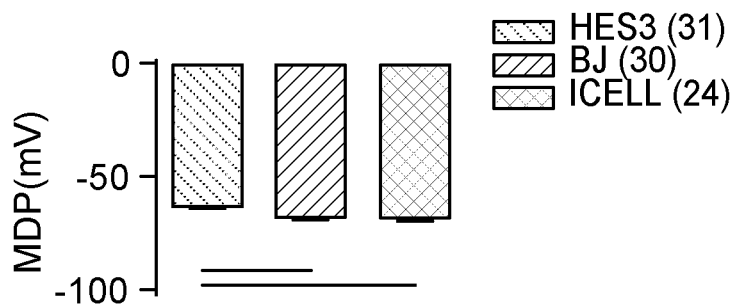
(FIG. 12B) Minimum diastolic potential and (FIG. 12C) Upstroke velocity. Action potential duration at (FIG. 12D) 30% repolarization ($APD_{30}$), 50% repolarization ($APD_{50}$) and 90% repolarization ($APD_{90}$). Data presented as mean±SEM, n≥3 tissue, One-way ANOVA with Tukey post hoc multiple comparison test. Numbers in brackets indicate the total number of individual cells sampled. Ventricular tissues (derived from BJ1D hiPSC-CMs) treated with (FIGS. 12E-12I) verapamil and (FIGS. 12J-12N) dofetilide.
Figure 12C:
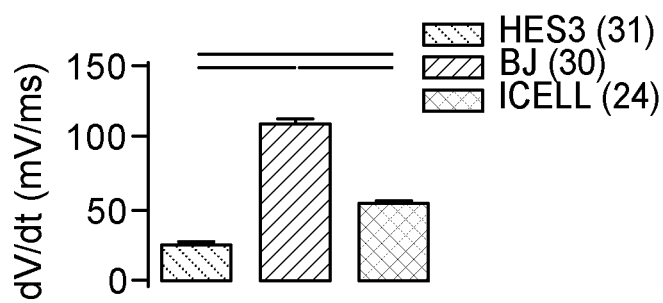
(FIGS. 12E, 12J) Representative action potential recordings, (FIGS. 12F, 12K) Action potential amplitude.
(FIGS. 12G, 12L) Minimum diastolic potential.
(FIGS. 12H, 12M) Upstroke velocity and (FIGS. 12I, 12N) $APD_{30}$, $APD_{50}$, and $APD_{90}$. Data presented as mean±SEM, n=3 tissue, One-way ANOVA with Tukey's post hoc comparison of test concentrations to 0 µM. Numbers in brackets indicate the total number of individual cells sampled at each concentration.
Figure 12D:
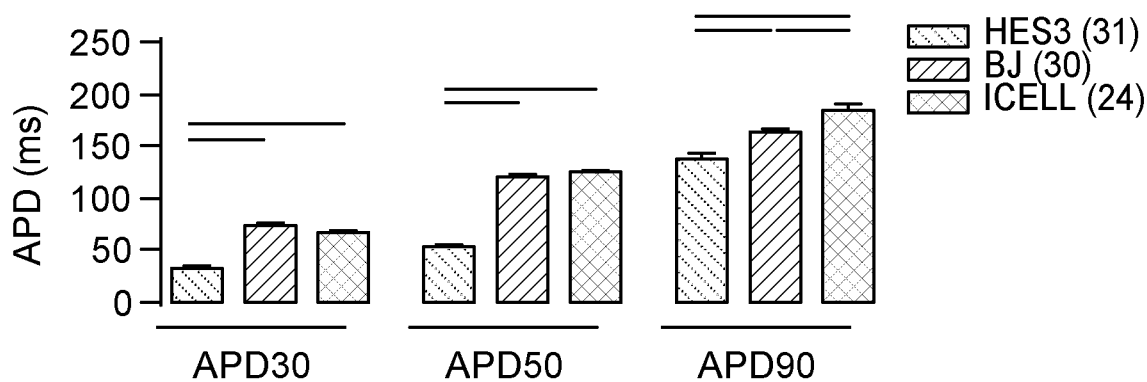
Figure 13A:
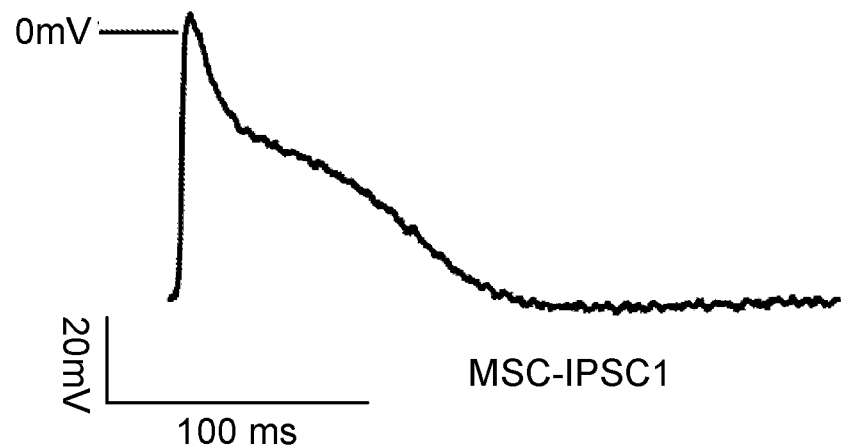
FIGS. 13A-13F show action potential characterization of atrial tissues generated from two different cell lines. MSC-IPS1 (FIG. 13A) and Hes3 (FIG. 13B) cell lines were assessed with sharp microelectrode recordings at the end of cultivation and exhibited some differences in action potential profiles, (FIG. 13C) Action potential amplitude, (FIG. 13D) Minimum diastolic potential, (FIG. 13E) Upstroke velocity and (FIG. 13F) Action potential duration at 30% repolarization ($APD_{30}$), 50% repolarization ($APD_{50}$) and 90% repolarization ($APD_{90}$). Numbers in brackets indicate the total number of individual cells sampled. Data presented as mean±SEM, n≥4 tissue, One-way ANOVA with Tukey post hoc multiple comparison test.
Figure 13B:
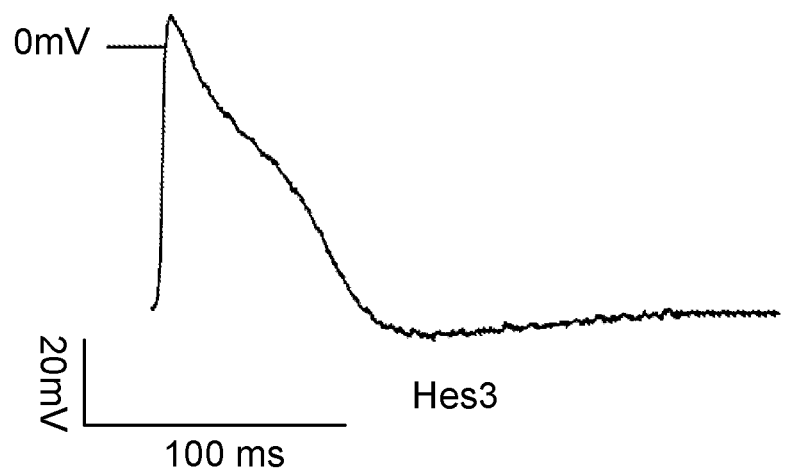
Figure 13C:
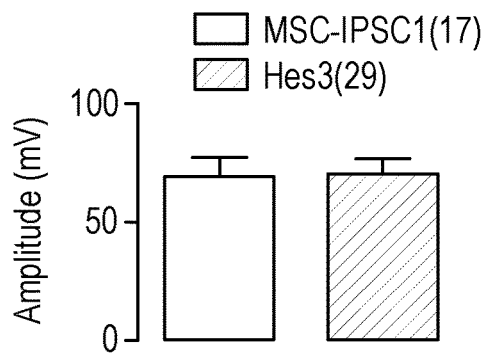
Figure 13D:
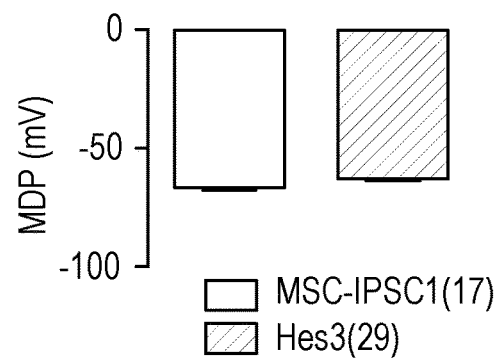
Figure 13E:
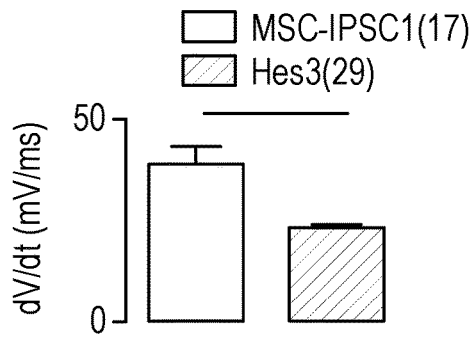
Figure 13F:
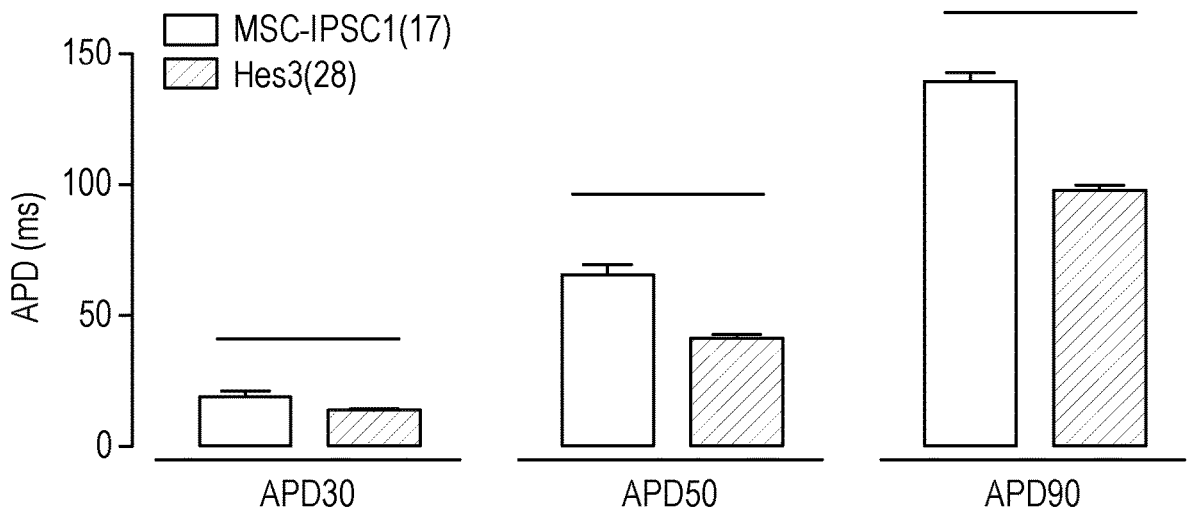

Another advantage of the platform is the requirement for the relatively small number of CMs (i.e. ~0.1 million/tissue) when compared with many previous studies which required between 0.5 and 2 million cells per tissue. Consequently, although the absolute active force per tissue is significantly lower in the current work compared to that reported in other studies, the force per cross-sectional area (or per cell) is on the order of those reported in other studies (FIG. 11O). These results suggest a possible community effect, such that the contribution of CM number to the collective contractile force in a tissue is non-linear. Yet, fold increase in the force between 1-3 Hz was much higher in the current ventricular preparations, compared to those reported in a recent landmark study (Ronaldson-Bouchard et al., 2018). Consistent with the previous work, electrical stimulation ramp-up to 6 Hz promotes maturation, however frequencies above 3 Hz may not result in 1:1 coupling.

Additional clear benefits of the Biowire II platform include the ability to compare atrial and ventricular myocardium. Our data indicate that both, the starting cell population (i.e. distinct directed differentiation protocols) and the electrical conditioning contribute to atrial vs. ventricular phenotype divergence of the cardiac tissues in terms of gene expression, immunostaining and electrophysiological properties. Electrical conditioning appeared to be particularly effective for ventricular preparations, causing upregulation of high density lipoprotein genes consistent with developmental metabolic changes that decrease the reliance of adult cardiomyocytes on glycolysis, while also strongly promoting sarcomeric organization, the expression of chamber-specific proteins such as MLC2v and driving electrical changes seen with maturation.

We observe profound physiological differences between the two cardiac tissue types. Specifically, ventricular tissues are quiescent at the end of cultivation in the absence of external stimulation and display a robust positive FFR, PRP and a fast conduction velocity which are the hallmarks of adult human myocardium that allow for enhanced pumping during periods of increased blood flow demand. Consistent with the native adult atrial muscle physiology, the atrial Biowires display a relatively flat FFR, minimal PRP and a slower conduction velocity. By contrast, most previous work reported a negative FFR for ventricular tissues and achieving a flat force-frequency relationship was considered to be an advance. We also report for the first time, human ventricular cardiac tissue displaying notches in the action potential profile which are associated with the presence of the rapidly activating and inactivating transient outward potassium currents, which are also hallmarks of the adult myocardium.

By contrast, the minimum diastolic potential of the tissues (−70 mV) was still somewhat depolarized compared to the adult myocardium levels (−80 to −90 mV), especially in atrial biowires, and this correlated with relatively slow upstroke velocities (~110 mV/ms) compared to adult myocardium (254-303 mV/ms), despite being faster than fetal myocardium (5-13 mV/ms). Nevertheless, the diastolic potentials in the Biowire II platform were either improved or in line with those reported in recent stem cell derived cardiac tissues.

Cardiac toxicity is the prime cause of drug withdrawals, with chamber-specific cardiotoxicity considered to be a major issue. Treatments for the atrial fibrillation are limited and some cause death to ventricular CMs. In this regard, we provide evidence for chamber-specific drug responses, founded on the presence of ultra-rapid delayed rectifier $K^+$ currents ($I_{Kur}$) and the parasympathetic-dependent acetylcholine-activated potassium current ($I_{Kach}$) in atrial tissues but not ventricular tissues. Specifically, we showed that very low concentrations of 4-AP (<50 µM) prolonged AP duration in atrial but not ventricular tissues; whereas the acetylcholine analogue, carbachol, shortened atrial APDs only. We also observed higher expression levels of KCNJ2 responsible for Kir2.1 protein production and the corresponding $I_{K1}$ current in ventricular tissues compared to atrial tissues.

Since cardiac hypertrophy in response to increased workload arising from conditions such as hypertension is a well-established risk factor for heart disease and failure, developing platforms to model these conditions would be highly desirable. Accordingly, we generated Biowires from ventricular CMs created from iPSCs derived from participants enrolled in the NHLBI HyperGEN-LVH study, an established epidemiological cohort focusing on LVH and its underlying risk factors, which started recruiting in 1996. Although all these patients suffer from prolonged hypertension, in association with marked elevations in cardiac workloads, they present with highly variable left ventricular hypertrophy. Our blinded studies, allowed the identification of three cell lines derived from Affected hypertensive participants with the greatest amount of LVH, in comparison to those cell lines derived from non-affected participants with normal LV mass and contractile function. Specifically, Biowires generated from the Affected participants exhibited an absence of active force generation after a prolonged culturing under a pacing protocol designed to mimic the increased workload, compared to the tissues derived from the Non-Affected participants that were still able to beat despite prolonged pacing at 3 Hz. In fact, prolonged rapid pacing is known to lead to heart failure in vivo. Therefore, the drop in the active force, between 6 weeks and 8 months, in the Non-Affected samples is an expected response. Clearly, the tissues derived from the Non-affected participants were better at resisting the rapid pacing protocol and maintaining contractility, compared to those derived from the Affected participants.

Remarkably, pathway analyses of RNA sequencing data from the Affected and Non-Affected tissues identified a significant enrichment in pathways linked to cardiac hypertrophy, enlargement, cardiac dilatation, cardiac dysfunction and heart failure. These expression differences reflect and are consistent with the underlying disease phenotype of LVH as well as the anticipated phenotype of end organ damage under continued stress related to LVH such as hypertensive heart disease ultimately leading to reduced contractility and heart failure. Therefore, our model may enable us to fully understand the disease mechanism responsible for progression from LVH to heart failure, as a platform for future drug development.

Described herein are heteropolar cardiac tissues with an atrial and ventricular end, that exhibit spatially constrained responses to drugs that have complex or incompletely understood mechanisms of action in the cardiovascular system, such as serotonin and ranolazine. The effects of serotonin on the cardiovascular system are complex. It has been reported to cause positive inotropy in atrial cardiomyocytes, and no inotropic effect in ventricular cardiomyocytes. The overall cardiovascular effect of serotonin are very broad consisting of bradycardia or tachycardia, hypotension or hypertension, and vasodilation or vasoconstriction.

Ranolazine is currently in clinical trials with Gilead. This drug is largely a Na+ channel blocker, affecting both atria and ventricle, albeit in different ways. There is some controversy related to how and whether this drug has atrial-selective effects. Calcium transient traces from atrio-ventricular Biowires were able to capture the complex effect of serotonin on the human heart muscle, revealing the positive inotropic effect of serotonin on the atrial end but not the ventricular end. Conduction velocity significantly slowed down at the atrial end, after introduction of ranolazine, but not at the ventricular end. The half-inactivation voltage of atrial cells is more negative than ventricular CMs by around −17 mV; therefore more sodium channels inactivate at baseline membrane for atrial CMs at stroke or takeoff point compared with ventricular CMs. Because ranolazine is effective on the inactive sodium channel, it affects atrial more than ventricular cells.

To generate atrio-ventricular Biowires from a single cell source, we used HES3-NKX2-5$^{eGFP/w}$ cells; and to facilitate imaging of cell location we used a combination of GFP+ HES3 atrial CM at one end and BJ1D ventricular cells at the other end. Although, BJ1D cells enabled us to prepare ventricular tissues with high conduction velocities (31.8±7.9 cm/s), in the range of those reported for the adult myocardium (30-100 cm/s), HES3 ventricular preparations achieved velocities of only 5.5±1.3 cm/s, leading to relatively low conduction velocities of HES3 based atrio-ventricular preparations. In addition to providing a useful technical solution for the spatially constrained cardiac cell co-culture, this platform can have positive implications in drug testing, by enabling testing on both atrial and ventricular tissues in a single pass, and thereby doubling the throughput.

References

Aggarwal, P., Turner, A., Matter, A., Kattman, S. J., Stoddard, A., Lorier, R., Swanson, B. J., Arnett, D. K., and Broeckel, U. (2014). RNA expression profiling of human iPSC-derived cardiomyocytes in a cardiac hypertrophy model. PloS one 9, e108051.

Ahn, S., Ardona, H. A. M., Lind, J. U., Eweje, F., Kim, S. L., Gonzalez, G. M., Liu, Q., Zimmerman, J. F., Pyrgiotakis, G., Zhang, Z., et al. (2018). Mussel-inspired 3D fiber scaffolds for heart-on-a-chip toxicity studies of engineered nanomaterials. Analytical and bioanalytical chemistry.

Balaji, S., Hewett, K. W., Krombach, R. S., Clair, M. J., Ye, X., and Spinale, F. G. (1999). Inducible lethal ventricular arrhythmias in swine with pacing-induced heart failure. Basic research in cardiology 94, 496-503.

Bean, B. P., Cohen, C. J., and Tsien, R. W. (1983). Lidocaine block of cardiac sodium channels. The Journal of general physiology 81, 613-642.

Blatter, L. A. (2017). The intricacies of atrial calcium cycling during excitation-contraction coupling. The Journal of general physiology 149, 857-865.

Blatter, L. A., Kockskamper, J., Sheehan, K. A., Zima, A. V., Huser, J., and Lipsius, S. L. (2003). Local calcium gradients during excitation-contraction coupling and *alternans* in atrial myocytes. The Journal of physiology 546, 19-31.

Boudou, T., Legant, W. R., Mu, A., Borochin, M. A., Thavandiran, N., Radisic, M., Zandstra, P. W., Epstein, J. A., Margulies, K. B., and Chen, C. S. (2012). A microfabricated platform to measure and manipulate the mechanics of engineered cardiac microtissues. Tissue engineering Part A 18, 910-919.

Bray, N. L., Pimentel, H., Melsted, P., and Pachter, L. (2016a). Erratum: Near-optimal probabilistic RNA-seq quantification. Nature biotechnology 34, 888.

Bray, N. L., Pimentel, H., Melsted, P., and Pachter, L. (2016b). Near-optimal probabilistic RNA-seq quantification. Nature biotechnology 34, 525-527.

Burashnikov, A., and Antzelevitch, C. (2008). How Do Atrial-Selective Drugs Differ From Antiarrhythmic Drugs Currently Used in the Treatment of Atrial Fibrillation? Journal of atrial fibrillation 1, 98-107.

Burashnikov, A., Di Diego, J. M., Zygmunt, A. C., Belardinelli, L., and Antzelevitch, C. (2007a). Atrium-selective sodium channel block as a strategy for suppression of atrial fibrillation—Differences in sodium channel inactivation between atria and ventricles and the role of ranolazine. Circulation 116, 1449-1457.

Burashnikov, A., Di Diego, J. M., Zygmunt, A. C., Belardinelli, L., and Antzelevitch, C. (2007b). Atrium-selective sodium channel block as a strategy for suppression of atrial fibrillation: differences in sodium channel inactivation between atria and ventricles and the role of ranolazine. Circulation 116, 1449-1457.

Castle, N. A., and Slawsky, M. T. (1993). Characterization of 4-aminopyridine block of the transient outward K+ current in adult rat ventricular myocytes. The Journal of pharmacology and experimental therapeutics 265, 1450-1459.

Chen, L. Y., Sotoodehnia, N., Buzkova, P., Lopez, F. L., Yee, L. M., Heckbert, S. R., Prineas, R., Soliman, E. Z., Adabag, S., Konety, S., et al. (2013). Atrial fibrillation and the risk of sudden cardiac death: the atherosclerosis risk in communities study and cardiovascular health study. JAMA internal medicine 173, 29-35.

Cyganek, L., Tiburcy, M., Sekeres, K., Gerstenberg, K., Bohnenberger, H., Lenz, C., Henze, S., Stauske, M., Salinas, G., Zimmermann, W. H., et al. (2018). Deep phenotyping of human induced pluripotent stem cell-derived atrial and ventricular cardiomyocytes. JCI insight 3.

Davia, K., Davies, C. H., and Harding, S. E. (1997). Effects of inhibition of sarcoplasmic reticulum calcium uptake on contraction in myocytes isolated from failing human ventricle. Cardiovascular research 33, 88-97.

Dawodu, A. A., Monti, F., Iwashiro, K., Schiariti, M., Chiavarelli, R., and Puddu, P. E. (1996). The shape of human atrial action potential accounts for different frequency-related changes in vitro. International journal of cardiology 54, 237-249.

Devalla, H. D., Schwach, V., Ford, J. W., Milnes, J. T., El-Haou, S., Jackson, C., Gkatzis, K., Elliott, D. A., Chuva de Sousa Lopes, S. M., Mummery, C. L., et al. (2015). Atrial-like cardiomyocytes from human pluripotent stem cells are a robust preclinical model for assessing atrial-selective pharmacology. EMBO molecular medicine 7, 394-410.

Domansky, K., Leslie, D. C., McKinney, J., Fraser, J. P., Sliz, J. D., Hamkins-Indik, T., Hamilton, G. A., Bahinski, A., and Ingber, D. E. (2013). Clear castable polyurethane elastomer for fabrication of microfluidic devices. Lab on a chip 13, 3956-3964.

Doss, M. X., Di Diego, J. M., Goodrow, R. J., Wu, Y., Cordeiro, J. M., Nesterenko, V. V., Barajas-Martinez, H., Hu, D., Urrutia, J., Desai, M., et al. (2012). Maximum diastolic potential of human induced pluripotent stem cell-derived cardiomyocytes depends critically on I(Kr). PloS one 7, e40288.

Drouin, E., Charpentier, F., Gauthier, C., Laurent, K., and Le Marec, H. (1995). Electrophysiologic characteristics of cells spanning the left ventricular wall of human heart: evidence for presence of M cells. Journal of the American College of Cardiology 26, 185-192.

Earl, C. Q., Linden, J., and Weglicki, W. B. (1986). Biochemical mechanisms for the inotropic effect of the cardiotonic drug milrinone. Journal of cardiovascular pharmacology 8, 864-872.

Eisen, A., Ruff, C. T., Braunwald, E., Nordio, F., Corbalan, R., Dalby, A., Dorobantu, M., Mercuri, M., Lanz, H., Rutman, H., et al. (2016). Sudden Cardiac Death in Patients With Atrial Fibrillation: Insights From the ENGAGE AF-TIMI 48 Trial. Journal of the American Heart Association 5.

Eising, G. P., Hammond, H. K., Helmer, G. A., Gilpin, E., and Ross, J., Jr. (1994). Force-frequency relations during heart failure in pigs. The American journal of physiology 267, H2516-2522.

Eng, G., Lee, B. W., Protas, L., Gagliardi, M., Brown, K., Kass, R. S., Keller, G., Robinson, R. B., and Vunjak-Novakovic, G. (2016). Autonomous beating rate adaptation in human stem cell-derived cardiomyocytes. Nature communications 7, 10312.

Eschenhagen, T., Eder, A., Vollert, I., and Hansen, A. (2012). Physiological aspects of cardiac tissue engineering. American journal of physiology Heart and circulatory physiology 303, H133-143.

Gennser, G., and Nilsson, E. (1970). Excitation and impulse conduction in the human fetal heart. Acta physiologica Scandinavica 79, 305-320.

Ginsburg, R., Bristow, M. R., Billingham, M. E., Stinson, E. B., Schroeder, J. S., and Harrison, D. C. (1983). Study of the normal and failing isolated human heart: decreased response of failing heart to isoproterenol. American heart journal 106, 535-540.

Gintant, G., Sager, P. T., and Stockbridge, N. (2016). Evolution of strategies to improve preclinical cardiac safety testing. Nature reviews Drug discovery 15, 457-471.

Grandi, E., Pandit, S. V., Voigt, N., Workman, A. J., Dobrev, D., Jalife, J., and Bers, D. M. (2011). Human atrial action potential and Ca2+ model: sinus rhythm and chronic atrial fibrillation. Circulation research 109, 1055-1066.

Helmer, G. A., McKirnan, M. D., Shabetai, R., Boss, G. R., Ross, J., Jr., and Hammond, H. K. (1996). Regional deficits of myocardial blood flow and function in left ventricular pacing-induced heart failure. Circulation 94, 2260-2267.

Hinson, J. T., Chopra, A., Nafissi, N., Polacheck, W. J., Benson, C. C., Swist, S., Gorham, J., Yang, L., Schafer, S., Sheng, C. C., et al. (2015). HEART DISEASE. Titin mutations in iPS cells define sarcomere insufficiency as a cause of dilated cardiomyopathy. Science 349, 982-986.

Horvath, A., Lemoine, M. D., Loser, A., Mannhardt, I., Flenner, F., Uzun, A. U., Neuber, C., Breckwoldt, K., Hansen, A., Girdauskas, E., et al. (2018). Low Resting Membrane Potential and Low Inward Rectifier Potassium Currents Are Not Inherent Features of hiPSC-Derived Cardiomyocytes. Stem cell reports 10, 822-833.

Huebsch, N., Loskill, P., Deveshwar, N., Spencer, C. I., Judge, L. M., Mandegar, M. A., Fox, C. B., Mohamed, T. M., Ma, Z., Mathur, A., et al. (2016). Miniaturized iPS-Cell-Derived Cardiac Muscles for Physiologically Relevant Drug Response Analyses. Scientific reports 6, 24726.

Iwashiro, K., Criniti, A., Sinatra, R., Dawodu, A. A., d'Amati, G., Monti, F., Pannarale, L., Bernucci, P., Brancaccio, G. L., Vetuschi, A., et al. (1997). Felodipine protects human atrial muscle from hypoxia-reoxygenation dysfunction: a force-frequency relationship study in an in vitro model of stunning. International journal of cardiology 62, 107-132.

Jackman, C. P., Carlson, A. L., and Bursac, N. (2016). Dynamic culture yields engineered myocardium with near-adult functional output. Biomaterials 111, 66-79.

Jahnel, U., Rupp, J., Ertl, R., and Nawrath, H. (1992). Positive inotropic response to 5-HT in human atrial but not in ventricular heart muscle. Naunyn-Schmiedeberg's archives of pharmacology 346, 482-485.

Kannel, W. B., and Benjamin, E. J. (2008). Status of the epidemiology of atrial fibrillation. The Medical clinics of North America 92, 17-40, ix.

Kattman, S. J., Witty, A. D., Gagliardi, M., Dubois, N. C., Niapour, M., Hotta, A., Ellis, J., and Keller, G. (2011). Stage-specific optimization of activin/nodal and BMP signaling promotes cardiac differentiation of mouse and human pluripotent stem cell lines. Cell stem cell 8, 228-240.

Kaumann, A. J., Sanders, L., Brown, A. M., Murray, K. J., and Brown, M. J. (1991). A 5-HT4-like receptor in human right atrium. Naunyn-Schmiedeberg's archives of pharmacology 344, 150-159.

King, M. K., Coker, M. L., Goldberg, A., McElmurray, J. H., 3rd, Gunasinghe, H. R., Mukherjee, R., Zile, M. R., O'Neill, T. P., and Spinale, F. G. (2003). Selective matrix metalloproteinase inhibition with developing heart failure: effects on left ventricular function and structure. Circulation research 92, 177-185.

Koivumaki, J. T., Korhonen, T., and Tavi, P. (2011). Impact of sarcoplasmic reticulum calcium release on calcium dynamics and action potential morphology in human atrial myocytes: a computational study. PLoS computational biology 7, e1001067.

Koncz, I., Szel, T., Bitay, M., Cerbai, E., Jaeger, K., Fulop, F., Jost, N., Virag, L., Orvos, P., Talosi, L., et al. (2011). Electrophysiological effects of ivabradine in dog and human cardiac preparations: potential antiarrhythmic actions. European journal of pharmacology 668, 419-426.

Lancaster, M. A., Renner, M., Martin, C. A., Wenzel, D., Bicknell, L. S., Hurles, M. E., Homfray, T., Penninger, J. M., Jackson, A. P., and Knoblich, J. A. (2013). Cerebral organoids model human brain development and microcephaly. Nature 501, 373-379.

Lee, J. H., Protze, S. I., Laksman, Z., Backx, P. H., and Keller, G. M. (2017). Human Pluripotent Stem Cell-Derived Atrial and Ventricular Cardiomyocytes Develop from Distinct Mesoderm Populations. Cell stem cell 21, 179-194 e174.

Lemoine, M. D., Krause, T., Koivumaki, J. T., Prondzynski, M., Schulze, M. L., Girdauskas, E., Willems, S., Hansen, A., Eschenhagen, T., and Christ, T. (2018). Human Induced Pluripotent Stem Cell-Derived Engineered Heart Tissue as a Sensitive Test System for QT Prolongation and Arrhythmic Triggers. Circulation Arrhythmia and electrophysiology 11, e006035.

Lemoine, M. D., Mannhardt, I., Breckwoldt, K., Prondzynski, M., Flenner, F., Ulmer, B., Hirt, M. N., Neuber, C., Horvath, A., Kloth, B., et al. (2017). Human iPSC-derived cardiomyocytes cultured in 3D engineered heart tissue show physiological upstroke velocity and sodium current density. Scientific reports 7, 5464.

Li, G. R., Feng, J., Wang, Z., Fermini, B., and Nattel, S. (1995). Comparative mechanisms of 4-aminopyridine-resistant Ito in human and rabbit atrial myocytes. The American journal of physiology 269, H463-472.

Lian, X., Hsiao, C., Wilson, G., Zhu, K., Hazeltine, L. B., Azarin, S. M., Raval, K. K., Zhang, J., Kamp, T. J., and Palecek, S. P. (2012). Robust cardiomyocyte differentiation from human pluripotent stem cells via temporal modulation of canonical Wnt signaling. Proceedings of the National Academy of Sciences of the United States of America 109, E1848-1857.

Lian, X., Zhang, J., Azarin, S. M., Zhu, K., Hazeltine, L. B., Bao, X., Hsiao, C., Kamp, T. J., and Palecek, S. P. (2013). Directed cardiomyocyte differentiation from human pluripotent stem cells by modulating Wnt/beta-catenin signaling under fully defined conditions. Nature protocols 8, 162-175.

Lind, J. U., Busbee, T. A., Valentine, A. D., Pasqualini, F. S., Yuan, H., Yadid, M., Park, S. J., Kotikian, A., Nesmith, A. P., Campbell, P. H., et al. (2017a). Instrumented cardiac microphysiological devices via multimaterial three-dimensional printing. Nature materials 16, 303-308.

Lind, J. U., Yadid, M., Perkins, I., O'Connor, B. B., Eweje, F., Chantre, C. O., Hemphill, M. A., Yuan, H., Campbell, P. H., Vlassak, J. J., et al. (2017b). Cardiac microphysiological devices with flexible thin-film sensors for higher-throughput drug screening. Lab on a chip 17, 3692-3703.

MacQueen, L. A., Sheehy, S. P., Chantre, C. O., Zimmerman, J. F., Pasqualini, F. S., Liu, X., Goss, J. A., Campbell, P. H., Gonzalez, G. M., Park, S.-J., et al. (2018). A tissue-engineered scale model of the heart ventricle. Nature Biomedical Engineering.

Mannhardt, I., Breckwoldt, K., Letuffe-Breniere, D., Schaaf, S., Schulz, H., Neuber, C., Benzin, A., Werner, T., Eder, A., Schulze, T., et al. (2016). Human Engineered Heart Tissue: Analysis of Contractile Force. Stem cell reports 7, 29-42. Martin, C., Sofia, A., Zhang, B. Y., Nunes, S. S., and Radisic, M. (2013). Fusible core molding for the fabrication of branched, perfusable, three-dimensional microvessels for vascular tissue engineering. Int J Artif Organs 36, 159-165.

Mathur, A., Loskill, P., Shao, K., Huebsch, N., Hong, S., Marcus, S. G., Marks, N., Mandegar, M., Conklin, B. R., Lee, L. P., et al. (2015). Human iPSC-based cardiac microphysiological system for drug screening applications. Scientific reports 5, 8883.

Messerli, F. H., Rimoldi, S. F., and Bangalore, S. (2017). The Transition From Hypertension to Heart Failure: Contemporary Update. JACC Heart failure 5, 543-551.

Money-Kyrle, A. R., Davies, C. H., Ranu, H. K., O'Gara, P., Kent, N. S., Poole-Wilson, P. A., and Harding, S. E. (1998). The role of cAMP in the frequency-dependent changes in contraction of guinea-pig cardiomyocytes. Cardiovascular research 37, 532-540.

Multani, M. M., Krombach, R. S., Hendrick, J. W., Baicu, S. C., Joffs, C., Sample, J. A., deGasparo, M., and Spinale, F. G. (2001). Long-term angiotensin-converting enzyme and angiotensin I-receptor inhibition in pacing-induced heart failure: effects on myocardial interstitial bradykinin levels. Journal of cardiac failure 7, 348-354.

Mummery, C., Ward-van Oostwaard, D., Doevendans, P., Spijker, R., van den Brink, S., Hassink, R., van der Heyden, M., Opthof, T., Pera, M., de la Riviere, A. B., et al. (2003). Differentiation of human embryonic stem cells to cardiomyocytes: role of coculture with visceral endoderm-like cells. Circulation 107, 2733-2740.

Nagueh, S. F., Shah, G., Wu, Y., Torre-Amione, G., King, N. M., Lahmers, S., Witt, C. C., Becker, K., Labeit, S., and Granzier, H. L. (2004). Altered titin expression, myocardial stiffness, and left ventricular function in patients with dilated cardiomyopathy. Circulation 110, 155-162.

Nunes, S. S., Miklas, J. W., Liu, J., Aschar-Sobbi, R., Xiao, Y., Zhang, B., Jiang, J., Masse, S., Gagliardi, M., Hsieh, A., et al. (2013). Biowire: a platform for maturation of human pluripotent stem cell-derived cardiomyocytes. Nature methods 10, 781-787.

O'Hara, T., Virag, L., Varro, A., and Rudy, Y. (2011). Simulation of the undiseased human cardiac ventricular action potential: model formulation and experimental validation. PLoS computational biology 7, e1002061.

Omens, J. H. (1998). Stress and strain as regulators of myocardial growth. Progress in biophysics and molecular biology 69, 559-572.

Oudit, G. Y., Kassiri, Z., Sah, R., Ramirez, R. J., Zobel, C., and Backx, P. H. (2001). The molecular physiology of the cardiac transient outward potassium current (I(to)) in normal and diseased myocardium. Journal of molecular and cellular cardiology 33, 851-872.

Park, I. H., Zhao, R., West, J. A., Yabuuchi, A., Huo, H., Ince, T. A., Lerou, P. H., Lensch, M. W., and Daley, G. Q. (2008). Reprogramming of human somatic cells to pluripotency with defined factors. Nature 451, 141-146.

Pimentel, H., Bray, N. L., Puente, S., Melsted, P., and Pachter, L. (2017). Differential analysis of RNA-seq incorporating quantification uncertainty. Nature methods 14, 687-690.

Radisic, M., Euloth, M., Yang, L., Langer, R., Freed, L. E., and Vunjak-Novakovic, G. (2003). High-density seeding of myocyte cells for cardiac tissue engineering. Biotechnol Bioeng 82, 403-414.

Ribeiro, M. C., Tertoolen, L. G., Guadix, J. A., Bellin, M., Kosmidis, G., D'Aniello, C., Monshouwer-Kloots, J., Goumans, M. J., Wang, Y. L., Feinberg, A. W., et al. (2015). Functional maturation of human pluripotent stem cell derived cardiomyocytes in vitro-correlation between contraction force and electrophysiology. Biomaterials 51, 138-150.

Riegler, J., Tiburcy, M., Ebert, A., Tzatzalos, E., Raaz, U., Abilez, O. J., Shen, Q., Kooreman, N. G., Neofytou, E., Chen, V. C., et al. (2015). Human Engineered Heart Muscles Engraft and Survive Long Term in a Rodent Myocardial Infarction Model. Circulation research 117, 720-730.

Ronaldson-Bouchard, K., Ma, S. P., Yeager, K., Chen, T., Song, L., Sirabella, D., Morikawa, K., Teles, D., Yazawa, M., and Vunjak-Novakovic, G. (2018). Advanced maturation of human cardiac tissue grown from pluripotent stem cells. Nature 556, 239-243.

Ruan, J. L., Tulloch, N. L., Razumova, M. V., Saiget, M., Muskheli, V., Pabon, L., Reinecke, H., Regnier, M., and Murry, C. E. (2016). Mechanical Stress Conditioning and Electrical Stimulation Promote Contractility and Force Maturation of Induced Pluripotent Stem Cell-Derived Human Cardiac Tissue. Circulation 134, 1557-1567.

Sala, L., Bellin, M., and Mummery, C. L. (2016). Integrating cardiomyocytes from human pluripotent stem cells in safety pharmacology: has the time come? British journal of pharmacology.

Santini, M., and Ricci, R. (2001). Atrial fibrillation coexisting with ventricular tachycardia: a challenge for dual chamber defibrillators. Heart 86, 253-254.

Saxena, P. R., and Villalon, C. M. (1990). Cardiovascular effects of serotonin agonists and antagonists. Journal of cardiovascular pharmacology 15 Suppl 7, S17-34.

Schaaf, S., Shibamiya, A., Mewe, M., Eder, A., Stohr, A., Hirt, M. N., Rau, T., Zimmermann, W. H., Conradi, L., Eschenhagen, T., et al. (2011). Human engineered heart tissue as a versatile tool in basic research and preclinical toxicology. PloS one 6, e26397.

Semsarian, C., Ahmad, I., Giewat, M., Georgakopoulos, D., Schmitt, J. P., McConnell, B. K., Reiken, S., Mende, U., Marks, A. R., Kass, D. A., et al. (2002). The L-type calcium channel inhibitor diltiazem prevents cardiomyopathy in a mouse model. The Journal of clinical investigation 109, 1013-1020.

Shim, J., Grosberg, A., Nawroth, J. C., Parker, K. K., and Bertoldi, K. (2012). Modeling of cardiac muscle thin films: pre-stretch, passive and active behavior. Journal of biomechanics 45, 832-841.

Sidorov, V. Y., Samson, P. C., Sidorova, T. N., Davidson, J. M., Lim, C. C., and Wikswo, J. P. (2017). I-Wire Heart-on-a-Chip I: Three-dimensional cardiac tissue constructs for physiology and pharmacology. Acta biomaterialia 48, 68-78.

Toepke, M. W., and Beebe, D. J. (2006). PDMS absorption of small molecules and consequences in microfluidic applications. Lab on a chip 6, 1484-1486.

Tran, R. T., Thevenot, P., Gyawali, D., Chiao, J. C., Tang, L., and Yang, J. (2010). Synthesis and characterization of a biodegradable elastomer featuring a dual crosslinking mechanism. Soft matter 6, 2449-2461.

Tulloch, N. L., Muskheli, V., Razumova, M. V., Korte, F. S., Regnier, M., Hauch, K. D., Pabon, L., Reinecke, H., and Murry, C. E. (2011). Growth of engineered human myocardium with mechanical loading and vascular coculture. Circulation research 109, 47-59.

van der Hooft, C. S., Heeringa, J., van Herpen, G., Kors, J. A., Kingma, J. H., and Stricker, B. H. (2004). Drug-induced atrial fibrillation. Journal of the American College of Cardiology 44, 2117-2124.

van Meer, B. J., de Vries, H., Firth, K. S. A., van Weerd, J., Tertoolen, L. G. J., Karperien, H. B. J., Jonkheijm, P., Denning, C., AP, I. J., and Mummery, C. L. (2017). Small molecule absorption by PDMS in the context of drug response bioassays. Biochemical and biophysical research communications 482, 323-328.

Venugopal, J. R., Prabhakaran, M. P., Mukherjee, S., Ravichandran, R., Dan, K., and Ramakrishna, S. (2012). Biomaterial strategies for alleviation of myocardial infarction. Journal of the Royal Society, Interface 9, 1-19.

Vicente, J., Johannesen, L., Mason, J. W., Crumb, W. J., Pueyo, E., Stockbridge, N., and Strauss, D. G. (2015). Comprehensive T wave morphology assessment in a randomized clinical study of dofetilide, quinidine, ranolazine, and verapamil. Journal of the American Heart Association 4.

Wang, G., McCain, M. L., Yang, L., He, A., Pasqualini, F. S., Agarwal, A., Yuan, H., Jiang, D., Zhang, D., Zangi, L., et al. (2014). Modeling the mitochondrial cardiomyopathy of Barth syndrome with induced pluripotent stem cell and heart-on-chip technologies. Nature medicine 20, 616-623.

Williams, R. R., Rao, D. C., Ellison, R. C., Arnett, D. K., Heiss, G., Oberman, A., Eckfeldt, J. H., Leppert, M. F., Province, M. A., Mockrin, S. C., et al. (2000). NHLBI family blood pressure program: methodology and recruitment in the HyperGEN network. Hypertension genetic epidemiology network. Annals of epidemiology 10, 389-400.

Yang, L., Soonpaa, M. H., Adler, E. D., Roepke, T. K., Kaltman, S. J., Kennedy, M., Henckaerts, E., Bonham, K., Abbott, G. W., Linden, R. M., et al. (2008). Human cardiovascular progenitor cells develop from a KDR+ embryonic-stem-cell-derived population. Nature 453, 524-528.

Yang, X., Pabon, L., and Murry, C. E. (2014). Engineering adolescence: maturation of human pluripotent stem cell-derived cardiomyocytes. Circulation research 114, 511-523.

Zang, W. J., Chen, L. N., Yu, X. J., Fang, P., Lu, J., and Sun, Q. (2005). Comparison of effects of acetylcholine on electromechanical characteristics in guinea-pig atrium and ventricle. Experimental physiology 90, 123-130.

Zhang, B., Montgomery, M., Chamberlain, M. D., Ogawa, S., Korolj, A., Pahnke, A., Wells, L. A., Masse, S., Kim, J., Reis, L., et al. (2016). Biodegradable scaffold with built-in vasculature for organ-on-a-chip engineering and direct surgical anastomosis. Nature materials 15, 669-678.

Example 3

We investigated the impact of four microenvironmental cues: cell seeding density, types and percentages of non-myocyte populations, the types of hydrogels used for tissue inoculation and the electrical conditioning regimes on the structural and functional assembly of human pluripotent stem cell-derived cardiac tissues. Utilizing a heart-on-a-chip system that is capable of continuous non-invasive monitoring of tissue contractions, we were able to study how different micro-environmental cues affect the assembly of the cardiomyocytes into a functional cardiac tissue. We have defined conditions that resulted in tissues exhibiting hallmarks of the mature human myocardium, such as positive force-frequency relationship and post-rest potentiation.

Our goal here was to characterize and optimize a user-friendly organ-on-a-chip platform for the cultivation of human pluripotent stem cell-derived cardiac tissues. Unlike common organ-on-a-chip platforms, the described chip is constructed of tissue culture polystyrene and flexible polymer wires that enable on-line tracking of contraction force. The platform, termed Biowire II, has open access for liquid dispensing and enables the creation of cylindrical cardiac microtissues suspended at a constant height. Here, we comprehensively explored different culture conditions including seeding density, non-myocyte populations, hydrogel scaffolds and electrical stimulation protocols to define a more controlled seeding and cultivation protocol engineering a mature, functional myocardial tissue that is ideal for drug testing and discovery applications.

Biowire II platform enables efficient use of stem cell-derived cardiomyocytes.

The Biowire II chip is a strip of patterned tissue culture plastic with eight rectangular microwells for cell seeding and tissue formation (FIG. 15B). The chip was made of polystyrene, commonly used tissue culture substrate, with two parallel poly(octamethylene maleate (anhydride) citrate) (POMaC) wires affixed at either end of the microwells with a small amount of low absorption adhesive. These wires allow tissues to attach and their displacement is used to estimate passive and active tension generation by the tissues.

Figure 16A:
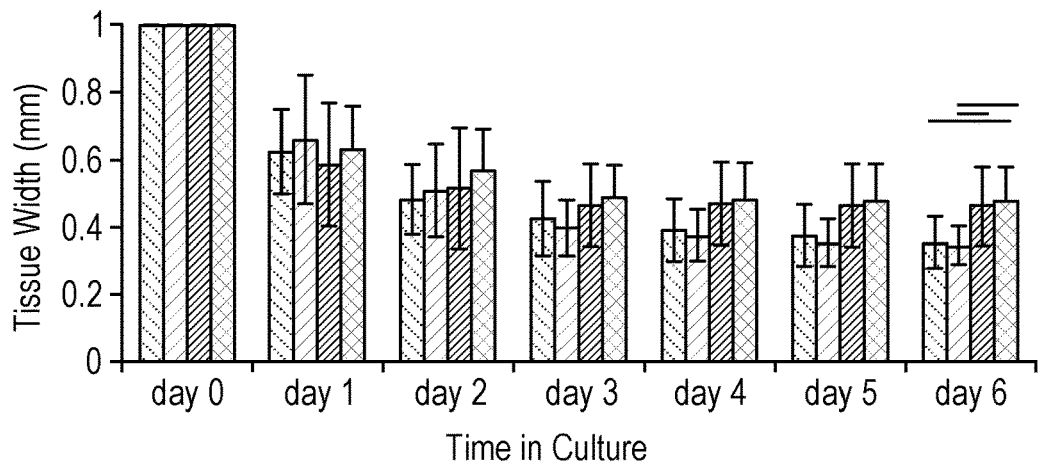

The dimensions of the tissue culture microwells (5 mm×1 mm×300 µm, L×W×H) were uniquely designed to contain small amounts of cells and facilitate tissue formation. The seeded cells remodel the matrix over the first week of culture, compacting the structure and creating a cylindrical tissue affixed to the polymer wire at each end. As the input cell number increased according to the following groups: 0.05, 0.1, 0.2, 0.3 million cells/tissue by varying the cell seeding density (25, 50, 100, 150 million/mL), we observed that more compaction of the hydrogel by the cells occurred in the 25 and 50 million/mL groups and less in the 100 and 150 million/mL groups (FIG. 16A).

Figure 16B:
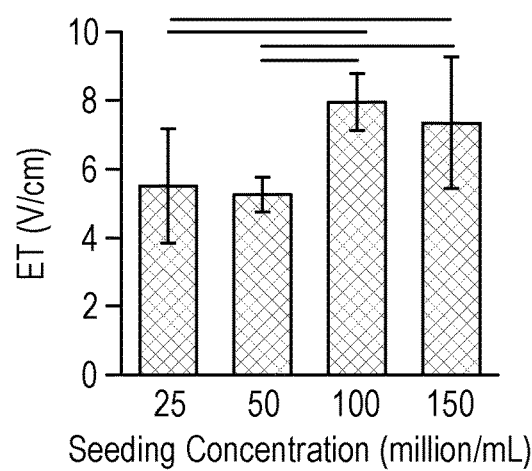
Figure 16C:
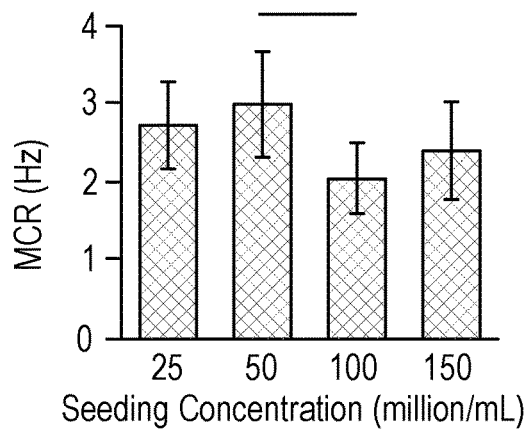

To monitor maturation and the quality of our tissues, we measured ET and MCR on day 6 after seeding, at which time the tissues had undergone cell-gel compaction. Tissues in the 25 and 50 million/mL groups had significantly lower ET than the ones in the 100 and 150 million/mL groups (FIG. 16B). In addition, 50 million/mL group had significantly higher MCR compared to the 100 million/mL group (FIG. 16C).

Figure 16D:
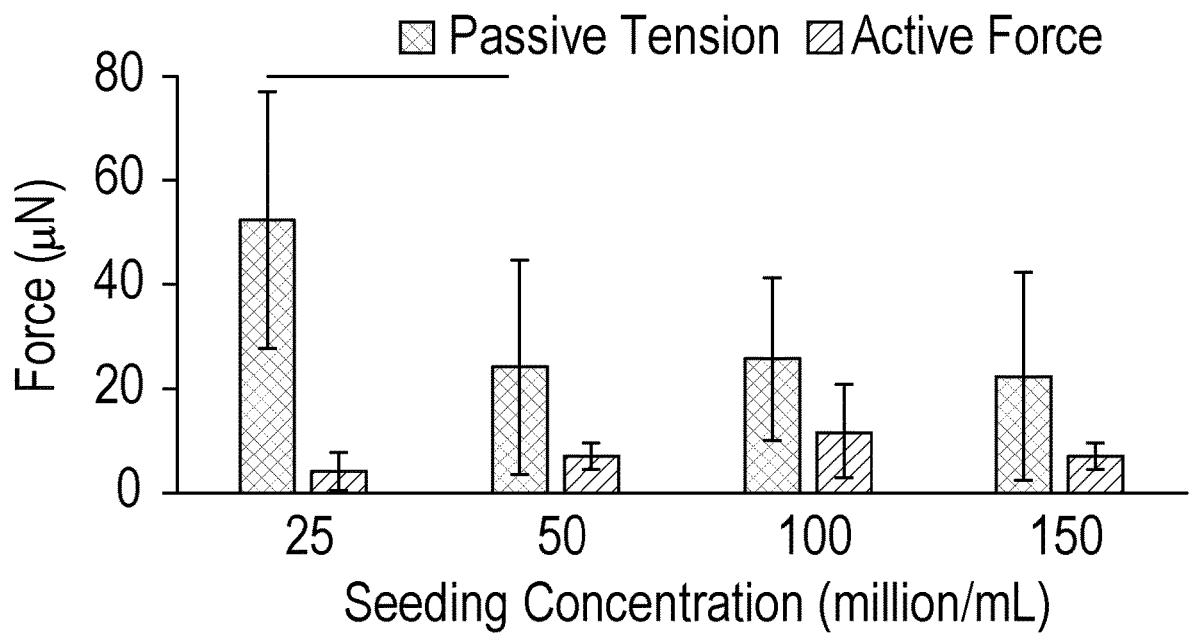
Figure 16E:
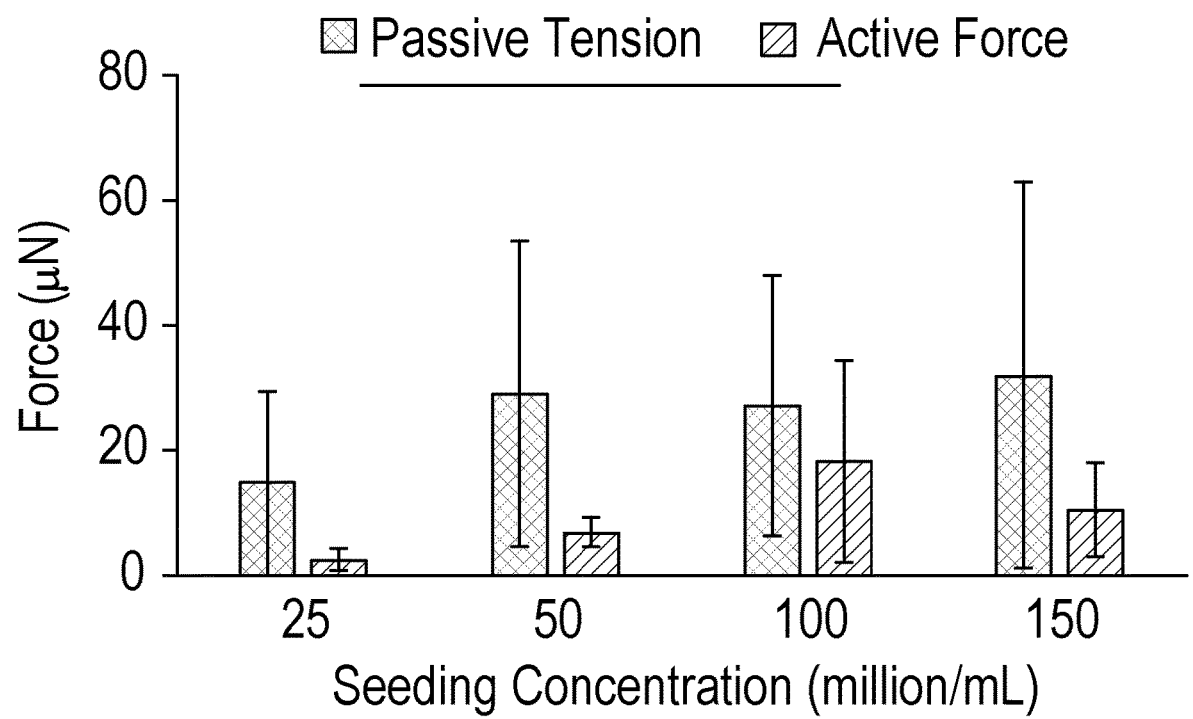
Figure 16F:
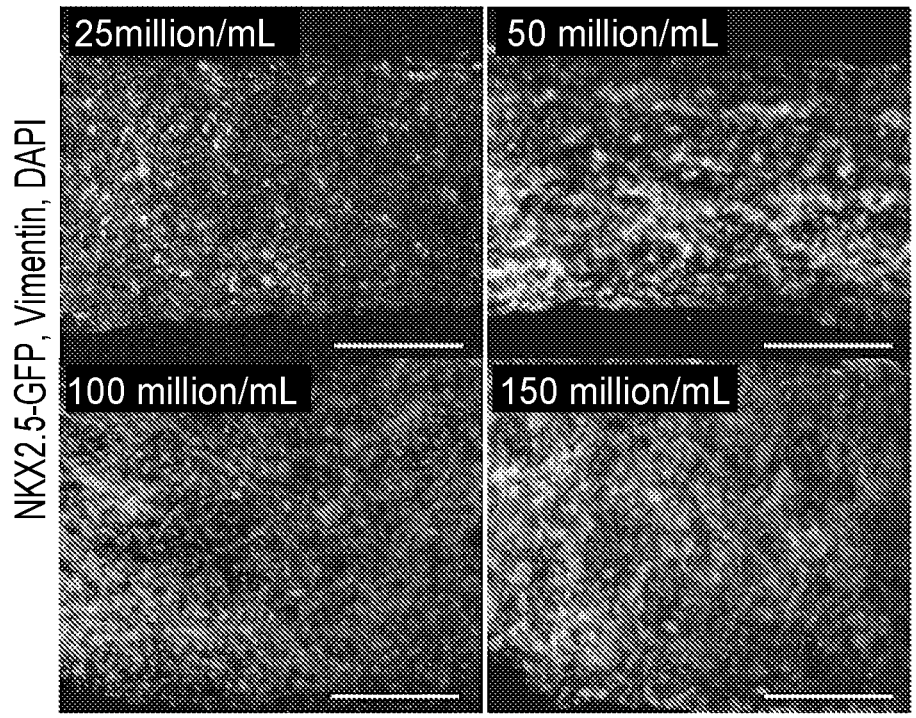

Tissues from the lowest seeding density exhibited the highest passive tension on day 7 (FIG. 16D). After 30 days of culture, passive tension was comparable in all groups (FIG. 16E). Active forces were the lowest in 25 million/mL group, which was significantly lower compared to the group of 100 million/mL.

Figure 16G:
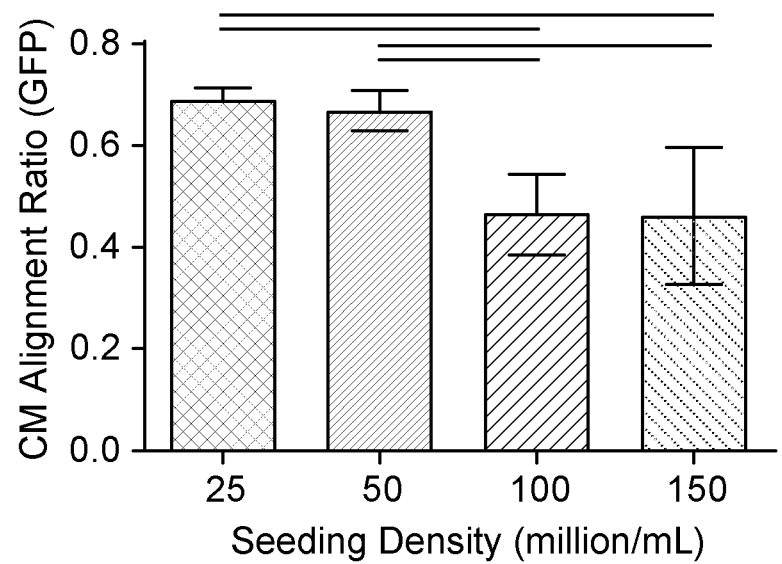

Confocal imaging of GFP labeled CMs, facilitated through the use of HES3-NKX2-5eGFP/w and Vimentin labeled non-cardiomyocyte populations, at day 7 (FIG. 16F), enabled us to quantify the cellular alignment of CMs in tissues of various groups (FIG. 16G). Quantitative analysis of GFP signal confirmed that groups seeded with 25 and 50 million cells/mL exhibited significantly better cellular alignment in compacted tissues compared to the groups seeded with 100 and 150 million cells/mL (FIG. 16G).

Figure 16H:
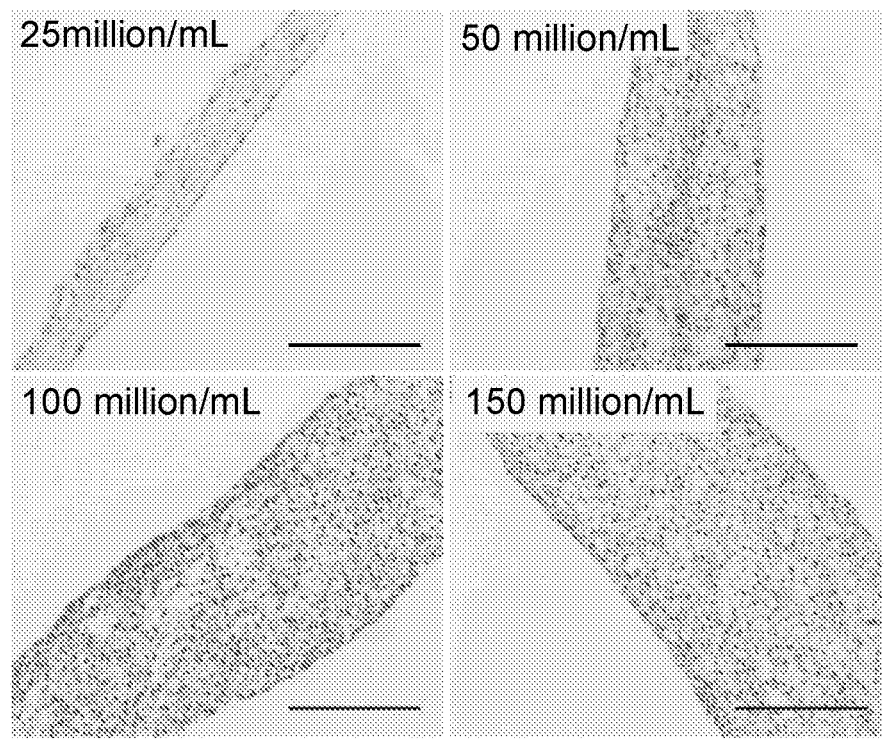
Figure 16I:
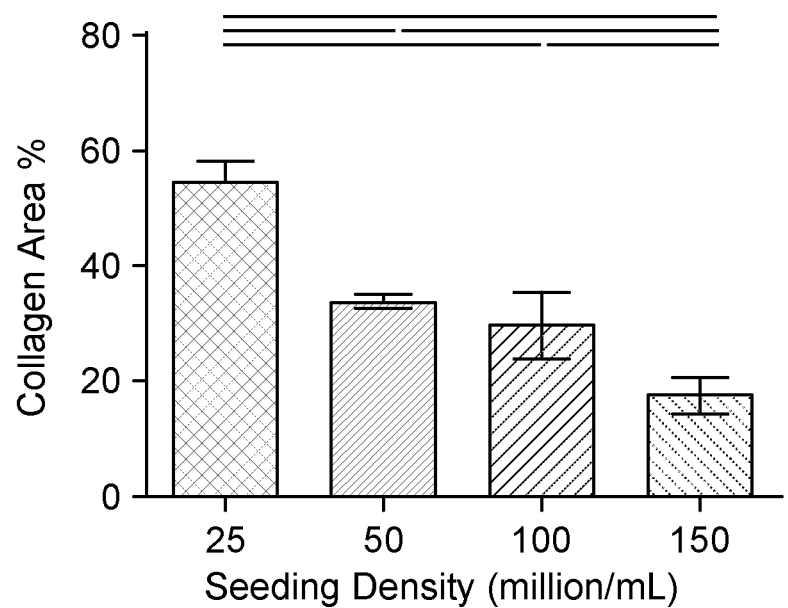

Mason's trichrome staining revealed the more pronounced presence of collagen in the tissues at the lower seeding densities after 30 days of culture (FIG. 16H). As expected, the lowest cell density group, the group of 25 million/mL, appeared to be the least cellular, consistent with the lowest active forces. Tissues seeded at a higher density exhibited lower collagen presence, without any visible collagen islands, as more cells can facilitate better remodeling of the collagen hydrogel used for seeding (FIG. 16I). More importantly, the yield of cells in the tissue after 30 days of culture was the lowest in the 25 million/mL group, at 31% of the seeded cell number, and comparable in all other groups at 75%-106% of the seeded cell number (FIG. 21). However, increasing cell number per tissue failed to yield higher active forces, thus motivating the use of lower cell numbers to maintain overall process efficiency.

One of the main goals of this work was to create a tissue with a minimal cell number to facilitate higher throughput studies in drug discovery. Engineered cardiac tissues often require 0.5-2 million CMs per tissue, motivating the work towards cell number optimization in order to create smaller tissues that require fewer cells, therefore, reducing the overall cost of the preparation and evaluation. We also sought to establish that this platform is effective when using cardiomyocytes derived from several sources (iPSCs and ESCs) as well as to demonstrate the properties of biowires generated from ventricular versus atrial cardiomyocytes derived from these stem cell source. Based on our findings, tissues with a seeding density of 50 million/mL (~0.1 million cells), exhibit better cellular alignment and absence of visible collagen islands, that are characteristic of a healthy myocardium in vivo, compared to the 25 million/mL group. In addition, the group seeded with 50 million/mL cells exhibited relatively high active forces throughout the entire culture period, comparable to those generated by seeding 100 and 150 million/mL. Therefore, we have kept our engineer cardiac tissues at a 50 million/mL seeding density to investigate how other micro-environmental cues affect the functional assembly of cardiac tissues.

Comparison of MSC and cFB as a Non-Myocyte Population

In cardiac tissue engineering, non-myocytes, such as MSCs or cFBs have been commonly added to the engineered ventricular tissues to help with the tissue formation in the short term and remodeling in the long term. As non-contracting and proliferating cells, FBs were considered undesirable during early cardiac tissue engineering studies and were routinely removed by a series of pre-plating steps. Over time tissue engineers learned to harness the power of FBs by introducing them strategically in defined percentages during co-culture with ventricular CMs, to obtain ventricular engineered cardiac tissues with enhanced structural and functional properties and an enhanced ability to survive in vivo. Alternatively, mesenchymal cell types such as MSCs have also be used to enhance the outcome of ventricular tissue engineering. No differences were observed in the functional outcome when either FBs or MSCs have been used previously in ventricular tissue engineering. In the context of ventricular cardiac tissues based on hESC-derived CMs, we also demonstrated enhanced matrix remodelling and functional properties in cultures with 75% CMs and 25% hESC-derived CD90+ mesodermal cells. Most recent studies describing the generation of atrial tissues used human foreskin or cardiac FBs or no additional non-myocytes, thus systematic comparison of FBs to MSC have not been made previously for atrial tissues, motivating our investigation here.

Figure 17A:
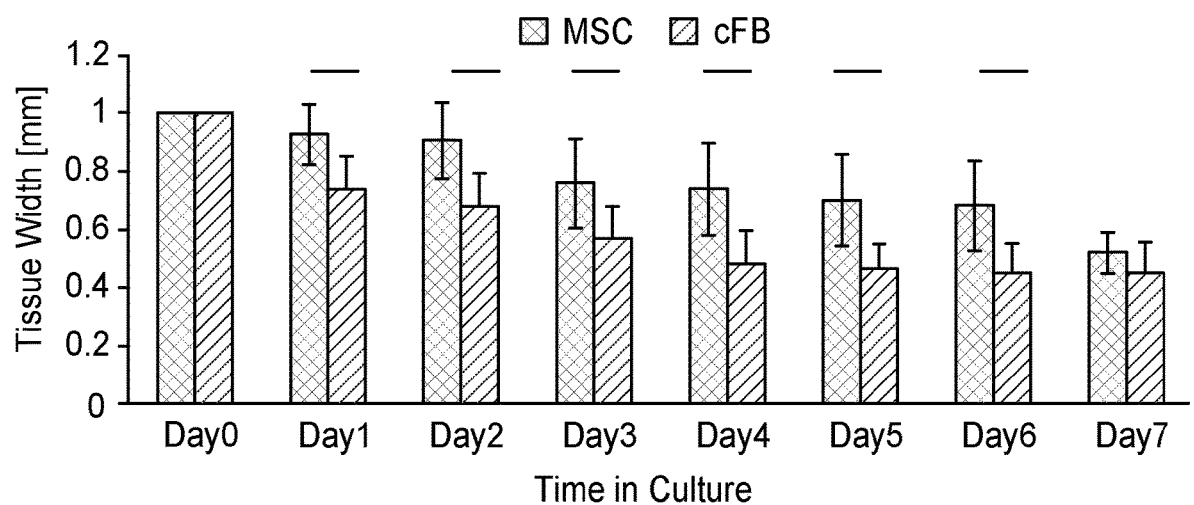
Figure 17B:
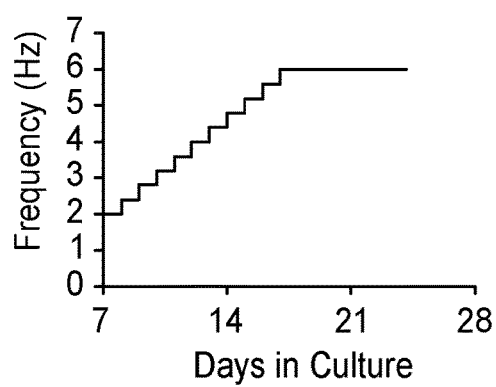
Figure 17C:
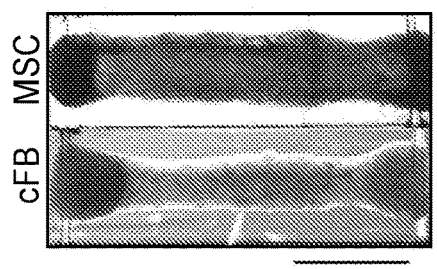
Figure 17D:
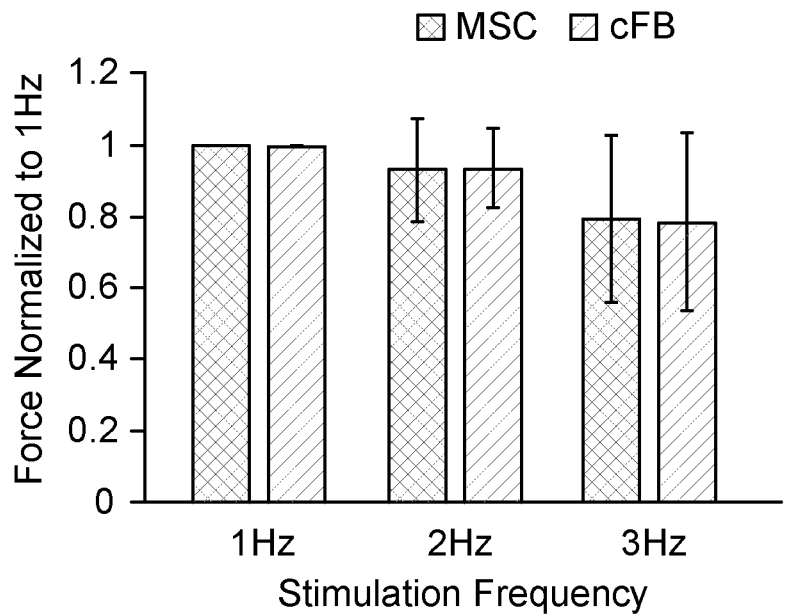
Figure 17E:
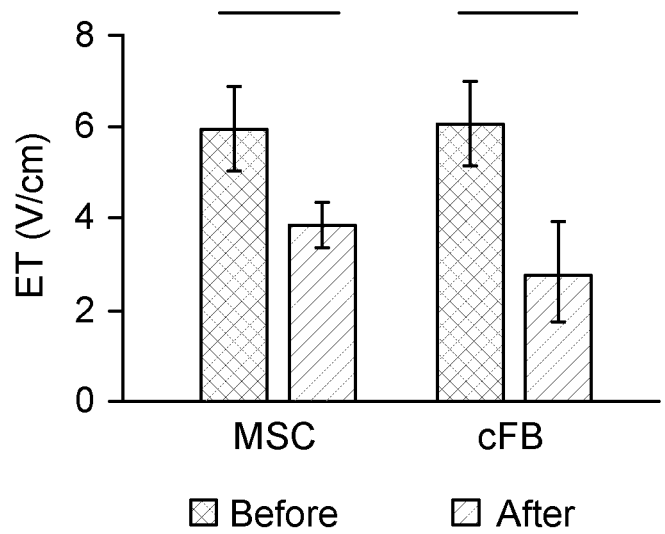
Figure 17F:
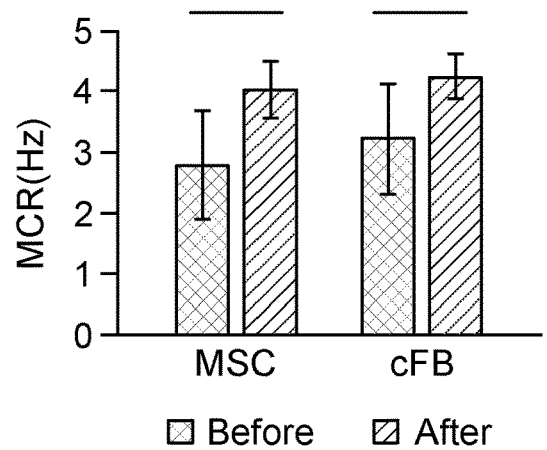

Initially, the compaction of tissues generated with MSCs was delayed compared to tissues with cFBs; however, by day 7 there were no measurable differences between the two sets of tissues (FIG. 17A). After day 7, both groups experienced electrical conditioning with an atrial specific protocol (FIG. 17B). At the end of cultivation, both tissue types exhibited a densely compacted appearance as shown in FIG. 17C. The non-myocyte population did not affect the FFR relationship, as equivalent values (FIG. 17D) were obtained. ET and MCR (FIGS. 17E and 17F) were improved remarkably with electrical conditioning during culture in both groups, without a significant difference between the MSC and the cFB group at either time point.

Figure 17G:
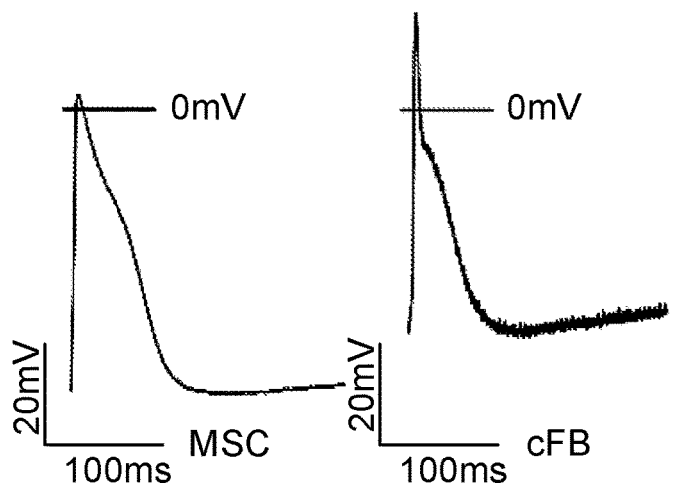
Figure 17H:
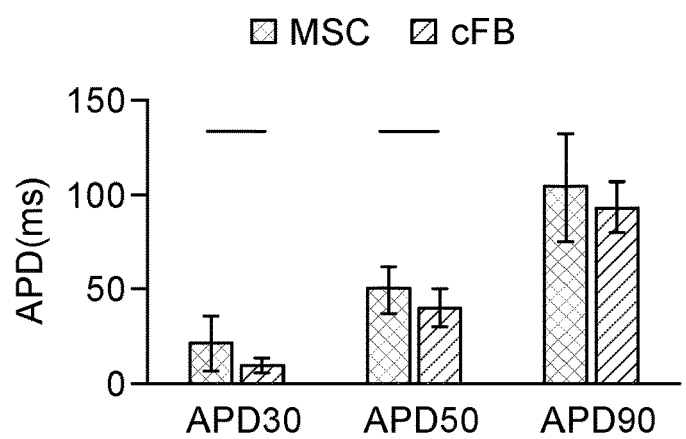
Figure 17I:
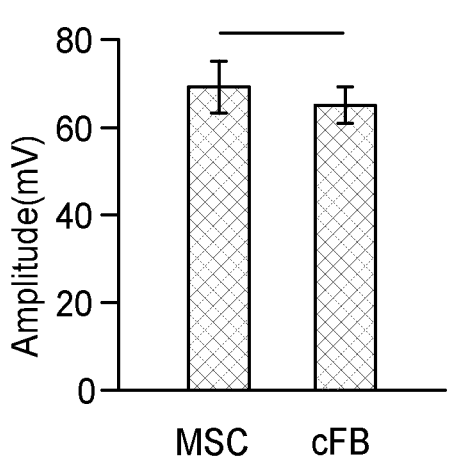
Figure 17J:
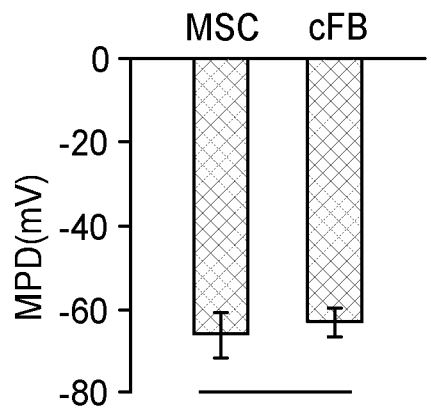
Figure 17K:
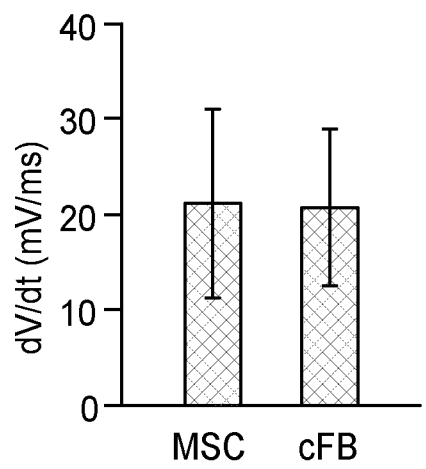

The two tissue groups exhibited differences in their action potential profiles (FIG. 17G). CMs in the tissues with cFB had a significantly shorter APD30 and APD50 than the CMs with MSCs, which is a hallmark of functional improvement for atrial CMs (FIG. 17H). CMs in the tissues with cFBs had significantly lower amplitude (FIG. 17I), less negative minimum diastolic potentials (FIG. 17J) and similar upstroke velocity (FIG. 17K) compared to the tissues with MSCs.

Cell-mediated compaction of the extracellular matrix (ECM) is an important modulator in tissue engineering, yet different cell types may influence the function of the tissues at the endpoint. Despite both MSCs and cFBs facilitate similar tissue formation, our results indicate that the effect of non-myocytes is more complex in terms of action potential properties. Furthermore, MSCs exhibit plasticity and the extent of integration and coupling to CMs is unknown. By contrast, cFBs exist in native myocardium and are electrically coupled with CMs through gap junctions which has been shown in mathematical modeling studies to modulate the electrical properties of the myocardium.

cFB percentage influences tissue function.

Figure 18A:
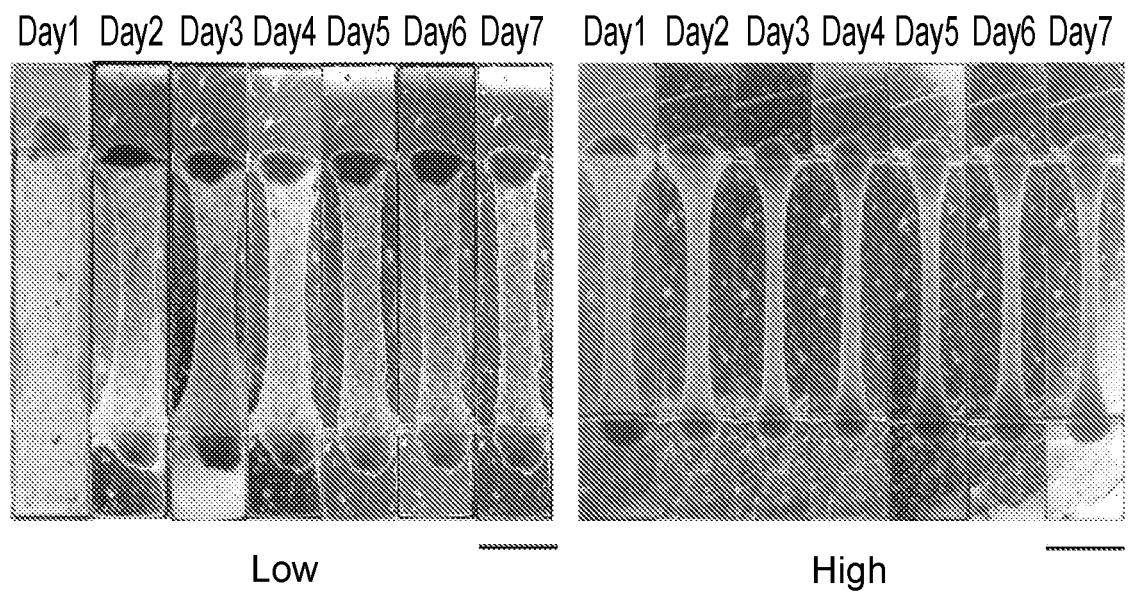
Figure 18B:
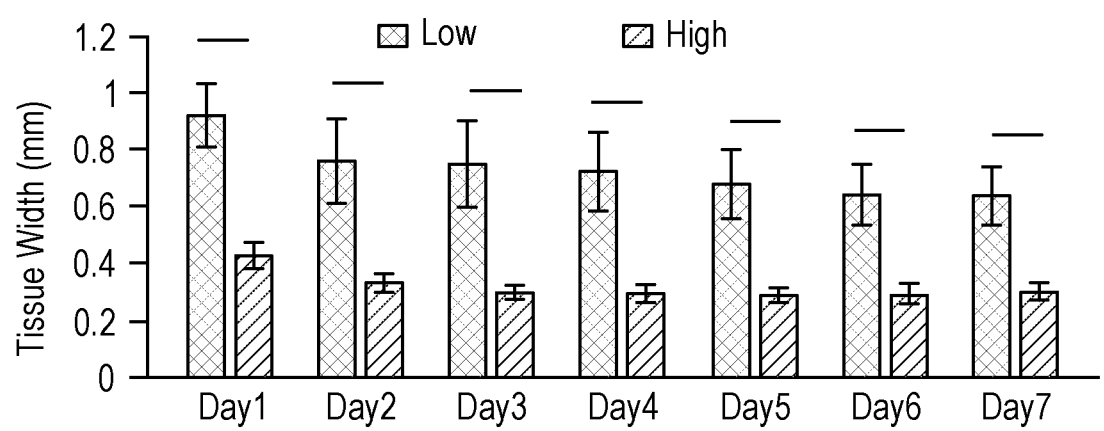
Figure 18C:
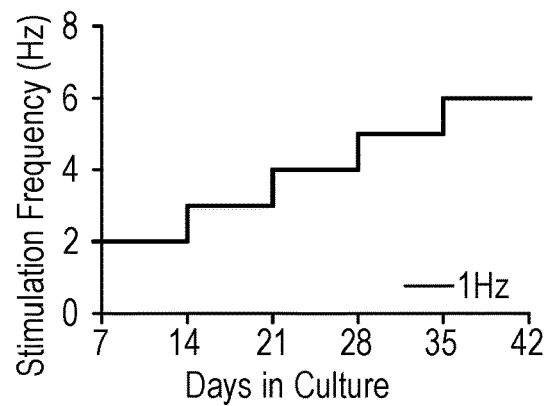
Figure 18D:
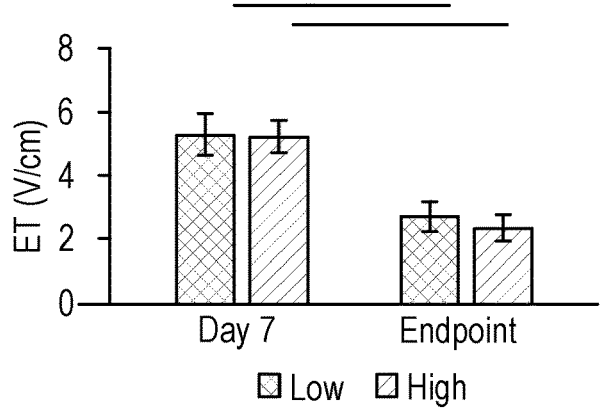
Figure 18E:
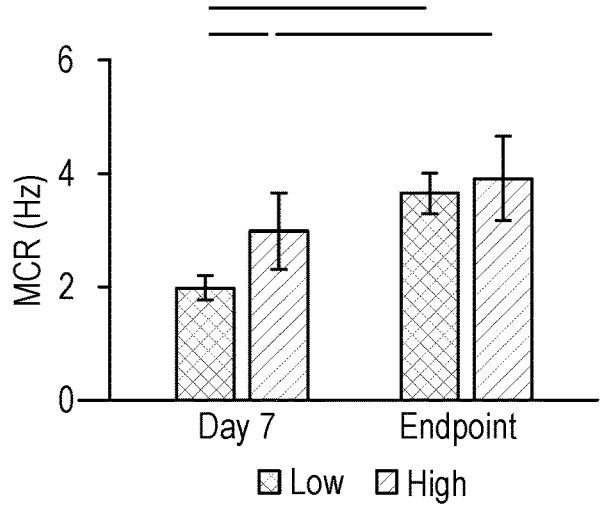

In addition to the non-myocyte population type, studies have shown that the percentage of non-myocytes within the microenvironment can also significantly influence the tissue function. Because of the heterogeneous nature of the cell population obtained directly from the ventricular differentiation culture, the CM population (NKX2.5+) was accounted for 76.1±13.0% of total cells on average. The remaining cells were non-myocytes. Here, we compared cardiac tissue function in tissues seeded with either 10% or 25% of additional cFBs in ventricular preparations to facilitate tissue remodeling. Therefore, total non-myocyte population vs. CM was actually equivalent to 3:7 in tissues with 10% additional cFB, i.e. low cFB group, and 4:6 in tissues with 25% additional cFB i.e. high cFB group. The initial 7-day compaction was significantly faster in the high cFB group (FIGS. 18A and 18B). After electrical conditioning (FIG. 18C), ET and MCR were significantly improved in both groups (FIGS. 18D and 18E). Positive FFR is a hallmark of human adult ventricular myocardium, whereas flat FFR is observed in the myocardium of newborns. Recent studies describe the first cultivated engineered cardiac tissue with positive FFR and a remarkable maturation level. Thus, achieving positive FFR became one of the important criteria to evaluate tissue function in our studies.

Figure 18F:
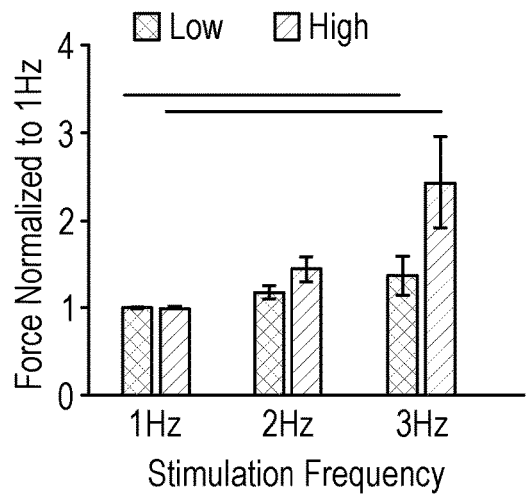
Figure 18G:
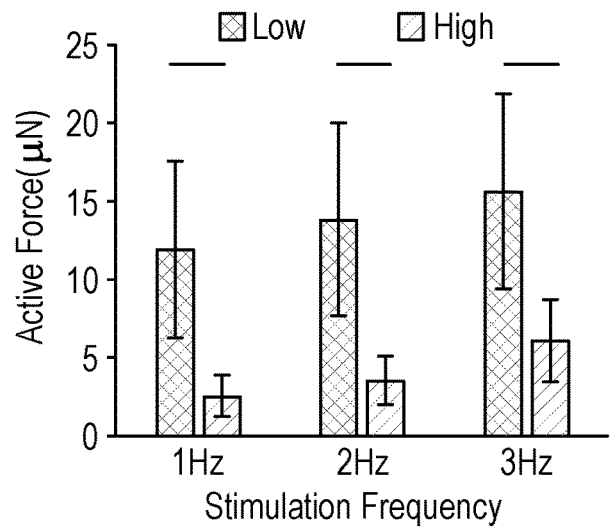
Figure 18H:
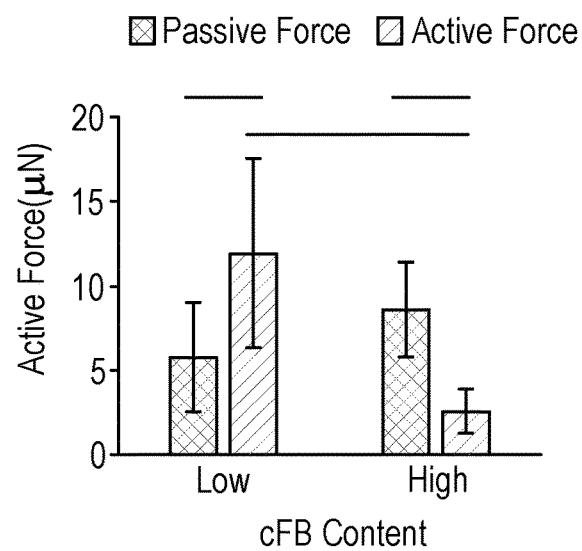

Here, a positive FFR was achieved for both the low cFB and high cFB group after electrical conditioning (FIG. 18F). Importantly, active forces from the low cFB group were significantly higher than those of the high cFB group when paced at the same frequency (FIG. 18G) with roughly 3-4 fold difference. This difference in the active force was achieved with the same number of seeded CMs, suggesting that the CMs in the tissues with low cFB have higher efficiency in their contractile machinery likely due to the improved electromechanical connectivity and mechanical coupling. Moreover, tissues from the low cFB group have significantly higher active forces than passive tensions, unlike the opposite trend from high cFB group (FIG. 18H). Higher active forces result in higher displacements of the polymer wire, which provides more accurate active force readouts from the platform.

Due to the nature of our system, the tissue experiences higher tension along the longitudinal direction of the microwell during remodeling, which facilitates the uniaxial contraction (FIG. 22). Previous studies suggest that cFBs can sense and align with this tension and therefore facilitate the alignment of CMs. Without adding cFBs to the tissue, the low level of cellular reorganization during the first week led to the formation of a thin film of CM sheet with minimal tissue contraction (FIG. 23). Previous studies also show that at low fibroblast density, impulse propagation in cardiac tissues is sustained when CMs couple to more depolarized fibroblasts. In our case, the preferred non-myocyte population is approximately 30% (low cFB group), which is consistent with other studies. However, a further increase in the fibroblast number within the tissue is thought to promote conduction blocks in the areas covered with large fibroblast numbers, thus increasing the tissue stiffness and slowing down conduction. Our results here are consistent with those findings.

Slower electrical conditioning improves tissue function and consistency.

Figure 19A:
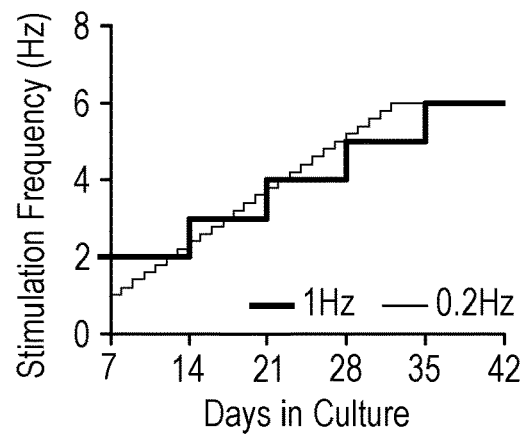
Figure 19B:
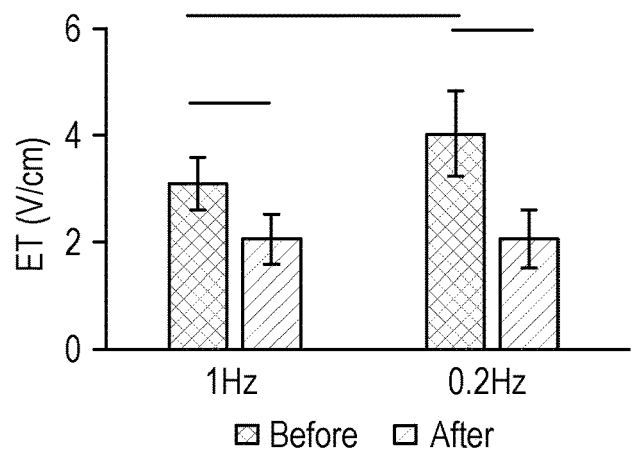
Figure 19C:
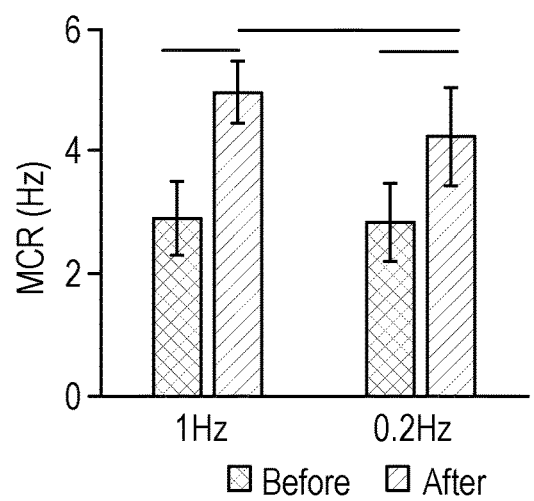
Figure 19D:
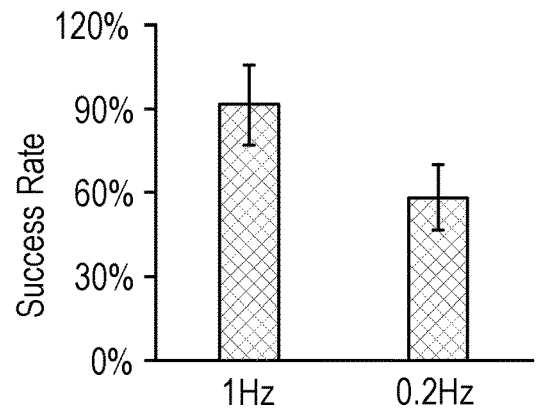
Figure 19E:
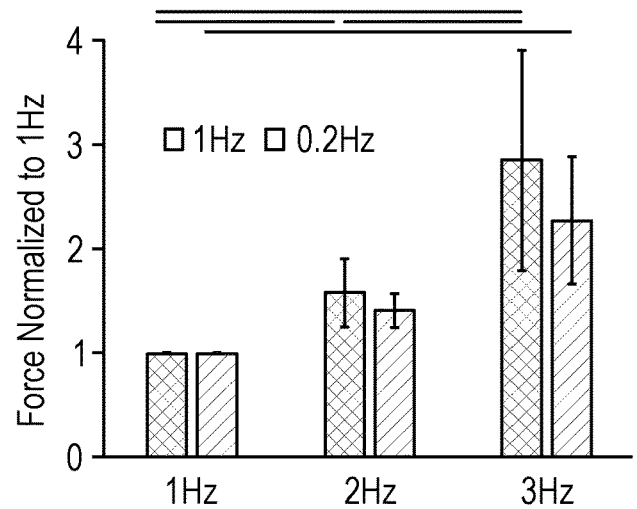

Progressive increase in the frequency of electrical conditioning is proven to be useful for cardiac tissue functional development. Here, we compared two conditioning protocols with different intensity of frequency increase: suprathreshold electrical conditioning of 1 Hz weekly step-up and 0.2 Hz daily step-up (FIG. 19A). ETs (FIG. 19B) were significantly decreased in both groups with electrical conditioning reaching approximately the same levels. MCRs increased after electrical conditioning in both groups. In addition, at the end of electrical conditioning MCR in the 1 Hz group was significantly higher than the MCR in the 0.2 Hz group (FIG. 19C). Similarly, the success rate for tissues to achieve positive FFR were also slightly higher in the 1 Hz than the 0.2 Hz group (FIG. 19D). The results were potentially due to the faster overall frequency step-up in 0.2 Hz group (equivalent to 1.4 Hz/week) compared to the 1 Hz group (1 Hz/week).

Figure 19F:
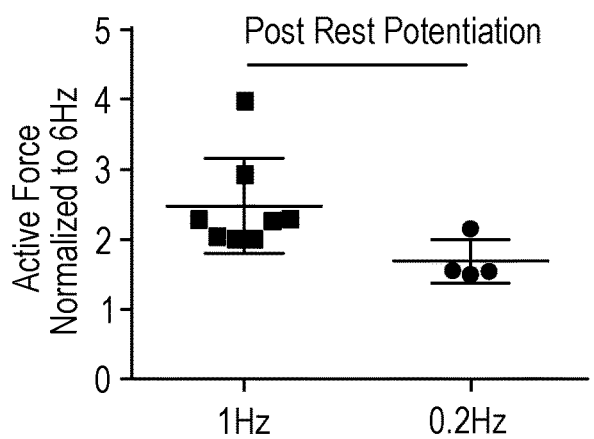
Figure 19G:
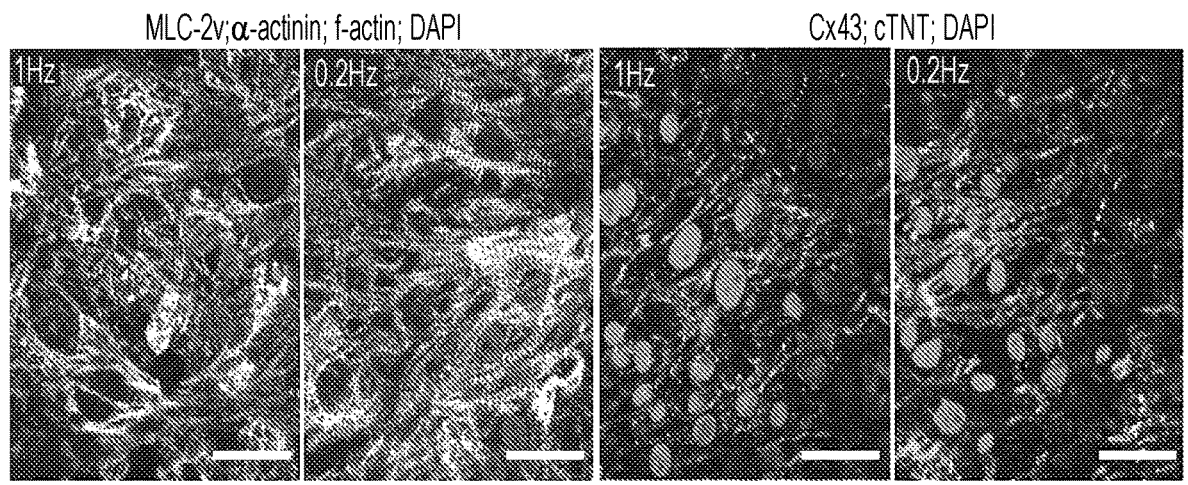
Figure 19H:
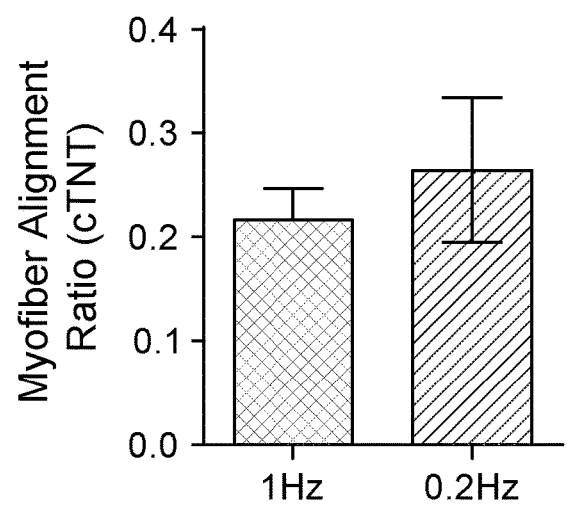

During the frequency ramp-up protocol, conceptually it is important for the tissue to capture the applied pacing frequency. Therefore, slower step-up may be more beneficial. Pronounced positive FFR from 1-3 Hz was observed in both groups without any significant difference (FIG. 19E), however, the percent of tissues able to achieve this at the end of the conditioning protocol was lower in the 0.2 Hz group compared to the 1 Hz group, which suggested that 0.2 Hz per day of frequency increase would be too fast for all tissues to achieve desired functional improvement (FIG. 19D). Post-rest potentiation (PRP) of force is another hallmark of the adult myocardium in addition to positive FFR. The PRP indicates the capacity of the sarcoplasmic reticulum (SR) in CMs to store, efficiently release and subsequently replenish $Ca2+$. Both of our stimulation protocols are able to generate tissues with positive FFR. However, tissues from the 1 Hz group developed a higher PRP than those of the 0.2 Hz group (FIG. 19F). Confocal images of MLC 2v, sarcomeric α-actinin, F-actin, cTNT and Cx43 demonstrated no appreciable differences between the groups (FIGS. 19G and 19H). Based on the improvements in the success rate and the functional properties, a weekly 1 Hz step-wise electrical conditioning may be a better approach in further studies.

Collagen/Fibrin hydrogel blend improves the intracellular organization.

Figure 20B:
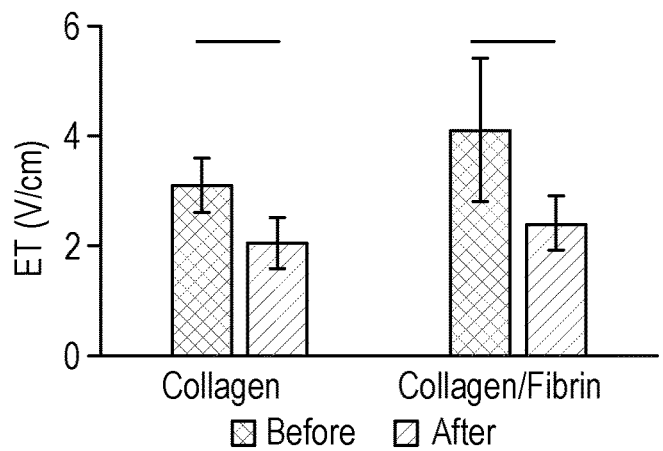
Figure 20C:
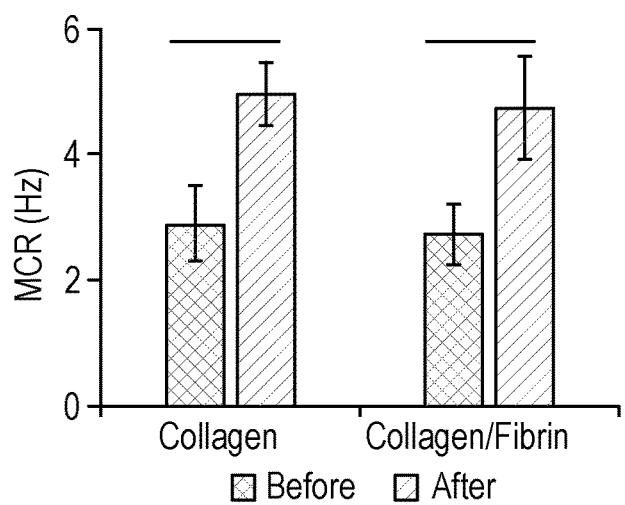
Figure 20D:
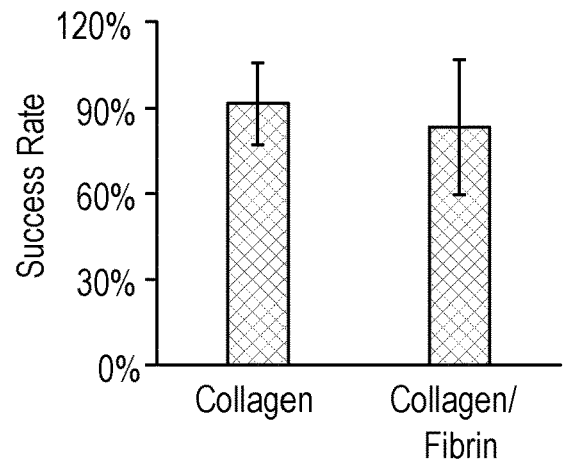

In cardiac tissue engineering, hydrogels are primarily used to immobilize cells right after seeding and maximize cardiomyocyte viability by providing structural and mechanical support as well as a biological niche for tissue assembly. Notable recent approaches managed to eliminate the use of hydrogels. However, in our system, the opening of the microwell is too large to enable successful tissue compaction and stabilization in the absence of hydrogels. Here, tissues seeded with Collagen hydrogel or Collagen/Fibrin hydrogel, two commonly used hydrogels in cardiac tissue engineering, were compared after conditioning with the 1 Hz step-up protocol (FIG. 20A). Tissues based on Collagen or a combined Collagen/Fibrin gel developed equivalent ET and MCR (FIGS. 20B, 20C). Success rate determined by the percentage of tissues that reached a positive FFR at the end of cultivation, was also equivalent between the two hydrogel groups (FIG. 20D).

Figure 20E:
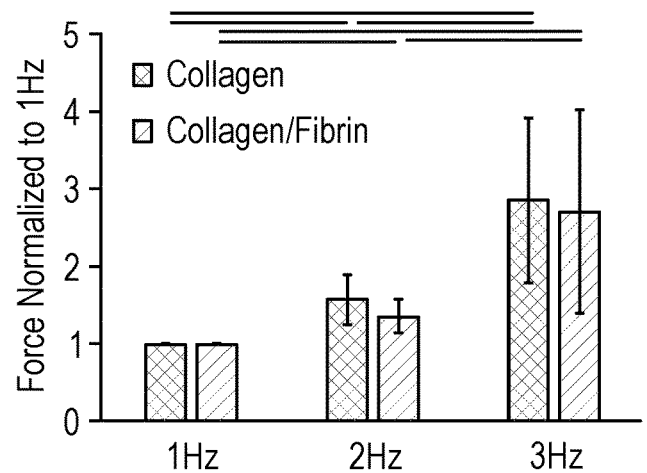
Figure 20F:
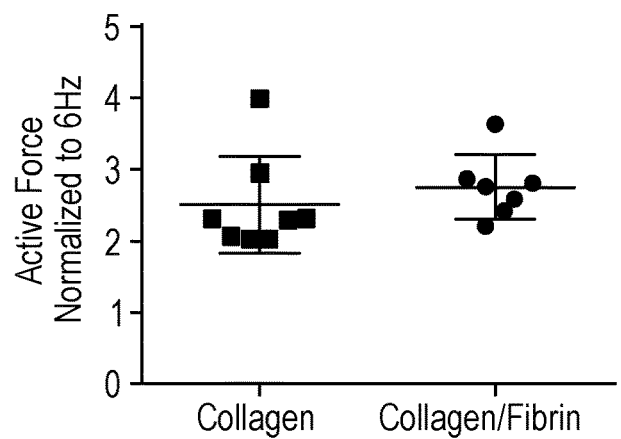
Figure 20G:
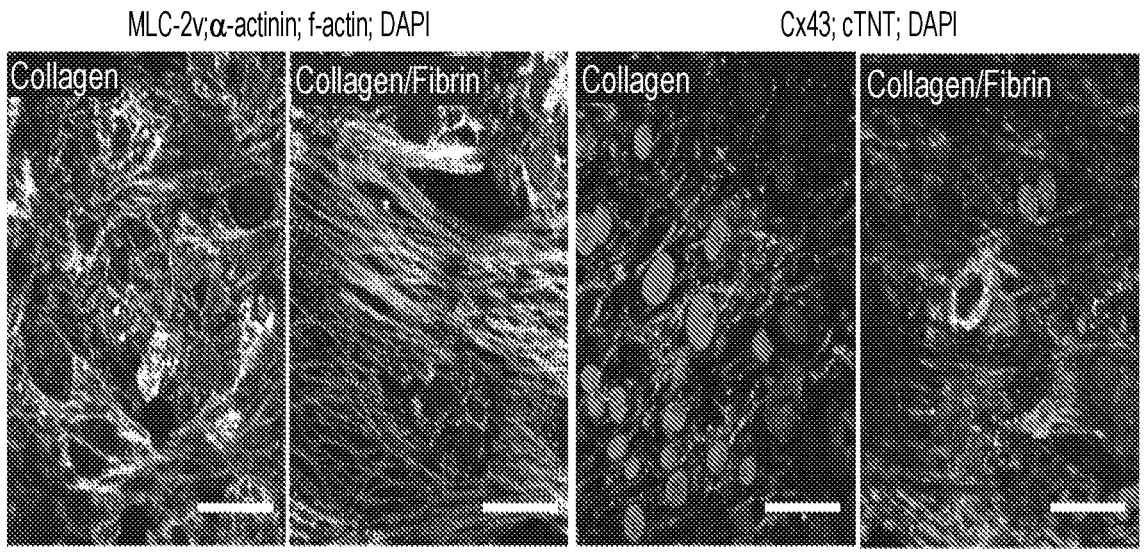
Figure 20H:
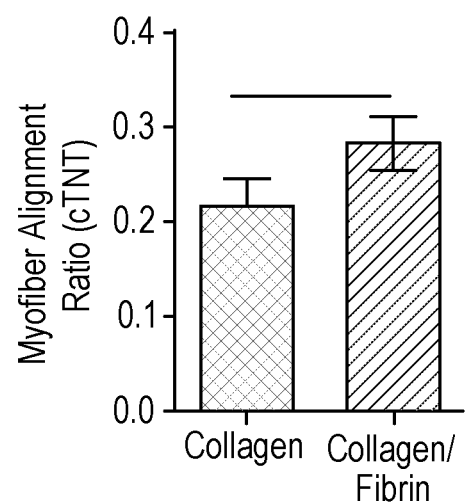

Pronounced positive FFR and robust PRP were observed in both hydrogel groups without significant differences (FIGS. 20E, 20F). Notably, tissues generated with the Collagen/Fibrin hydrogel had more aligned and organized structural proteins, i.e. myosin light chain 2v, sarcomeric α-actinin, F-actin and troponin T, compared to those tissues cultivated from the Collagen hydrogel (FIG. 20G, both left and right panel). The myofiber alignment was quantified from confocal images of cTNT staining and a significantly better alignment was shown in Collagen/Fibrin group (FIG. 20H). In addition, confocal images of Cx43 staining demonstrated the robust presence of this gap junctional protein in both groups (FIG. 20G, right panel).

According to these results, we concluded that both hydrogels were able to serve as a scaffold for tissue formation and maturation. Despite no measurable differences in contractile function, tissues in the Collagen/Fibrin group appeared to have an improved organization of intracellular structural and functional proteins compared to the Collagen only group.

Although collagen and fibrin hydrogels have similar microscopic structures, the shear modulus of pure Collagen hydrogel was reported to be only half that of the Collagen/Fibrin hydrogel, according to the studies that used identical Collagen/Fibrin ratio as we have explored here. Lower elastic modulus, higher ultimate tensile stress and toughness were observed in the Collagen/Fibrin gels compared to the pure Collagen gels in the previous studies. In addition, the mechanism of tissue compaction is closely related to cell migration, both of which can be linked to fibrin and its degradation products. These differences in chemical and mechanical properties may contribute to better CM alignment and enhanced intracellular organization in the tissues seeded with the fibrin-containing hydrogel.

This study focused on delineating microenvironmental factors governing human cardiac tissue formation in a unique organ-on-a-chip platform that is constructed entirely of cytocompatible low-absorption plastic and enables direct, non-destructive and continuous monitoring of the active force and passive tension of the developing tissue. The optimized microenvironmental factors enabled us to create miniaturized human cardiac tissues with as little as 0.1 million cells, while still obtaining hallmarks of adult-like functionality and maturation such as positive FFR and substantial PRPs. We found that the optimal seeding density for tissue formation was 50 million/mL. As a non-myocyte population for co-culture, cFBs enabled enhancement of electrophysiological properties consistent with cardiac chamber specificity. Further increasing the percentage of added cFBs was found to have detrimental effects on functional properties such as active force. Electrical conditioning was found to consistently enhance structural and functional properties in all groups. Moreover, the slower the frequency step-up, the more cardiac tissues successfully achieved the desired maturity as measured by the tissues ability to achieve a positive FFR. Finally, when comparing hydrogel scaffolds, a collagen hydrogel blended with fibrin enhanced intracellular organization of CMs. Controlling all the microenvironmental cues presented here may give rise to cardiac tissues that have a significant potential to improve the robustness and fidelity of stem cell-derived adult-like cardiac tissue models for use in drug development and disease modelling applications.

The Fabrication of Biowire Chip

A repeating pattern consisting of rectangular microwells (5 mm×1 mm×300 µm, L×W×H) interconnected by two parallel grooves (200 µm×100 µm, W×H) was designed and fabricated by soft lithography. The negative polydimethylsiloxane (PDMS) master was made by plasma bonding a sheet of patterned PDMS (Mold #1) to a silicon wafer and was used to hot emboss the microwells into a clear polystyrene sheet. Poly(octamethylene maleate (anhydride) citrate) (POMaC) polymer wires (100 µm×100 µm×8 cm, W×H×L) were prepared separately. PDMS mold (Mold #2) with channels (100 µm×100 µm×8 cm, W×H×L) was lightly pressed against the clean glass slide. The POMaC prepolymer was perfused through the channels and crosslinked with UV exposure. After peeling off the PDMS from the glass slide, POMaC wires were exposed and manually placed into the two parallel grooves patterned into the polystyrene sheet. Approximately 41 mg (after curing) of clear polyurethane 2-part adhesive (SP 1552-2, GS Polymers, Inc.) was used to fix the POMaC wires in place in order to obtain a single strip of 8 microwells. (FIG. 15A) The column of eight microwells was cut and used for tissue culture, as shown in the photograph (FIG. 15B).

Cells and Generation of Engineered Cardiac Tissue

Predominantly ventricular cardiomyocytes (CMs) were derived from the human embryonic stem cell (hESC) lines HES3-NKX2-5gfp/w and the human induced pluripotent stem cell (hiPSC) line BJ1D using published differentiation protocols. Ventricular cell populations from BJ1D iPSCs contained 74.7±6.3% (n=9) of CMs, based on cardiac troponin T expression analysis with flow cytometry at day 21 of the differentiation. Ventricular cells from HES3-NKX2.5gfp/w hESCs contained 76.1±13.0% (n=6) CMs, based on GFP+ expression analysis with flow cytometry at day 21 of the differentiation.

Predominantly atrial cardiomyocytes were derived from HES3-NKX2-5gfp/w hESCs using an atrial-specific EB differentiation protocol as described. Briefly, all-trans retinoic acid (0.5 µM, Sigma 82625) was added during the cardiac mesoderm specification stage (days 3-5 of differentiation) to promote atrial cardiogenesis. Atrial cardiomyocytes from HES3-NKX2-5gfp/w hESCs were analyzed and defined based on the proportion of NKX2.5+, cTNT+ and MLC2v– cells using flow cytometry on day 20 of differentiation, 79.1±8.0%, n=10. Differentiated cells were dissociated to single cells for subsequent tissue seeding, as previously described.

Flow Cytometry

Cells were obtained by dissociating differentiation cultures with collagenase (200 unit/mL). The cells were fixed with 4% paraformaldehyde (Sigma 158127) in PBS for 10 min at room temperature while shielding from light, to prevent bleaching of GFP fluorescence. For HES3-NKX2-5gfp/w hESC derived ventricular CMs, no further staining was required. For the rest of the cell types, cells were blocked with 5% fetal bovine serum (FBS) (Life Technologies 12483020) in phosphate buffered saline (PBS) for 30 min and followed by permeabilization with PBS containing 5% FBS and 0.1% Triton X (Alfa Aesar A16046) for 10 min on ice. Mouse anti-cardiac Troponin T (cTnT) (ThermoFisher MS295-P; 1:200) and donkey anti-mouse-Alexa Fluor 488 (Abcam ab150105; 1:400) were used subsequently to stain CMs. For HES3-NKX2-5gfp/w hESC derived atrial CMs, additional rabbit anti-myosin light chain-2v (Santa Cruz sc-15370), and Donkey anti-rabbit IgG (H+L), AlexaFluor555 (Thermo Fisher A31572) were used to identify atrial specification.

Hydrogel Preparation and Seeding Conditions

Collagen hydrogel (0.5 mL at 3.0 mg/mL) was prepared with high concentration rat tail collagen (9.82 mg/mL, Corning 354249) with 15% (v/v) Matrigel (Corning 354230), deionized sterile $H_2O$ and 10% (v/v) M199 (Sigma M0650) and neutralized by $NaHCO_3$(E COM SX0320-1) and NaOH (Caledon 7860-1-70). A Collagen/Fibrin hydrogel was prepared by combining the Collagen hydrogel with 33 mg/mL fibrinogen (Sigma-Aldrich F3879) in a 3:1 ratio. When the Collagen/Fibrin hydrogel was used, fibrin conversion to fibrinogen polymer was facilitated by the addition of 0.5 µL of 25 IU/mL thrombin (Sigma-Aldrich) to each well prior to seeding. Aprotinin (10 µM, Sigma A3428) was added in the first week of culture to the media in order to maintain the integrity of fibrin.

For seeding, CMs were dissociated from embryoid bodies or monolayers, they were mixed with the supporting cells, pelleted and resuspended in the specified hydrogel according to the experimental design, then 2 µL of cell-hydrogel mixture was added to each well. In all experiments, the tissues were kept in culture for 7 days to allow for remodeling and compaction around the POMaC wires prior to electrical conditioning.

To optimize seeding density, dissociated cardiac cells (HES3) and cardiac fibroblasts (LONZA, Clonetics™ NHCF-V) were mixed in a 10:2.5 cell number ratio, then they were seeded at four different concentrations: 25, 50, 100, 150 million per mL into the Biowire II wells.

Cardiac fibroblasts (cFB) and mesenchymal stem cells (MSC) were compared as non-myocyte populations for atrial tissue formation. Dissociated cardiac cells (HES3) and cFBs or MSC were mixed in 10:1.5 cell number ratios respectively.

To determine the appropriate fraction of non-myocytes, dissociated cardiac cells (HES3) and cardiac fibroblasts were mixed in 10:1 and 10:2.5 cell number ratios, for low cFB and high cFB groups respectively.

For hydrogel optimization, dissociated cardiac cells (BJ1D) and cFBs were mixed in 10:1 cell number ratio, in collagen hydrogel or collagen/fibrin hydrogel at 50 million per mL.

For electrical conditioning optimization, dissociated cardiac cells (BJ1D) and cFBs were mixed in 10:1 cell number ratio, in collagen hydrogel at 50 million per mL.

Electrical Stimulation

On day 7, tissues were transferred to an electrical stimulation chamber, as previously described, for electrical conditioning. Briefly, for ventricular tissues frequency was ramped up by 1 Hz per week from 2 Hz to 6 Hz unless otherwise specified. For the optimization of electrical conditioning, two protocols were compared: 1 Hz weekly increase from 2-6 Hz and 0.2 Hz daily increase from 1-6 Hz. For atrial preparations, the frequency was increased daily by 0.4 Hz, from 2 Hz to 6 Hz, then retained at 6 Hz for 1 week.

Evaluation of Active Force and Passive Tension

POMaC wires have an intrinsic autofluorescence in the blue channel, enabling us to determine wire deflection from the movies of tissue contraction taken in the blue channel (10× objective; $\lambda_{ex}$=350 nm, $\lambda_{em}$=470 nm; 100 frames/s, 5 ms exposure). To determine the force-frequency relationship (FFR), the tissues were electrically paced from 1-6 Hz (20 sec/each frequency). After the last period of high-frequency pacing, a short period of rest was induced by turning the stimulator off, followed by reinitiation of pacing at 1 Hz to determine post-rest potentiation (PRP). All imaging was performed by Olympus IX81 inverted fluorescent microscope and CellSens software (Olympus Corporation).

Sequential images from the blue channel recording were analyzed using a custom MatLab code that traced the maximum deflection of the POMaC wire. Total (at peak contraction) and passive (at rest) POMaC wire deflections were converted to force measurements (µN) using the force calibration curves described elsewhere. The active force was calculated as the difference between the total and passive tension. The custom MatLab code was used to calculate the passive tension, active force, contraction and relaxation duration, and upstroke and relaxation velocity.

Immunostaining, Confocal Microscopy and Myofiber Alignment Quantification

Tissues were fixed with 4% paraformaldehyde, permeabilized with 0.2% Tween20™ and blocked with 10% fetal bovine serum (FBS). The following primary antibodies were used: mouse anti-cardiac Troponin T (cTnT) (ThermoFisher MS295-P; 1:200), rabbit anti-Connexin 43 (Cx-43) (Abcam ab11370; 1:200), mouse anti-a-actinin (Abcam ab9465; 1:200), rabbit anti-myosin light chain-2v (Santa Cruz ab9465; 1:200). The following secondary antibodies were used: donkey anti-mouse-Alexa Fluor 488 (Abcam ab150105; 1:400) and donkey anti-rabbit-Alexa Fluor 594 (Abcam ab150080; 1:200). Phalloidin-Alexa Fluor 660 (Invitrogen A22285; 1:200) was used to stain F-actin fibers. Conjugated vimentin-Cy3 (Sigma C9080; 1:200) was used to stain for vimentin. Confocal microscopy images were obtained using an Olympus FluoView 1000 laser scanning confocal microscope (Olympus Corporation).

The alignment ratio was calculated using ImageJ plugin OrientationJ (Biomedical Imaging Group). The distribution analysis was performed using a Gaussian filter with a window of 2 pixels (cTNT) and 10 pixels (GFP+).

Brightfield Images from Histological Staining and the Quantification of Collagen Paraffin-embedded tissues were sectioned at 5 µm thickness. Masson's trichrome staining was then performed to reveal the collagen fibers, cells and cell nuclei followed by brightfield imaging on Olympus IX81 inverted microscope.

Area of collagen staining was determined by ImageJ color threshold analysis with Blue (0-255), green (180-255) and red (120-210). The total area of tissue was determined by manually tracing the tissue edges and measuring pixel numbers in the enclosed area.

Determination of Excitation Threshold and Maximum Capture Rate

Excitation Threshold (ET) and Maximum Capture Rate (MCR) of tissues were measured in the stimulation chamber connected to an electrical stimulator (S88x Stimulator, GRASS, Astromed). The tissues in the stimulation chamber were placed in a preconditioned environmental chamber (37° C. and 5% $CO_2$). The beating of the tissues was monitored under brightfield with electrical pacing. To find ET, the frequency and the duration of the monophasic electrical pulses were set to 1 Hz and 2 ms, respectively. The minimum voltage needed to induce the synchronous contraction of the tissue, i.e. ET, was tested by starting from 1 V/cm and increasing the stimulation amplitude in increments of 0.1 V/cm until the synchrony of tissue contraction was achieved. To find MCR, the voltage was set to twice the average ET for all tissues in the stimulation chamber. The maximum frequency allowing synchronous contraction, i.e. MCR, was found by increasing the stimulation frequency in 0.1 Hz increments starting from 1 Hz until the synchrony of tissue contraction was clearly interrupted.

Intracellular Recordings

Tissues were perfused with 35-37° C. Kreb's Solution (Sigma K4002) (118 mM NaCl, 4.2 mM KCl, 1.2 mM $KH_2PO_4$, 1.2 mM $MgSO_4$, 1.8 mM $CaCl_2$, 23 mM $NaHCO_3$, 2 mM Na-pyruvate and 20 mM glucose, equilibrated with 95% $O_2$ and 5% $CO_2$, pH 7.4). They were paced at twice the ET. The action potential was recorded with high impedance microelectrodes (60-90 MΩ) filled with 3 M KCl, connected to an Axopatch 200 B amplifier (Axon Instruments). Recordings were performed in current clamp mode at 10 kHz by clampex 10 and signals were analyzed using the Clampfit 10 Data Analysis Module of the pCLAMP™ 10 Electrophysiology Data Acquisition & Analysis Software (Axon Instruments). The movement of the tissue was minimized by perfusing with 10 µM blebbistatin (Toronto Research Chemicals) for 20 min.

DNA Quantification

Tissues were harvested from the Biowire II platform to estimate the total number of cells from each tissue after 30 days of culture. The tissues were lysed with 1× cell lysis buffer (Cell Signalling 9803) for 1 h in room temperature and then homogenized with the ultra-sonicator for 2 seconds. The supernatant was collected and analyzed with Quant-iT PicoGreen dsDNA Assay Kit (Thermo Fisher P11496) according to the manufacturer's protocol. The fluorescent nucleic acid signal from each cardiac tissue was correlated to a standard curve generated by extracting and measuring DNA from a known number of cardiac cells.

Statistics

Statistical analysis was performed using Prism 6.0 and SigmaPlot 12.0. All data are represented as mean±standard derivation (SD). Indicated sample sizes (n) represent individual tissue samples. For intracellular recordings, sample size (n) represents the number of cells analyzed from three or more independent experiments. Differences between experimental groups were analyzed by Student's t-test or Mann-Whitney test or one-way ANOVA or ANOVA on ranks. Experiments with two different variables were analyzed with two-way ANOVA. Holm-Sidak and Tukey's multiple comparison methods were used with one-way and two-way ANOVA. Dunn's multiple comparison method was used with ANOVA on ranks. $P<0.05$ was considered significant for all statistical tests.

REFERENCES

Y. Zhao, A. Korolj, N. Feric, M. Radisic, Human pluripotent stem cell-derived cardiomyocyte based models for cardiotoxicity and drug discovery, Expert opinion on drug safety 15(11) (2016) 1455-1458.

Y. Zhao, N. T. Feric, N. Thavandiran, S. S. Nunes, M. Radisic, The role of tissue engineering and biomaterials in cardiac regenerative medicine, The Canadian journal of cardiology 30(11) (2014) 1307-22.

G. Gintant, P. T. Sager, N. Stockbridge, Evolution of strategies to improve preclinical cardiac safety testing, Nature reviews. Drug discovery 15(7) (2016) 457-71.

L. Sala, M. Bellin, C. L. Mummery, Integrating cardiomyocytes from human pluripotent stem cells in safety pharmacology: has the time come?, British journal of pharmacology (2016).

T. Boudou, W. R. Legant, A. Mu, M. A. Borochin, N. Thavandiran, M. Radisic, P. W. Zandstra, J. A. Epstein, K. B. Margulies, C. S. Chen, A microfabricated platform to measure and manipulate the mechanics of engineered cardiac microtissues, Tissue engineering. Part A 18(9-10) (2012) 910-9.

C. P. Jackman, A. L. Carlson, N. Bursac, Dynamic culture yields engineered myocardium with near-adult functional output, Biomaterials 111 (2016) 66-79.

N. Huebsch, P. Loskill, N. Deveshwar, C. I. Spencer, L. M. Judge, M. A. Mandegar, C. B. Fox, T. M. Mohamed, Z. Ma, A. Mathur, A. M. Sheehan, A. Truong, M. Saxton, J. Yoo, D. Srivastava, T. A. Desai, P. L. So, K. E. Healy, B. R. Conklin, Miniaturized iPS-Cell-Derived Cardiac Muscles for Physiologically Relevant Drug Response Analyses, Scientific reports 6 (2016) 24726.

S. S. Nunes, J. W. Miklas, J. Liu, R. Aschar-Sobbi, Y. Xiao, B. Zhang, J. Jiang, S. Masse, M. Gagliardi, A. Hsieh, N. Thavandiran, M. A. Laflamme, K. Nanthakumar, G. J. Gross, P. H. Backx, G. Keller, M. Radisic, Biowire: a platform for maturation of human pluripotent stem cell-derived cardiomyocytes, Nature methods 10(8) (2013) 781-7.

S. Nattel, Electrical coupling between cardiomyocytes and fibroblasts: experimental testing of a challenging and important concept, Cardiovascular research 114(3) (2018) 349-352.

F. B. Sachse, A. P. Moreno, J. A. Abildskov, Electrophysiological modeling of fibroblasts and their interaction with myocytes, Annals of biomedical engineering 36(1) (2008) 41-56.

K. Ronaldson-Bouchard, S. P. Ma, K. Yeager, T. Chen, L. Song, D. Sirabella, K. Morikawa, D. Teles, M. Yazawa, G. Vunjak-Novakovic, Advanced maturation of human cardiac tissue grown from pluripotent stem cells, Nature 556(7700) (2018) 239-243.

A. Singh, A. Singh, D. Sen, Mesenchymal stem cells in cardiac regeneration: a detailed progress report of the last 6 years (2010-2015), Stem cell research & therapy 7(1) (2016) 82.

B. Zhang, A. Korolj, B. F. L. Lai, M. Radisic, Advances in organ-on-a-chip engineering, Nature Reviews Materials 3(8) (2018) 257-278.

K. Domansky, D. C. Leslie, J. McKinney, J. P. Fraser, J. D. Sliz, T. Hamkins-Indik, G. A. Hamilton, A. Bahinski, D. E. Ingber, Clear castable polyurethane elastomer for fabrication of microfluidic devices, Lab on a chip 13(19) (2013) 3956-64.

I. Mannhardt, K. Breckwoldt, D. Letuffe-Breniere, S. Schaaf, H. Schulz, C. Neuber, A. Benzin, T. Werner, A. Eder, T. Schulze, B. Klampe, T. Christ, M. N. Hirt, N. Huebner, A. Moretti, T. Eschenhagen, A. Hansen, Human Engineered Heart Tissue: Analysis of Contractile Force, Stem cell reports 7(1) (2016) 29-42.

B. Zhang, M. Montgomery, M. D. Chamberlain, S. Ogawa, A. Korolj, A. Pahnke, L. A. Wells, S. Masse, J. Kim, L. Reis, A. Momen, S. S. Nunes, A. R. Wheeler, K. Nanthakumar, G. Keller, M. V. Sefton, M. Radisic, Biodegradable scaffold with built-in vasculature for organ-on-a-chip engineering and direct surgical anastomosis, Nature materials 15(6) (2016) 669-78.

I. Rashedi, N. Talele, X. H. Wang, B. Hinz, M. Radisic, A. Keating, Collagen scaffold enhances the regenerative properties of mesenchymal stromal cells, PloS one 12(10) (2017) e0187348.

N. Bursac, M. Papadaki, R. J. Cohen, F. J. Schoen, S. R. Eisenberg, R. Carrier, G. Vunjak-Novakovic, L. E. Freed, Cardiac muscle tissue engineering: toward an in vitro model for electrophysiological studies, The American journal of physiology 277(2) (1999) H433-44.

O. Caspi, A. Lesman, Y. Basevitch, A. Gepstein, G. Arbel, I. H. Habib, L. Gepstein, S. Levenberg, Tissue engineering of vascularized cardiac muscle from human embryonic stem cells, Circulation research 100(2) (2007) 263-72.

A. Lesman, M. Habib, O. Caspi, A. Gepstein, G. Arbel, S. Levenberg, L. Gepstein, Transplantation of a tissue-engineered human vascularized cardiac muscle, Tissue engineering. Part A 16(1) (2010) 115-25.

R. K. Iyer, L. L. Chiu, M. Radisic, Microfabricated poly (ethylene glycol) templates enable rapid screening of triculture conditions for cardiac tissue engineering, Journal of biomedical materials research. Part A 89(3) (2009) 616-31.

R. K. Iyer, L. L. Chiu, G. Vunjak-Novakovic, M. Radisic, Biofabrication enables efficient interrogation and optimization of sequential culture of endothelial cells, fibroblasts and cardiomyocytes for formation of vascular cords in cardiac tissue engineering, Biofabrication 4(3) (2012) 035002.

R. K. Iyer, D. Odedra, L. L. Chiu, G. Vunjak-Novakovic, M. Radisic, VEGF Secretion by Non-Myocytes Modulates Connexin-43 Levels in Cardiac Organoids, Tissue engineering. Part A (2012).

H. Naito, I. Melnychenko, M. Didie, K. Schneiderbanger, P. Schubert, S. Rosenkranz, T. Eschenhagen, W. H. Zimmermann, Optimizing engineered heart tissue for therapeutic applications as surrogate heart muscle, Circulation 114(1 Suppl) (2006) 172-8.

K. R. Stevens, K. L. Kreutziger, S. K. Dupras, F. S. Korte, M. Regnier, V. Muskheli, M. B. Nourse, K. Bendixen, H. Reinecke, C. E. Murry, Physiological function and transplantation of scaffold-free and vascularized human cardiac muscle tissue, Proceedings of the National Academy of Sciences of the United States of America 106(39) (2009) 16568-73.

N. Thavandiran, N. Dubois, A. Mikryukov, S. Masse, B. Beca, C. A. Simmons, V. S. Deshpande, J. P. McGarry, C. S. Chen, K. Nanthakumar, G. M. Keller, M. Radisic, P. W. Zandstra, Design and formulation of functional pluripotent stem cell-derived cardiac microtissues, Proceedings of the National Academy of Sciences of the United States of America 110(49) (2013) E4698-707.

N. L. Tulloch, V. Muskheli, M. V. Razumova, F. S. Korte, M. Regnier, K. D. Hauch, L. Pabon, H. Reinecke, C. E. Murry, Growth of engineered human myocardium with mechanical loading and vascular coculture, Circulation research 109(1) (2011) 47-59.

L. Cyganek, M. Tiburcy, K. Sekeres, K. Gerstenberg, H. Bohnenberger, C. Lenz, S. Henze, M. Stauske, G. Salinas, W. H. Zimmermann, G. Hasenfuss, K. Guan, Deep phenotyping of human induced pluripotent stem cell-derived atrial and ventricular cardiomyocytes, JCI insight 3(12) (2018).

Y. Zhao, N. Rafatian, N. T. Feric, B. J. Cox, R. Aschar-Sobbi, E. Y. Wang, P. Aggarwal, B. Zhang, G. Conant, K. Ronaldson-Bouchard, A. Pahnke, S. Protze, J. H. Lee, L. Davenport Huyer, D. Jekic, A. Wickeler, H. E. Naguib, G. M. Keller, G. Vunjak-Novakovic, U. Broeckel, P. H. Backx, M. Radisic, A Platform for Generation of Chamber-Specific Cardiac Tissues and Disease Modeling, Cell 176(4) (2019) 913-927 e18.

Y. Zhao, N. Rafatian, N. T. Feric, B. Cox, R. Aschar-Sobbi, E. Y. Wang, P. Aggarwal, B. Zhang, G. Conant, K. Ronaldson-Bouchard, A. Pahnke, S. Protze, J. H. Lee, L. Davenport Huyer, D. Jekic, A. Wickeler, H. Naguib, G. M. Keller, G. Vunjak-Novakovic, U. Broeckel, P. H.

Backx, M. Radisic, A platform for generation of chamber specific cardiac tissues and disease modelling, Cell in press (2018).

M. Lemme, B. M. Ulmer, M. D. Lemoine, A. T. L. Zech, F. Flenner, U. Ravens, H. Reichenspurner, M. Rol-Garcia, G. Smith, A. Hansen, T. Christ, T. Eschenhagen, Atrial-like Engineered Heart Tissue: An In Vitro Model of the Human Atrium, Stem cell reports 11(6) (2018) 1378-1390.

E. Bell, H. P. Ehrlich, D. J. Buttle, T. Nakatsuji, Living tissue formed in vitro and accepted as skin-equivalent tissue of full thickness, Science 211(4486) (1981) 1052-4.

C. Vasquez, N. Benamer, G. E. Morley, The cardiac fibroblast: functional and electrophysiological considerations in healthy and diseased hearts, Journal of cardiovascular pharmacology 57(4) (2011) 380-8.

M. M. Maleckar, J. L. Greenstein, W. R. Giles, N. A. Trayanova, Electrotonic Coupling between Human Atrial Myocytes and Fibroblasts Alters Myocyte Excitability and Repolarization, Biophysical journal 97(8) (2009) 2179-2190.

R. F. Wiegerinck, A. Cojoc, C. M. Zeidenweber, G. Ding, M. Shen, R. W. Joyner, J. D. Fernandez, K. R. Kanter, P. M. Kirshbom, B. E. Kogon, M. B. Wagner, Force frequency relationship of the human ventricle increases during early postnatal development, Pediatric research 65(4) (2009) 414-9.

M. Tiburcy, J. E. Hudson, P. Balfanz, S. Schlick, T. Meyer, M. L. Chang Liao, E. Levent, F. Raad, S. Zeidler, E. Wingender, J. Riegler, M. Wang, J. D. Gold, I. Kehat, E. Wettwer, U. Ravens, P. Dierickx, L. W. van Laake, M. J. Goumans, S. Khadj eh, K. Toischer, G. Hasenfuss, L. A. Couture, A. Unger, W. A. Linke, T. Araki, B. Neel, G. Keller, L. Gepstein, J. C. Wu, W. H. Zimmermann, Defined Engineered Human Myocardium With Advanced Maturation for Applications in Heart Failure Modeling and Repair, Circulation 135(19) (2017) 1832-1847.

S. Rhee, Fibroblasts in three dimensional matrices: cell migration and matrix remodeling, Exp Mol Med 41(12) (2009) 858-865.

J. J. Tomasek, G. Gabbiani, B. Hinz, C. Chaponnier, R. A. Brown, Myofibroblasts and mechano-regulation of connective tissue remodelling, Nat Rev Mol Cell Bio 3(5) (2002) 349-363.

Y. Xie, A. Garfinkel, P. Camelliti, P. Kohl, J. N. Weiss, Z. Qu, Effects of fibroblast-myocyte coupling on cardiac conduction and vulnerability to reentry: A computational study, Heart rhythm: the official journal of the Heart Rhythm Society 6(11) (2009) 1641-9.

V. Jacquemet, C. S. Henriquez, Loading effect of fibroblast-myocyte coupling on resting potential, impulse propagation, and repolarization: insights from a microstructure model, American journal of physiology. Heart and circulatory physiology 294(5) (2008) H2040-52.

K. M. Herum, I. G. Lunde, A. D. McCulloch, G. Christensen, The Soft- and Hard-Heartedness of Cardiac Fibroblasts: Mechanotransduction Signaling Pathways in Fibrosis of the Heart, J Clin Med 6(5) (2017).

K. N. J., K. R. J., M. A. J., K. L. K. Coulombe, Optimizing Blended Collagen-Fibrin Hydrogels for Cardiac Tissue Engineering with Human iPSC-derived Cardiomyocytes, ACS Biomaterials Science & Engineering DOI: 10.1021/acsbiomaterials.8b01112 (2018).

S. Schaaf, A. Shibamiya, M. Mewe, A. Eder, A. Stohr, M. N. Hirt, T. Rau, W. H. Zimmermann, L. Conradi, T. Eschenhagen, A. Hansen, Human engineered heart tissue as a versatile tool in basic research and preclinical toxicology, PloS one 6(10) (2011) e26397.

V. K. Lai, S. P. Lake, C. R. Frey, R. T. Tranquillo, V. H. Barocas, Mechanical behavior of collagen-fibrin co-gels reflects transition from series to parallel interactions with increasing collagen content, Journal of biomechanical engineering 134(1) (2012) 011004.

Y. P. Kong, B. Carrion, R. K. Singh, A. J. Putnam, Matrix identity and tractional forces influence indirect cardiac reprogramming, Scientific reports 3 (2013) 3474.

C. L. Cummings, D. Gawlitta, R. M. Nerem, J. P. Stegemann, Properties of engineered vascular constructs made from collagen, fibrin, and collagen-fibrin mixtures, Biomaterials 25(17) (2004) 3699-706.

H. Nomura, M. Naito, A. Iguchi, W. D. Thompson, E. B. Smith, Fibrin gel induces the migration of smooth muscle cells from rabbit aortic explants, Thrombosis and haemostasis 82(4) (1999) 1347-52.

L. A. Sporn, L. A. Bunce, C. W. Francis, Cell proliferation on fibrin: modulation by fibrinopeptide cleavage, Blood 86(5) (1995) 1802-10.

M. R. Neidert, E. S. Lee, T. R. Oegema, R. T. Tranquillo, Enhanced fibrin remodeling in vitro with TGF-beta1, insulin and plasmin for improved tissue-equivalents, Biomaterials 23(17) (2002) 3717-31.

C. Martin, A. Sofla, B. Y. Zhang, S. S. Nunes, M. Radisic, Fusible core molding for the fabrication of branched, perfusable, three-dimensional microvessels for vascular tissue engineering, Int J Artif Organs 36(3) (2013) 159-165.

Y. Zhao, E. Y. Wang, L. H. Davenport, Y. Liao, K. Yeager, G. Vunjak-Novakovic, M. Radisic, B. Zhang, A Multi-material Microphysiological Platform Enabled by Rapid Casting of Elastic Microwires, Advanced healthcare materials (2019) e1801187.

R. T. Tran, P. Thevenot, D. Gyawali, J. C. Chiao, L. Tang, J. Yang, Synthesis and characterization of a biodegradable elastomer featuring a dual crosslinking mechanism, Soft matter 6(11) (2010) 2449-2461.

X. Lian, C. Hsiao, G. Wilson, K. Zhu, L. B. Hazeltine, S. M. Azarin, K. K. Raval, J. Zhang, T. J. Kamp, S. P. Palecek, Robust cardiomyocyte differentiation from human pluripotent stem cells via temporal modulation of canonical Wnt signaling, Proceedings of the National Academy of Sciences of the United States of America 109(27) (2012) E1848-57.

X. Lian, J. Zhang, S. M. Azarin, K. Zhu, L. B. Hazeltine, X. Bao, C. Hsiao, T. J. Kamp, S. P. Palecek, Directed cardiomyocyte differentiation from human pluripotent stem cells by modulating Wnt/beta-catenin signaling under fully defined conditions, Nature protocols 8(1) (2013) 162-75.

J. H. Lee, S. I. Protze, Z. Laksman, P. H. Backx, G. M. Keller, Human Pluripotent Stem Cell-Derived Atrial and Ventricular Cardiomyocytes Develop from Distinct Mesoderm Populations, Cell stem cell 21(2) (2017) 179-194 e4.

Y. Zhao, N. Rafatian, N. Feric, B. Cox, R. Aschar-Sobbi, Y. Wang, P. Aggarwal, B. Zhang, G. Conant, K. Ronaldson-Bouchard, A. Pahnke, S. Protze, J. H. Lee, L. Davenport Huyer, D. Jekic, A. Wickeler, H. Naguib, G. Keller, G. Vunjak-Novakovic, U. Broeckel, B. P., M. Radisic, A platform for generation of chamber specific cardiac tissues and disease modeling, Cell (2018).

S. S. Nunes, N. Feric, A. Pahnke, J. W. Miklas, M. Li, J. Coles, M. Gagliardi, G. Keller, M. Radisic, Human Stem Cell-Derived Cardiac Model of Chronic Drug Exposure, ACS Biomaterials Science & Engineering 3(9) (2017) 11.

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A composite cardiac tissue grown in vitro, the composite cardiac tissue having a cylindrical geometry, the composite cardiac tissue comprising an atrial tissue at a first longitudinal end of the composite cardiac tissue and a ventricular tissue at an opposite second longitudinal end of the composite cardiac tissue, wherein the atrial tissue is connected to the ventricular tissue via a transition zone between the atrial tissue at the first longitudinal end of the composite cardiac tissue and the ventricular tissue at the second longitudinal end of the composite cardiac tissue, the transition zone comprising tissue with mixed atrial and ventricular properties, wherein a first action potential (AP) measurement taken at the atrial tissue has a first amplitude, a second AP measurement of taken at the ventricular tissue has a second amplitude higher than the first amplitude, and a third AP measurement taken at the transition zone has a third amplitude that is intermediate between the first and second amplitudes.

2. The composite cardiac tissue of claim 1, having at least about 30% of cells substantially aligned in the same direction.

3. The composite cardiac tissue of claim 1, further comprising a hydrogel, wherein at least a portion of the cells are encapsulated inside the hydrogel.

4. The composite cardiac tissue of claim 3, wherein the hydrogel comprises collagen, intestinal submucosa, cellulose, a proteoglycan, heparin sulfate, chondroitin sulfate, keratin sulfate, hyaluronic acid, elastin, fibronectin, thrombin, laminin, fibrin, chitosan, alginate, solubilized basement membrane extracted from Engelbreth-Hold-Swarm (EHS) mouse sarcoma cells, agarose, decellularized extracellular matrix, polyethylene glycol, silicone, or a combination thereof.

5. The composite cardiac tissue of claim 1, wherein the ventricular tissue is characterized by higher expression of myosin light chain-2v (MLC2v) compared to the atrial tissue.

6. The composite cardiac tissue of claim 4, wherein the hydrogel comprises collagen and fibrin.

7. The composite cardiac tissue of claim 1, wherein the composite cardiac tissue has a volume of about 0.1-2.5 mm$^3$.

8. The composite cardiac tissue of claim 1, wherein the composite cardiac tissue has a length of at least about 3 mm.

9. A method for producing a composite cardiac tissue in vitro, the composite cardiac having an atrial tissue and a ventricular tissue in connection with each other, the method comprising:
 (a) providing atrial cardiomyocytes at a first longitudinal end of a microwell and ventricular cardiomyocytes at a second opposing longitudinal end of the microwell;
 (b) applying an electrical stimulation at a first frequency to the atrial and ventricular cardiomyocytes for a first period of time, the first frequency being equal to or greater than a suprathreshold frequency;
 (c) increasing the frequency of the electrical stimulation at a rate of at least about 0.05 Hz/day until the frequency is at a second frequency of no more than about 6 Hz; and
 (d) maintaining the electrical stimulation at the second frequency for a second period of time, thereby producing the composite cardiac tissue having a cylindrical geometry, the composite cardiac tissue comprising the atrial tissue at a first longitudinal end of the composite cardiac tissue and the ventricular tissue at an opposite second longitudinal end of the composite cardiac tissue, the atrial tissue being connected to the ventricular tissue via a transition zone between the atrial tissue at the first longitudinal end of the composite cardiac tissue and the ventricular tissue at the second longitudinal end of the composite cardiac tissue, the transition zone comprising tissue with mixed atrial and ventricular properties, wherein a first action potential (AP) measurement taken at the atrial tissue has a first amplitude, a second AP measurement of taken at the ventricular tissue has a second amplitude higher than the first amplitude, and a third AP measurement taken at the transition zone has a third amplitude that is intermediate between the first and second amplitudes.

10. The method of claim 9, wherein the first frequency is about 1-3 Hz.

11. The method of claim 9, wherein the rate is no more than about 1 Hz/day.

12. The method of claim 9, wherein step (d) comprises producing the ex vivo tissue having at least about 30% of cells substantially aligned in the same direction.

13. The method of claim 9, wherein at least a portion of the atrial and ventricular cardiomyocytes are encapsulated inside a hydrogel.

14. The method of claim 13, wherein the hydrogel comprises, intestinal submucosa, cellulose, a proteoglycan, heparin sulfate, chondroitin sulfate, keratin sulfate, hyaluronic acid, elastin, fibronectin, thrombin, laminin, fibrin, chitosan, alginate, solubilized basement membrane extracted from Engelbreth-Hold-Swarm (EHS) mouse sarcoma cells, agarose, decellularized extracellular matrix, polyethylene glycol, silicone, or a combination thereof.

* * * * *